US011053222B2

(12) United States Patent
Hermanson et al.

(10) Patent No.: US 11,053,222 B2
(45) Date of Patent: Jul. 6, 2021

(54) FLUORESCENT COMPOUNDS

(71) Applicants: Pierce Biotechnology, Inc., Rockville, IL (US); Dyomics GmbH, Jena (DE)

(72) Inventors: Greg Hermanson, Loves Park, IL (US); Peter T. Czerney, Weimar (DE); Surbhi Desai, Rockford, IL (US); Matthias S. Wenzel, Jena (DE); Boguslawa Dworecki, Rockford, IL (US); Frank G. Lehmann, Jena (DE)

(73) Assignees: Pierce Biotechnology, Inc., Rockville, IL (US); Dyomics GmbH, Jena (DE)

( * ) Notice: Subject to any disclaimer, the term of this patent is extended or adjusted under 35 U.S.C. 154(b) by 24 days.

(21) Appl. No.: 16/436,512

(22) Filed: Jun. 10, 2019

(65) Prior Publication Data

US 2019/0359596 A1    Nov. 28, 2019

Related U.S. Application Data

(63) Continuation of application No. 15/817,561, filed on Nov. 20, 2017, now Pat. No. 10,351,551, which is a continuation of application No. 13/330,993, filed on Dec. 20, 2011, now Pat. No. 10,053,447.

(60) Provisional application No. 61/425,446, filed on Dec. 21, 2010, provisional application No. 61/446,319, filed on Feb. 24, 2011, provisional application No. 61/480,840, filed on Apr. 29, 2011, provisional application No. 61/482,933, filed on May 5, 2011.

(51) Int. Cl.
*C07D 403/06*    (2006.01)
*C07D 209/10*    (2006.01)

(52) U.S. Cl.
CPC ......... *C07D 403/06* (2013.01); *C07D 209/10* (2013.01)

(58) Field of Classification Search
CPC .... A61K 51/00; A61K 51/04; A61K 2121/00; A61K 2123/00; A61K 51/041; A61K 51/044; A61K 51/08; A61K 51/088; A61K 51/10; A61K 51/06; C07D 209/00; C07D 209/04; C07D 209/10; C07D 403/00; C07D 403/02; C07D 403/06
USPC ...... 424/1.11, 1.49, 1.65, 1.69, 9.1, 9.2, 9.6; 514/1, 1.1, 19.2, 19.3, 19.4, 19.5, 19.6; 530/300
See application file for complete search history.

(56) References Cited

U.S. PATENT DOCUMENTS

| | | |
|---|---|---|
| 1,524,791 A | 2/1925 | Konig |
| 4,839,265 A | 6/1989 | Ohno et al. |
| 4,981,977 A | 1/1991 | Southwick et al. |
| 5,268,486 A | 12/1993 | Waggoner et al. |
| 5,486,616 A | 1/1996 | Waggoner et al. |
| 5,556,959 A | 9/1996 | Brush et al. |
| 5,569,587 A | 10/1996 | Waggoner |
| 5,569,766 A | 10/1996 | Waggoner et al. |
| 5,627,027 A | 5/1997 | Waggoner |
| 5,846,737 A | 12/1998 | Kang |
| 5,972,838 A | 10/1999 | Pearce et al. |
| 5,986,086 A | 11/1999 | Brush et al. |
| 6,048,982 A | 4/2000 | Waggoner |
| 6,083,485 A | 7/2000 | Licha et al. |
| 6,136,612 A | 10/2000 | Della Ciania et al. |
| 6,225,050 B1 | 5/2001 | Waggoner |
| 6,258,340 B1 | 7/2001 | Licha et al. |
| 6,342,326 B1 | 1/2002 | Milton |
| 6,534,041 B1 | 3/2003 | Licha et al. |
| 6,641,093 B2 | 11/2003 | Coudrais |
| 6,673,334 B1 | 1/2004 | Achilefu et al. |
| 6,761,878 B2 | 7/2004 | Achilefu et al. |
| 6,924,372 B2 | 8/2005 | Czerney et al. |
| 6,939,532 B2 | 9/2005 | Achilefu et al. |
| 6,974,873 B2 | 12/2005 | Leung et al. |
| 6,977,305 B2 | 12/2005 | Leung et al. |
| 7,172,907 B2 | 2/2007 | Chen et al. |
| 7,175,831 B2 | 2/2007 | Achilefu et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |
| 8,431,111 B2 | 4/2013 | Nairne et al. |
| 8,889,884 B1 | 11/2014 | Hermanson et al. |
| 9,097,667 B2 | 8/2015 | Mao et al. |

(Continued)

FOREIGN PATENT DOCUMENTS

AU    2006200511    2/2006
DE       4445065 A1    6/1996

(Continued)

OTHER PUBLICATIONS

Search Report issued by the German Patent Office regarding App #10 2006 029 454.8 dated Oct. 10, 2006 (with English language summary).
Search Report issued by the German Patent Office regarding App #10 2006 057 345.5 dated May 21, 2007 (with English language summary).
International Search Report and Written Opinion PCT/US2013/028252, issued by the European Patent Office, dated Apr. 25, 2013 (12 pages).

(Continued)

*Primary Examiner* — D. L. Jones
(74) *Attorney, Agent, or Firm* — McNeill Baur PLLC

(57) ABSTRACT

Compounds used as labels with properties comparable to known fluorescent compounds. The compounds can be conjugated to proteins and nucleic acids for biological imaging and analysis. Synthesis of the compounds, formation and use of the conjugated compounds, and specific non-limiting examples of each are provided.

12 Claims, 50 Drawing Sheets

(56) References Cited

U.S. PATENT DOCUMENTS

| | | |
|---|---|---|
| 9,249,307 B2 | 2/2016 | Hermanson et al. |
| 9,365,598 B2 | 6/2016 | Hermanson et al. |
| 9,676,787 B2 | 6/2017 | Hermanson et al. |
| 9,751,868 B2 | 9/2017 | Hermanson et al. |
| 9,791,450 B2 | 10/2017 | Mao et al. |
| 10,000,467 B2 | 6/2018 | Hermanson et al. |
| 10,053,447 B2 * | 8/2018 | Hermanson .......... C07D 403/06 |
| 10,125,120 B2 | 11/2018 | Hermanson et al. |
| 10,351,551 B2 * | 7/2019 | Hermanson .......... C07D 403/06 |
| 2001/0055567 A1 | 12/2001 | Licha et al. |
| 2002/0064794 A1 | 5/2002 | Leung et al. |
| 2002/0077487 A1 | 6/2002 | Leung et al. |
| 2004/0166515 A1 | 8/2004 | Terpetschnig et al. |
| 2004/0241095 A1 | 12/2004 | Achilefu et al. |
| 2006/0004188 A1 | 1/2006 | Leung et al. |
| 2006/0099638 A1 | 5/2006 | Leung et al. |
| 2007/0128659 A1 | 6/2007 | Czerney et al. |
| 2007/0178512 A1 | 8/2007 | Leung et al. |
| 2007/0203343 A1 | 8/2007 | West et al. |
| 2008/0233050 A1 | 9/2008 | Achilefu et al. |
| 2009/0035809 A1 | 2/2009 | Leung et al. |
| 2009/0305410 A1 | 12/2009 | Mao et al. |
| 2010/0040547 A1 | 2/2010 | Frangioni |
| 2010/0196282 A1 | 8/2010 | Nairne et al. |
| 2010/0215585 A1 | 8/2010 | Frangioni |
| 2010/0267937 A1 | 10/2010 | West et al. |
| 2010/0303732 A1 | 12/2010 | Bahner |
| 2011/0065896 A1 | 3/2011 | Licha et al. |
| 2011/0171678 A1 | 7/2011 | Leung et al. |
| 2011/0178397 A1 | 7/2011 | Bahner |
| 2012/0114563 A1 | 5/2012 | Carter et al. |
| 2012/0156140 A1 | 6/2012 | Hermanson et al. |
| 2013/0045488 A1 | 2/2013 | Hermanson et al. |
| 2013/0230465 A1 | 9/2013 | Hermanson et al. |
| 2013/0230466 A1 | 9/2013 | Hermanson et al. |
| 2014/0106349 A1 | 4/2014 | Mao et al. |
| 2014/0255312 A1 | 9/2014 | Hermanson et al. |
| 2015/0119281 A1 | 4/2015 | Hermanson et al. |
| 2015/0322078 A1 | 11/2015 | Hermanson et al. |
| 2016/0168383 A1 | 6/2016 | Hermanson et al. |
| 2016/0176852 A1 | 6/2016 | Hermanson et al. |
| 2016/0176853 A1 | 6/2016 | Hermanson et al. |
| 2018/0002340 A1 | 1/2018 | Hermanson et al. |
| 2018/0118723 A1 | 5/2018 | Hermanson et al. |
| 2018/0134689 A1 | 5/2018 | Hermanson et al. |
| 2018/0327387 A1 | 11/2018 | Hermanson et al. |
| 2019/0084964 A1 | 3/2019 | Hermanson et al. |

FOREIGN PATENT DOCUMENTS

| | | |
|---|---|---|
| DE | 19717904 A1 | 10/1998 |
| DE | 19926460 A1 | 12/1999 |
| DE | 10046215 A1 | 4/2002 |
| EP | 1 152 008 | 11/2001 |
| EP | 1181940 | 2/2002 |
| EP | 1322710 | 7/2003 |
| EP | 1770129 | 4/2007 |
| EP | 1792949 | 6/2007 |
| EP | 1801165 | 6/2007 |
| EP | 2325263 | 7/2010 |
| GB | 434875 | 9/1935 |
| JP | 03217837 | 9/1991 |
| JP | 5-313304 | 11/1993 |
| WO | 96/17628 | 6/1996 |
| WO | 98/48838 | 11/1998 |
| WO | 00/075237 | 12/2000 |
| WO | 02/26891 | 4/2002 |
| WO | 02/32466 A1 | 4/2002 |
| WO | 2004/065491 A1 | 8/2004 |
| WO | 05/044923 | 5/2005 |
| WO | 2005/044923 | 5/2005 |
| WO | 05/103162 | 11/2005 |
| WO | 06/020947 | 2/2006 |
| WO | 2008/017079 | 2/2008 |
| WO | 2009/016180 | 2/2009 |
| WO | 2009/016181 | 2/2009 |
| WO | 2009/078970 A1 | 6/2009 |
| WO | 10/091126 | 8/2010 |
| WO | 2010/106169 | 9/2010 |
| WO | 2012/088007 A1 | 6/2012 |
| WO | 2012/129128 A1 | 9/2012 |

OTHER PUBLICATIONS

International Search Report of the World Intellectual Property Bureau for PCT/US2011/065975, dated Mar. 15, 2012.

Written Opinion of the World Intellectual Property Bureau for PCT/US2011/065975, dated Mar. 15, 2012.

International Preliminary Report on Patentability, PCT/US/2011/065975, dated Jul. 4, 2013 (8 pages).

Examination Report, Great Britain Application No. 1214580.1, dated May 31, 2013 (4 pages).

Extended European Search Report, European Patent Application No. 15198169.3 (dated Mar. 29, 2016, 8 pages).

Extended European Search Report and Written Opinion issued in European Patent Application No. 16169172.0 (dated Jul. 14, 2016, 7 pages).

Second Office Action with English translation issued in Chinese Patent Application No. 201380005497.X (dated Apr. 28, 2016, 21 pages).

Rejection Decision with English translation issued in Chinese Patent Application No. 201380005497.X (dated Nov. 2, 2016, 11 pages).

United Kingdom Search and Examination Report GB1214580.1, dated Nov. 22, 2012, 4 pages.

Office Action in European Patent Application No. 15198169.3, dated Jan. 13, 2017, 3 pages.

Office Action in European Patent Application No. 15198169.3, dated Jul. 13, 2017, 4 pages.

Alvarez-Maubecin, V. et al. Functional Coupling Between Neurons and Glia. The Journal of Neuroscience. Jun. 1, 2000, 20(11):4091-4098.

Bharaj, B.S. et al. Rapid sequencing of the p53 gene with a new automated DNA sequencer. Clinical Chemistry. 44:7 1397-1403 1998.

Biotium. Product brochure titled CF™ Dyes The next-generation dyes for protein labeling. Apr. 6, 2006.

Burns, M.A. et al. An Integrated Nanoliter DNA Analysis Device. Science. vol. 282, pp. 484-487, Oct. 16, 1998.

DeRisi, J.L. et al. Exploring the Metabolic and Genetic Control of Gene Expression on a Genomic Scale. Science. vol. 278, pp. 680-686, Oct. 24, 1997.

Fradelizi, J. et al. Quantitative Measurement of Proteins by Western Blotting with Cy5™-Coupled Secondary Antibodies. BioTechniques. 26:484-494 Mar. 1999.

Gragg, J. L. Synthesis of Near-Infrared Heptamethine Cyanine Dyes. Chemistry Theses. Paper 28 (2010). http://digitalarchive.gsu.edu/chemistry_theses/28.

Hermanson, Bioconjugate Techniques, 2nd Ed., London, Elsevier Inc. 2008, pp. 464-474; 690-697.

Licha et al. Synthesis and Characterization of Cyanine Dye—Poly(ethylene Glycol) Conjugates as Contrast Agents for In Vivo Fluorescence Imaging. SPIE 3196 (1998) 98-102.

MacBeath, G. and S.L. Schreiber. Printing Proteins as Microarrays for High-Throughput Function Determination. Science. vol. 289, pp. 1760-1763, Sep. 8, 2000.

Manders, E.M.M. et al. Direct Imaging of DNA in Living Cells Reveals the Dynamics of Chromosome Formation. The Journal of Cell Biology. vol. 144, No. 5, Mar. 8, 1999 813-821.

Mank, A.J.G. et al., Visible Diode Laser-Induced Fluorescence Detection in Liquid Chromatography after Precolumn Derivatization of Amines. Anal. Chem. vol. 67, pp. 1742-1748, 1995.

Mujumdar, R.B. et al. Cyanine Dye Labeling Reagents: Sulfoindocyanine Succinimidyl Esters. Bioconjug Chem. vol. 4, No. 2, pp. 105-111, Mar./Apr. 1993.

Patonay, G., et al. Noncovalent Labeling of Biomolecules with Red and Near-Infrared Dyes. Molecules. 9, 40-49, 2004.

(56) References Cited

OTHER PUBLICATIONS

Pharmacia Biotech. Table of Contents p. 294 and p. 295 of the Pharmacia Biotech Catalogue. 1994.
Riefke et al. Tumor Detection with Cyanine Dye-Poly(ethylene Glycol) Conjugates as Contrast Agents for Near-Infrared Imaging. SPIE 3196 (1998) 103-110.
Roman, B.L. et al. Non-Radioisotopic AFLP Method Using PCR Primers Fluorescently Labeled with Cy™ 5. BioTechniques. vol. 26, No. 2, pp. 236-238, Feb. 1999.
Schena, M. et al. Parallel human genome analysis: Microarray-based expression monitoring of 1000 genes. Proc. Natl. Acad. Sci. USA. vol. 93, pp. 10614-10619, Oct. 1996.
Shao, F. et al. Monofunctional Carbocyanine Dyes for Bio- and Bioorthogonal Conjugation. Bioconjugate Chemistry. 19(12): 2487-2491, Dec. 2008.
Strekowski (ed.), Heterocyclic Polymethine Dyes: Synthesis, Properties and Applications, (2008) Springer-Verlag, Berlin Heidelberg, pp. 1-241.
Voss, H. et al. Automated Cycle Sequencing with Taquenase™: Protocols for Internal Labeling, Dye Primer and "Doublex" Simultaneous Sequencing. BioTechniques. vol. 23, No. 2, pp. 312-318, Aug. 1997.
Wilchek and Miron Activation of Sepharose with N,N'-disuccinimidyl carbonate. Applied Biochemistry and Biotechnology, vol. 11, pp. 191-193 (1985).

\* cited by examiner rabbit IgG (ng/well)

Biotinylated BSA (ng/well)

mouse IgG (ng/well)

| S/B (@ 125 ng coating) | 2.5X | 7.5X | 10X | 15X |
|---|---|---|---|---|
| DyLight 750-GAM | 134.9 | 207.9 | 191.5 | 161.2 |
| 755 Compound 1 (isomer 1)-GAM | 127.5 | 182.4 | 158.5 | 137.2 |
| 755 Compound 1 (isomer 2)-GAM | 87.1 | 158.7 | 136.5 | 101.2 |
| Alexa 750-GAM | 108.0 | 109.6 | 71.1 | 53.5 |

| S/B (@ 125 ng coating) | 2.5X | 7.5X | 10X | 15X |
|---|---|---|---|---|
| DyLight 750-GAR | 76.2 | 139.5 | 100.8 | 102.9 |
| 755 Compound 1 (isomer 1)-GAR | 50.5 | 122.5 | 80.8 | 84.0 |
| 755 Compound 1 (isomer 2)-GAR | 50.9 | 97.3 | 63.2 | 64.6 |
| Alexa 750-GAR | 66.0 | 65.5 | 39.6 | 33.6 |

| S/B (25ng coating) | 3X | 5X |
|---|---|---|
| DyLight 750-SA | 76.7 | 84.8 |
| 755 Compound 1 (isomer 1)-SA | 70.2 | 84.3 |
| 755 Compound 1 (isomer 2)-SA | 77.2 | 92.3 |
| Alexa 750-SA | 79.8 | 52.0 |

FIG. 70

| S/B @ 125 ng coating | 2.5X | 7.5X | 10X | 15X |
|---|---|---|---|---|
| DyLight 750-GAM | 2.7 | 3.6 | 3.5 | 3.9 |
| 755 Compound 1 (isomer 1)-GAM | 4.5 | 3.8 | 3.4 | 3.8 |
| 755 Compound 1 (isomer 2)-GAM | 2.6 | 4.1 | 3.0 | 3.9 |
| Alexa 750-GAM | 2.3 | 2.7 | 2.4 | 2.6 |

FIG. 71

| S/B @ 1000 ng coating | 2.5X | 7.5X | 10X | 15X |
|---|---|---|---|---|
| DyLight 750-GAM | 30.3 | 41.8 | 40.3 | 46.7 |
| 755 Compound 1 (isomer 1)-GAM | 30.6 | 42.9 | 44.7 | 41.2 |
| 755 Compound 1 (isomer 2)-GAM | 22.7 | 41.7 | 41.6 | 37.6 |
| Alexa 750-GAM | 22.9 | 29.4 | 28.7 | 21.8 |

FIG. 76

| S/B @ 125 ng coating | 2.5X | 7.5X | 10X | 15X |
|---|---|---|---|---|
| DyLight 750-GAR | 2.1 | 2.4 | 2.8 | 2.7 |
| 755 Compound 1 (isomer 1)-GAR | 1.8 | 2.7 | 2.6 | 2.6 |
| 755 Compound 1 (isomer 2)-GAR | 1.7 | 2.4 | 4.6 | 2.8 |
| Alexa750-GAR | 2.4 | 2.4 | 4.5 | 2.2 |

FIG. 77

| S/B @ 1000 ng coating | 2.5X | 7.5X | 10X | 15X |
|---|---|---|---|---|
| DyLight 750-GAR | 17.7 | 23.3 | 32.9 | 28.6 |
| 755 Compound 1 (isomer 1)-GAR | 14.7 | 26.8 | 29.9 | 31.3 |
| 755 Compound 1 (isomer 2)-GAR | 15.2 | 28.7 | 32.0 | 32.7 |
| Alexa750-GAR | 20.6 | 17.8 | 21.1 | 16.4 |

FIG. 80

|  | @ 200ng coating | @ 25ng coating |
|---|---|---|
| DyLight 750-SA (3X) | 33.9 | 4.5 |
| 755 Compound 1 (isomer 1)-SA (3X) | 24.4 | 2.9 |
| 755 Compound 1 (isomer 2)-SA (3X) | 24.6 | 3.0 |
| Alexa750-SA (3X) | 22.4 | 4.5 |

FIG. 81

|  | @ 200ng coating | @ 25ng coating |
|---|---|---|
| DyLight 750-SA (5X) | 14.5 | 3.1 |
| 755 Compound 1 (isomer 1)-SA (5X) | 13.5 | 3.3 |
| 755 Compound 1 (isomer 2)-SA (5X) | 17.6 | 3.1 |
| Alexa 750-SA (5X) | 12.2 | 2.3 |

FLUORESCENT COMPOUNDS

This application is a continuation of U.S. patent application Ser. No. 15/817,561, filed Nov. 20, 2017, now U.S. Pat. No. 10,351,551, which is a continuation of U.S. patent application Ser. No. 13/330,993, filed Dec. 20, 2011, now U.S. Pat. No. 10,053,447, which claims the benefit of U.S. Provisional Application Nos. 61/425,446 filed Dec. 21, 2010; 61/446,319 filed Feb. 24, 2011; 61/480,840 filed Apr. 29, 2011; and 61/482,933 filed May 5, 2011; each of which is expressly incorporated by reference herein in its entirety.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their t-system. Compounds that have insufficient hydrophilicity undergo non-specific interactions with various surfaces, resulting in problems when attempting purify the corresponding conjugate, and an unsatisfactory signal to noise ratio.

Efforts are directed to reducing undesirable properties by introducing substituents that increase the hydrophilicity of the compounds. For example, sulfonic acid function substituents have been introduced into the cyanine chromophore. U.S. Pat. No. 6,083,485 (Licha) and U.S. Pat. Nos. 6,977,305 and 6,974,873 (Molecular Probes) disclose cyanine compounds having one of the common methyl groups in the 3-position of the terminal indole heterocycle substituted by a ω-carboxyalkyl function, and in which the previously present (e.g. in Cy3 or Cy5) N-alkyl or N-ω-carboxyalkyl functions are replaced by N-ω-alkyl sulfonic acid functions. WO 05/044923 discloses cyanine compounds having the common methyl substituent in the 3-position of the terminal indole heterocycle substituted by a N-ω-alkyl sulfonic acid function. In these publications, cyanine compounds having more than two sulfonic acid function substituents exhibited higher solubility and correspondingly a lower tendency to dimer formation, in comparison to cyanine compounds (Cy3, Cy5) described in U.S. Pat. No. 5,627,027.

The disclosed cyanine compounds are useful as labels in optical, especially fluorescence optical, determination and detection methods. The compounds have high hydrophilicity, high molar absorbance, high photo-stability, and high storage stability. These compounds can be excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules such as proteins (e.g., antigens, antibodies, etc.), DNA and/or RNA segments, etc. with the corresponding complimentary species. Thus, among other embodiments, the compounds are useful to measure enzyme kinetics, receptor-ligand interactions, and nucleic acid hybridization kinetics in vitro and/or in vivo. The compounds are useful for the pharmacological characterization of receptors and/or drugs. Applications include, but are not limited to, uses in medicine, pharmacy, biological sciences, materials sciences, environmental control, detection of organic and inorganic micro samples occurring in nature, etc.

The following nomenclature is used to describe various embodiments:

550 Compound 1 (ethylene glycol group)
550 Compound 2 (diethylene glycol group)
550 Compound 3 (polyethylene glycol (3) group)
550 Compound 4 (polyethylene glycol (4) group)
550 Compound 5 (polyethylene glycol (5) group)
550 Compound 6 (polyethylene glycol (6) group)
550 Compound 1 (isomer 1)
550 Compound 1 (isomer 2)
550 Compound 2 (isomer 1)
550 Compound 2 (isomer 2)
550 Compound 3 (isomer 1)
550 Compound 3 (isomer 2)
550 Compound 4 (isomer 1)
550 Compound 4 (isomer 2)
550 Compound 5 (isomer 1)
550 Compound 5 (isomer 2)
550 Compound 6 (isomer 1)
550 Compound 6 (isomer 2)
650 Compound 1 (ethylene glycol group)
650 Compound 2 (diethylene glycol group)
650 Compound 3 (polyethylene glycol (3) group)
650 Compound 4 (polyethylene glycol (4) group)
650 Compound 5 (polyethylene glycol (5) group)
650 Compound 6 (polyethylene glycol (6) group)
650 Compound 1 (isomer 1)
650 Compound 1 (isomer 2)
650 Compound 2 (isomer 1)
650 Compound 2 (isomer 2)
650 Compound 3 (isomer 1)
650 Compound 3 (isomer 2)
650 Compound 4 (isomer 1)
650 Compound 4 (isomer 2)
650 Compound 5 (isomer 1)
650 Compound 5 (isomer 2)
650 Compound 6 (isomer 1)
650 Compound 6 (isomer 2)
650 Compound 1 (substituted polymethine)
650 Compound 2 (substituted polymethine)
650 Compound 3 (substituted polymethine)
650 Compound 4 (substituted polymethine)
650 Compound 5 (substituted polymethine)
650 Compound 6 (substituted polymethine)
755 Compound 1 (ethylene glycol group)
755 Compound 2 (diethylene glycol group)
755 Compound 3 (polyethylene glycol (3) group)
755 Compound 4 (ethylene glycol group)
755 Compound 5 (diethylene glycol group)
755 Compound 6 (polyethylene glycol (3) group)
755 Compound 1 (isomer 1)
755 Compound 1 (isomer 2)
755 Compound 2 (isomer 1)
755 Compound 2 (isomer 2)
755 Compound 3 (isomer 1)
755 Compound 3 (isomer 2)
755 Compound 4 (isomer 1)
755 Compound 4 (isomer 2)
755 Compound 5 (isomer 1)
755 Compound 5 (isomer 2)

755 Compound 6 (isomer 1)
755 Compound 6 (isomer 2)
755 Compound 1 (substituted polymethine)
755 Compound 2 (substituted polymethine)
755 Compound 3 (substituted polymethine)
755 Compound 4 (substituted polymethine)
755 Compound 5 (substituted polymethine)
755 Compound 6 (substituted polymethine)

In one embodiment, the cyanine compounds have, in a N-position of one heterocycle, an ethylene glycol group, and the other heterocycle has, in a N-position, a function for conjugating the compound to a biomolecule.

In one embodiment, the cyanine compounds have, in a N-position of one heterocycle, an ethylene glycol polymer (i.e., poly(ethylene) glycol abbreviated as PEG), and the other heterocycle has, in a N-position, a function for conjugating the compound to a biomolecule.

In one embodiment, the compound is a compound according to general formula I

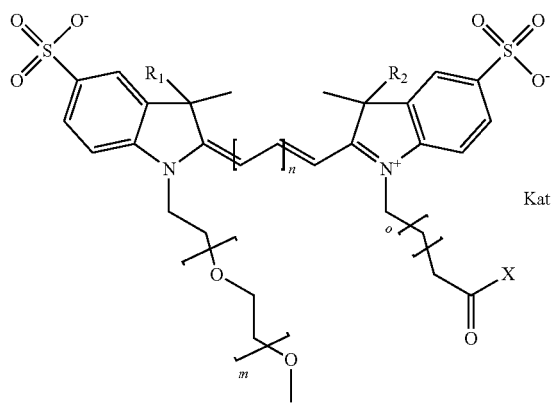

wherein each of $R^1$ and $R^2$ is the same or different and is independently selected from the group consisting of an aliphatic, heteroaliphatic, or sulfoalkyl group; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO—STP, —NR-L-CO-TFP, —NR-L-CO-benzotriazole, —NR-L-CHO, —NR-L-maleimide, and —NR-L-NH—CO—CH2—I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive.

In one embodiment, the compound is a compound according to general formula I, wherein each of R1 and R2 is sulfoalkyl; X is —OH, —NHS, —O-TFP, or —NR-L-maleimide; m is 0; o is 3; and n is 1. In one embodiment, the compound is a compound according to general formula I, wherein each of R1 and R2 is sulfoalkyl; X is —OH, —NHS, —O-TFP, or —NR-L-maleimide; m is 1; o is 3; and n is 1. In one embodiment, the compound is a compound according to general formula I, wherein each of R1 and R2 is sulfoalkyl; X is —OH, —NHS, —O-TFP, or —NR-L-maleimide; m is 2; o is 3; and n is 1. In one embodiment, the compound is a compound according to general formula I, wherein each of R1 and R2 is sulfoalkyl; X is —OH, —NHS, —O-TFP, or —NR-L-maleimide; m is 3; o is 3; and n is 1. In one embodiment, the compound is a compound according to general formula I, wherein each of R1 and R2 is sulfoalkyl; X is —OH, —NHS, —O-TFP, or —NR-L-maleimide; m is 4; o is 3; and n is 1. In one embodiment, the compound is a compound according to general formula I, wherein each of R1 and R2 is sulfoalkyl; X is —OH, —NHS, —O-TFP, or —NR-L-maleimide; m is 5; o is 3; and n is 1.

In one embodiment, the compound is a compound according to general formula I, wherein each of R1 and R2 is sulfoalkyl; X is —OH, —NHS, —O-TFP, or —NR-L-maleimide; m is 0; o is 3; and n is 2. In one embodiment, the compound is a compound according to general formula I, wherein each of R1 and R2 is sulfoalkyl; X is —OH, —NHS, —O-TFP, or —NR-L-maleimide; m is 1; o is 3; and n is 2. In one embodiment, the compound is a compound according to general formula I, wherein each of R1 and R2 is sulfoalkyl; X is —OH, —NHS, —O-TFP, or —NR-L-maleimide; m is 2; o is 3; and n is 2. In one embodiment, the compound is a compound according to general formula I, wherein each of R1 and R2 is sulfoalkyl; X is —OH, —NHS, —O-TFP, or —NR-L-maleimide; m is 3; o is 3; and n is 2. In one embodiment, the compound is a compound according to general formula I, wherein each of R1 and R2 is sulfoalkyl; X is —OH, —NHS, —O-TFP, or —NR-L-maleimide; m is 4; o is 3; and n is 2. In one embodiment, the compound is a compound according to general formula I, wherein each of R1 and R2 is sulfoalkyl; X is —OH, —NHS, —O-TFP, or —NR-L-maleimide; m is 5; o is 3; and n is 2.

In one embodiment, the compound is a compound according to general formula I, wherein each of R1 and R2 is sulfoalkyl; X is —OH, —NHS, —O-TFP, or —NR-L-maleimide; m is 0; o is 3; and n is 3. In one embodiment, the compound is a compound according to general formula I, wherein each of R1 and R2 is sulfoalkyl; X is —OH, —NHS, —O-TFP, or —NR-L-maleimide; m is 1; o is 3; and n is 3. In one embodiment, the compound is a compound according to general formula I, wherein each of R1 and R2 is sulfoalkyl; X is —OH, —NHS, —O-TFP, or —NR-L-maleimide; m is 2; o is 3; and n is 3. In one embodiment, the compound is a compound according to general formula I, wherein each of R1 and R2 is sulfoalkyl; X is —OH, —NHS, —O-TFP, or —NR-L-maleimide; m is 3; o is 3; and n is 3. In one embodiment, the compound is a compound according to general formula I, wherein each of R1 and R2 is sulfoalkyl; X is —OH, —NHS, —O-TFP, or —NR-L-maleimide; m is 4; o is 3; and n is 3. In one embodiment, the compound is a compound according to general formula I, wherein each of R1 and R2 is sulfoalkyl; X is —OH, —NHS, —O-TFP, or —NR-L-maleimide; m is 5; o is 3; and n is 3.

In one embodiment, an isolated enantiomeric mixture selected from diastereomer Ia of general formula I

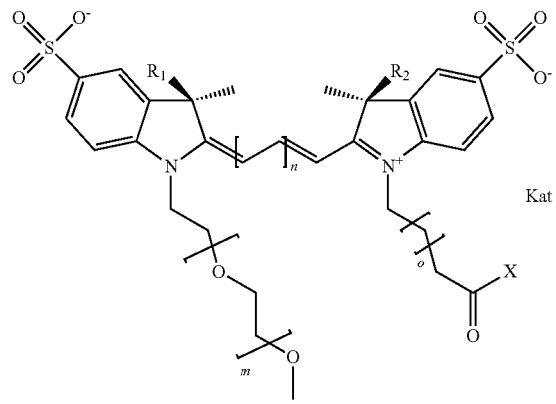

or diastereomer Ib of general formula I

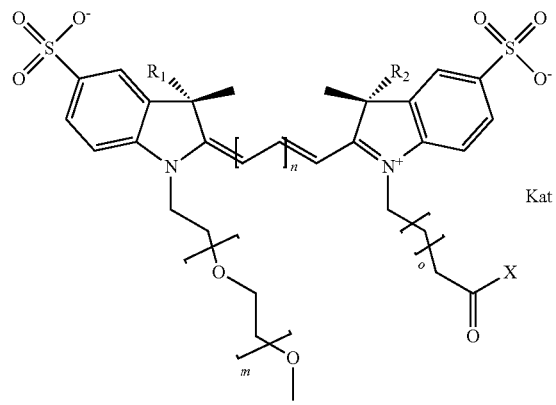

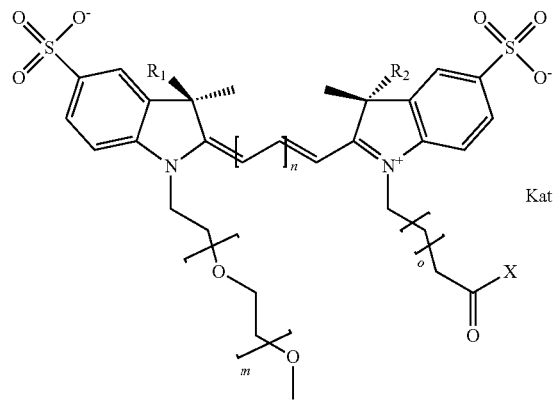

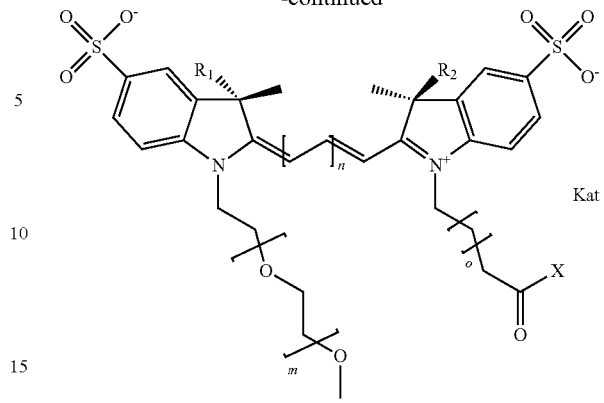

is provided, wherein each of $R^1$ and $R^2$ is the same or different and is independently selected from the group consisting of an aliphatic, heteroaliphatic, sulfoalkyl group, or heteroaliphatic with terminal $SO_3$; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO—STP, —NR-L-CO-TFP, —NR-L-CO-benzotriazole, —NR-L-CHO, —NR-L-maleimide, and —NR-L-NH—CO—CH2—I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive.

In one embodiment, the compound has general formula II

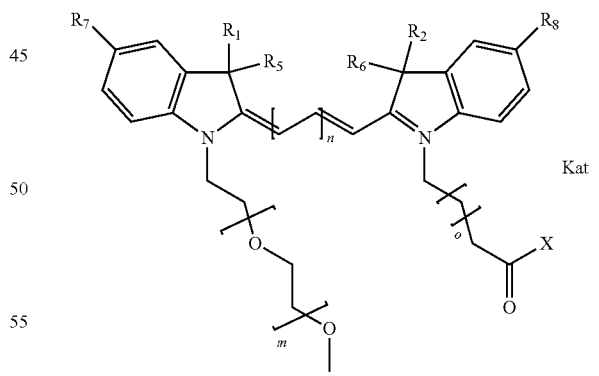

where each of $R^1$, $R^2$, $R^5$, and $R^6$ is the same or different and is independently selected from the group consisting of an aliphatic, heteroaliphatic, or sulfoalkyl group; each of $R^7$ and $R^8$ is the same or different and is independently selected from either H or $SO_3$; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH₂, —NR-L-NH—NH₂, —NR-L-CO₂H, —NR-L-CO—NHS, —NR-L-CO—STP, —NR-L-CO-TFP, —NR-L-CO-benzotriazole, —NR-L-CHO, —NR-L-maleimide, and —NR-L-NH—CO—CH2—I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive.

In one embodiment, the compound is 550 Compound 1

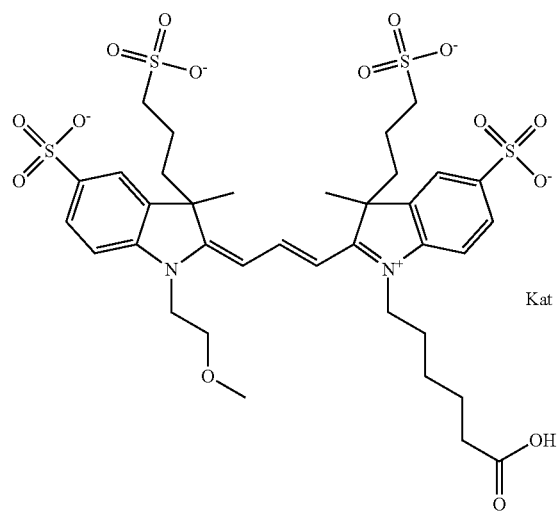 [SMILES: COCCN1/C(=C/C=C/C2=[N+](CCCCCC(=O)O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

550 Compound 1 (2-{(E)-3-[1-(5-carboxypentyl)-3-methyl-5-sulfo-3-(3-sulfopropyl)-1,3-dihydro-indol-(2E)-ylidene]-propenyl}-1-(2-methoxy-ethyl)-3-methyl-5-sulfo-3-(3-sulfo-propyl)-3H-indolium) contains an ethylene glycol on the indole N of the left heterocycle, i.e., a methylated ethylene glycol, as shown in the structure above, and the ethylene glycol can be represented in abbreviated format as —[C—C—O]₁-, which is used throughout. The methyl group on the ethylene glycol prevents the terminal —OH from oxidation. Oxidation is known to occur, over time, on an unprotected terminus of an ethylene glycol group, diethylene glycol group, or polyethylene glycol group, collectively referred to herein as an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 550 Compound 1, but one skilled in the art appreciates that activation is not limited to these examples. One non-limiting example of an activated compound is the NHS-ester of 550 Compound 1, shown below:

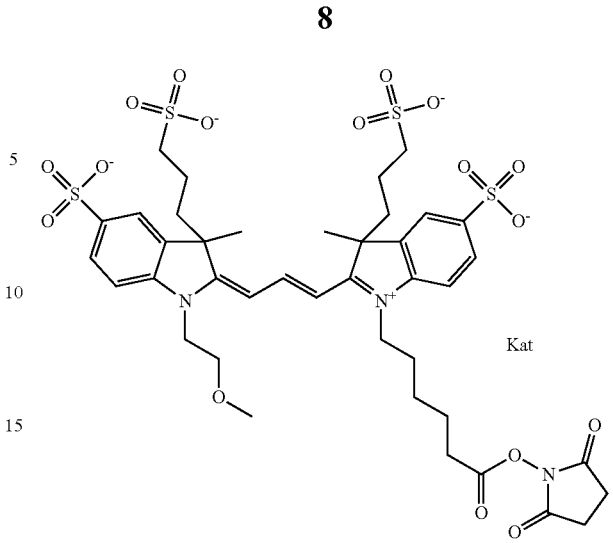

In one embodiment, the compound is a NHS-ester of 550 Compound 1 where, according to general formula I, o is 1, shown below:

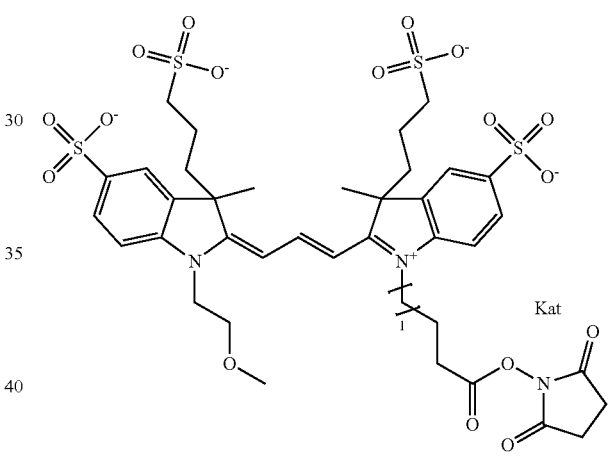

In one embodiment, the compound is an NHS-ester of 550 Compound 1 where, according to general formula I, o is 5, shown below:

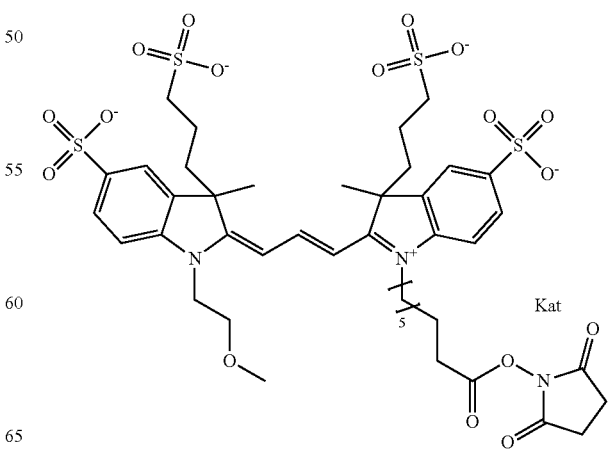

In one embodiment, the compound is described by the following general formula III, where m=1-6, and p=1-6:

One non-limiting example of a NHS-ester of 550 Compound 1, according to general formula III, where m=1 and p=2, is shown below:

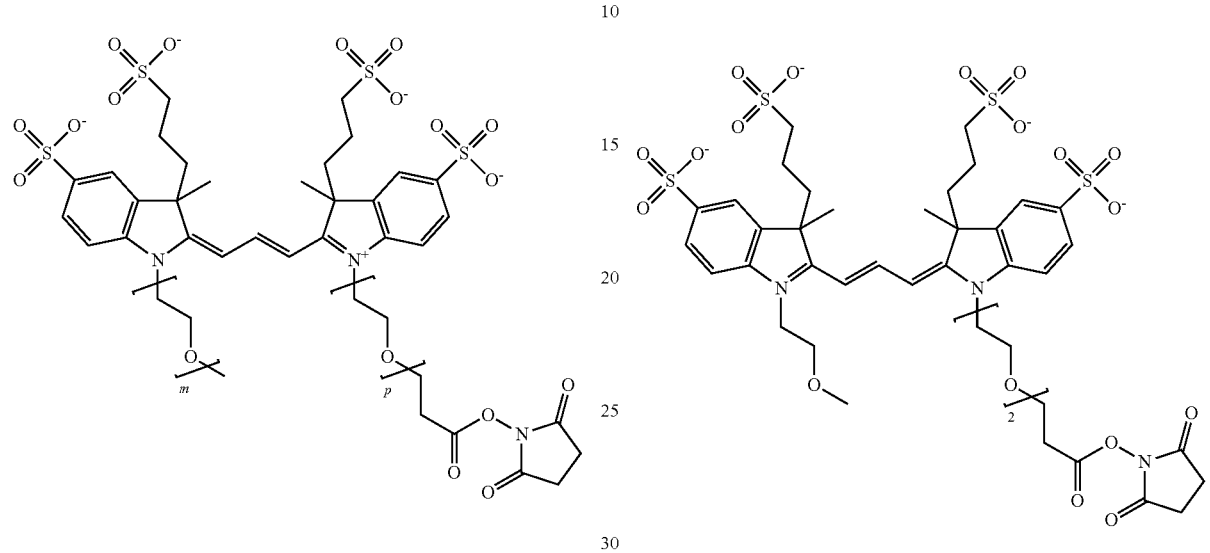

One non-limiting example of a NHS-ester of 550 Compound 1, according to general formula III, where m=1 and p=1, is shown below:

One non-limiting example of a NHS-ester of 550 Compound 1, according to general formula III, where m=1 and p=3, is shown below:

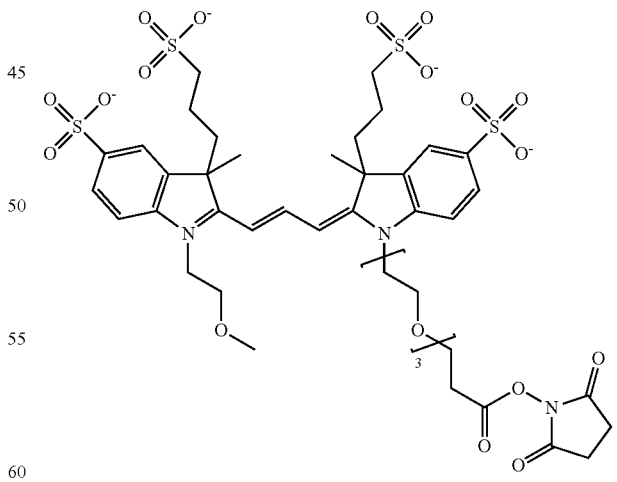

One non-limiting example of a NHS-ester of 550 Compound 1, according to general formula III, where m=1 and p=4, is shown below:

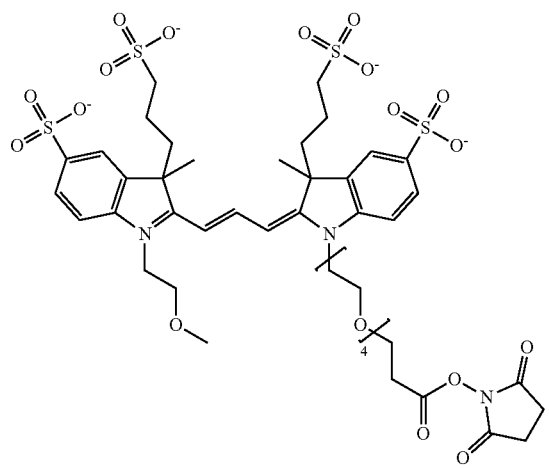

One non-limiting example of a NHS-ester of 550 Compound 1, according to general formula III, where m=1 and p=5, is shown below:

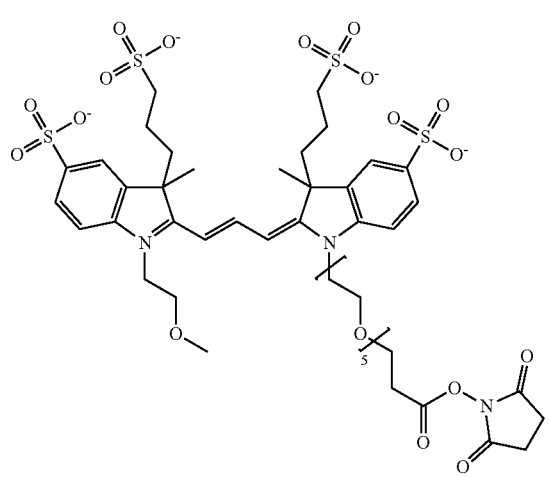

One non-limiting example of a NHS-ester of 550 Compound 1, according to general formula III, where m=1 and p=6, is shown below:

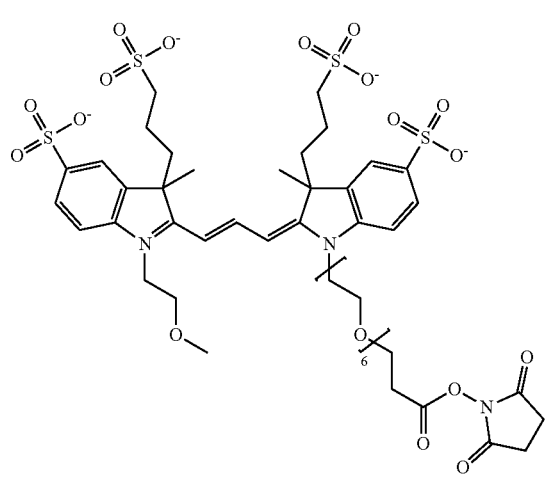

One non-limiting example of a NHS-ester of 550 Compound 2, according to general formula III, where m=2 and p=1, is shown below:

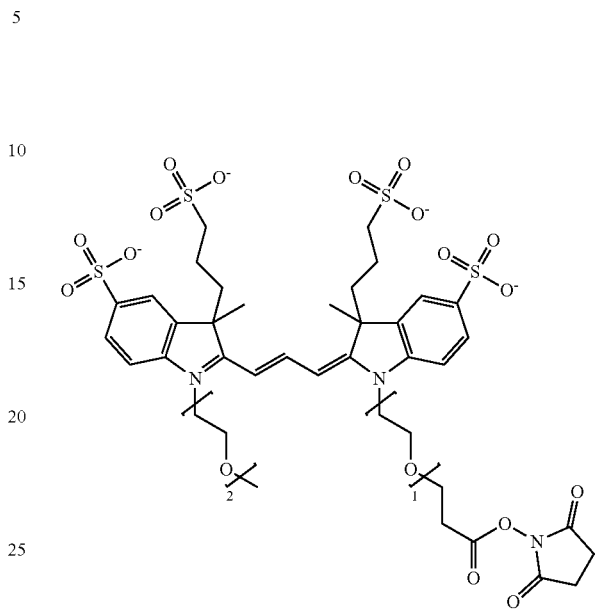

One non-limiting example of a NHS-ester of 550 Compound 2, according to general formula III, where m=2 and p=2, is shown below:

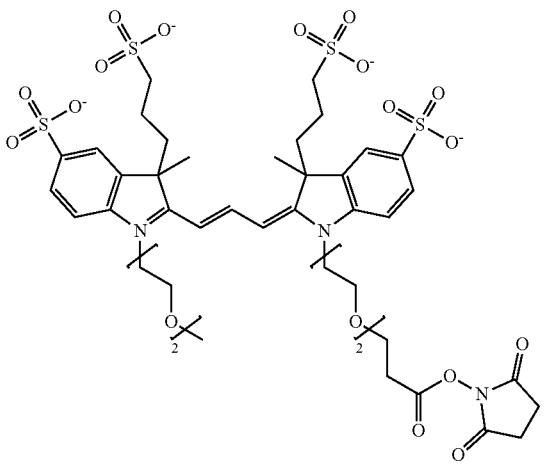

One non-limiting example of a NHS-ester of 550 Compound 2, according to general formula III, where m=2 and p=3, is shown below:

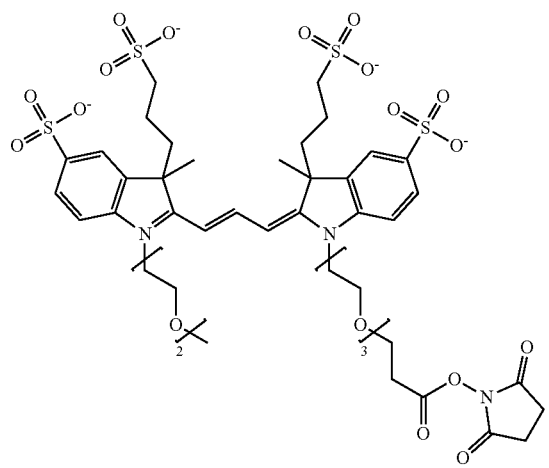

One non-limiting example of a NHS-ester of 550 Compound 3, according to general formula III, where m=3 and p=1, is shown below:

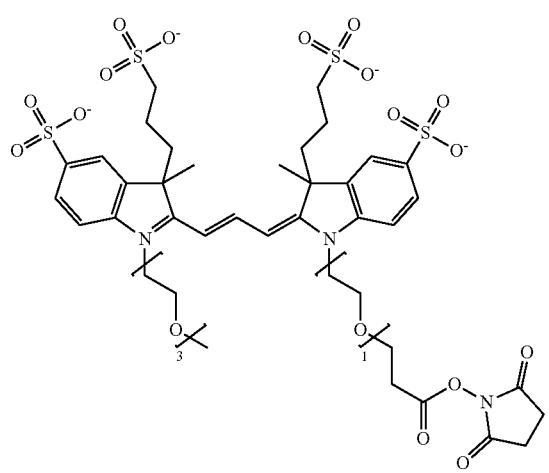

One non-limiting example of a NHS-ester of 550 Compound 3, according to general formula III, where m=3 and p=2, is shown below:

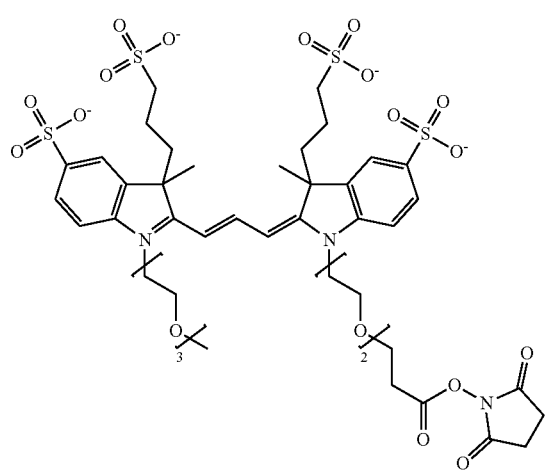

One non-limiting example of a NHS-ester of 550 Compound 3, according to general formula III, where m=3 and p=3, is shown below:

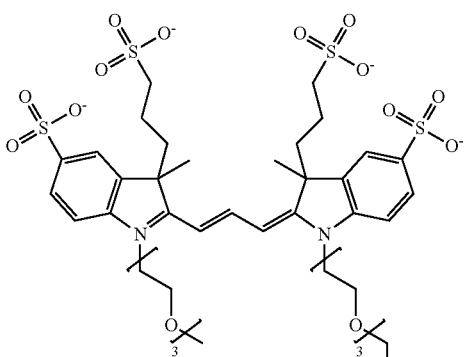

One non-limiting example of a NHS-ester of 550 Compound 4, according to general formula III, where m=4 and p=1, is shown below:

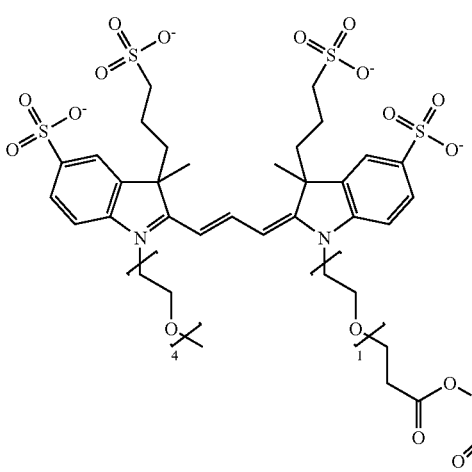

One non-limiting example of a NHS-ester of 550 Compound 5, according to general formula III, where m=5 and p=1, is shown below:

One non-limiting example of a NHS-ester of 550 Compound 6, according to general formula III, where m=6 and p=1, is shown below:

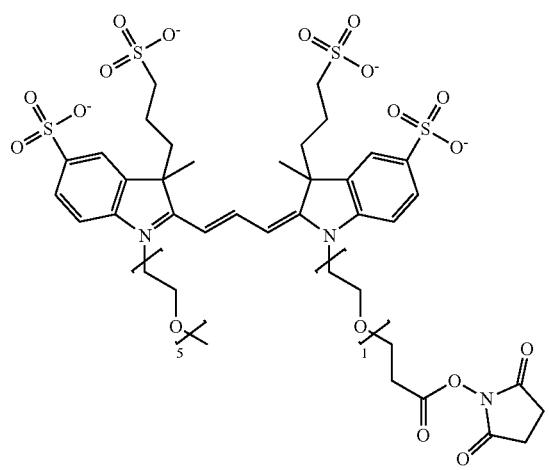

One non-limiting example of an activated 550 Compound 1 is a tetrafluorophenyl (TFP)-ester form of 550 Compound 1, shown below:

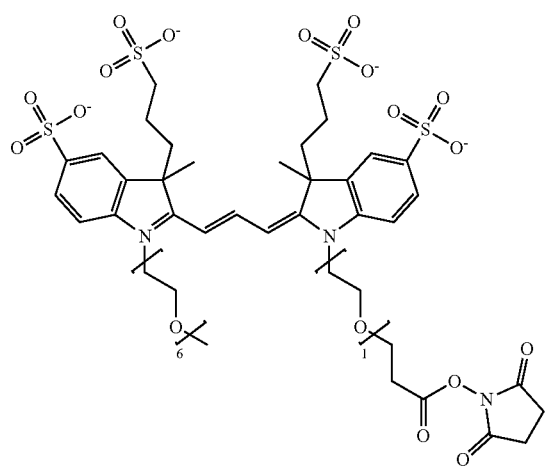

One non-limiting example of an activated 550 Compound 1 is a sulfotetrafluorophenyl (STP)-ester form of 550 Compound 1, shown below:

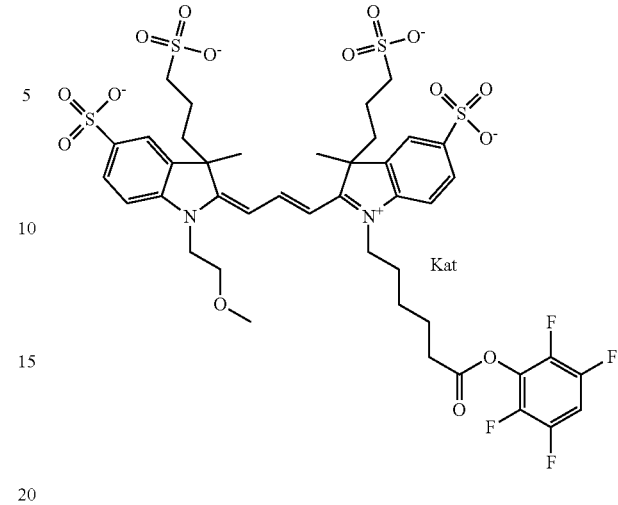

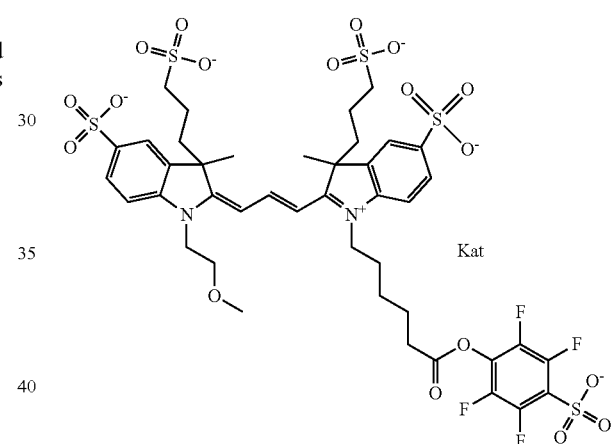

One non-limiting example of an activated 550 Compound 1 is a hydrazide form of 550 Compound 1, shown below:

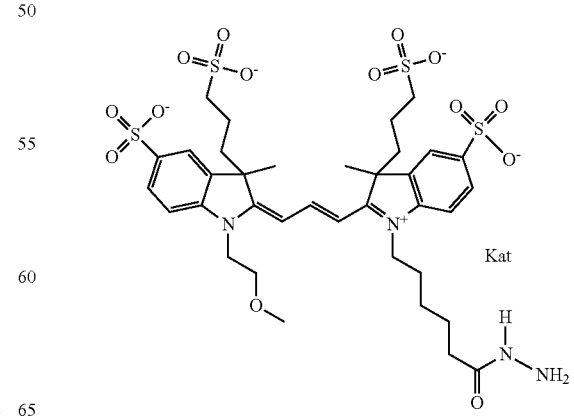

One non-limiting example of an activated 550 Compound 1 is a maleimide form of 550 Compound 1, shown below:

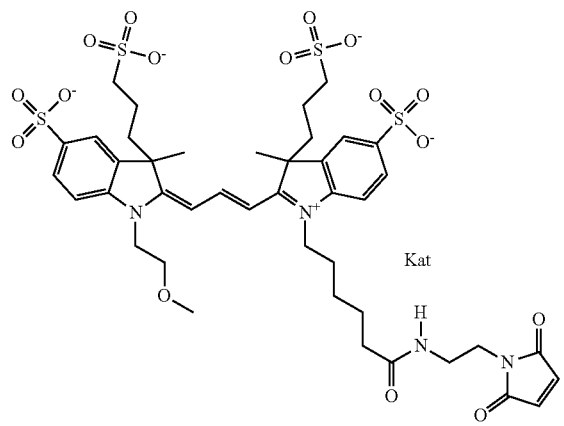 [SMILES: COCCN1/C(=C/C=C/C2=[N+](CCCCCC(=O)NCCN3C(=O)C=CC3=O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

In one embodiment, the compound is 550 Compound 2

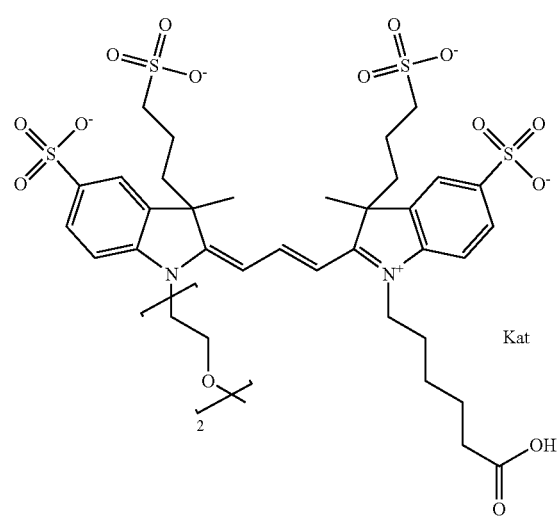

550 Compound 2 (2-{(E)-3-[1-(5-Carboxypentyl)-3-methyl-5-sulfo-3-(3-sulfopropyl)-1,3-dihydro-indol-(2E)-ylidene]-propenyl}-1-[2-(2-methoxy-ethoxy)-ethyl]-3-methyl-5-sulfo-3-(3-sulfo-propyl)-3H-indolium) contains a diethylene glycol on the indole N of the left heterocycle. 550 Compound 2, with the diethylene glycol shown in abbreviated notation used throughout, represents the following structure.

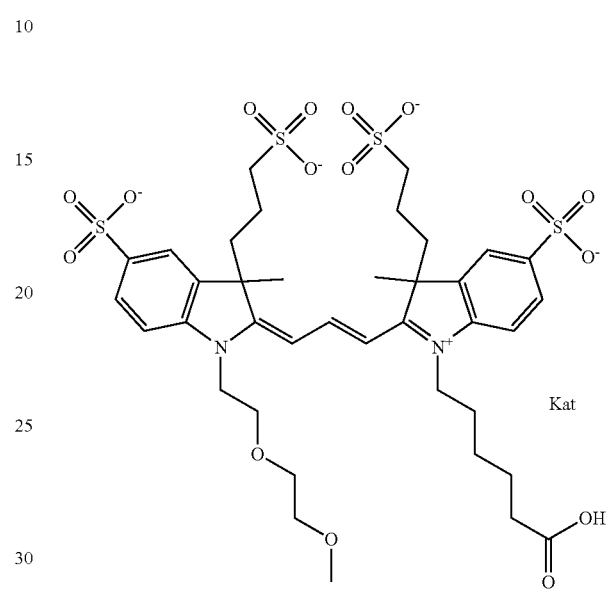

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 2 is activated as described above, one non-limiting example of which is the NHS-ester form of 550 Compound 2, shown below.

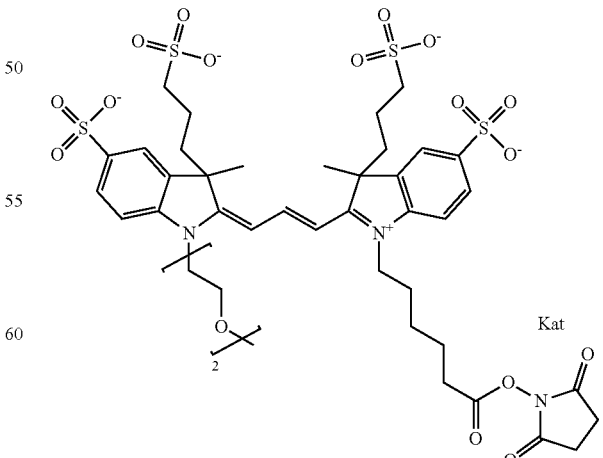

In one embodiment, the compound is 550 Compound 3

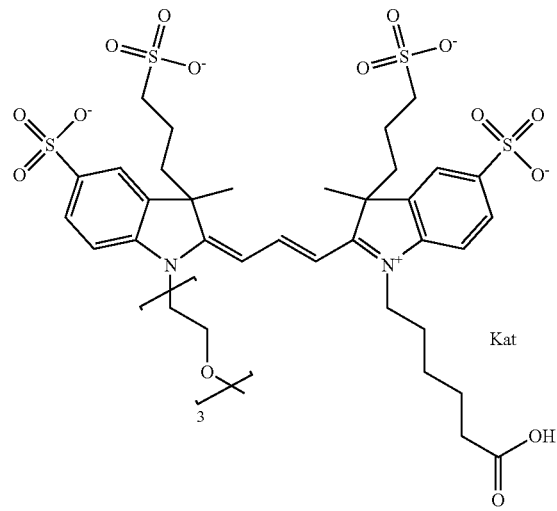

550 Compound 3 (2-{(E)-3-[1-(5-Carboxypentyl)-3-methyl-5-sulfo-3-(3-sulfopropyl)-1,3-dihydro-indol-(2E)-ylidene]-propenyl}-1-{2-[2-(2-methoxy-ethoxy)-ethoxy]-ethyl}-3-methyl-5-sulfo-3-(3-sulfo-propyl)-3H-indolium) contains a (poly)ethylene glycol on the indole N of the left heterocycle. 550 Compound 3, with the (poly)ethylene glycol shown in abbreviated notation used throughout, represents the following structure.

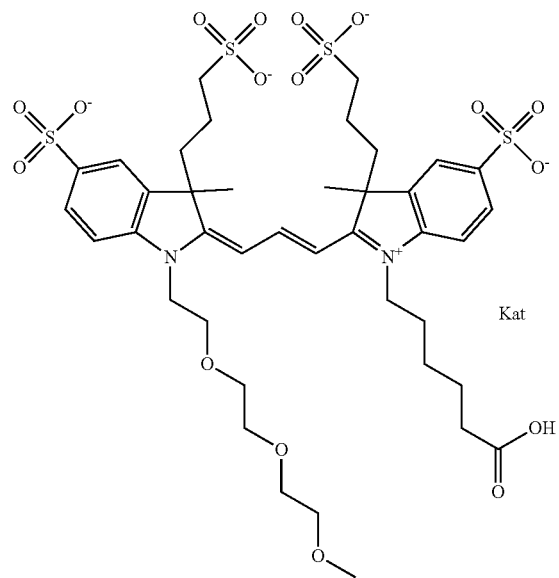 [SMILES: COCCOCCOCCN1/C(=C/C=C/C2=[N+](CCCCCC(=O)O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 3 is activated as described above.

In one embodiment, the compound is 550 Compound 4

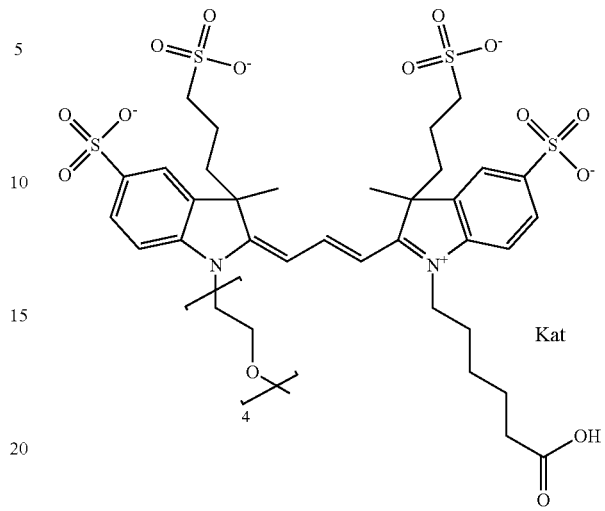

550 Compound 4 (1-(5-carboxypentyl)-3-methyl-2-((1E,3E)-3-(3-methyl-5-sulfonato-3-(3-sulfonatopropyl)-1-(2,5,8,11-tetraoxatridecan-13-yl)indolin-2-ylidene)prop-1-en-1-yl)-3-(3-sulfonatopropyl)-3H-indol-1-ium-5-sulfonate) contains a (poly)ethylene glycol on the indole N of the left heterocycle. 550 Compound 4, with the (poly)ethylene glycol shown in abbreviated notation used throughout, represents the following structure.

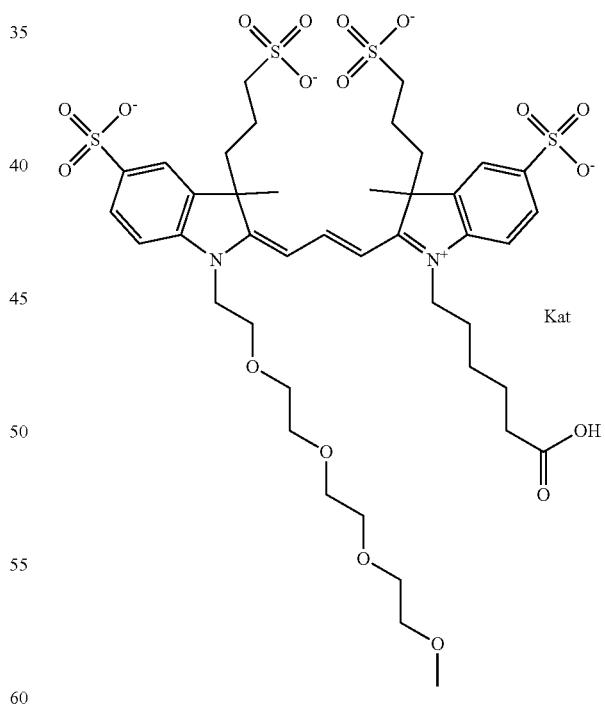

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 4 is activated as described above.

In one embodiment, the compound is 550 Compound 5

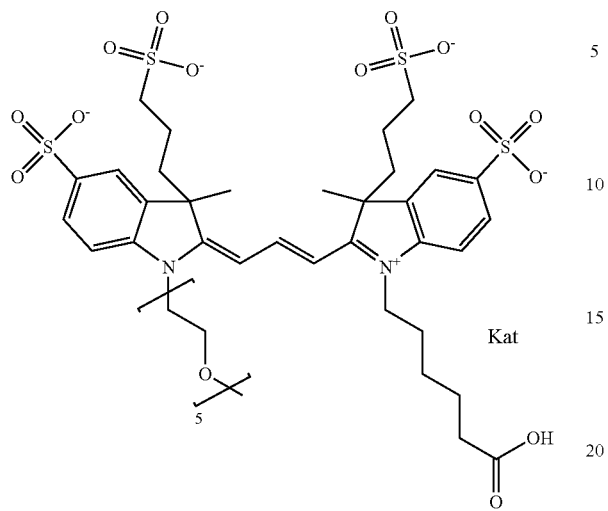

550 Compound 5 (2-((1E,3E)-3-(1-(2,5,8,11,14-pentaoxahexadecan-16-yl)-3-methyl-5-sulfonato-3-(3-sulfonatopropyl)indolin-2-ylidene)prop-1-en-1-yl)-1-(5-carboxypentyl)-3-methyl-3-(3-sulfonatopropyl)-3H-indol-1-ium-5-sulfonate) contains a (poly)ethylene glycol on the indole N of the left heterocycle. 550 Compound 5, with the (poly)ethylene glycol shown in abbreviated notation used throughout, represents the following structure.

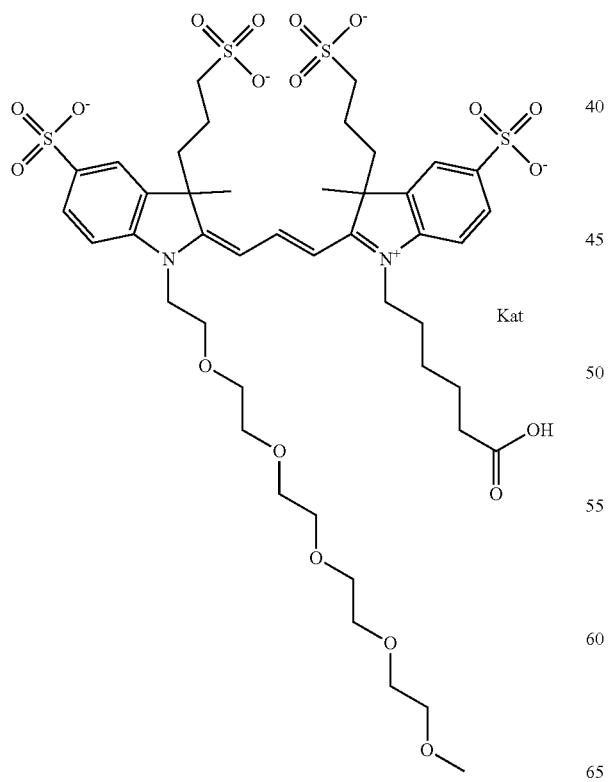

The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 550 Compound 5 is activated as described above.

In one embodiment, the compound is 550 Compound 6

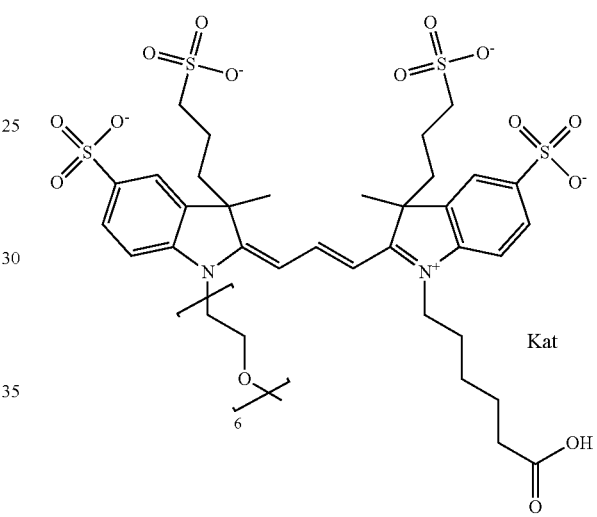

550 Compound 6 (1-(5-carboxypentyl)-3-methyl-2-((1E,3E)-3-(3-methyl-1-(2,5,8,11,14,17-hexaoxanonadecan-19-yl)-5-sulfonato-3-(3-sulfonatopropyl)indolin-2-ylidene)prop-1-en-1-yl)-3-(3-sulfonatopropyl)-3H-indol-1-ium-5-sulfonate) contains a (poly)ethylene glycol on the indole N of the left heterocycle. 550 Compound 6, with the (poly)ethylene glycol shown in abbreviated notation used throughout, represents the following structure.

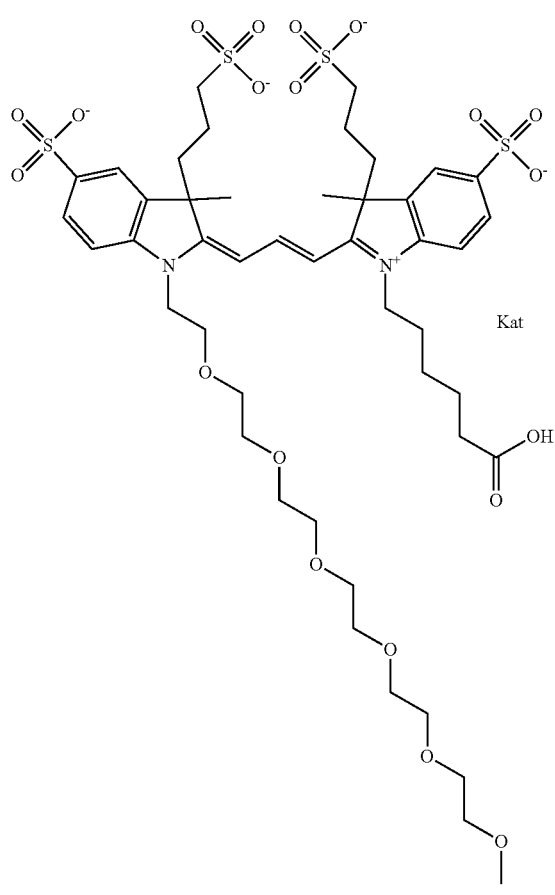 [SMILES: COCCOCCOCCOCCOCCOCCN1/C(=C/C=C/C2=[N+](CCCCCC(=O)O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 550 Compound 6 is activated as described above.

In embodiments, the compound contains one or more substitutions of the polymethine linker. In one embodiment, the compound has general formula IV

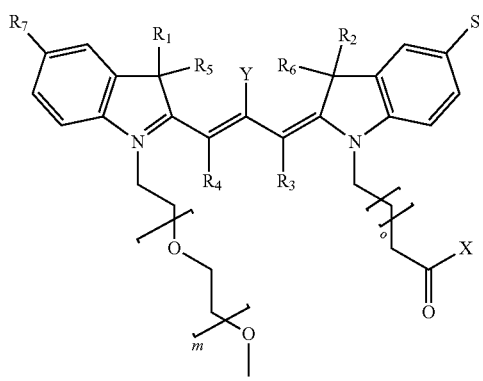

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or $SO_3$; X is selected from —OH, —SH, —NH$_2$, —NH—NH$_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—I, or —NR-L-NH—CO—CH$_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group; and Y is selected from the group consisting of hydrogen, alkyl, sulfoalkyl, fluorine, chlorine, or bromine.

One non-limiting example is a substituted polymethine form of 550 Compound 1, shown below:

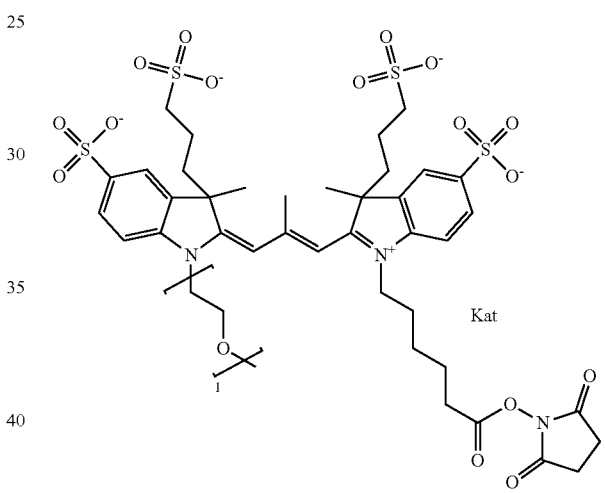

One non-limiting example is a substituted polymethine form of 550 Compound 2, shown below:

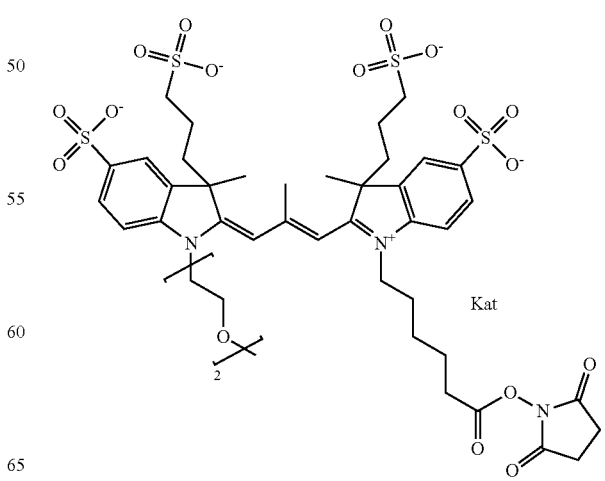

One non-limiting example is a substituted polymethine form of 550 Compound 3, shown below:

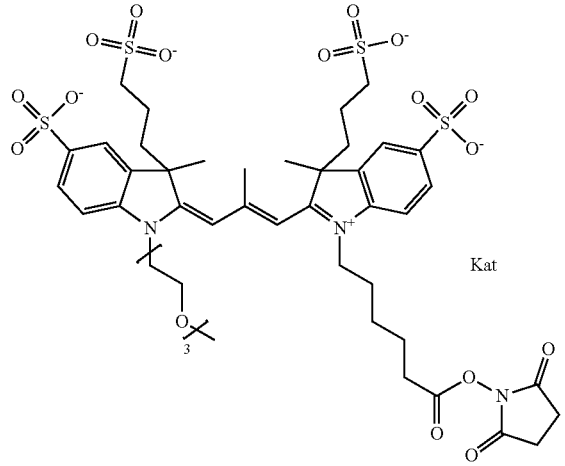

One non-limiting example is a substituted polymethine form of 550 Compound 4, shown below:

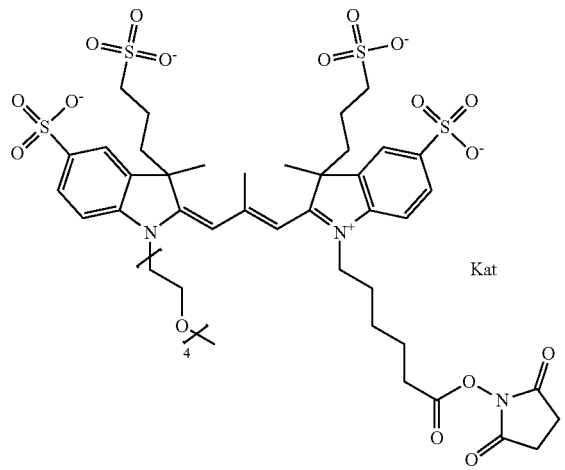

One non-limiting example is a substituted polymethine form of 550 Compound 5, shown below:

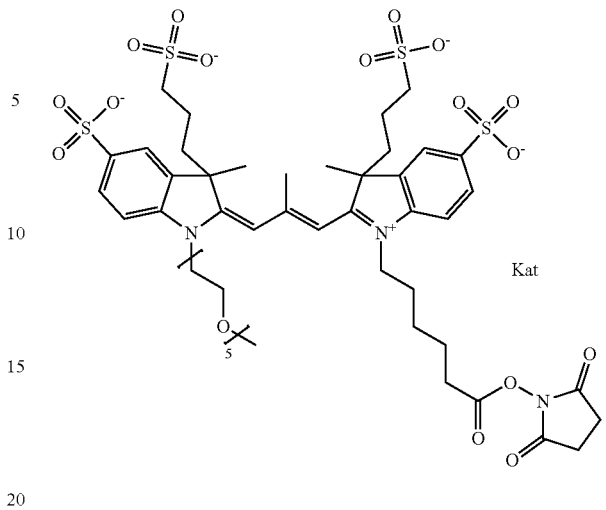

One non-limiting example is a substituted polymethine form of 550 Compound 6, shown below:

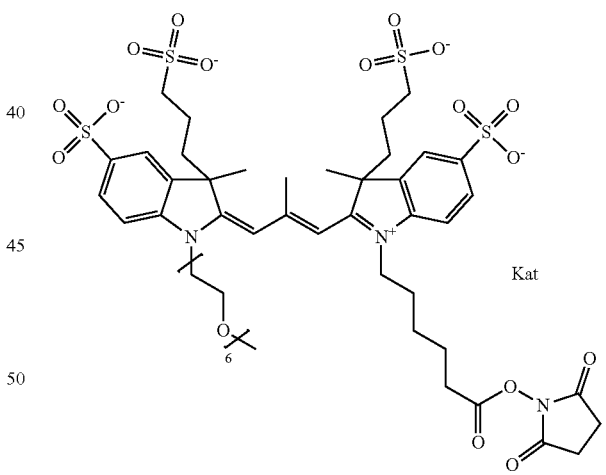

One non-limiting example is a substituted polymethine form of 550 having an ethylene glycol, diethylene glycol, or polyethylene glycol as described for general formula III, such as the compound shown below:

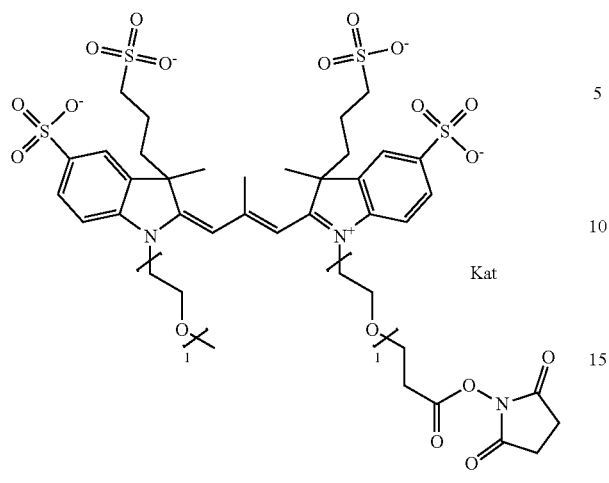

In embodiments, the degree of sulfonation is varied to, e.g., vary the compound's degree of hydrophilicity or hydrophobicity. One non-limiting example is a monosulfonate form of 550 Compound 1, shown below, but it is understood that the single sulfo group can be at any of the described positions:

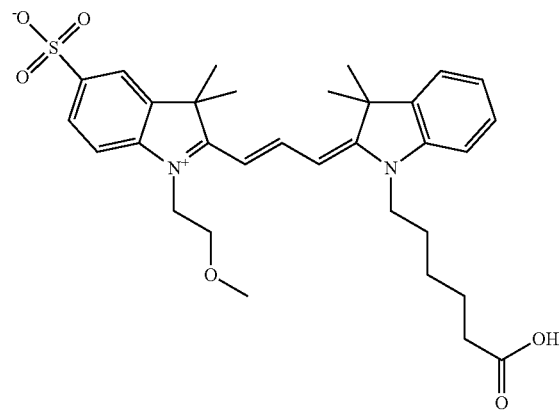

One non-limiting example is a disulfonate form of 550 Compound 1, shown below, but it is understood that the two sulfo groups can be at any of the described positions:

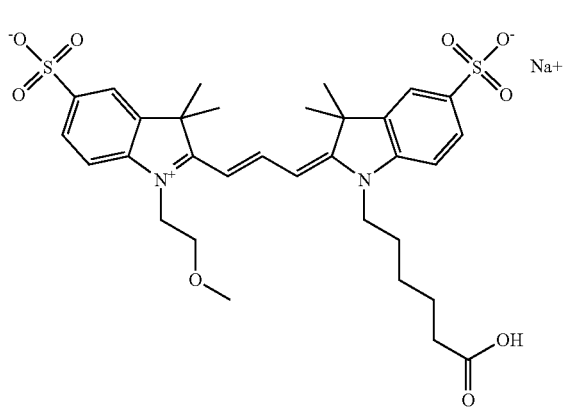

One non-limiting example is a trisulfonate form of 550 Compound 1, shown below, but it is understood that each of the three sulfo groups can be at any of the described positions:

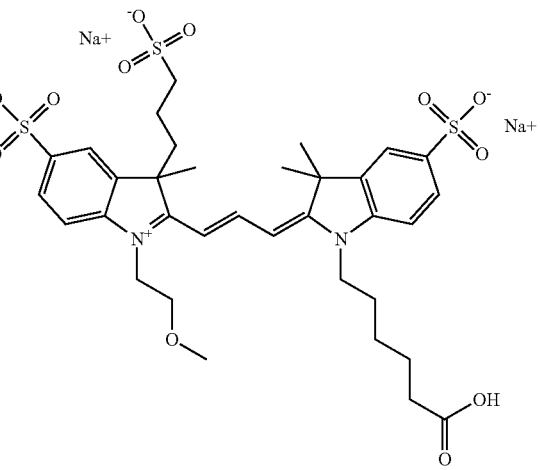

One non-limiting example is a tetrasulfonate form of 550 Compound 1, shown below, but it is understood that each of the four sulfo groups can be at any of the described positions:

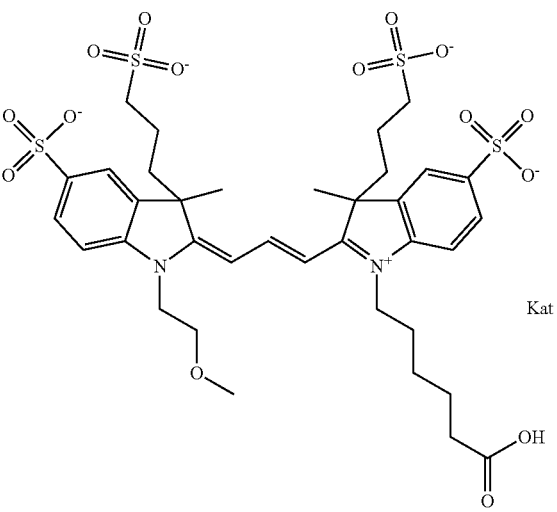

In one embodiment, the compound has general formula V

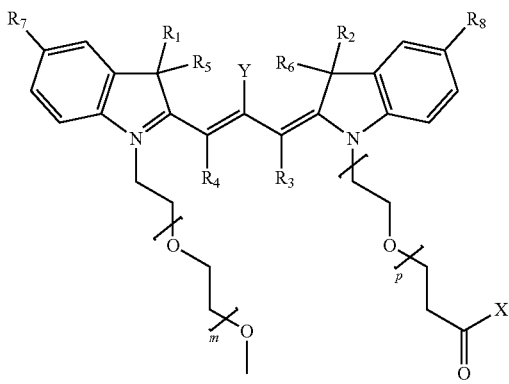

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or $SO_3$; X is selected from —OH, —SH, —$NH_2$, —NH—$NH_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, or —NR-L-NH—CO—$CH_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, or a heteroaliphatic group; and Y is selected from the group consisting of hydrogen, alkyl, sulfoalkyl, fluorine, chlorine, or bromine.

In one embodiment, the compound is 650 Compound 1

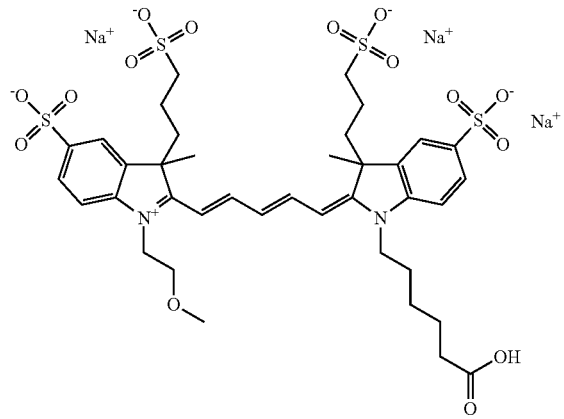

650 Compound 1 (2-{(1E,3E)-5-[1-(5-Carboxypentyl)-3-methyl-5-sulfo-3-(3-sulfopropyl)-1,3-dihydro-indol-(2E)-ylidene]-penta-1,3-dienyl}-1-(2-methoxy-ethyl)-3-methyl-5-sulfo-3-(3-sulfopropyl)-3H-indolium tri sodium salt) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus (i.e., an unprotected ethylene glycol group, diethylene glycol group, or polyethylene glycol group). Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 650 Compound 1, but one skilled in the art appreciates that activation is not limited to these examples. One non-limiting example of an activated compound is the NHS-ester of 650 Compound 1, shown below:

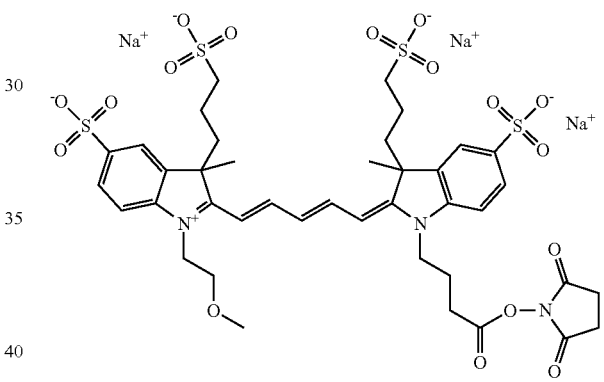

In one embodiment, the compound is a NHS-ester of 650 Compound 1 where, according to general formula I, o is 1, shown below:

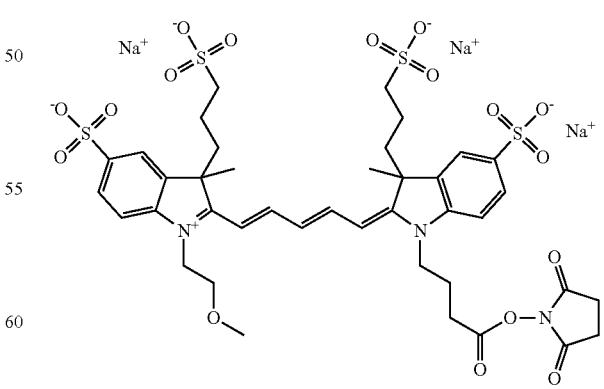

In one embodiment, the compound is an NHS-ester of 650 Compound 1 where, according to general formula I, o is 5, shown below:

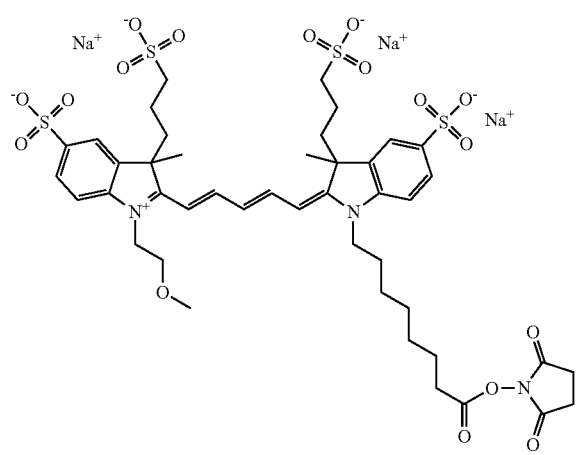

In one embodiment, the compound is described by the following general formula VI, where m=1-6, and p=1-6:

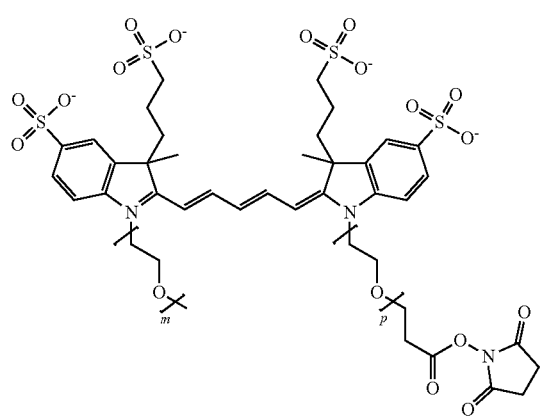

One non-limiting example of a NHS-ester of 650 Compound 1, according to formula VI, where m=1 and p=1, is shown below:

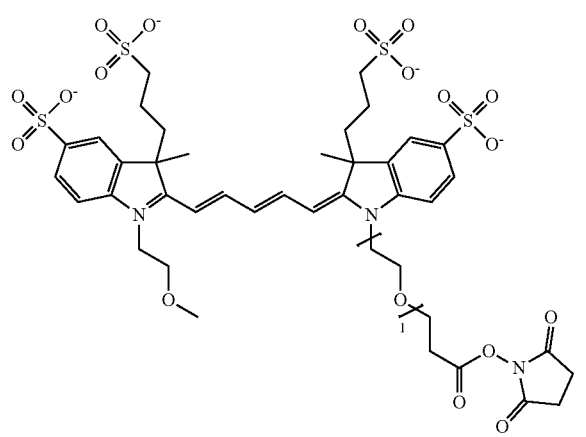

One non-limiting example of a NHS-ester of 650 Compound 1, according to general formula VI, where m=1 and p=2, is shown below:

One non-limiting example of a NHS-ester of 650 Compound 1, according to general formula VI, where m=1 and p=3, is shown below:

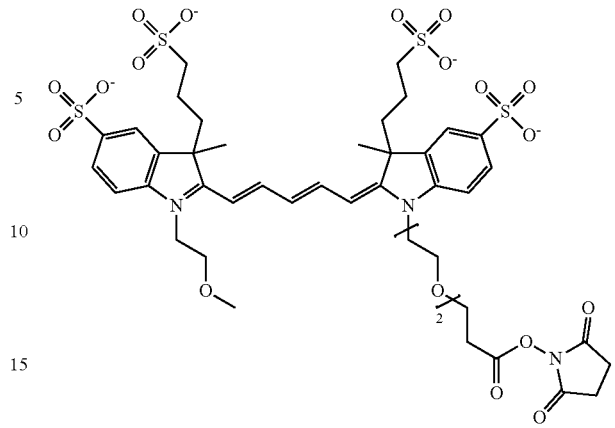

One non-limiting example of a NHS-ester of 650 Compound 1, according to general formula VI, where m=1 and p=4, is shown below:

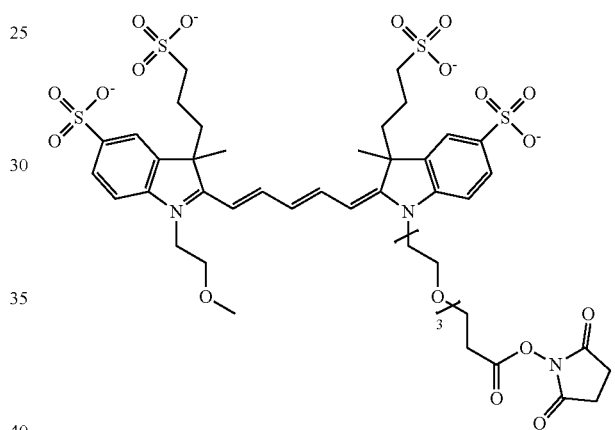

One non-limiting example of a NHS-ester of 650 Compound 1, according to general formula VI, where m=1 and p=5, is shown below:

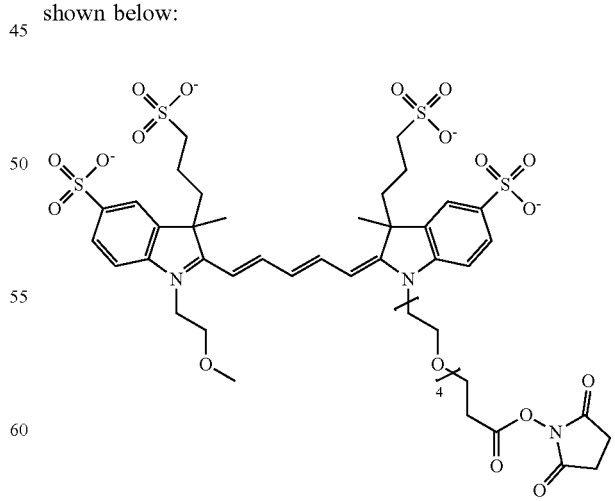

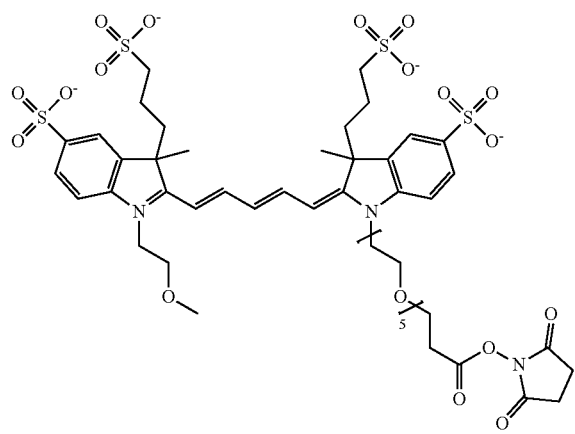

One non-limiting example of a NHS-ester of 650 Compound 1, according to general formula VI, where m=1 and p=6, is shown below:

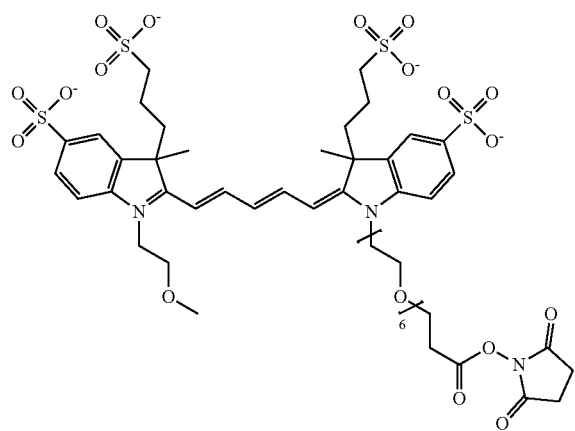

One non-limiting example of a NHS-ester of 650 Compound 2, according to general formula VI, where m=2 and p=1, is shown below:

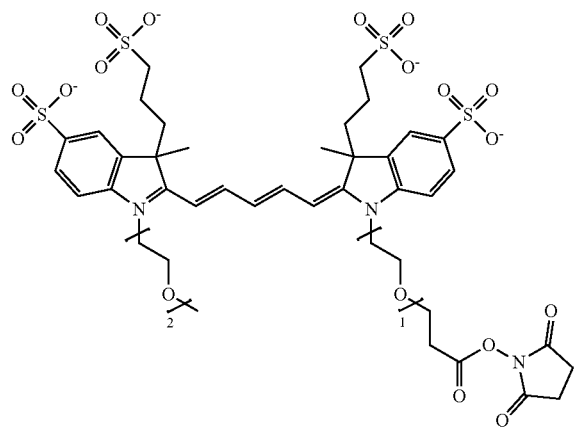

One non-limiting example of a NHS-ester of 650 Compound 2, according to general formula VI, where m=2 and p=2, is shown below:

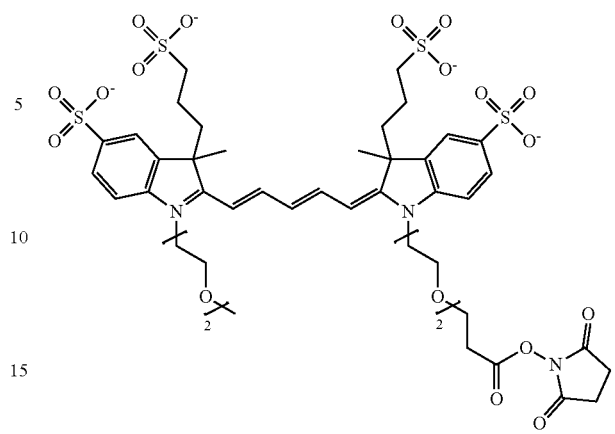

One non-limiting example of a NHS-ester of 650 Compound 2, according to general formula VI, where m=2 and p=3, is shown below:

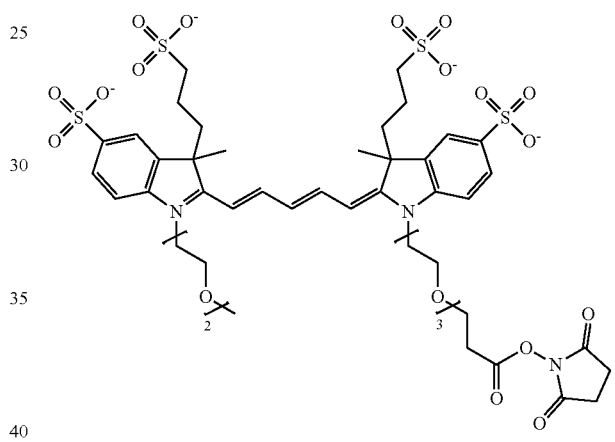

One non-limiting example of a NHS-ester of 650 Compound 3, according to general formula VI, where m=3 and p=1, is shown below:

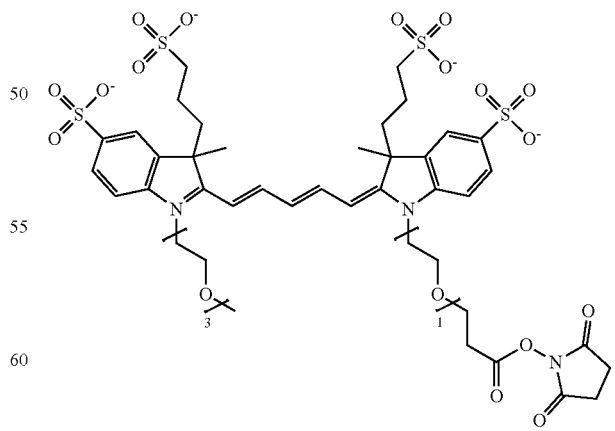

One non-limiting example of a NHS-ester of 650 Compound 3, according to general formula VI, where m=3 and p=2, is shown below:

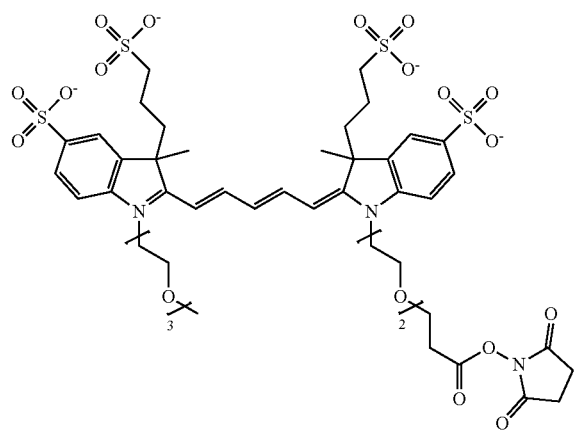

One non-limiting example of a NHS-ester of 650 Compound 3, according to general formula VI, where m=3 and p=3, is shown below:

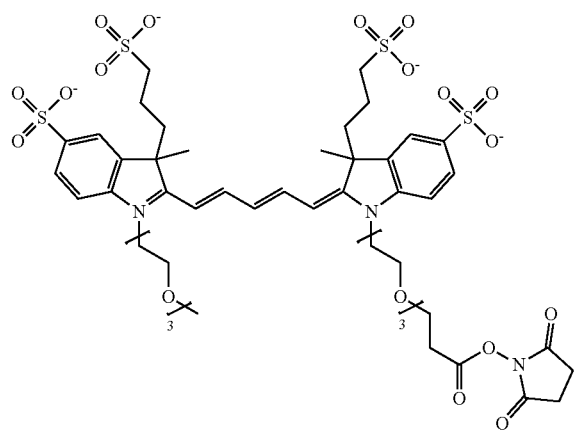

One non-limiting example of a NHS-ester of 650 Compound 4, according to general formula VI, where m=4 and p=1, is shown below:

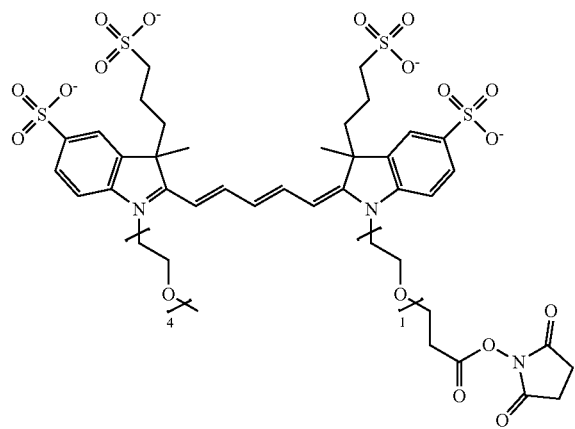

One non-limiting example of a NHS-ester of 650 Compound 5, according to general formula VI, where m=5 and p=1, is shown below:

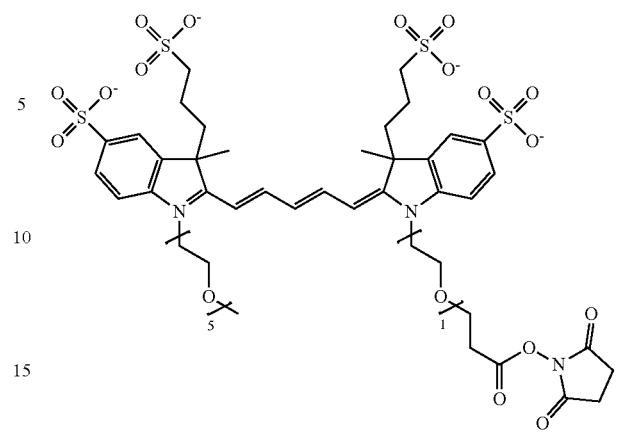

One non-limiting example of a NHS-ester of 650 Compound 6, according to general formula VI, where m=6 and p=1, is shown below:

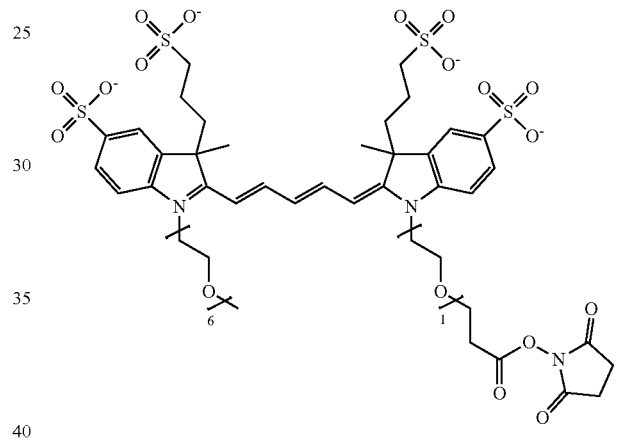

One non-limiting example of an activated 650 Compound 1 is the tetrafluorophenyl (TFP)-ester of 650 Compound 1, shown below:

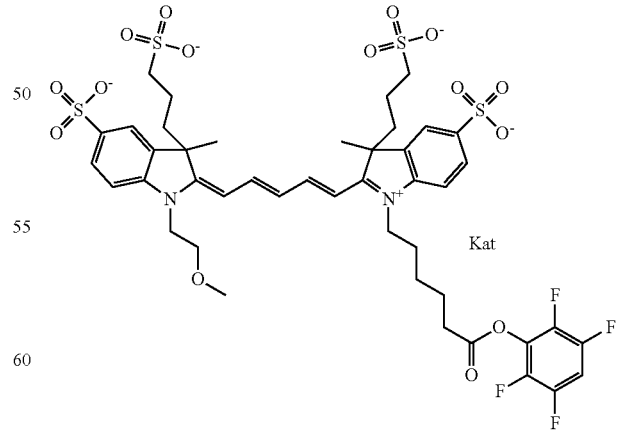

One non-limiting example of an activated 650 Compound 1 is the sulfotetrafluorophenyl (STP)-ester of 650 Compound 1, shown below:

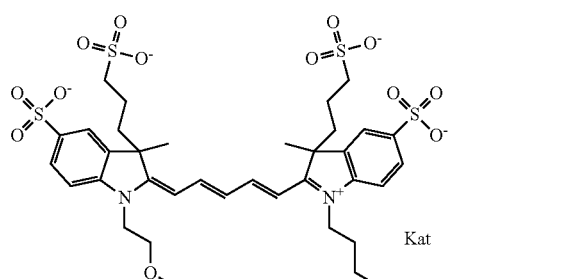

One non-limiting example of an activated 650 Compound 1 is the hydrazide of 650 Compound 1, shown below:

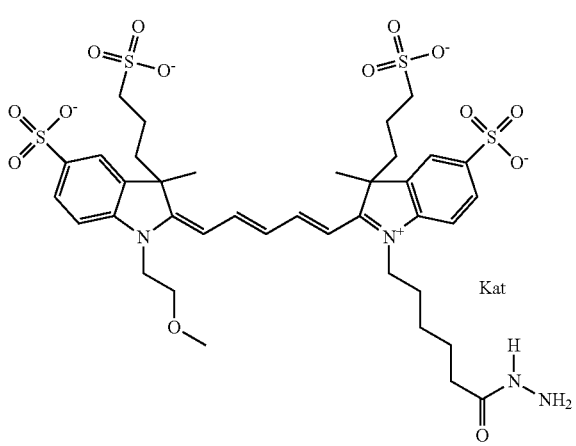 [SMILES: COCCN1/C(=C/C=C/C=C/C2=[N+](CCCCCC(=O)NN)c3ccc(S(=O)(=O)[O-])cc3C2(C)CCCS(=O)(=O)[O-])C(C)(CCCS(=O)(=O)[O-])c2cc(S(=O)(=O)[O-])ccc21]

One non-limiting example of an activated 650 Compound 1 is the maleimide of 650 Compound 1, shown below:

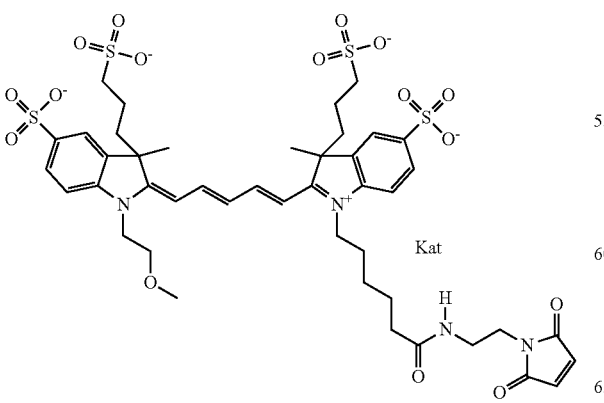

In one embodiment, the compound is 650 Compound 2

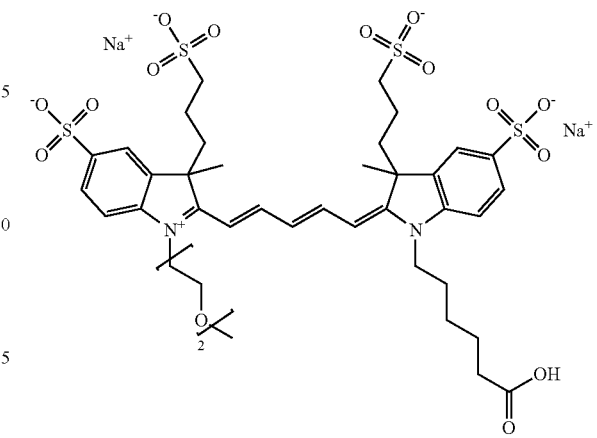

650 Compound 2 (2-{(1E,3E)-5-[1-(5-carboxypentyl)-3-methyl-5-sulfo-3-(3-sulfopropyl)-1,3-dihydroindol-(2E)-ylidene]-penta-1,3-dienyl}-1-[2-(2-methoxy-ethoxy)-ethyl]-3-methyl-5-sulfo-3-(3-sulfopropyl)-3H-indolium tri sodium salt.) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 2 is activated as described above, one non-limiting example of which is the NHS-ester form of 650 Compound 2, shown below.

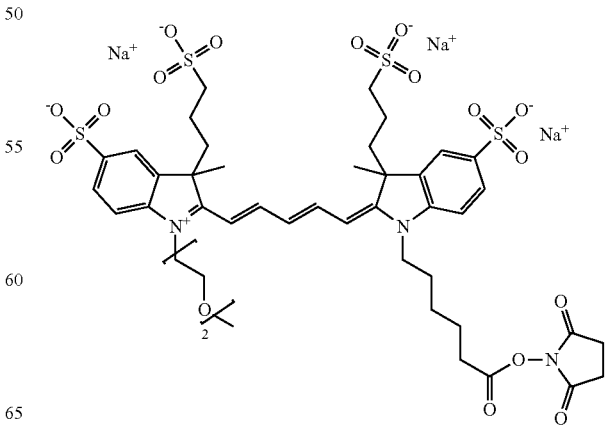

In one embodiment, the compound is 650 Compound 3

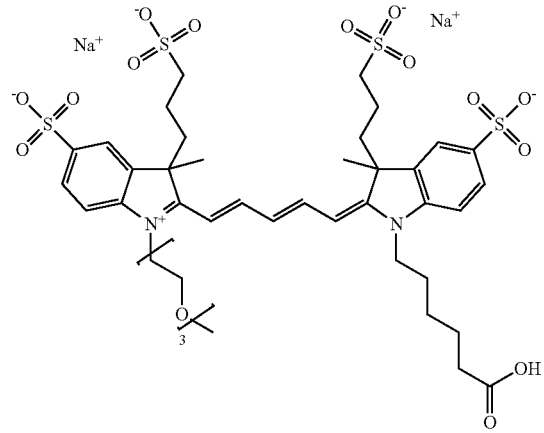

650 Compound 3 (2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-{2-[2-(2-methoxy-ethoxy)-ethoxy]-ethyl}-3-methyl-5-sulfo-3-(3-sulfopropyl)-3H-indolium tri sodium salt) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 3 is activated as described above, one non-limiting example of which is the NHS-ester form of 650 Compound 3, shown below.

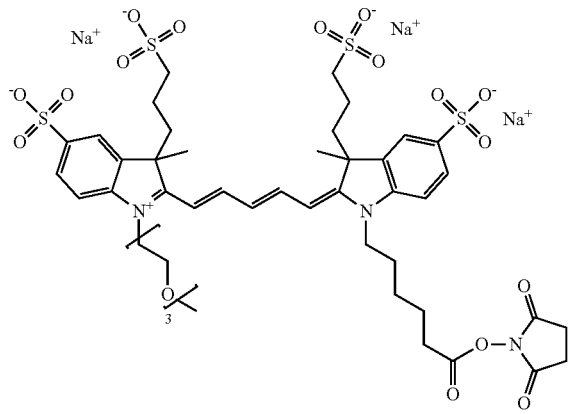

In one embodiment, the compound is 650 Compound 4

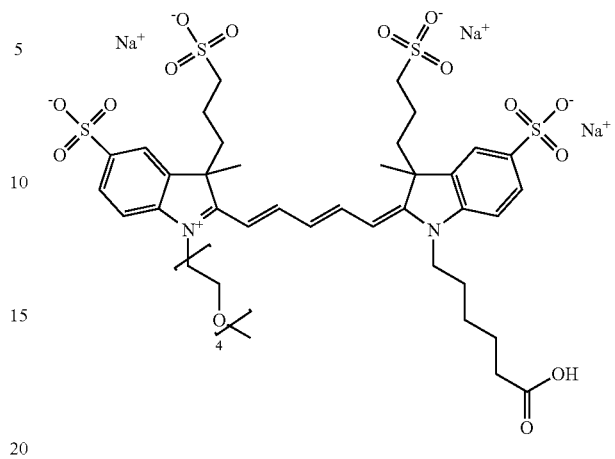

650 Compound 4 (2-((1E,3E,5E)-5-(1-(5-carboxypentyl)-3-methyl-5-sulfonato-3-(3-sulfonatopropyl)indolin-2-ylidene)penta-1,3-dien-1-yl)-3-methyl-3-(3-sulfonatopropyl)-1-(2,5,8,11-tetraoxatridecan-13-yl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 4 is activated as described above.

In one embodiment, the compound is 650 Compound 5

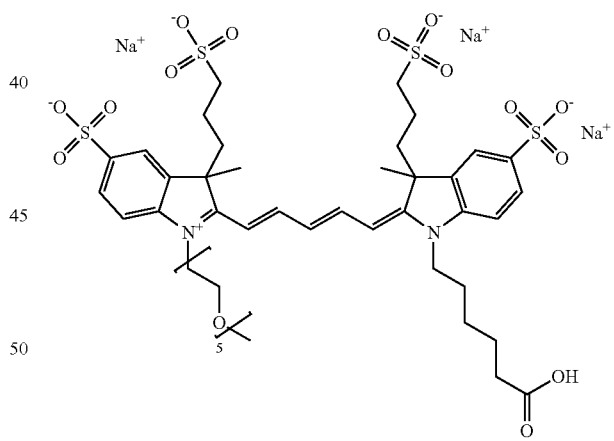

650 Compound 5 (2-((1E,3E,5E)-5-(1-(5-carboxypentyl)-3-methyl-5-sulfonato-3-(3-sulfonatopropyl)indolin-2-ylidene)penta-1,3-dien-1-yl)-1-(2,5,8,11,14-pentaoxahexadecan-16-yl)-3-methyl-3-(3-sulfonatopropyl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 5 is activated as described above.

In one embodiment, the compound is 650 Compound 6

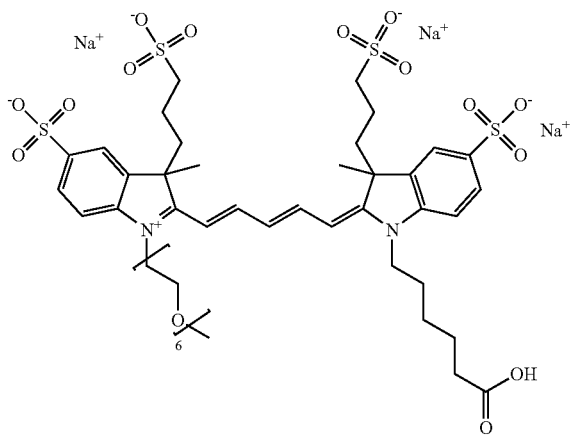

650 Compound 6 (2-((1E,3E,5E)-5-(1-(5-carboxypentyl)-3-methyl-5-sulfonato-3-(3-sulfonatopropyl)indolin-2-ylidene)penta-1,3-dien-1-yl)-3-methyl-1-(2,5,8,11,14,17-hexaoxanonadecan-19-yl)-3-(3-sulfonatopropyl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 650 Compound 6 is activated as described above.

In embodiments, the compound contains one or more substitutions of the polymethine linker. In one embodiment, the compound has general formula VII

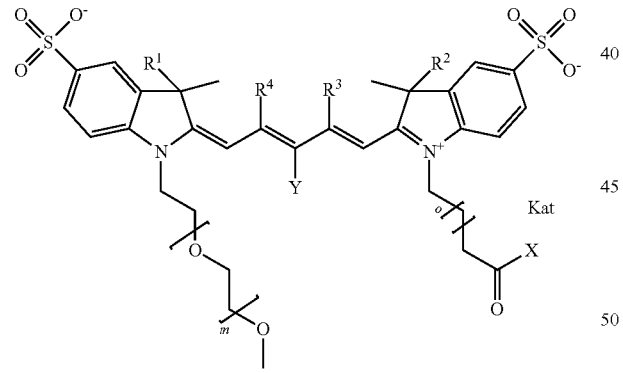

wherein each of $R^1$ and $R^2$ is the same or different and is independently selected from the group consisting of an aliphatic, heteroaliphatic, or sulfoalkyl group; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO—STP, —NR-L-CO-TFP, —NR-L-CO-benzotriazole, —NR-L-CHO, —NR-L-maleimide, and —NR-L-NH—CO—CH$_2$—I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH=CH—, —OCH=CH— where each of q and q' is the same or different and is an integer from 2 to 6 inclusive; and Y is selected from the group consisting of hydrogen, alkyl, sulfoalkyl, fluorine, chlorine, bromine, a substituted or unsubstituted aryl-, phenoxy- and a phenylmercapto function.

In one embodiment, the compound of general formula VII wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

In one embodiment, an isolated enantiomeric mixture selected from diastereomer Ia of general formula VII

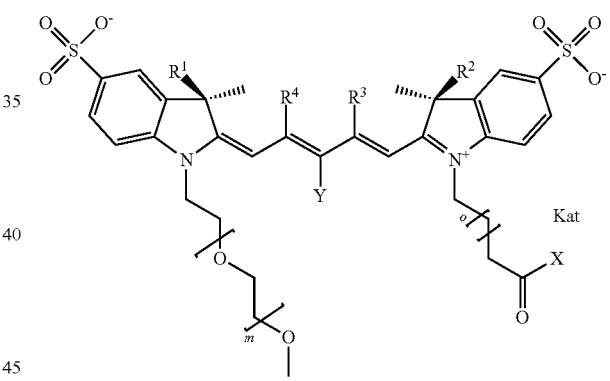

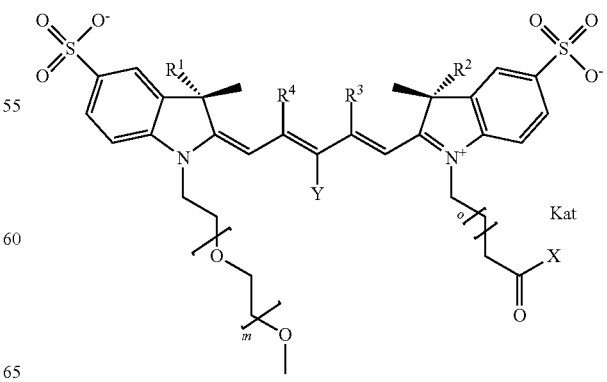

or diastereomer Ib of general formula VII

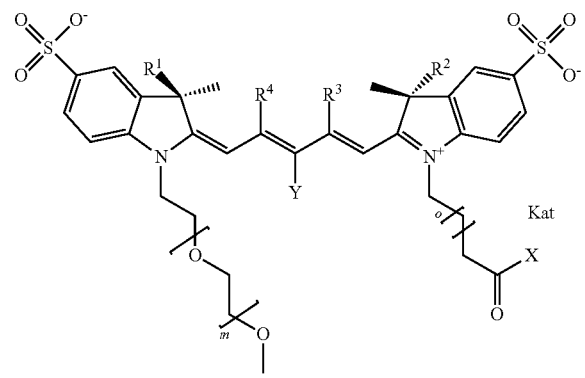

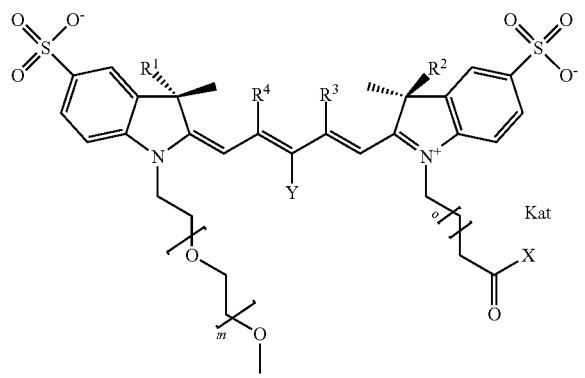

is provided, wherein each of $R^1$ and $R^2$ is the same or different and is independently selected from the group consisting of an aliphatic, heteroaliphatic, sulfoalkyl group, or heteroaliphatic with terminal $SO_3$; X is selected from the group consisting of —OH, —SH, —$NH_2$, —NH—$NH_2$, —F, —Cl, —Br, I, —NHS (hydroxysuccinimidyl/sulfosuccinimidyl), —O—TFP (2,3,5,6-tetrafluorophenoxy), —O—STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO—STP, —NR-L-CO-TFP, —NR-L-CO-benzotriazole, —NR-L-CHO, —NR-L-maleimide, and —NR-L-NH—CO—$CH_2$—I, where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group, or $R^3$ and $R^4$ together form a cyclic structure where $R^3$ and $R^4$ are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- and a phenylmercapto function.

In one embodiment, the compound has general formula VIII

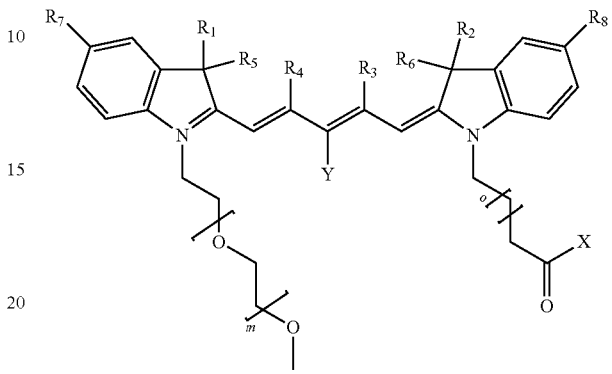

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or $SO_3$; X is selected from —OH, —SH, —$NH_2$, —NH—$NH_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, or —NR-L-NH—CO—$CH_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- or phenylmercapto function.

In one embodiment, the compound of general formula VIII wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —$(CH_2)_q$— and CH=CH, where q is an integer from 1 to 2 inclusive, to result in a 3-, 4-, or 5-membered ring.

One non-limiting example is a substituted polymethine form of 650 Compound 1, shown below:

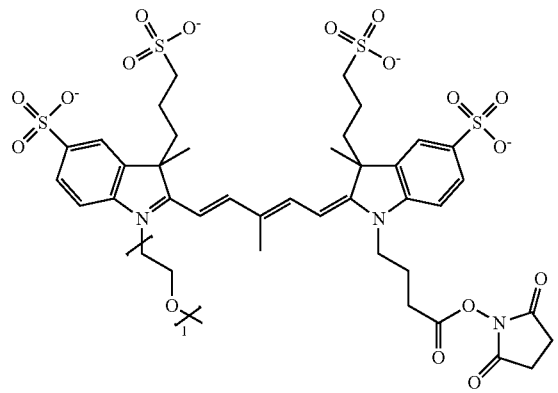

One non-limiting example is a substituted polymethine form of 650 Compound 2, shown below:

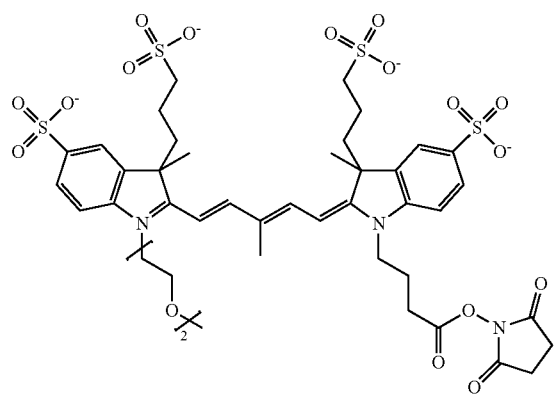

One non-limiting example is a substituted polymethine form of 650 Compound 3, shown below:

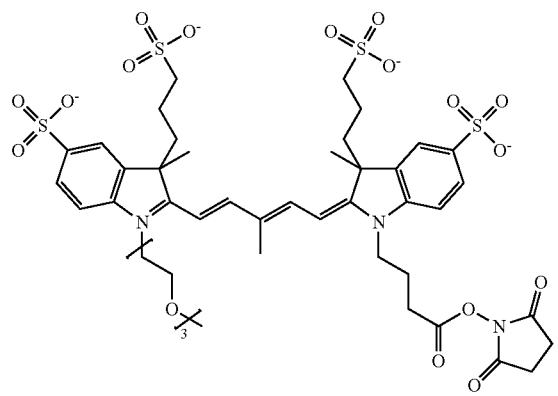

One non-limiting example is a substituted polymethine form of 650 Compound 4, shown below:

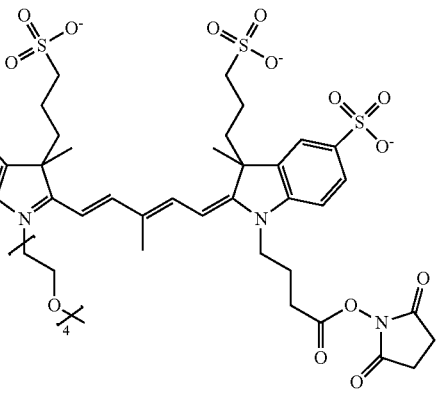

One non-limiting example is a substituted polymethine form of 650 Compound 5, shown below:

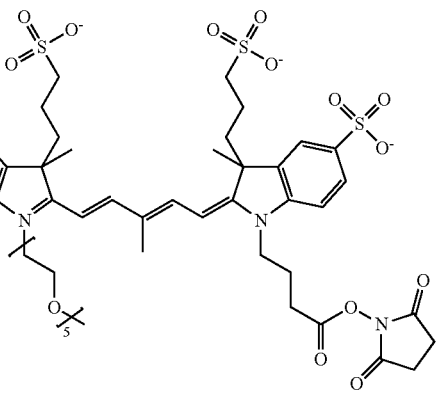

One non-limiting example is a substituted polymethine form of 650 Compound 6, shown below:

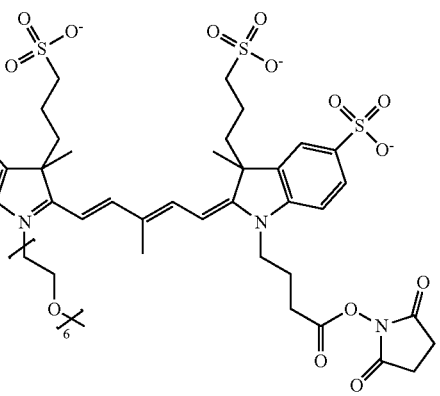

One non-limiting example is a substituted polymethine form of 650 having an ethylene glycol, diethylene glycol, or polyethylene glycol as described for general formula VI, such as the compound shown below:

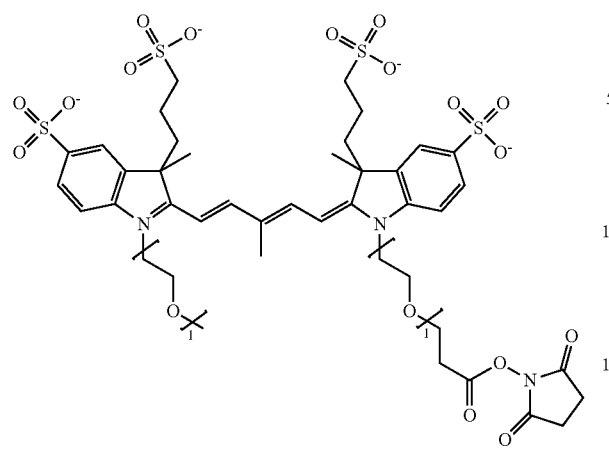

One non-limiting example is a substituted polymethine form of 650 Compound 1, shown below:

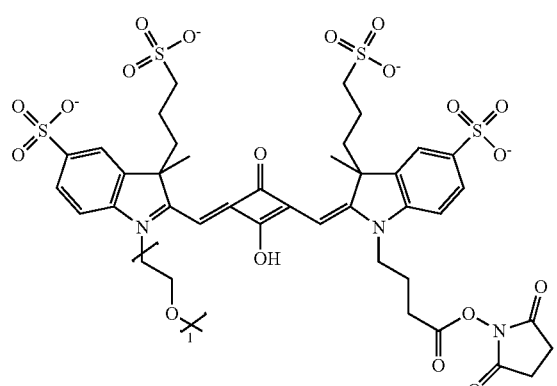

One non-limiting example is a substituted polymethine form of 650 Compound 2, shown below:

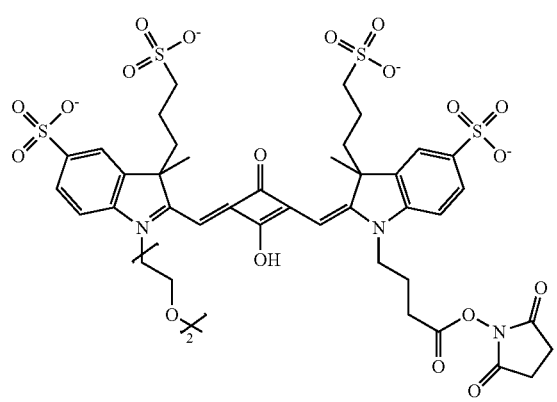

One non-limiting example is a substituted polymethine form of 650 Compound 3, shown below:

One non-limiting example is a substituted polymethine form of 650 Compound 4, shown below:

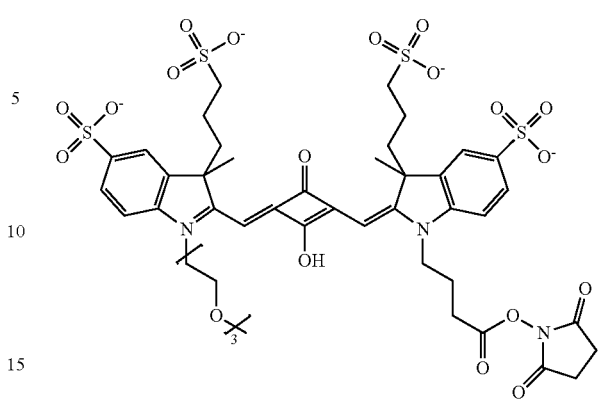

One non-limiting example is a substituted polymethine form of 650 Compound 5, shown below:

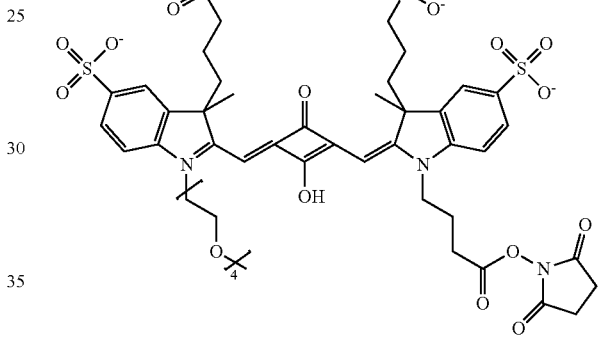

One non-limiting example is a substituted polymethine form of 650 Compound 6, shown below:

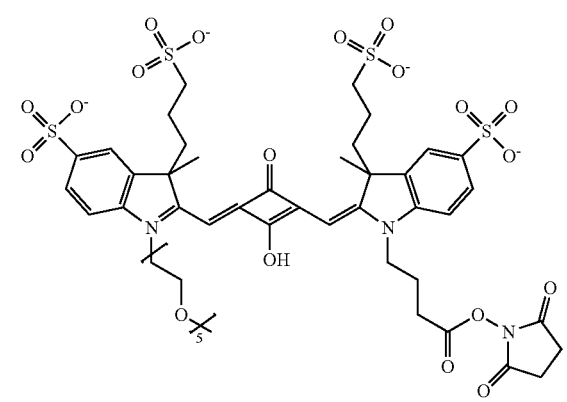

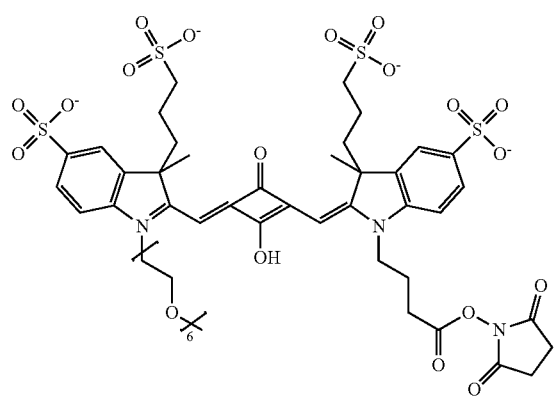

One non-limiting example is a substituted polymethine form of 650 having an ethylene glycol, diethylene glycol, or polyethylene glycol as described for general formula VI, such as the compound shown below:

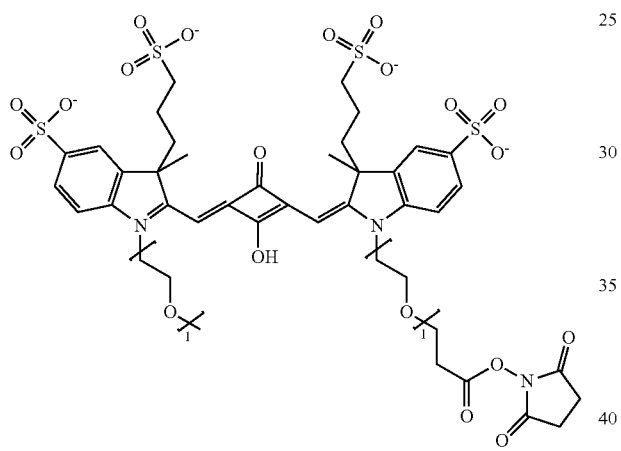

In embodiments, the degree of sulfonation is varied to, e.g., vary the compound's degree of hydrophilicity or hydrophobicity. One non-limiting example is a monosulfonate form of 650 Compound 1, shown below, but it is understood that the single sulfo group can be at any of the described positions:

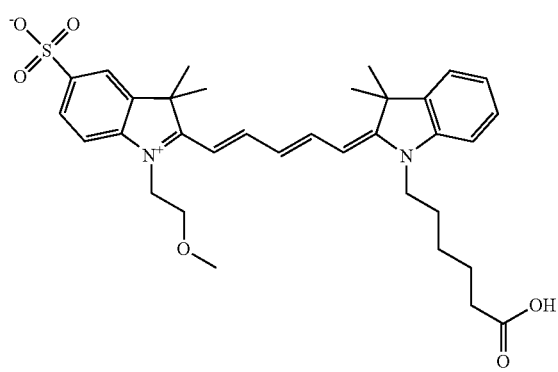

One non-limiting example is a disulfonate form of 650 Compound 1, shown below, but it is understood that each of the two sulfo groups can be at any of the described positions:

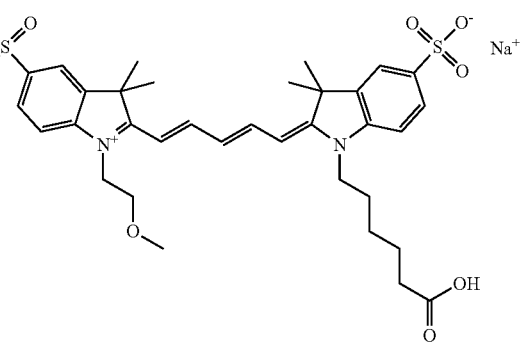

One non-limiting example is a trisulfonate form of 650 Compound 1, shown below, but it is understood that each of the three sulfo groups can be at any of the described positions:

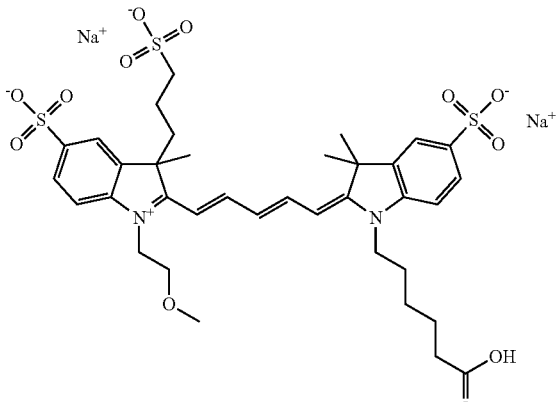

One non-limiting example is a trisulfonate form of 650 Compound 1, shown below, but it is understood that each of the three sulfo groups can be at any of the described positions:

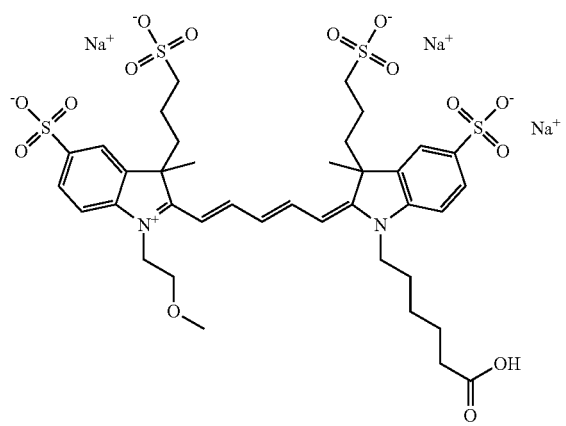

In one embodiment, the compound has general formula IX

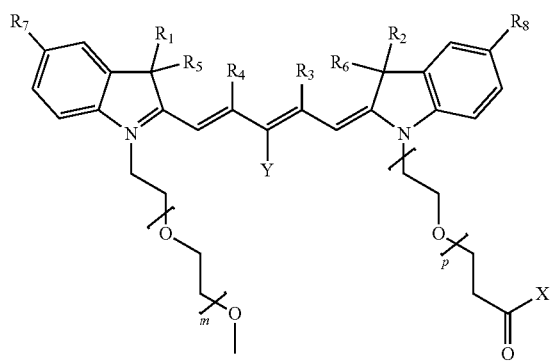

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or $SO_3$; X is selected from —OH, —SH, —$NH_2$, —NH—$NH_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, or —NR-L-NH—CO—$CH_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- or phenylmercapto function.

In one embodiment, the compound of general formula IX wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —$(CH_2)_q$— and CH=CH, where q is an integer from 1 to 2 inclusive, to result in a 3-, 4-, or 5-membered ring.

In one embodiment, the compound is 755 Compound 1

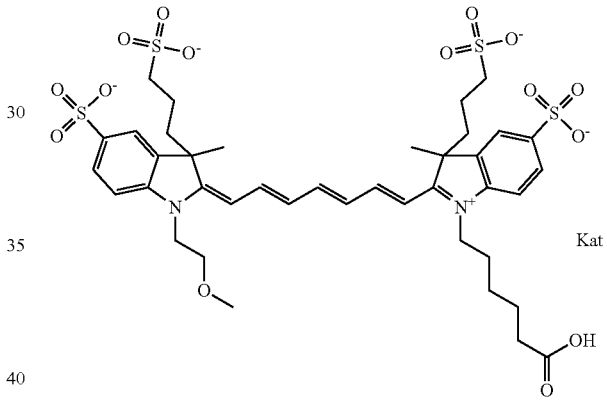

755 Compound 1 (2-{(1E,3E,5E)-7-[1-(5-carboxypentyl)-3-methyl-5-sulfo-3-(3-sulfopropyl)-1,3-dihydro-indol-(2E)-ylidene]-hepta-1,3,5-trienyl}-1-(2-methoxy-ethyl)-3-methyl-5-sulfo-3-(3-sulfopropyl)-3H-indolium tri sodium salt) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus (i.e., an unprotected terminus of an ethylene glycol group, diethylene glycol group, or polyethylene glycol group). Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 755 Compound 1, but one skilled in the art appreciates that activation is not limited to these examples. One non-limiting example of an activated compound is the NHS-ester of 755 Compound 1, shown below:

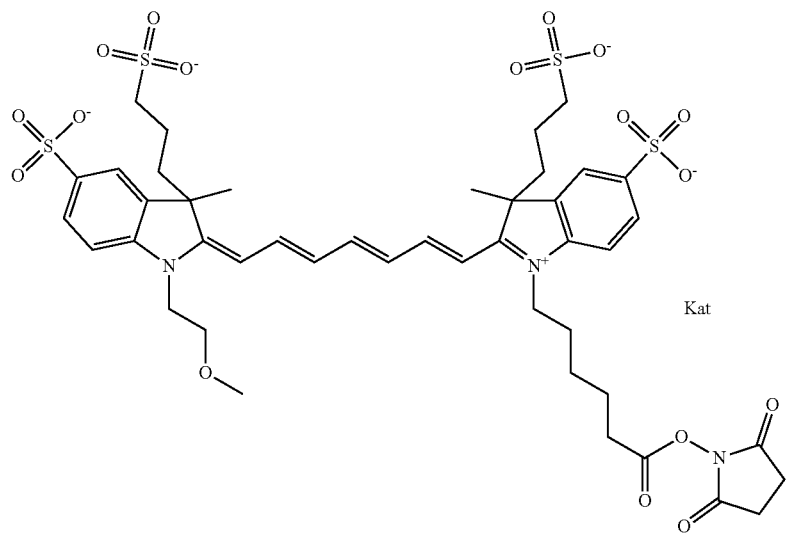
In one embodiment, the compound is an NHS-ester of 755 Compound 1 where, according to general formula I, o is 1, shown below:
In one embodiment, the compound is an NHS-ester of 755 Compound 1 where, according to general formula I, o is 5, shown below:
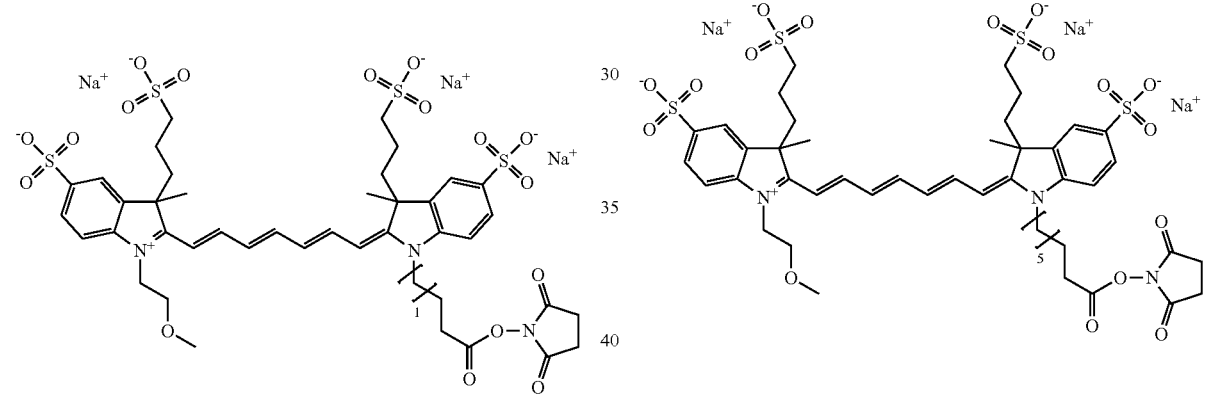
In one embodiment, the compound is described by the following general formula X, where m=1-6, and p=1-6:
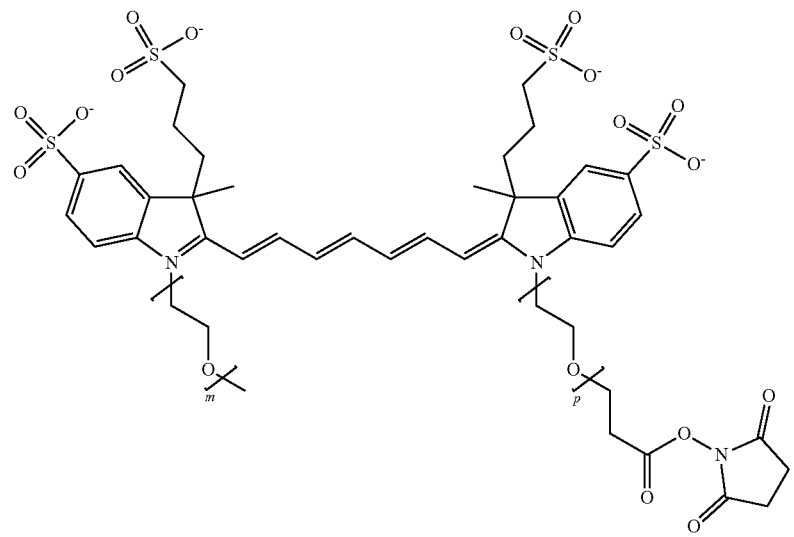

One non-limiting example of a NHS-ester of 755 Compound 1, according to general formula X, where m=1 and p=1, is shown below:
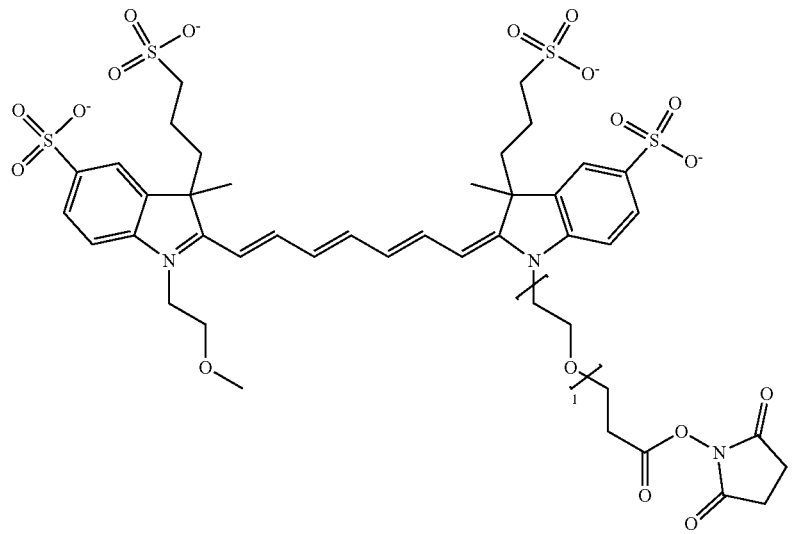
One non-limiting example of a NHS-ester of 755 Compound 1, according to general formula X, where m=1 and p=2, is shown below:
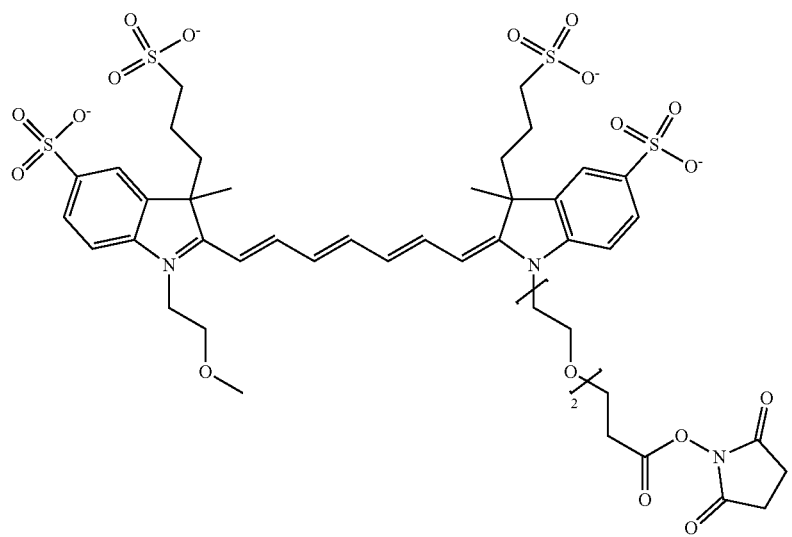
One non-limiting example of a NHS-ester of 755 Compound 1, according to general formula X, where m=1 and p=3, is shown below:

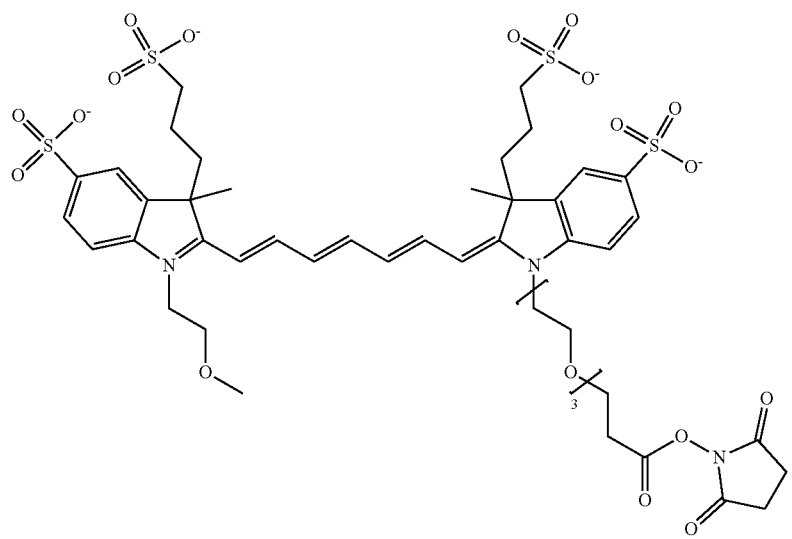
One non-limiting example of a NHS-ester of 755 Compound 1, according to general formula X, where m=1 and p=4, is shown below:
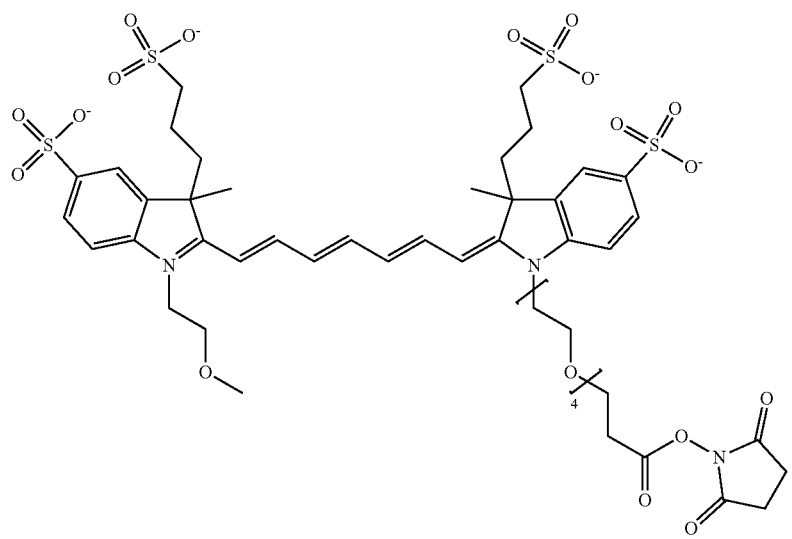
One non-limiting example of a NHS-ester of 755 Compound 1, according to general formula X, where m=1 and p=5, is shown below:

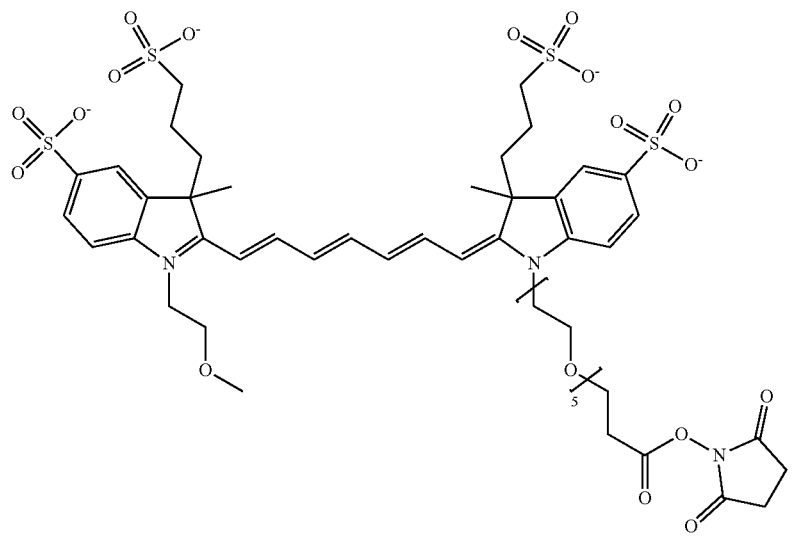
One non-limiting example of a NHS-ester of 755 Compound 1, according to general formula X, where m=1 and p=6, is shown below:
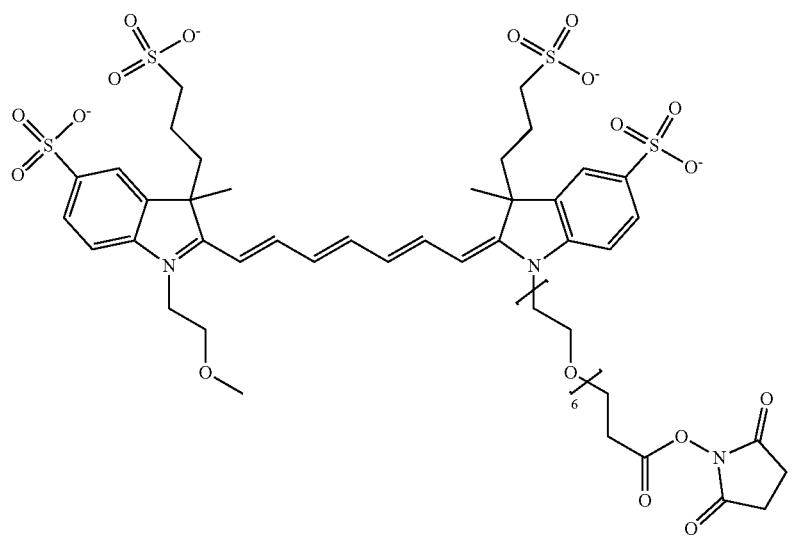
One non-limiting example of a NHS-ester of 755 Compound 2, according to general formula X, where m=2 and p=1, is shown below:

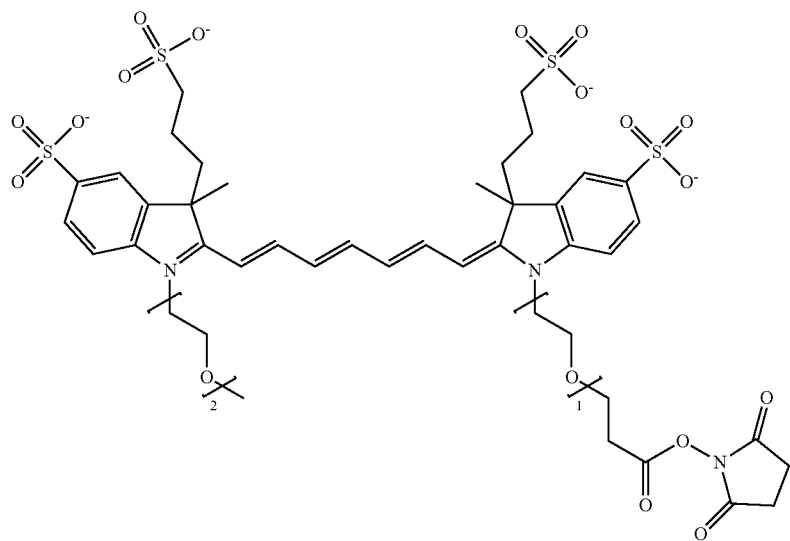
One non-limiting example of a NHS-ester of 755 Compound 2, according to general formula X, where m=2 and p=2, is shown below:
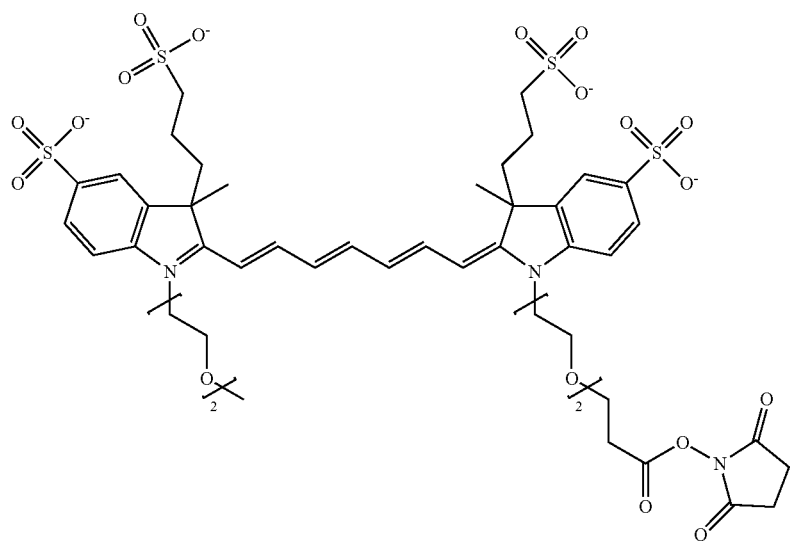
One non-limiting example of a NHS-ester of 755 Compound 2, according to general formula X, where m=2 and p=3, is shown below:

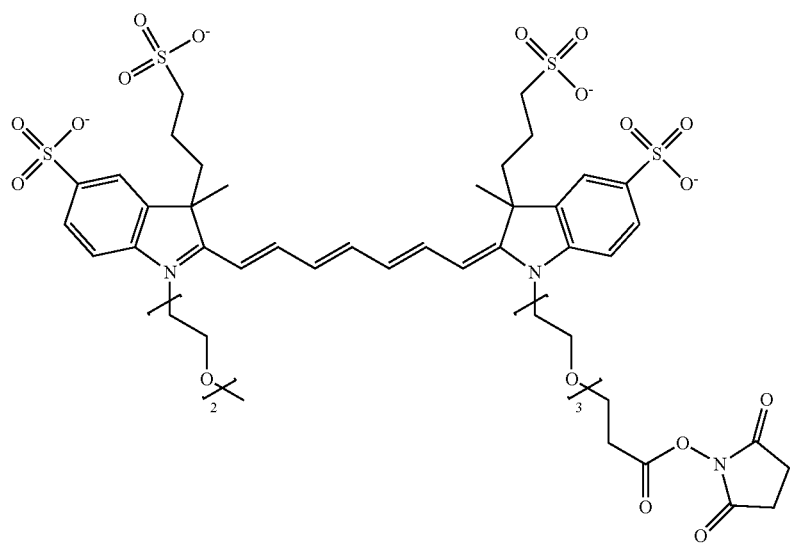
One non-limiting example of a NHS-ester of 755 Compound 3, according to general formula X, where m=3 and p=1, is shown below:
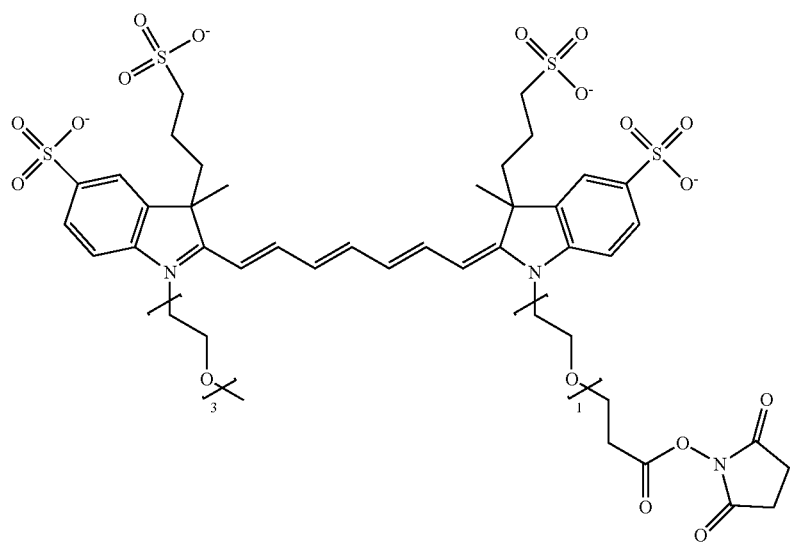
One non-limiting example of a NHS-ester of 755 Compound 3, according to general formula X, where m=3 and p=2, is shown below:

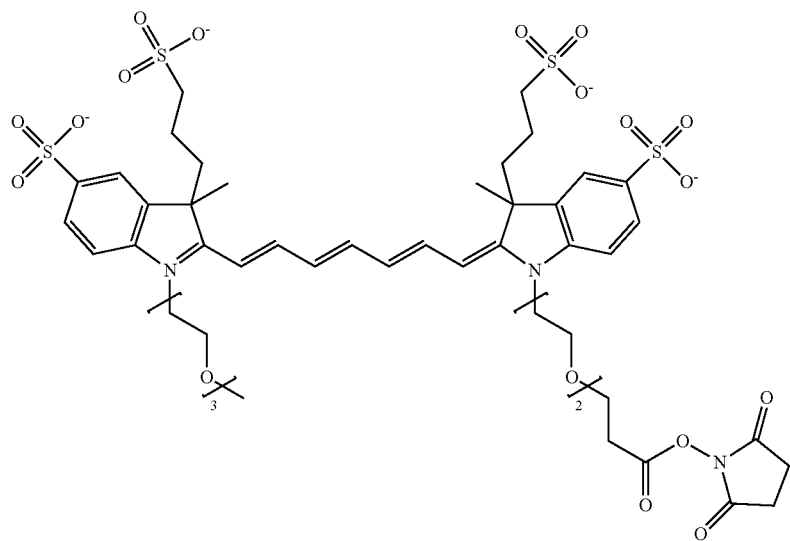
One non-limiting example of a NHS-ester of 755 Compound 3, according to general formula X, where m=3 and p=3, is shown below:
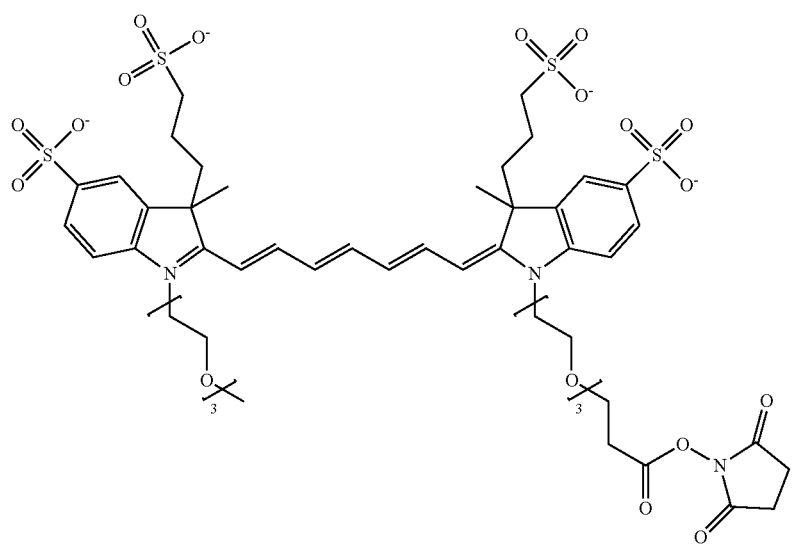
One non-limiting example of a NHS-ester of 755 Compound 4, according to general formula X, where m=4 and p=1, is shown below:

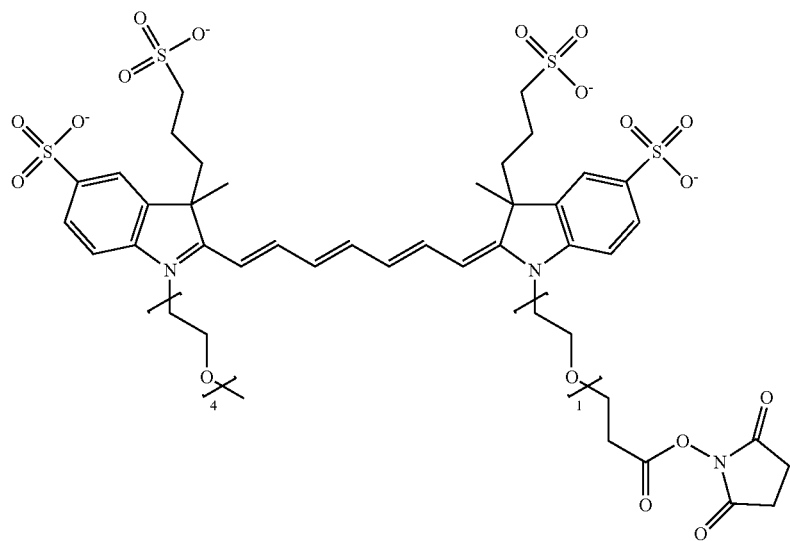
One non-limiting example of a NHS-ester of 755 Compound 5, according to general formula X, where m=5 and p=1, is shown below:
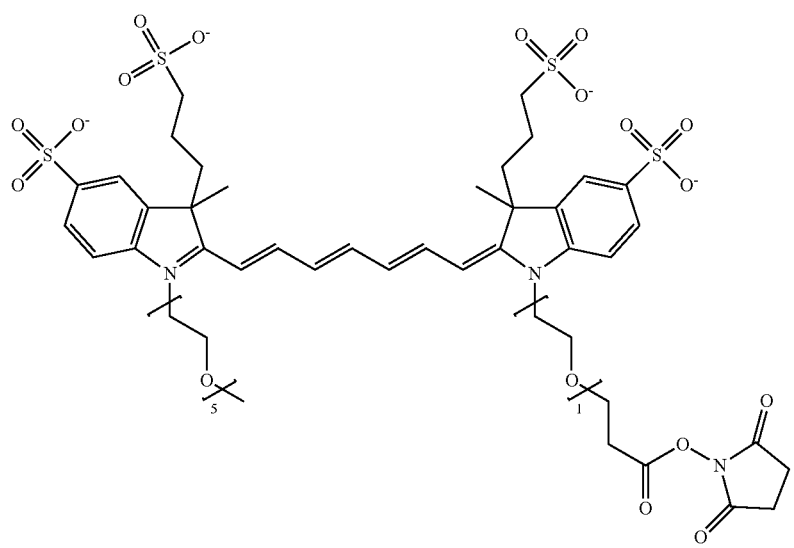
One non-limiting example of a NHS-ester of 755 Compound 6, according to general formula X, where m=6 and p=1, is shown below:

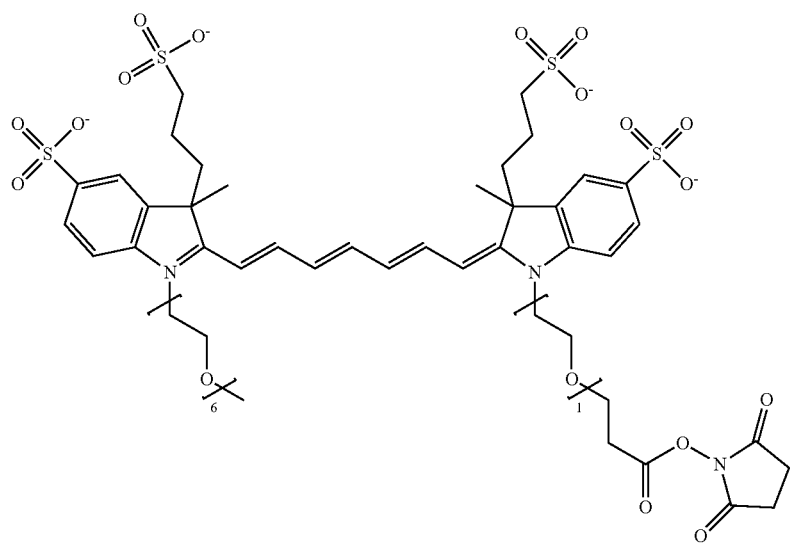
One non-limiting example of an activated 755 Compound 1 is a tetrafluorophenyl (TFP)-ester form of 755 Compound 1, shown below:
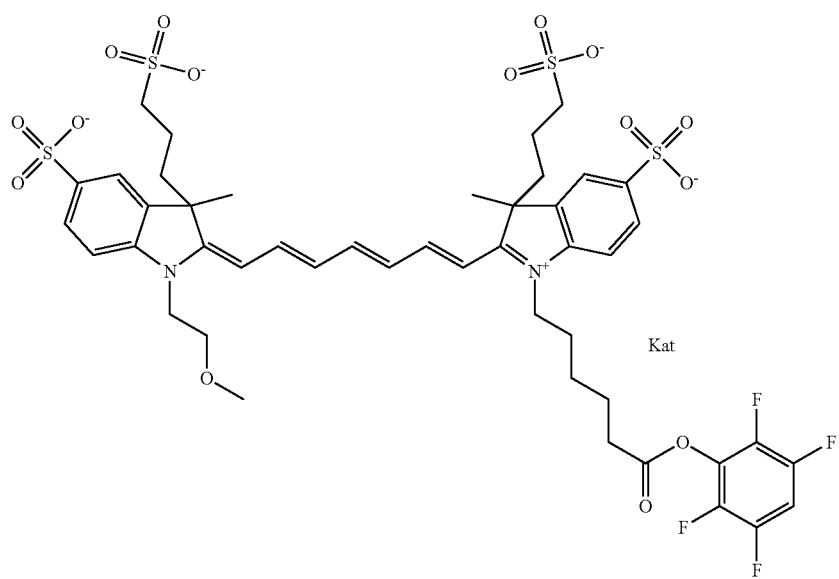 [SMILES: COCCN1/C(=C/C=C/C=C/C=C/C2=[N+](CCCCCC(=O)Oc3c(F)c(F)cc(F)c3F)c3ccc(S(=O)(=O)[O-])cc3C2(C)CCCS(=O)(=O)[O-])C(C)(CCCS(=O)(=O)[O-])c2cc(S(=O)(=O)[O-])ccc21]
One non-limiting example of an activated 755 Compound 1 is a sulfotetrafluorophenyl (STP)-ester form of 755 Compound 1, shown below:

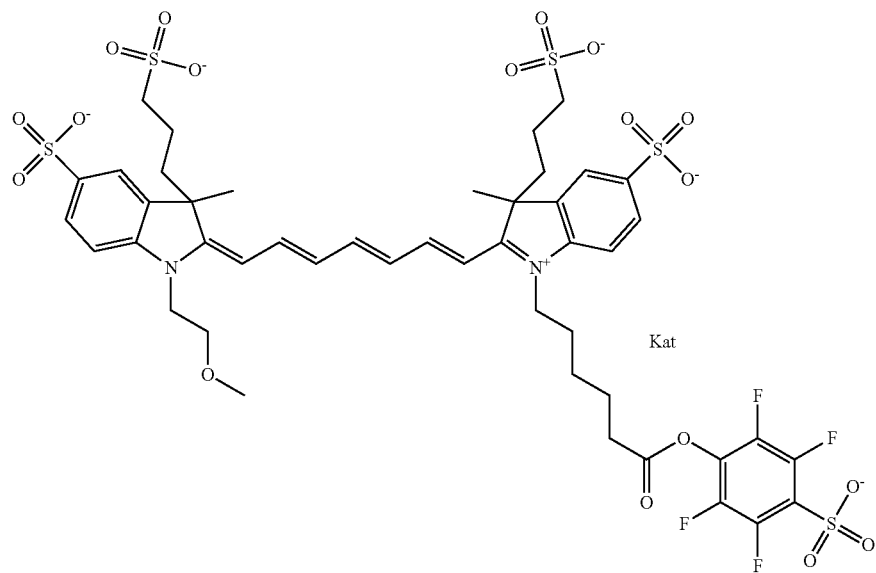 [SMILES: COCCN1/C(=C/C=C/C=C/C=C/C2=[N+](CCCCCC(=O)Oc3c(F)c(F)c(S(=O)(=O)[O-])c(F)c3F)c3ccc(S(=O)(=O)[O-])cc3C2(C)CCCS(=O)(=O)[O-])C(C)(CCCS(=O)(=O)[O-])c2cc(S(=O)(=O)[O-])ccc21]
One non-limiting example of an activated 755 Compound 1 is a hydrazide form of 755 Compound 1, shown below:
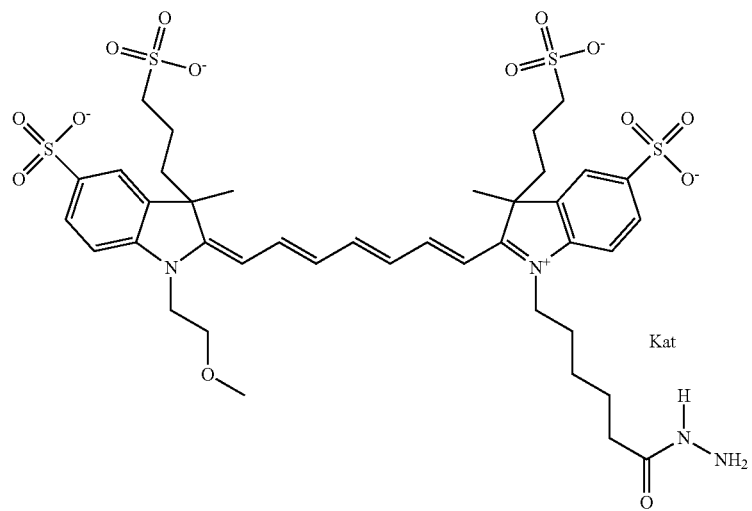 [SMILES: COCCN1/C(=C/C=C/C=C/C=C/C2=[N+](CCCCCC(=O)NN)c3ccc(S(=O)(=O)[O-])cc3C2(C)CCCS(=O)(=O)[O-])C(C)(CCCS(=O)(=O)[O-])c2cc(S(=O)(=O)[O-])ccc21]
One non-limiting example of an activated 755 Compound 1 is a maleimide form of 755 Compound 1, shown below:

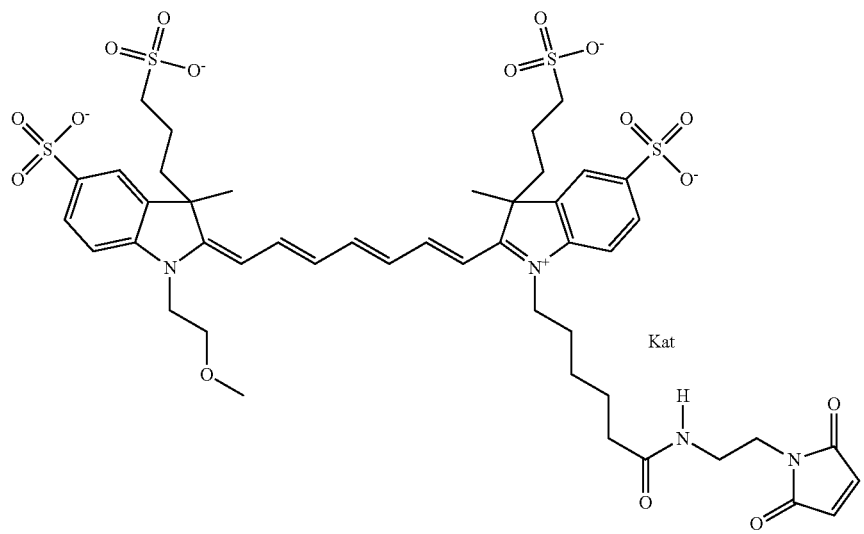 [SMILES: COCCN1/C(=C/C=C/C=C/C=C/C2=[N+](CCCCCC(=O)NCCN3C(=O)C=CC3=O)c3ccc(S(=O)(=O)[O-])cc3C2(C)CCCS(=O)(=O)[O-])C(C)(CCCS(=O)(=O)[O-])c2cc(S(=O)(=O)[O-])ccc21]

In one embodiment, the compound is 755 Compound 2

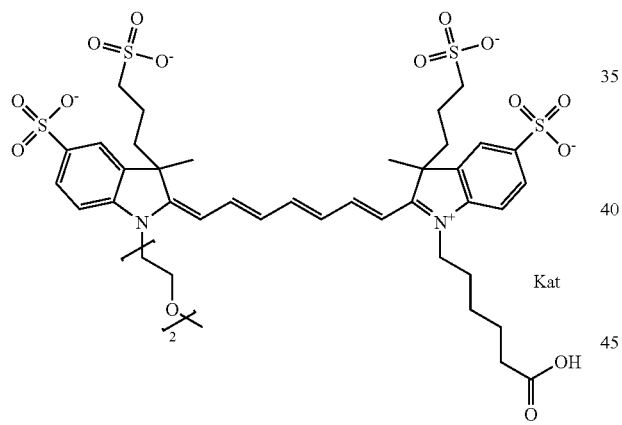

755 Compound 2 (2-{(1E,3E,5E)-7-[1-(5-carboxypentyl)-3-methyl-5-sulfo-3-(3-sulfopropyl)-1,3-dihydro-indol-(2E)-ylidene]-hepta-1,3,5-trienyl}-1-(2-methoxy-ethoxy)-3-methyl-5-sulfo-3-(3-sulfopropyl)-3H-indolium) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 2 is activated as described above, one non-limiting example of which is the NHS-ester form of 755 Compound 2, shown below.

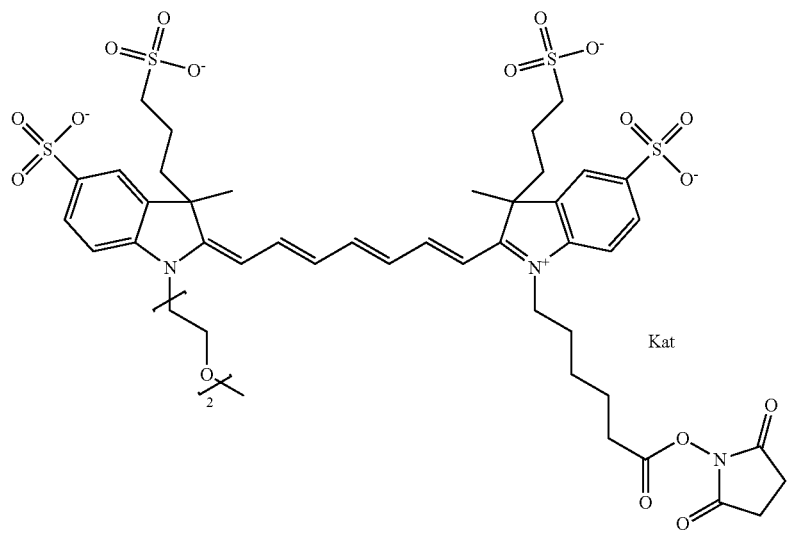

In one embodiment, the compound is 755 Compound 3

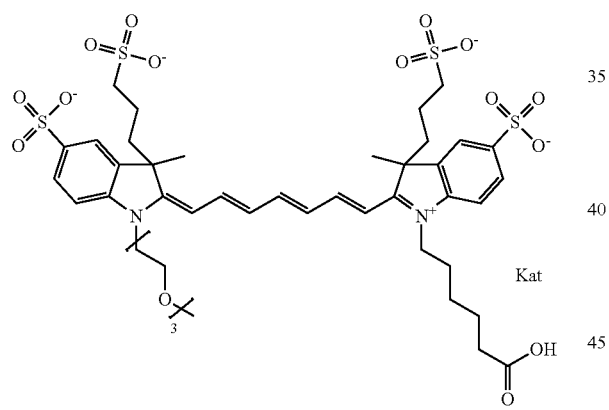

755 Compound 3 (2-{(1E,3E,5E)-7-[1-(5-carboxypentyl)-3-methyl-5-sulfo-3-(3-sulfopropyl)-1,3-dihydro-indol-(2E)-ylidene]-hepta-1,3,5-trienyl}-1-{2-[2-(2-methoxyethoxy)-ethoxy]-ethyl}-3-methyl-5-sulfo-3-(3-sulfopropyl)-3H-indolium) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 3 is activated as described above, one non-limiting example of which is the NHS-ester form of 755 Compound 3, shown below.

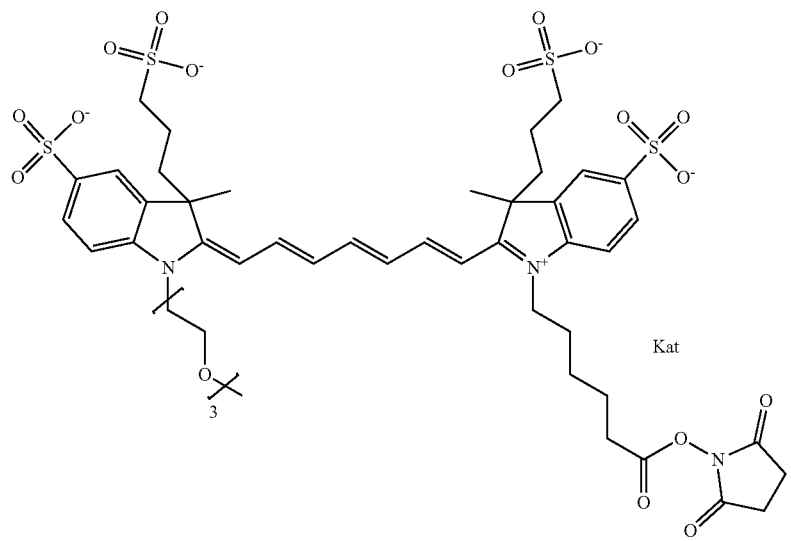

In one embodiment, the compound is 755 Compound 4

In one embodiment, the compound is 755 Compound 5

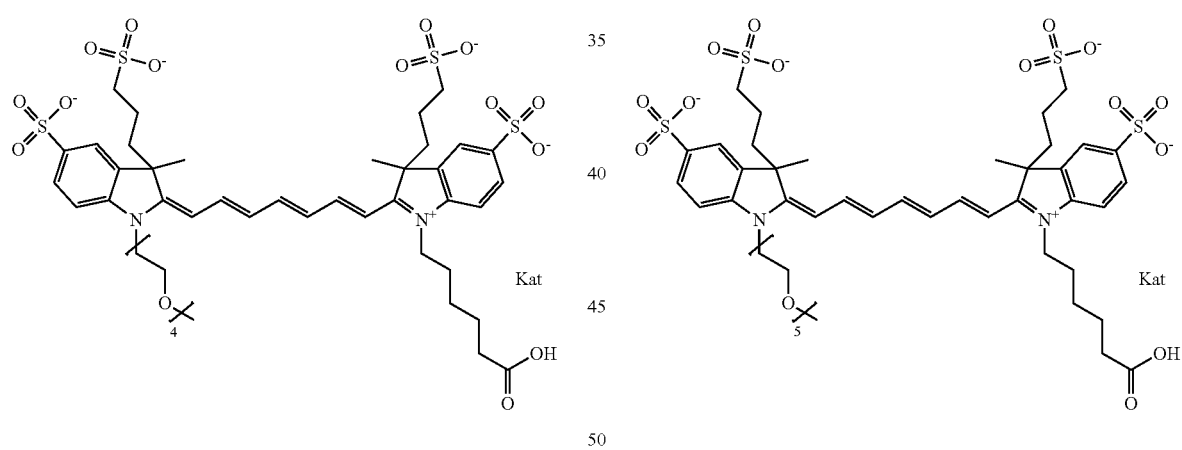

755 Compound 4 (1-(5-carboxypentyl)-3-methyl-24-(1E,3E,5E,7E)-7-(3-methyl-5-sulfonato-3-(3-sulfonatopropyl)-1-(2,5,8,11-tetraoxatridecan-13-yl)indolin-2-ylidene)hepta-1,3,5-trien-1-yl)-3-(3-sulfonatopropyl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 4 is activated as described above.

755 Compound 5 (2-((1E,3E,5E,7E)-7-(1-(2,5,8,11,14-pentaoxahexadecan-16-yl)-3-methyl-5-sulfonato-3-(3-sulfonatopropyl)indolin-2-ylidene)hepta-1,3,5-trien-1-yl)-1-(5-carboxypentyl)-3-methyl-3-(3-sulfonatopropyl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 755 Compound 5 is activated as described above.

In one embodiment, the compound is 755 Compound 6

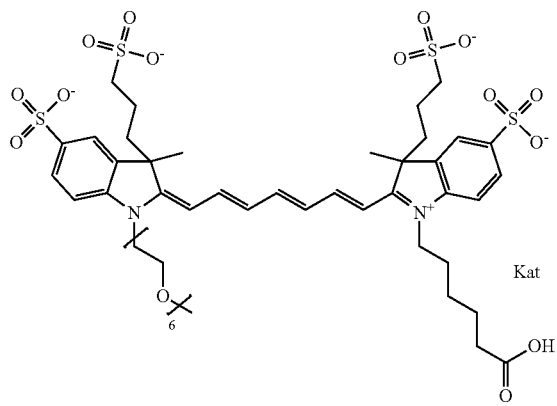

755 Compound 6 (1-(5-carboxypentyl)-3-methyl-2-((1E,3E,5E,7E)-7-(3-methyl-1-(2,5,8,11,14,17-hexaoxanonadecan-19-yl)-5-sulfonato-3-(3-sulfonatopropyl)indolin-2-ylidene)hepta-1,3,5-trien-1-yl)-3-(3-sulfonatopropyl)-3H-indol-1-ium-5-sulfonate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 755 Compound 6 is activated as described above.

In embodiments, the compound contains one or more substitutions of the polymethine linker. In one embodiment, the compound has general formula XI

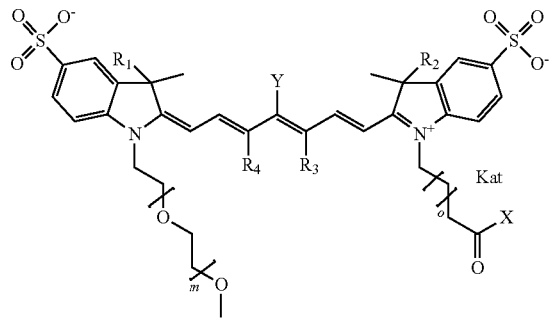

wherein each of $R^1$ and $R^2$ is the same or different and is independently selected from the group consisting of an aliphatic, heteroaliphatic, or sulfoalkyl group; X is selected from the group consisting of —OH, —SH, —NH$_2$, —NH—NH$_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO—STP, —NR-L-CO-TFP, —NR-L-CO-benzotriazole, —NR-L-CHO, —NR-L-maleimide, —NR-L-NH—CO—CH$_2$—I, and —NR-L-NH—CO—CH$_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- and a phenylmercapto function.

In one embodiment, the compound of general formula XI wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

In one embodiment, the compound has general formula XII

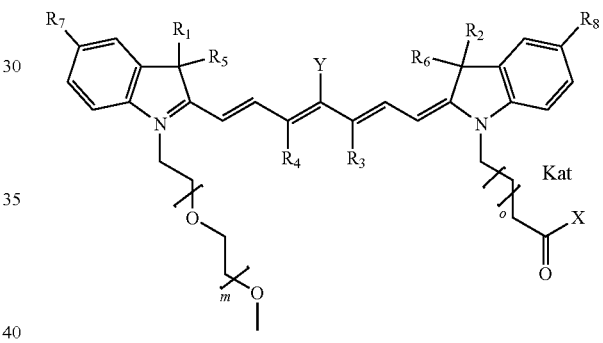

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or SO$_3$; X is selected from —OH, —SH, —NH$_2$, —NH—NH$_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—I, or —NR-L-NH—CO—CH$_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- or phenylmercapto function.

In one embodiment, the compound of general formula XII wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

One non-limiting example is a substituted polymethine form of 755 Compound 1, shown below:

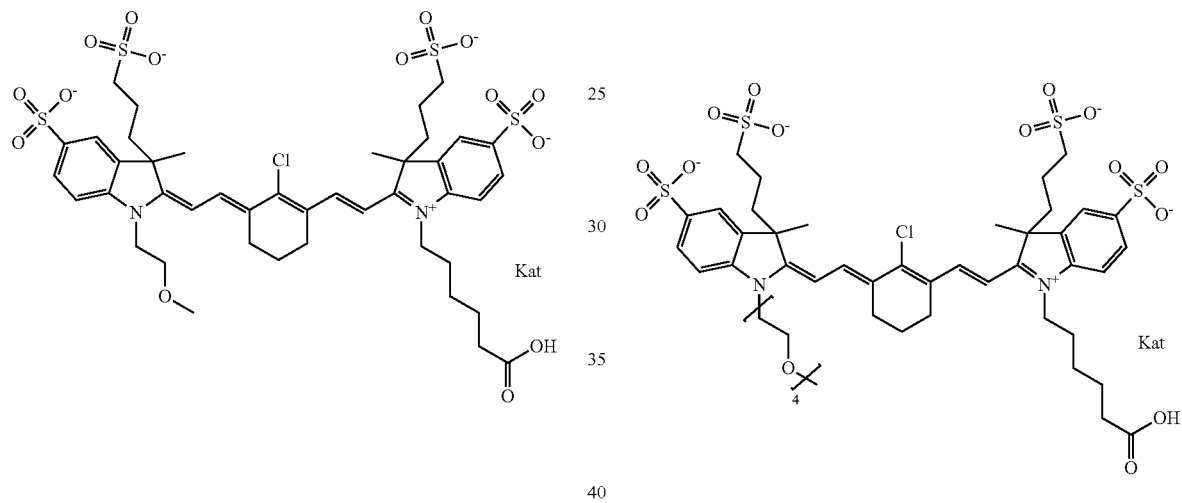

One non-limiting example is a substituted polymethine form of 755 Compound 2, shown below:

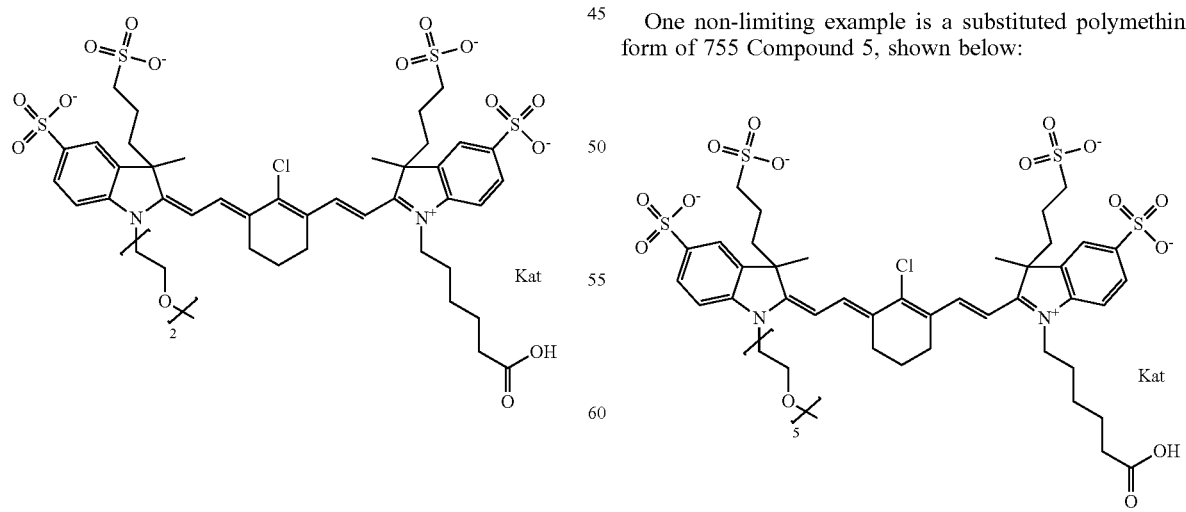

One non-limiting example is a substituted polymethine form of 755 Compound 3, shown below:

One non-limiting example is a substituted polymethine form of 755 Compound 4, shown below:

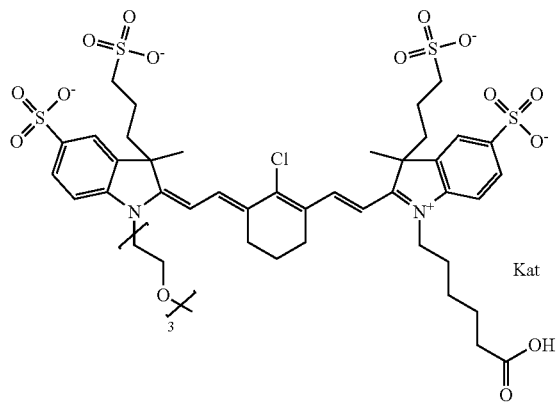

One non-limiting example is a substituted polymethine form of 755 Compound 5, shown below:

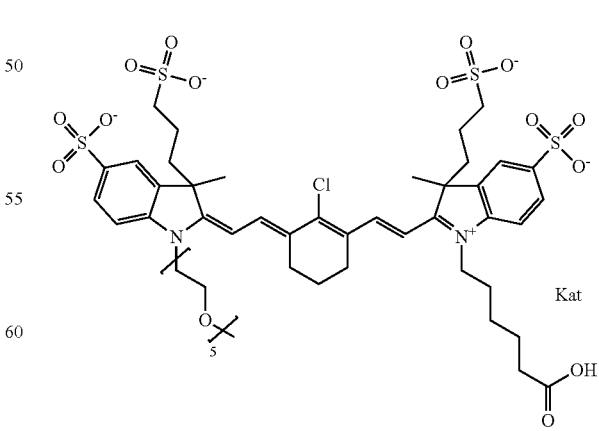

One non-limiting example is a substituted polymethine form of 755 Compound 6, shown below:

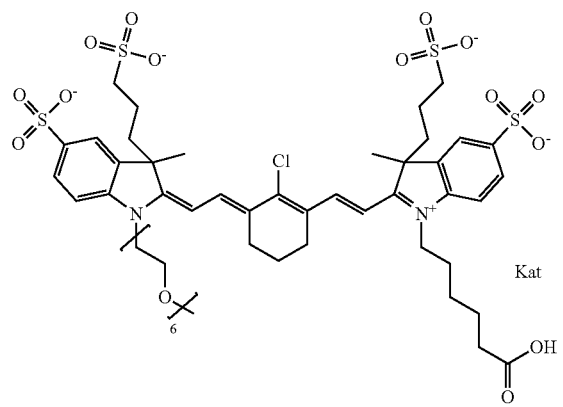

One non-limiting example is a substituted polymethine form of 755 having an ethylene glycol, diethylene glycol, or polyethylene glycol as described for general formula X, such as the compound shown below:

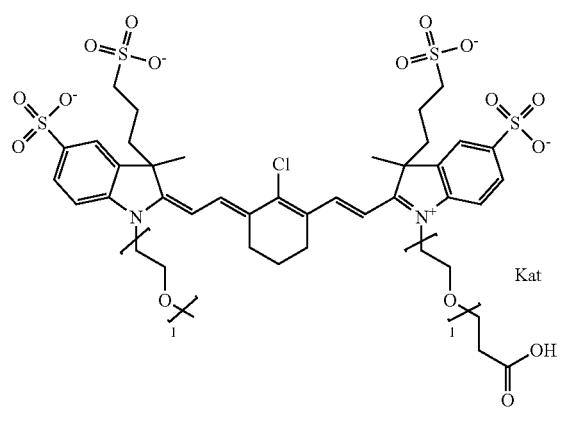

In embodiments, the degree of sulfonation is varied to, e.g., vary the compound's degree of hydrophlilicity or hydrophobicity. One non-limiting example is a monosulfonate form of 755 Compound 1, shown below, but it is understood that the single sulfo group can be at any of the described positions:

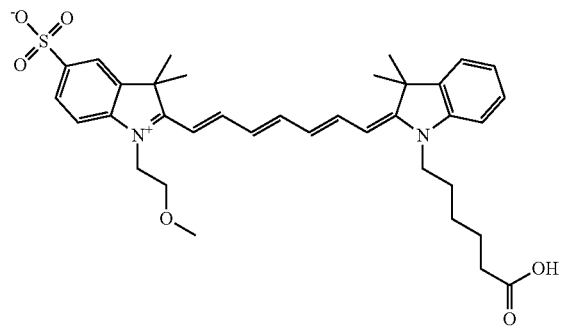

One non-limiting example is a disulfonate form of 755 Compound 1, shown below, but it is understood that the each of the two sulfo groups can be at any of the described positions:

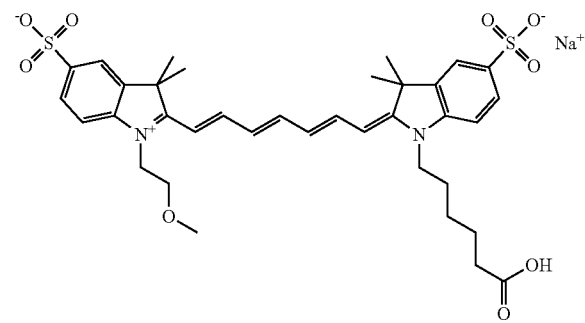

One non-limiting example is a trisulfonate form of 755 Compound 1, shown below, but it is understood that the each of the three sulfo groups can be at any of the described positions:

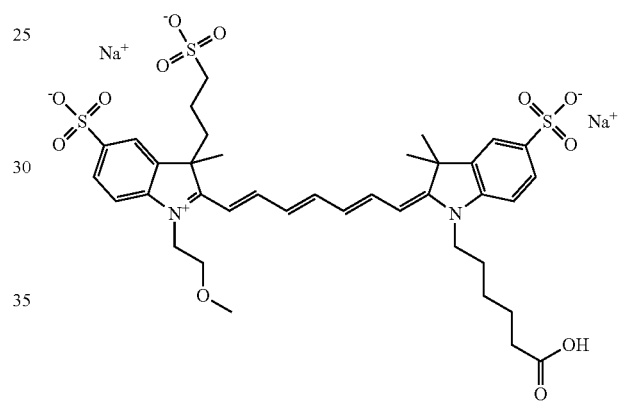

One non-limiting example is a tetrasulfonate form of 755 Compound 1, shown below, but it is understood that the each of the four sulfo groups can be at any of the described positions:

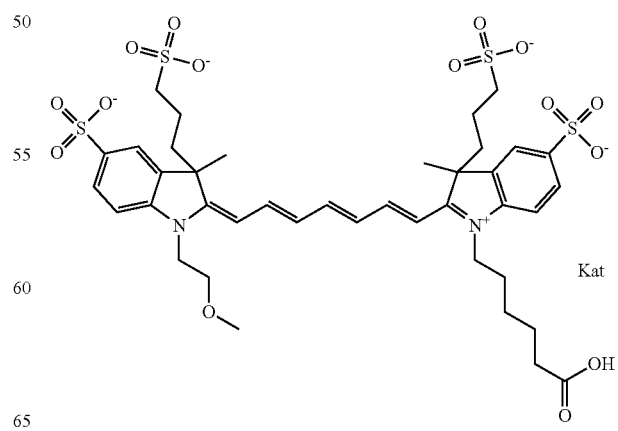

In one embodiment, the compound has general formula XIII

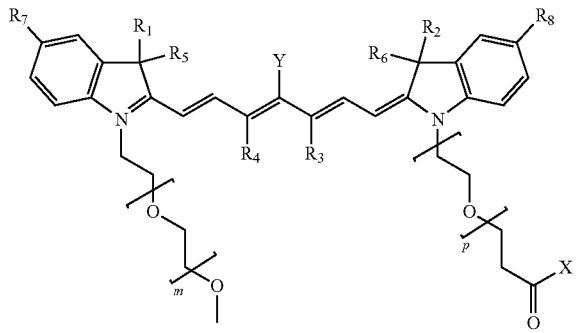

where each of $R^1$, $R^2$, $R^5$, and $R^6$ is the same or different and is independently selected from an aliphatic, heteroaliphatic, or sulfoalkyl group; each of $R^7$ and $R^8$ is the same or different and is independently selected from H or $SO_3$; X is selected from —OH, —SH, —NH$_2$, —NH—NH$_2$, —F, —Cl, —Br, —I, —NHS (hydroxysuccinimidyl/sulfosuccinimidyl), —O-TFP (2,3,5,6-tetrafluorophenoxy), —O—STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—I, or —NR-L-NH—CO—CH$_2$—Br where R is —H or an aliphatic or heteroaliphatic group, and L is selected from the group consisting of a divalent linear, crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; p is an integer from 1 to 6 inclusive; each of R3 and R4 is the same or different and is independently hydrogen, an aliphatic group, or a heteroaliphatic group, or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy- or phenylmercapto function.

In one embodiment, the compound of general formula XIII wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

The disclosed compounds are used and are useful as chromophores and/or fluorophores. For example, they can be used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

The present compounds, containing the disclosed functionality or functionalities, may be synthesized using methods known in the art, e.g., as described as follows with all references expressly incorporated by reference herein in their entirety.

The core indocyanine structure without additional functionalities, along with its synthesis, was described by König in U.S. Pat. No. 1,524,791 and BP 434875, and included 3-, 5-, and 7-membered polymethine chains.

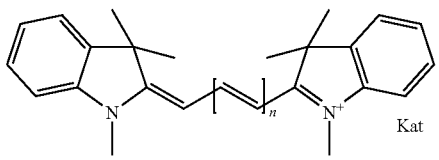

Synthesis of numerous modifications of the core indocyanine structure have been described. Such modifications provided various functionalities, e.g., synthesis of N-isothiocyanato-alkyl- and aromatic-carboxyalkyl-functionalized indocyanines were described in U.S. Pat. Nos. 5,627,027; 6,048,982; 4,981,977; U.S. Publication No. 2006/0199949; Southwick, Anal. Chem. 67 (1995)1742-48).

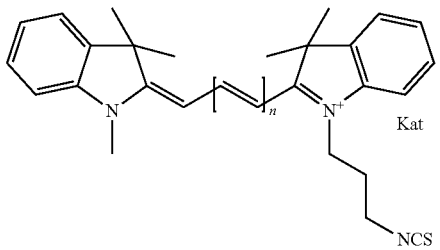

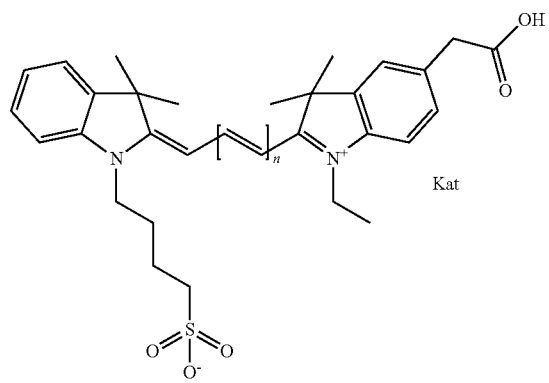

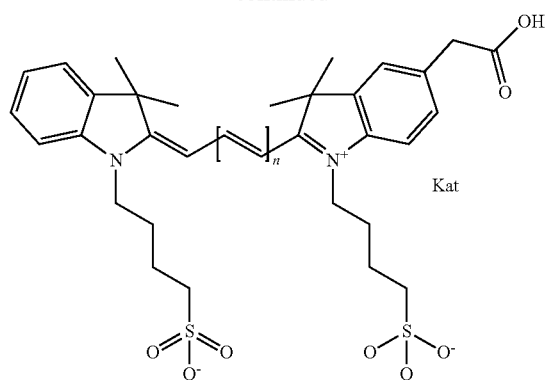
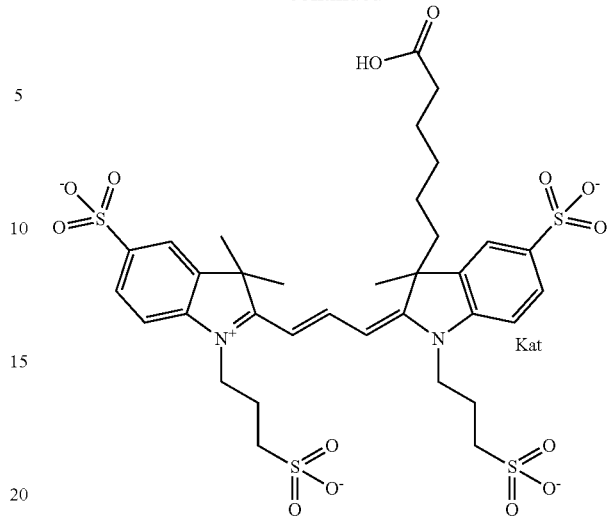
Synthesis of indocyanines with one or two N-carboxyalkyl functionalities were described in U.S. Pat. Nos. 5,268,486; 5,486,616; 5,569,587; 5,569,766; JP 03217837.
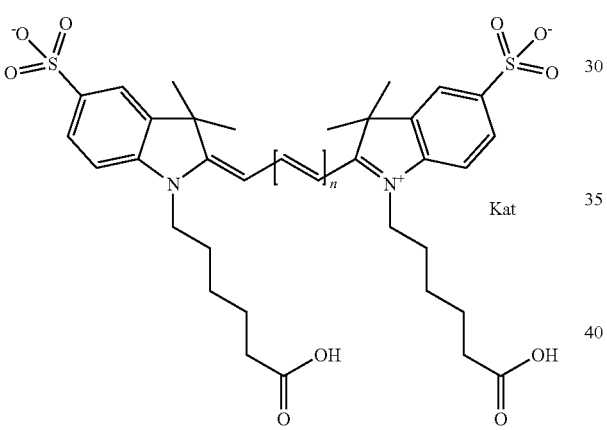
Synthesis of indocyanines containing C-carboxyalkyl groups were described in JP 05-313304; U.S. Publication Nos. 2006/0099638, 2006/0004188; 2002/0077487; 2002/0064794; U.S. Pat. Nos. 6,977,305 and 6,974,873.
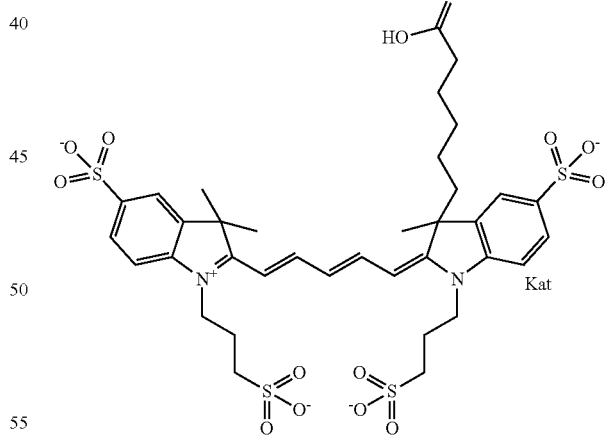
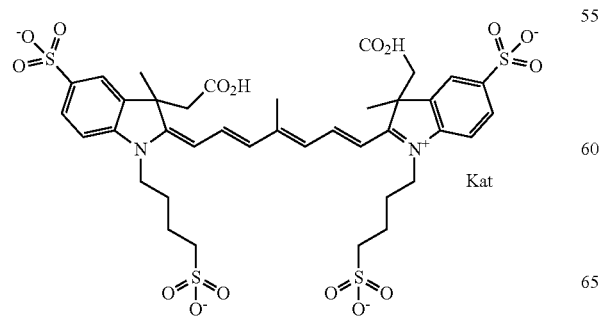
Synthesis of indocyanines with N- and C-sulfoalkyl groups were described in JP 05-313304; WO 2005/044923; U.S. Publication No. 2007/0203343.

89    90
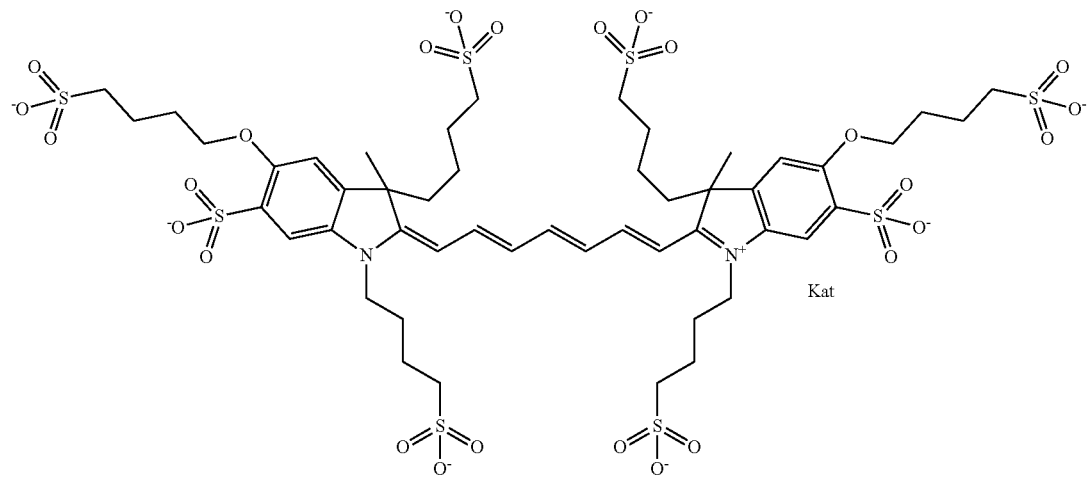
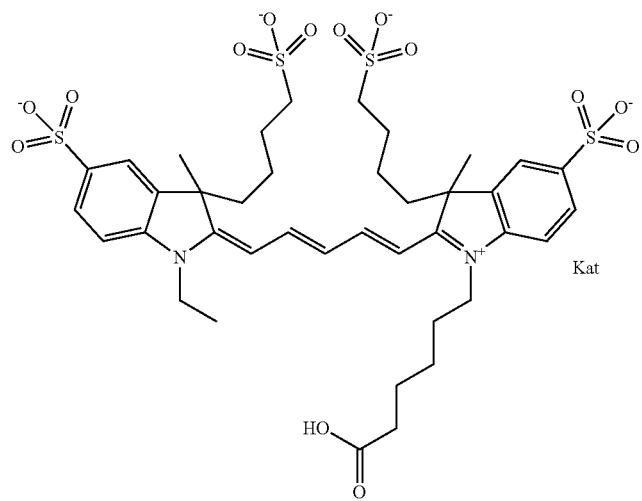
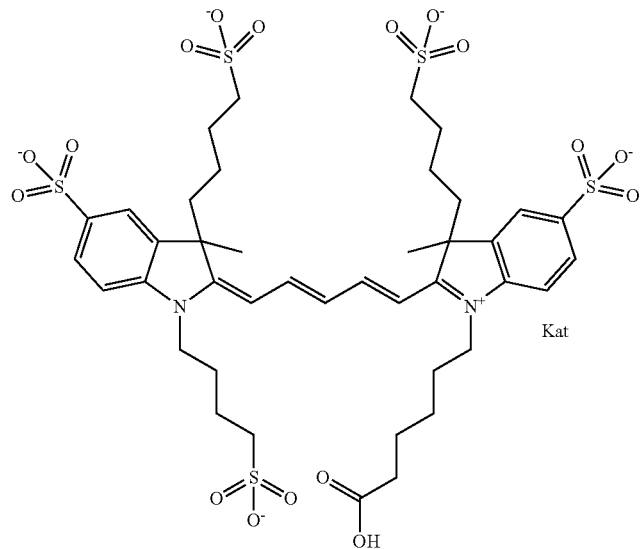

-continued
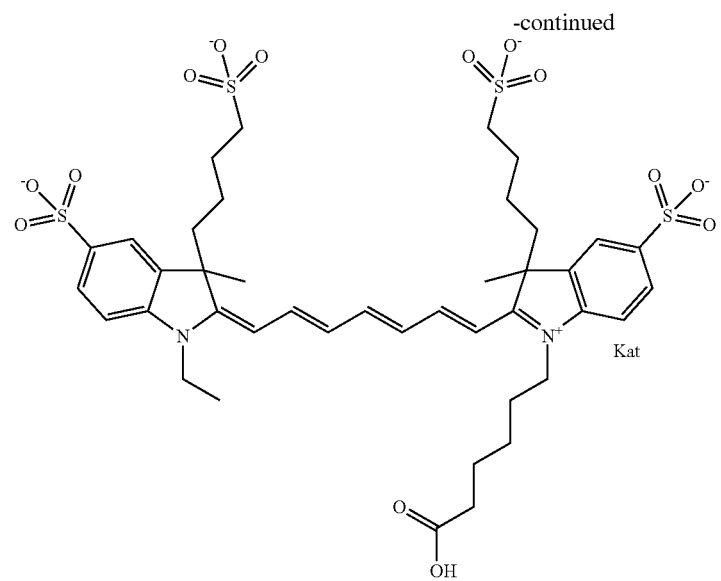
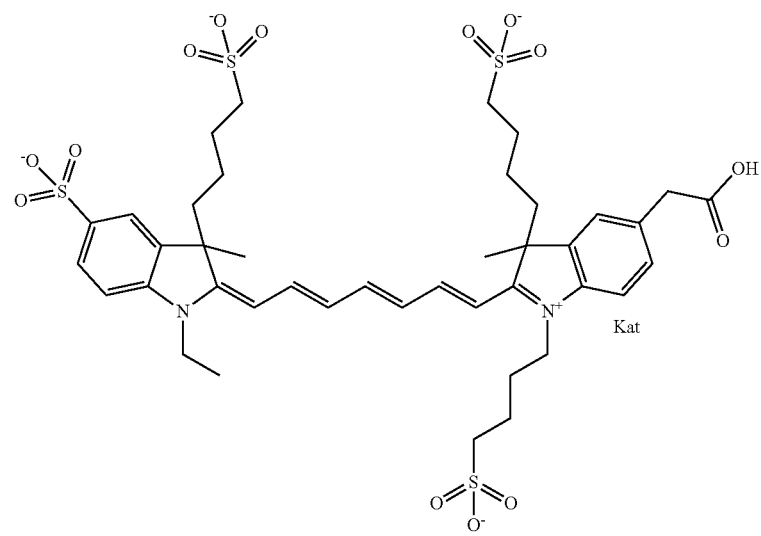

Synthesis of indocyanines with mixed C-carboxyalkyl and C-sulfoalkyl were described in EP 1792949 and U.S. Pat. No. 7,745,640.

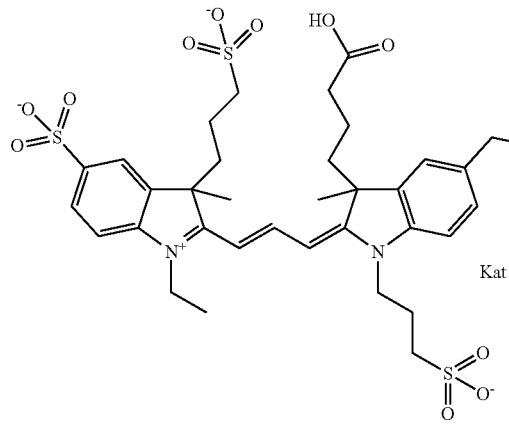

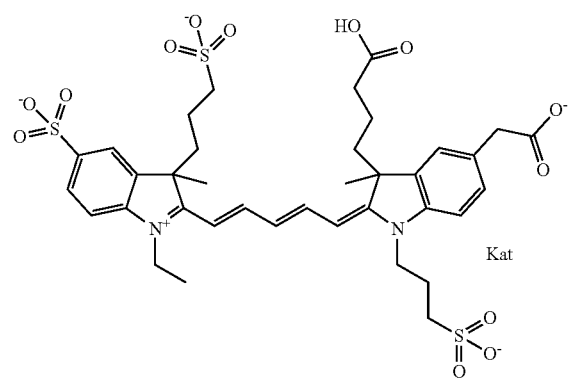

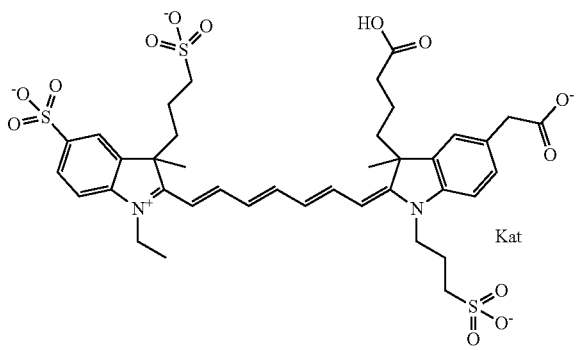

Synthesis of indocyanaines having a PEG-containing, N-carboxyalkyl spacer were described in U.S. Pat. No. 6,939,532.

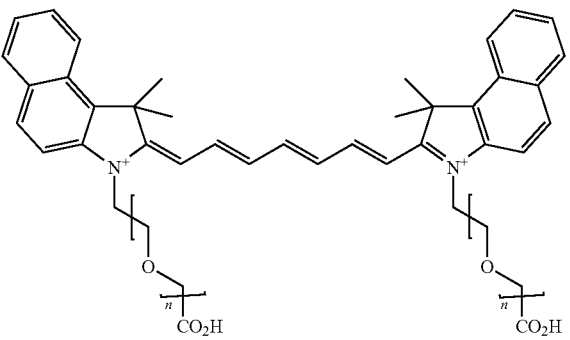

Functionalization of the N-carboxyalkyl with an amino-functionalized PEG-alkyl chain, and N- and C-substituted PEG-alkyl chains, were described in U.S. Publication No. 2009/0305410.

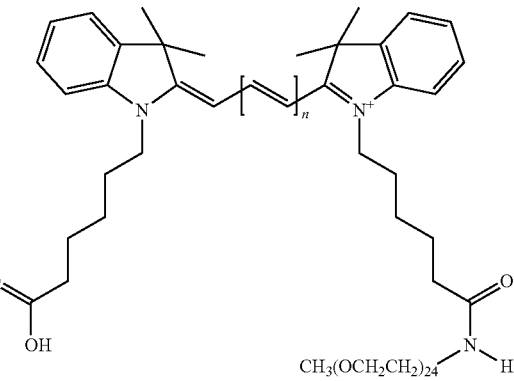

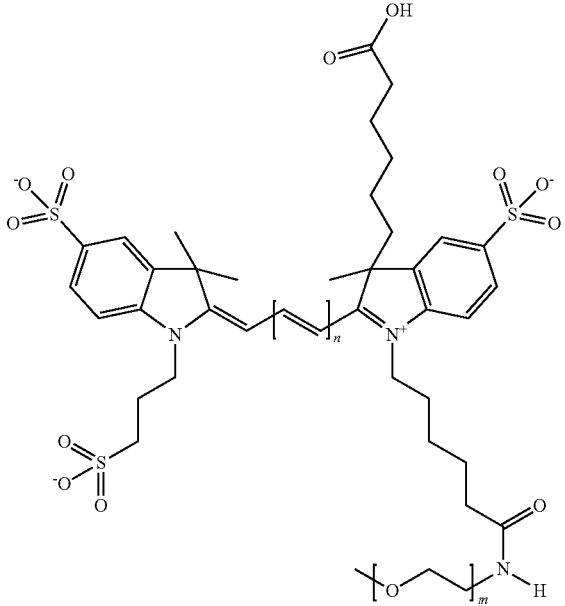

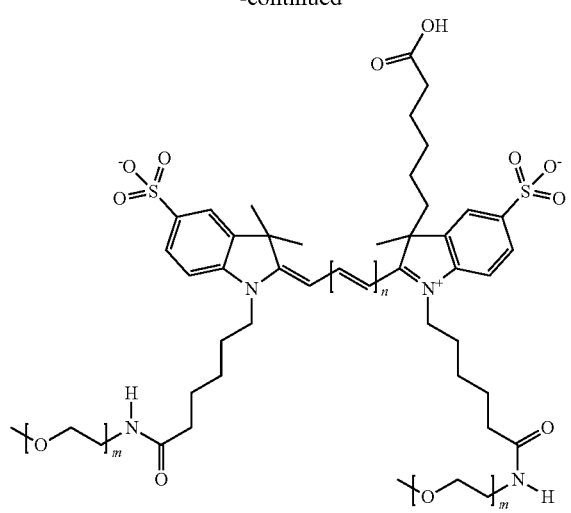
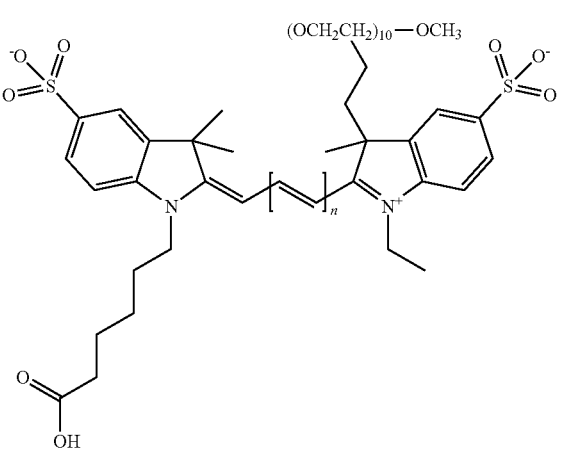
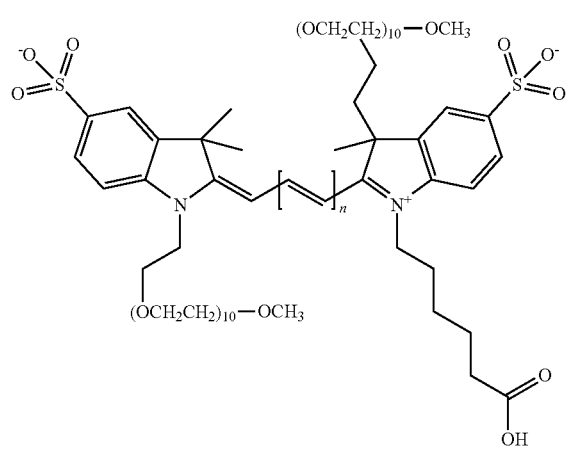
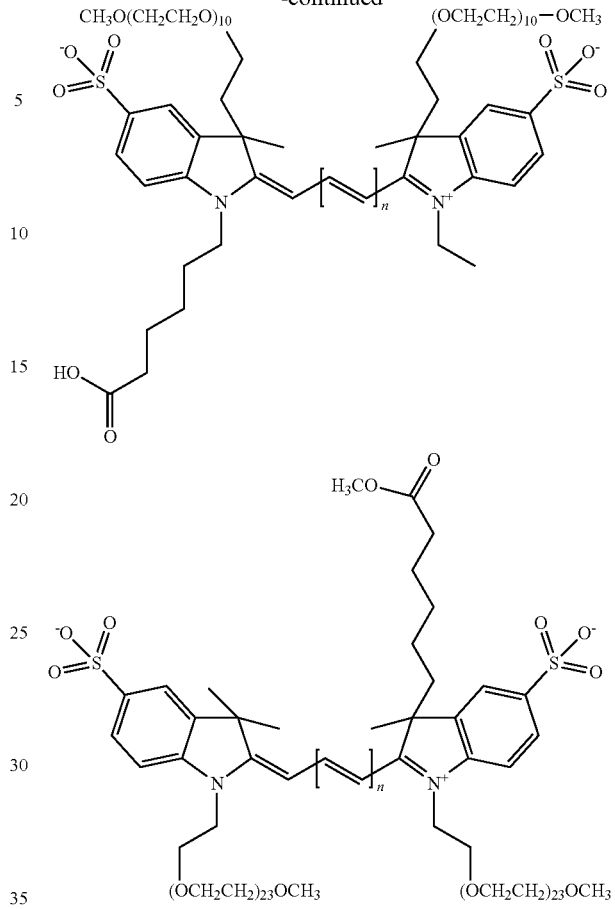

Synthesis of various polymethine bridge substitutions, and other functionalizations of indocyanines, were described in Strekowski, Heterocyclic Polymethine Dyes: Synthesis, Properties and Applications, (2008) Springer-Verlag, Berlin Heidelberg; Gragg, "Synthesis of Near-Infrared Heptamethine Cyanine Dyes" (2010). Chemistry Theses. Paper 28. http://digitalarchive.gsu.edu/chemistry_theses/28; Patonay et al. (2004) Noncovalent Labeling of Biomolecules with Red and Near-Infrared Dyes. Molecules 9 (2004) 40-49; and U.S. Pat. No. 7,172,907. Examples 1-18 also disclose synthesis reactions for the compounds.

In one embodiment, the compound is synthesized by a condensation reaction, known to one skilled in the art, of the two differently substituted indole heterocycles separated by a (poly)methine linker or bridge, e.g., C1, C3, or C5. Other synthesis methods are possible. As only one example, one of the indole heterocycles is first reacted with the C1, C3, or C5 linker. The 1:1 condensation product is isolated, and then condensed with the second indole heterocycle to result in the cyanine compound. The sequence of reacting the indole heterocycles is irrelevant. Thus, a plurality of differently functionalized, strongly hydrophilic, diastereomeric compounds that differ in total charge and specificity/reactivity of the active groups used for their immobilization, were prepared.

Conjugates of the compounds were prepared by covalently coupling the compounds to a biomolecule using the functional substituent on the N-position of the indole ring. This functional substituent was activated by routine protein chemistry reaction methods known to one skilled in the art.

The activated compound may be converted to, e.g., and without limitation, a N-hydroxysuccinimide (NHS)-ester, an acid fluoride, a tetrafluorophenyl (TFP)- or sulfotetrafluorophenyl (STP)-ester, an iodoacetyl group, a maleimide, a hydrazide, a sulfonyl chloride, or a phenylazide. Methods for preparing such compounds are known to one skilled in the art. In one embodiment, the activated substituent was then reacted with an amino group on the biomolecule under conditions to conjugate the desired biomolecule.

In one embodiment, a non-activated carboxyl group on the N-position of the indole in the compound was coupled to an amine using a carbodimide.

In one embodiment, a N-hydroxysuccinimidyl ester (X=—NHS) of a compound was formed as follows: 20 µmol dye with X=OH (carboxyalkyl group), 8 mg (40 µmol) dicyclohexylcarbodiimide, and 5 mg (40 µmol) N-hydroxysuccinimide were dissolved in 2 ml DMF and 100 µl water. Six µl (40 µmol) triethylamine was added. The reaction mixture was stirred at room temperature (about 20° C. to about 22° C.) for 24 hours and then filtered. The solvent was removed and the residue was washed with diethylether. The reaction proceeded quantitatively.

In one embodiment, a maleimide (X=—NH—$CH_2CH_2$-maleimide) of a compound is formed as follows: 20 µmol dye with X=—NHS (N-hydroxysuccinimid-ester) was dissolved in 2 ml DMF and 100 µl water and mixed with 7.6 mg (30 µmol) 2-maleimidoethylamine-trifluoracetate and 5 µl (30 µmol) N-ethyldiisopropyl-amine. The reaction mixture is stirred for 3 h at room temperature (about 20° C. to about 22° C.). The solvent was evaporated under reduced pressure. The residue is washed with diethylether and acetone and dried in vacuum. The reaction proceeds quantitatively.

In one embodiment, a iodoacetamide (X=—NH—$CH_2CH_2$—NH—CO—$CH_2$—I) of a compound is formed as follows: 20 µmol dye with X=—NHS (N-hydroxysuccinimid-ester) was dissolved in 2 ml DMF and 100 µl water, followed by addition of 40 mg (300 µmol) ethylendiamin-dihydrochloride and 26 µl (150 µmol) N-ethyldiisopropyl-amine. The reaction mixture is stirred for 3 h at room temperature (about 20° C. to about 22° C.). The solvent is then evaporated under reduced pressure, the residue was dissolved in methanol, and the ethylendiamindihydrochlorid was removed by filtration. The methanol is evaporated under reduced pressure. The residue is dissolved in 2 ml dry DMF, followed by addition of 7 mg (25 µmol) N-succinimidyl iodoacetate and 4 µl (25 µmol) N-ethyldiisopropylamine. The reaction mixture is stirred for 3 h at room temperature. The solvent was evaporated under reduced pressure and the residue was purified by reverse phase HPLC.

Coupling between the compound and the biomolecule may be performed as follows. The compound was reacted with the biomolecule in an organic or aqueous solution at pH between pH 5-pH 12 inclusive. The compound need not be dissolved in an organic solvent, such as dimethyl formamide (DMF) or dimethyl sulfoxide (DMSO) prior to adding the biomolecule. In one embodiment, coupling reaction may be performed in a 100% aqueous solution. In one embodiment, the coupling reaction occurs at room temperature (about 20° C. to about 22° C.).

To form a composition (dye), at least one biocompatible excipient was added to the compound(s), as known to one of ordinary skill in the art. Excipients include, but are not limited to, buffers, solubility enhancing agents, stabilizing agents, etc.

In one embodiment, a kit for performing an assay method comprises a disclosed compound, and instructions for performing the method using the compound.

The disclosed activated compounds (i.e., the compound modified with a reactive group) are useful to label macromolecules (e.g., antibodies, streptavidin, etc) using methods known to one skilled in the art, e.g., Hermanson, Bioconjugate Techniques, 2nd Ed., London, Elsevier Inc. 2008. The reaction was carried out for 1-2 h at room temperature (about 20° C. to about 22° C.), and then desalted by dialyzing against several changes of phosphate buffered saline (pH 7.2) or purified by gel filtration to remove the unreacted fluorescent dye. The resulting compound-biomolecule conjugate was used to detect, e.g., specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibited fluorescent properties. In this embodiment, they were used in optical methods including fluorescence optical qualitative and quantitative determination methods. Examples of such methods include, but are not limited to, microscopy, immunoassays, hybridization methods, chromatographic and electrophoretic methods, fluorescence resonance energy transfer (FRET) systems, high throughput screenings, analysis of receptor-ligand interactions on a microarray, etc.

Compounds of any of the embodiments were used as dyes for optical labelling of organic or inorganic biomolecules, also referred to as recognition units. Recognition units are molecules having specificity and/or affinity for a specific group of molecules. Examples of recognition units include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences that bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormones), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. The ionic interactions between these recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates were used in optical, including fluorescence optical, qualitative and/or quantitative determination methods to diagnose properties of cells (molecular imaging), in biosensors (point of care measurements), for investigation of the genome, and in miniaturizing technologies. Microscopy, cytometry, cell sorting, fluorescence correlation spectroscopy (FCS), ultra high throughput screening (uHTS), multicolor fluorescence in situ hybridisation (mc-FISH), FRET-systems and microarrays (DNA- and protein-chips) are exemplary application fields. As known to one skilled in the art, a microarray is a grid-like arrangement where more than two different molecules are immobilized in a known predefined region on at least one surface, and is useful to evaluate receptor ligand interactions. As known to one skilled in the art, a receptor is a naturally occurring or synthetic molecule that exhibits an affinity to a given ligand. Receptors can be used in a pure form or bound to another specie. Receptors can be coupled covalently or noncovalently to a binding partner either directly or indirectly (e.g., through a coupling mediator). Receptor examples include, but are not limited to, agonists and antagonists for cell membrane receptors, toxins and other poisons, viral epitopes, hormones (e.g., opiates, steroids), hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. As known to one skilled in the art, a ligand is a molecule that is recognized by a certain receptor. Ligand examples include, but are not limited to, agonists and antagonists for cell membrane receptors, toxins and other poisons, viral epitopes, hormones (e.g., opiates, steroids), hormone receptors, peptides, enzymes, enzyme substrates, drugs acting as cofactors, lectins, sugars, oligonucleotides, nucleic acids, oligosaccharides, proteins, antibodies, etc.

BRIEF DESCRIPTION OF THE DRAWINGS

FIG. 70 shows signal-to-background ratio of a functional assay with some inventive compounds and commercial dyes.

FIG. 71 shows signal-to-background ratio of a functional assay with some inventive compounds and commercial dyes.

FIG. 76 shows signal-to-background ratio of a functional assay with some inventive compounds and commercial dyes.

FIG. 77 shows signal-to-background ratio of a functional assay with some inventive compounds and commercial dyes.

FIG. 80 shows signal-to-background ratio of a functional assay with some inventive compounds and commercial dyes.

FIG. 81 shows signal-to-background ratio of a functional assay with some inventive compounds and commercial dyes.

Figure 1:
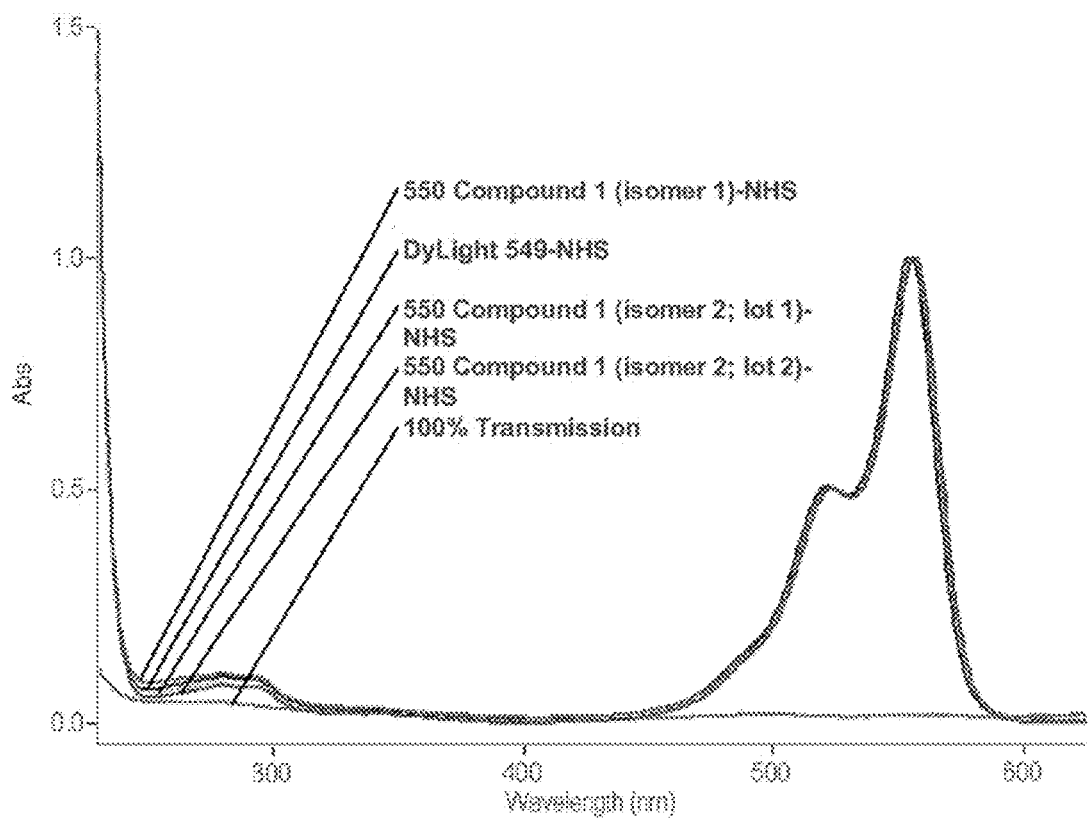
FIG. 1 shows absorption profiles of some inventive compounds and commercial dyes.

The following examples disclose properties of the inventive compounds relative to commercially available fluorescent dyes. Signal-to-noise ratio (S/N) is the ratio between the desired signal and the mean of the blank, accounting for the standard deviation of the signal and the blank. Signal-to-background ratio (S/B) is the ratio between the desired average signal and the average blank.

550 Compound 1 was compatible with gel filtration and Pierce Dye Removal Resin (PDRR) demonstrating its versatility and ease of purification. 550 Compound 1 exhibited similar labeling efficiency of goat anti-mouse (GAM), goat anti-rabbit (GAR), and streptavidin (SA), compared to DyLight 549-NHS ester. The performance of 550 Compound 1 conjugates (GAM, GAR, SA) in the functional assay was similar to DyLight 549 conjugates (GAM, GAR, SA) in terms of signal-to-noise. In an immunofluorescence experiment using 550 Compound 1 conjugates (GAM, GAR), 550 Compound 1 exhibited at least similar performance to DyLight 549 conjugates (GAM, GAR), and in some cases superior performance (e.g., mouse α-tubulin binding assay).

650 Compound 1 was compatible with gel filtration and PDRR demonstrating its versatility and ease of purification. 650 Compound 1 exhibited similar labeling efficiency of goat anti-mouse (GAM), goat anti-rabbit (GAR), and streptavidin (SA), compared to DyLight 649-NHS ester. The performance of 650 Compound 1 conjugates (GAM, GAR, SA) in the functional assay was superior to DyLight 649 conjugates (GAM, GAR, SA) in terms of signal to noise. In an immunofluorescence experiment using 650 Compound 1 conjugates (GAM, GAR), 650 Compound 1 exhibited at least similar performance to DyLight 649 conjugates (GAM, GAR), and in some cases superior performance (e.g., mouse α-tubulin binding assay).

650 Compound 2, having a (poly)ethylene glycol, was compatible with gel filtration and PDRR, demonstrating its versatility and ease of purification. 650 Compound 2 exhibited similar labeling efficiency of GAM, GAR, and SA, compared to DyLight 649-NHS ester. The performance of 650 Compound 2 conjugates (GAM, GAR, SA) in the functional assay was superior to DyLight 649 conjugates (GAM, GAR, SA) in terms of signal to noise. In an immunofluorescence experiment using 650 Compound 2 conjugates (GAM, GAR), 650 Compound 2 exhibited at least similar performance to DyLight 649 conjugates (GAM, GAR), and in some cases superior performance (e.g., mouse α-tubulin binding assay).

650 Compound 3, having a (poly)ethylene glycol, was compatible with gel filtration and PDRR, demonstrating its versatility and ease of purification. 650 Compound 3 exhibited similar labeling efficiency of GAM, GAR, and SA, compared to DyLight 649-NHS ester. The performance of 650 Compound 3 conjugates (GAM, GAR, SA) in the functional assay was superior to DyLight 649 conjugates (GAM, GAR, SA) in terms of signal to noise. In an immunofluorescence experiment using 650 Compound 3 conjugates (GAM, GAR), 650 Compound 3 exhibited at least similar performance to DyLight 649 conjugates (GAM, GAR), and in some cases superior performance (e.g., mouse α-tubulin binding assay).

755 Compound 1 (isomer 1)-NHS and 755 Compound 1 (isomer 2)-NHS were compatible with gel filtration, dialysis, and PDRR, demonstrating their versatility and ease of purification. 755 Compound 1 (isomer 1)-NHS showed slightly lower labeling efficiency of GAM and GAR compared to DyLight 750-NHS, however 755 Compound 1 (isomer 1)-NHS showed higher labeling efficiency of GAM and GAR compared to 755 Compound 1 (isomer 2)-NHS. Both 755 Compound 1 (isomer 1)-NHS and 755 Compound 1 (isomer 2)-NHS showed similar labeling efficiency of SA compared to DyLight 750-NHS.

The inventive compounds thus provide at least equivalent, and in some cases, superior performance as dyes when compared to commercially available known dyes such as DyLight® series dyes 549, 649, and 750 series dyes, and Alexa Fluor 555 and 647 dyes.

The following non-limiting examples further describe the compounds, methods, compositions, uses, and embodiments.

EXAMPLE 1

Synthesis of 4-methyl-5-oxohexane sulfonic Acid Used to Synthesize Example 2 Compound 2,3-dimethyl-3-(3-sulfopropyl)-3H-indole-5-sulfonic Acid di-potassium Salt and Example 8 Compound 1,2-dimethyl-1-(3-sulfopropyl)-1H-benzo[e]indole-6,8-disulfonic Acid tripotassium Salt

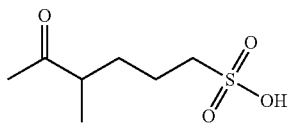

Sodium hydride (2.1 g, 80 wt %=69 mmol) was slurried in 10 ml of dry THF. The suspension was cooled to 0° C. and a solution of ethyl-2-methylacetoacetate (10 g, 69 mmol) in 10 ml of dry THF was added dropwise. The solution was stirred at room temperature for 1 h. A solution of 1,3-propanesultone (8.42 g, 69 mmol) in 10 ml of dry THF was added dropwise. Once the addition was complete, the solution was stirred for 2 h at 40° C. The solution was evaporated to dryness. The residue was dissolved in 100 ml water. The aqueous solution was extracted twice with ethylacetate, then 100 ml concentrated HCl was added and the solution was refluxed for 2 h. The solvent was evaporated in vacuum. The residue was purified by column chromatography (silica, methanol/dichloromethane) to give 4-methyl-5-oxohexane sulfonic acid. Yield 10 g; MS (ESI-): 193.2 [M]$^-$

EXAMPLE 2

Synthesis of 2,3-dimethyl-3-(3-sulfopropyl)-3H-indole-5-sulfonic Acid di-potassium Salt Used to Synthesize Example 3 Compound 1-(2-methoxy-ethyl)-2,3-dimethyl-5-sulfo-3-(3-sulfo-propyl)-3H-indolium and Example 4 Compound 1-[2-(2-methoxy-ethoxy)-ethyl]-2,3-dimethyl-5-sulfo-3-(3-sulfo-propyl)-3H-indolium and Example 5 Compound 1-{2-[2-(2-methoxy-ethoxy)-ethoxy]-ethyl}-2,3-dimethyl-5-sulfo-3-(3-sulfo-propyl)-3H-indolium and Example 6 Compound 1-(5-carboxy-pentyl)-2,3-dimethyl-5-sulfo-3-(3-sulfopropyl)-3H-indolium

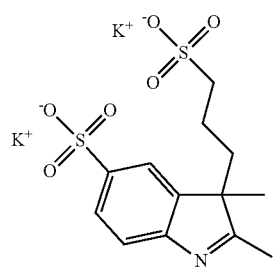

Ten g (51 mmol) 4-hydrazino-benzene sulfonic acid and 9.85 g (51 mmol) 4-methyl-5-oxohexane sulfonic acid were dissolved in 50 ml acetic acid. The solution was heated at 140° C. for 4 h. The solvent was evaporated in vacuum. The oily residue was dissolved in 20 ml methanol, then 50 ml of a saturated solution of KOH in 2-propanol was added to yield a yellow precipitate. The solid was filtered off and dried in vacuum. Yield 11 g, MS (ESI-): 172.5 [M]$^{2-}$

EXAMPLE 3

Synthesis of 1-(2-methoxy-ethyl)-2,3-dimethyl-5-sulfo-3-(3-sulfo-propyl)-3H-indolium Used to Synthesize 550, 650, 755 Compound 1

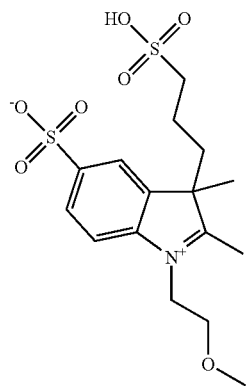

A mixture of 5 g (12.4 mmol) 2,3-dimethyl-3-(3-sulfopropyl)-3H-indole-5-sulfonic acid dipotassium salt and 5.89 g (25.6 mmol) 2-methoxyethyl-p-toluene sulfonate was heated under argon for 24 h. The residue was purified by column chromatography (reversed phase silica, methanol/water, TFA). Yield 2.3 g, MS (ESI-): 404.1 [M-H]⁻

EXAMPLE 4

Synthesis of 1-[2-(2-methoxy-ethoxy)-ethyl]-2,3-dimethyl-5-sulfo-3-(3-sulfo-propyl)-3H-indolium Used to Synthesize 550, 650, 755 Compound 2

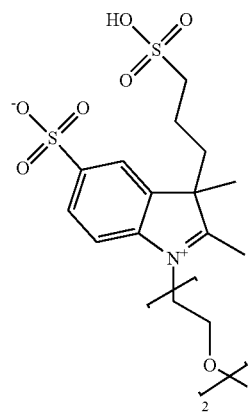

A mixture of 5 g (12.4 mmol) 2,3-dimethyl-3-(3-sulfopropyl)-3H-indole-5-sulfonic acid dipotassium salt and 7.1 g (25.6 mmol) [2-(2-methoxyethoxy)ethoxy]-p-toluene sulfonate was heated under argon for 24 h. The residue was purified by column chromatography (reversed phase silica, methanol/water, TFA). Yield 2.0 g. MS (ESI-): 448.2 [M-H]⁻

EXAMPLE 5

Synthesis of 1-{2-[2-(2-methoxy-ethoxy)-ethoxy]-ethyl}-2,3-dimethyl-5-sulfo-3-(3-sulfo-propyl)-3H-indolium Used to Synthesize 550, 650, 755 Compound 3

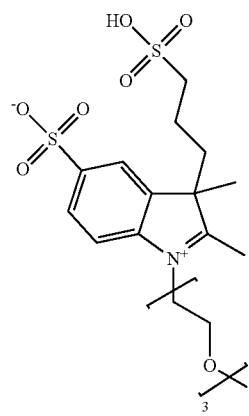

A mixture of 5 g (12.8 mmol) 2,3-dimethyl-3-(3-sulfopropyl)-3H-indole-5-sulfonic acid dipotassium salt and 8.14 g (25.6 mmol) [2-[2-(2-methoxyethoxy)ethoxy]ethoxy]p-toluene sulfonate was heated under argon for 24 h. The residue was purified by column chromatography (reversed phase silica, methanol/water, TFA). Yield 1.9 g, MS (ESI-): 492.1 [M-H]⁻

EXAMPLE 6

Synthesis of 1-(5-carboxypentyl)-2,3-dimethyl-5-sulfo-3-(3-sulfopropyl)-3H-indolium Used to Synthesize Example 7 Compound 1-(5-carboxypentyl)-3-methyl-2-((E)-2-phenylamino-vinyl)-5-sulfo-3-(3-sulfo-propyl)-3H-indolium and Example 8 Compound 1-(5-carboxypentyl)-3-methyl-2-((I E,3E)-4-phenylamino-buta-1,3-dienyl)-5-sulfo-3-(3-sulfopropyl)-3H-indolium and Example 9 Compound 1-(5-carboxypentyl)-3-methyl-2-((I E,3E,5E)-6-phenylamino-hexa-1,3,5-trienyl)-5-sulfo-3-(3-sulfopropyl)-3H-indolium

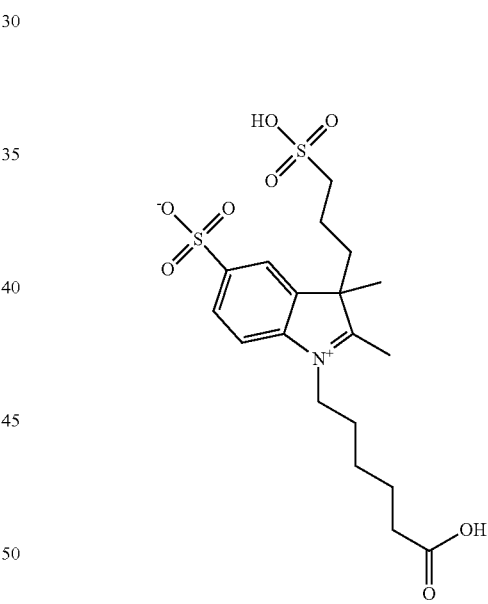

Both 5 g (15.7 mmol) 6-hydrazino-naphthalene-1,3-disulfonic acid and 4.93 g (25 mmol) 4-methyl-5-oxohexane sulfonic acid were dissolved in 50 ml acetic acid. The solution was heated at 140° C. for 4 h. The solvent was evaporated in a vacuum. The oily residue was dissolved in 20 ml methanol, then 50 ml of a saturated solution of KOH in 2-propanol was added to yield a yellow precipitate. The solid was filtered off and dried in vacuum. Yield 4.1 g, MS (ESI-): 158.2 [M]³⁻

EXAMPLE 7

Synthesis of 1-(5-carboxypentyl)-3-methyl-2-((E)-2-phenylamino-vinyl)-5-sulfo-3-(3-sulfo-propyl)-3H-indolium Used to Synthesize 550 Compounds

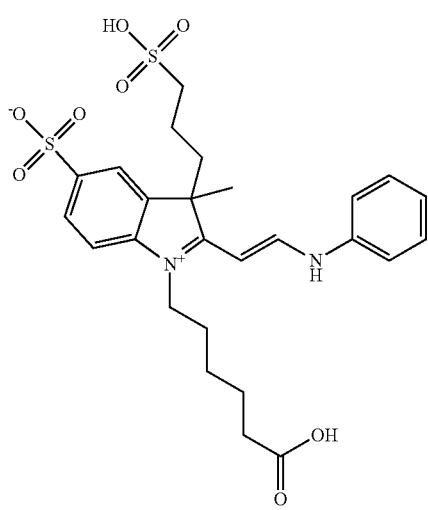

A combination of 0.92 g (2 mmol) 1-(5-carboxypentyl)-2,3-dimethyl-5-sulfo-3-(3-sulfopropyl)-3H-indolium and 0.43 g (2.2 mmol) N,N'-diphenylformamidine was dissolved in 20 ml methanol and stirred for 4 h under reflux. The solvent was removed under vacuum. The residue was washed carefully with ethyl acetate. A dark yellow solid was obtained which was processed without further purification. MS (ESI-): 563.1 [M-H]⁻

EXAMPLE 8

Synthesis of 1-(5-carboxypentyl)-3-methyl-2-((1E,3E)-4-phenylamino-buta-1,3-dienyl)-5-sulfo-3-(3-sulfopropyl)-3H-indolium Used to Synthesize 650 Compounds

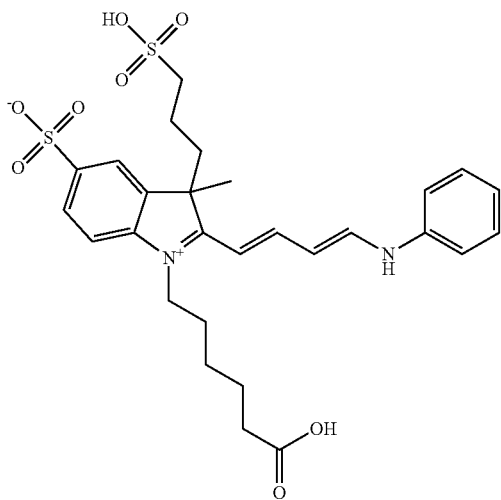

A combination of 0.92 g (2 mmol) 1-(5-carboxypentyl)-2,3-dimethyl-5-sulfo-3-(3-sulfopropyl)-3H-indolium and 0.57 g (2.2 mmol) malonaldehyde-bisphenylimine-hydrochloride were dissolved in 10 ml acetic acid and 10 ml acetic anhydride and stirred for 4 h at 120° C. The solvent was removed under vacuum. The residue was washed carefully with ethyl acetate. A dark brown solid was obtained which was processed without further purification. MS (ESI-): 589.2 [M-H]⁻

EXAMPLE 9

Synthesis of 1-(5-carboxypentyl)-3-methyl-2-((1E,3E,5E)-6-phenylamino-hexa-1,3,5-trienyl)-5-sulfo-3-(3-sulfopropyl)-3H-indolium Used to Synthesize 755 Compounds

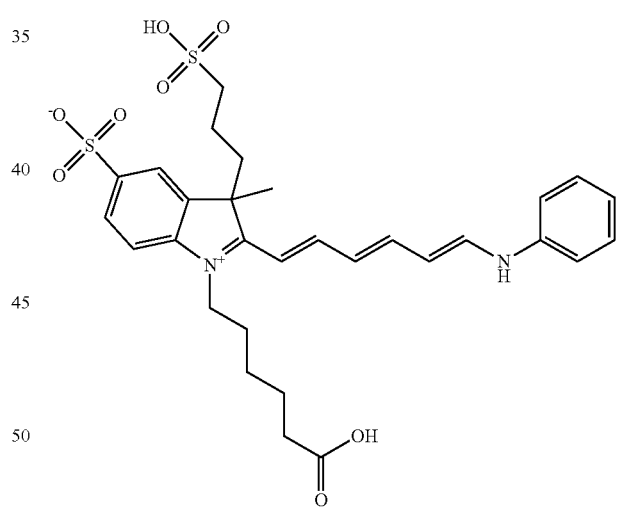

A combination of 0.92 g (2 mmol) 1-(5-carboxypentyl)-2,3-dimethyl-5-sulfo-3-(3-sulfopropyl)-3H-indolium and 0.63 g (2.2 mmol) glutacondianil-hydrochloride were dissolved in 10 ml acetic acid and 10 ml acetic anhydride and stirred for 4 h at 120° C. The solvent was removed under vacuum. The residue was washed carefully with ethyl acetate. A dark solid was obtained which was processed without further purification. MS (ESI-): 615.2 [M-H]⁻

EXAMPLE 10

Synthesis of 550 Compound 1

2-{(E)-3-[1-(5-carboxypentyl)-3-methyl-5-sulfo-3-(3-sulfopropyl)-1,3-dihydro-indol-(2E)-ylidene]-propenyl}-1-(2-methoxy-ethyl)-3-methyl-5-sulfo-3-(3-sulfo-propyl)-3H-indolium tri sodium Salt

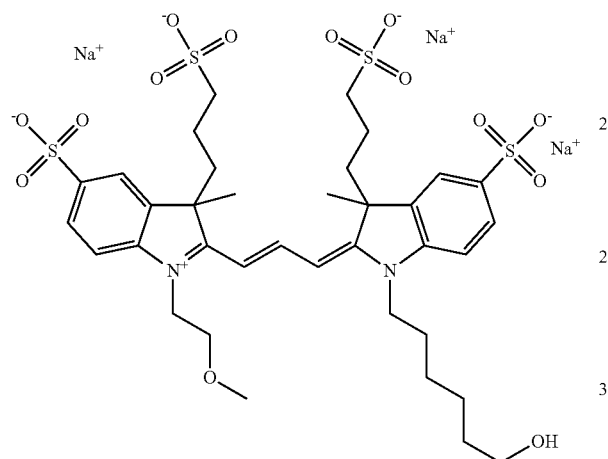

Five hundred sixty-four mg (1 mmol) 1-(5-carboxypentyl)-3-methyl-2-((E)-2-phenylamino-vinyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1), followed by 200 mg sodium acetate. The solution was stirred under reflux for 15 min. After cooling to room temperature, 20 ml diethylether was added. The resulting precipitate (mixture of the diastereomers 550 Compound 1 (isomer 1) and 550 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (550 Compound 1 (isomer 1)). The diastereomer that eluted second from the column was termed diastereomer 2 (550 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 550 Compound 1 (isomer 1) and 550 Compound 1 (isomer 2)) were dried in high vacuum.

550 Compound 1 (isomer 1):

yield: 12%

UV-vis (PBS): $\lambda max=557$ nm, $\lambda em=572$ nm

MS (ESI-) [M/z]: 291.2 $[M]^{3-}$; 448.3 $[M+Na]^{2-}$

550 Compound 1 (isomer 2):

yield: 23%

UV-vis (PBS): $\lambda max=557$ nm, $\lambda em=572$ nm

MS (ESI-) [M/z]: 291.1 $[M]^{3-}$; 448.2 $[M+Na]^{2-}$

EXAMPLE 11

Synthesis of 550 Compound 2

2-{(E)-3-[1-(5-carboxypentyl)-3-methyl-5-sulfo-3-(3-sulfopropyl)-1,3-dihydro-indol-(2E)-ylidene]-propenyl}-1-[2-(2-methoxy-ethoxy)-ethyl]-3-methyl-5-sulfo-3-(3-sulfo-propyl)-3H-indolium tri sodium Salt

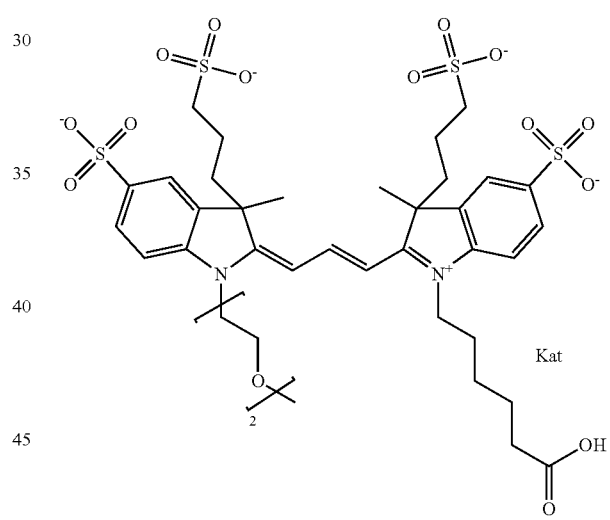

Both 1 mmol 1-(5-carboxypentyl)-3-methyl-2-((E)-2-phenylamino-vinyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 Compound 2 and 550-2 Compound 2) was extracted by suction, washed with ether and dried.

The residue was purified by column chromatography (RP-18, acetonitrile/water and concentrated HCl), thereby separating the diastereomers from each other, as described in Example 10.

EXAMPLE 12

Synthesis of 550 Compound 3

2-{(E)-3-[1-(5-carboxypentyl)-3-methyl-5-sulfo-3-(3-sulfopropyl)-1,3-dihydro-indol-(2E)-ylidene]-propenyl}-1-{2-[2-(2-methoxy-ethoxy)-ethoxy]-ethyl}-3-methyl-5-sulfo-3-(3-sulfo-propyl)-3H-indolium tri sodium salt

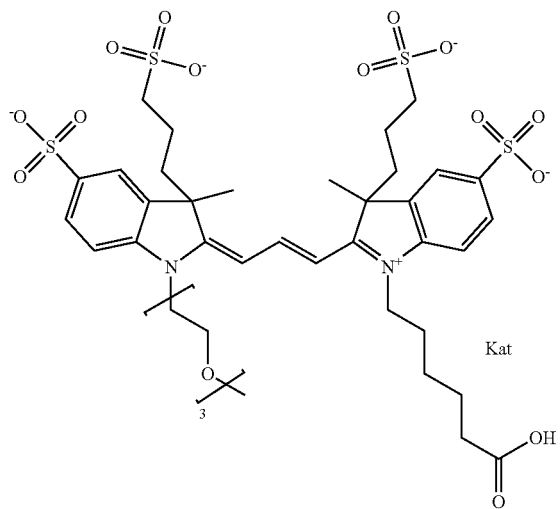

One mmol 1-(5-carboxypentyl)-3-methyl-2-((E)-2-phenylamino-vinyl)-5-sulfo-3-(3-sulfopropyl)-3H-indolium and 1 mmol 1-{2-[2-(2-methoxy-ethoxy)-ethoxy]-ethyl}-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 550-1 Compound 2 and 550-2 Compound 2) was extracted by suction, washed with ether and dried.

The residue was purified by column chromatography (RP-18, acetonitrile/water and concentrated HCl), thereby separating the diastereomers from each other, as described in Example 10.

EXAMPLE 13

650 Compound 1

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-(2-methoxy-ethyl)-3-methyl-5-sulfo-3-(3-sulfopropyl)-3H-indolium tri sodium salt

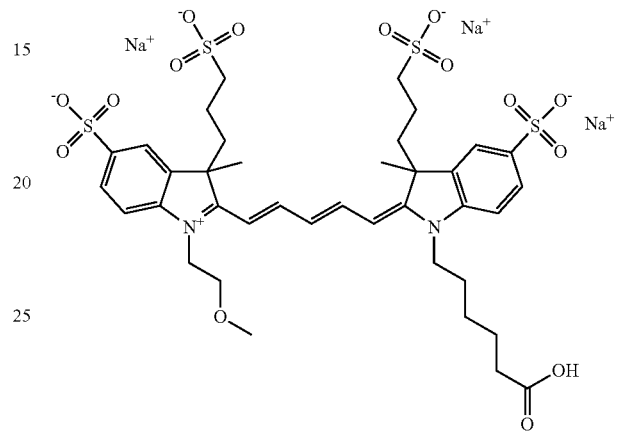

Both 90 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 650 Compound 1 (isomer 1) and 650 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (650 Compound 1 (isomer 1)). The diastereomer that eluted second from the column was termed diastereomer 2 (650 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 650 Compound 1 (isomer 1) and 650 Compound 1 (isomer 2)) were dried in high vacuum.

650 Compound 1 (isomer 1):

yield: 11%

UV-vis (PBS): $\lambda$max=654 nm, $\lambda$em=672 nm

MS (ESI-) [M/z]: 299.7 $[M]^{3-}$; 461.0 $[M+Na]^{2-}$

650 Compound 1 (isomer 2):

yield: 24%

UV-vis (PBS): $\lambda$max=654 nm, $\lambda$em=672 nm

MS (ESI-) [M/z]: 299.6 $[M]^{3-}$; 461.1 $[M+Na]^{2-}$

EXAMPLE 14

650 Compound 2

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-[2-(2-methoxy-ethoxy)-ethyl]-3-methyl-5-sulfo-3-(3-sulfopropyl)-3H-indolium tri sodium Salt

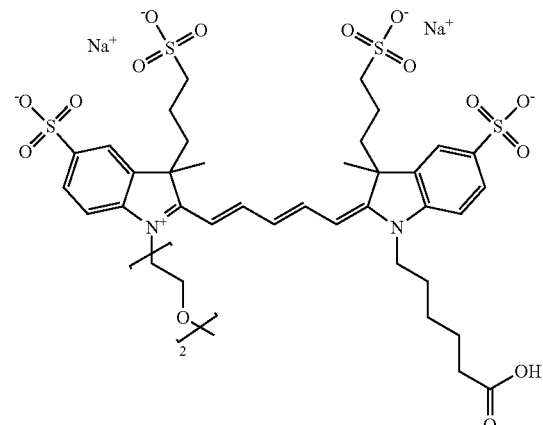

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 449 mg (1 mmol) 1-[2-(2-methoxy-ethoxy)-ethyl]-2,3-dimethyl-5-sulfo-3-(3-sulfopropyl)-3H-indolium were dissolved in 20 ml of acetic acid/acetic anhydride (1/1) followed by the addition of 200 mg of sodium acetate. The synthesis and work-up were carried out according to Example 13.

650-1 Compound 2:
yield: 11%
UV-vis (PBS): λmax=654 nm, λem=672 nm
MS (ESI-) [M/z]: 314.4 [M]$^{3-}$; 483.0 [M+Na]$^{2-}$
650-2 Compound 2:
yield: 16%
UV-vis (PBS): λmax=654 nm, λem=672 nm
MS (ESI-) [M/z]: 314.5 [M]$^{3-}$; 483.1 [M+Na]$^{2-}$

EXAMPLE 15

650 Compound 3

Synthesis of 2-{(1E,3E)-5-[1-(5-carboxypentyl)-3-methyl-5-sulfo-3-(3-sulfopropyl)-1,3-dihydro-indol-(2E)-ylidene]-penta-1,3-dienyl}-1-{2-[2-(2-methoxy-ethoxy)-ethoxy]-ethyl}-3-methyl-5-sulfo-3-(3-sulfopropyl)-3H-indolium tri sodium Salt—650 Compound 3

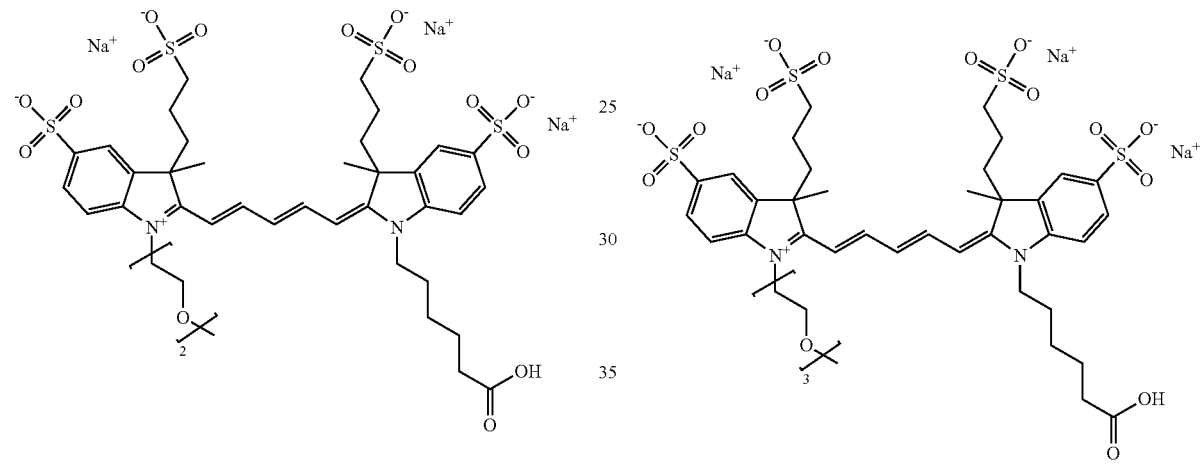

Both 564 mg (1 mmol) 1-(5-carboxypentyl)-3-methyl-2-((1E,3E)-4-phenylamino-buta-1,3-dienyl)-5-sulfo-3-(3-sulfopropyl)-3H-indolium and 493 mg (1 mmol) 1-{2-[2-(2-methoxy-ethoxy)-ethoxy]-ethyl}-2,3-dimethyl-5-sulfo-3-(3-sulfopropyl)-3H-indolium were dissolved in 20 ml acetic acid/acetic anhydride (1/1) followed by the addition of 200 mg sodium acetate. The synthesis and work-up were carried out according to Example 13.

650-1 Compound 3:
yield: 10%
UV-vis (PBS): λmax=654 nm, λem=672 nm
MS (ESI-) [M/z]: 329.2 [M]$^{3-}$; 505.0 [M+Na]$^{2-}$
650-2 Compound 3:
yield: 23%
UV-vis (PBS): λmax=654 nm, λem=672 nm
MS (ESI-) [M/z]: 329.1 [M]$^{3-}$; 505.1 [M+Na]$^{2-}$

EXAMPLE 16

Synthesis of 755 Compound 1

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethyl)-3-methyl-5-sulfo-3-(3-sulfopropyl)-3H-indolium tri sodium Salt

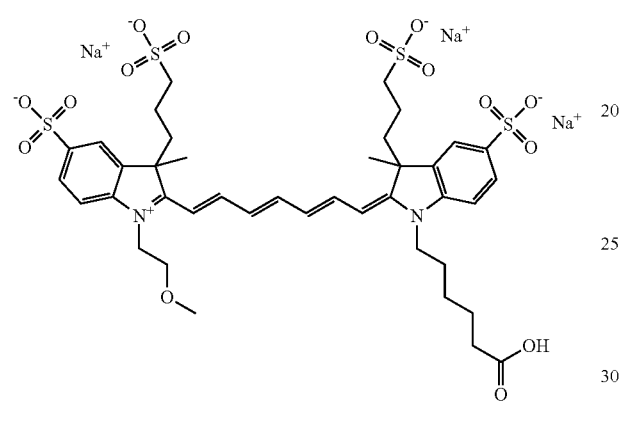

Six hundred and sixteen mg (1 mmol) 1-(5-Carboxypentyl)-3-methyl-2-((1E,3E,5E)-6-phenylamino-hexa-1,3,5-trienyl)-5-sulfo-3-(3-sulfopropyl)-3H-indolium and 404 mg (1 mmol) 1-(2-methoxy-ethyl)-2,3-dimethyl-5-sulfo-3-(3-sulfopropyl)-3H-indolium were dissolved in 20 ml of acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 755 Compound 1 (isomer 1) and 755 Compound 1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (755 Compound 1 (isomer 1)). The diastereomer that eluted second from the column was termed diastereomer 2 (755 Compound 1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 755 Compound 1 (isomer 1) and 755 Compound 1 (isomer 2)) were dried in high vacuum.

755 Compound 1 (Isomer 1):

yield: 8%

UV-vis (PBS): $\lambda$max=752 nm; $\lambda$em=778 nm

MS (ESI-) [M/z]: 308.4 $[M]^{3-}$; 474.2 $[M+Na]^{2-}$

755 Compound 1 (Isomer 2):

yield: 16%

UV-vis (PBS): $\lambda$max=752 nm; $\lambda$em=778 nm

MS (ESI-) [M/z]: 308.4 $[M]^{3-}$; 474.2 $[M+Na]^{2-}$.

EXAMPLE 17

Synthesis of 755 Compound 2

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-(2-methoxy-ethoxy)-3-methyl-5-sulfo-3-(3-sulfopropyl)-3H-indolium

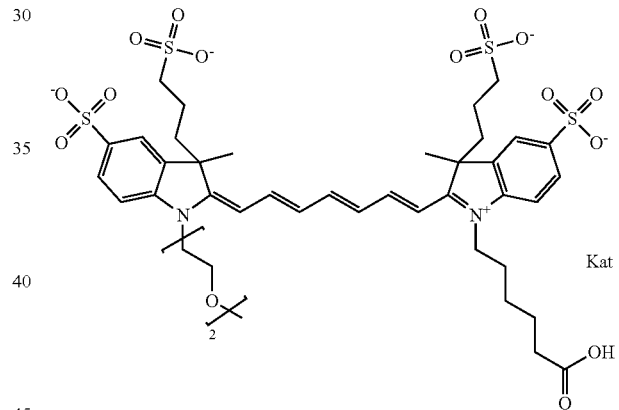

Both 1 mmol 1-(5-Carboxypentyl)-3-methyl-2-((1E,3E,5E)-6-phenylamino-hexa-1,3,5-trienyl)-5-sulfo-3-(3-sulfopropyl)-3H-indolium and 1 mmol 1-[2-(2-methoxy-ethoxy)-ethyl]-2,3-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 2 (isomer 1) and 755 compound 2 (isomer 2)) was extracted by suction, washed with ether and dried. The residue is purified by column chromatography (RP-18, acetonitrile/water and concentrated HCl), thereby separating the diastereomers from each other, as described in Example 16.

EXAMPLE 18

Synthesis of 755 Compound 3

2-{(1E,3E,5E)-7-[1-(5-Carboxypentyl)-3-methyl-5-sulfo-3-(3-sulfopropyl)-1,3-dihydro-indol-(2E)-ylidene]-hepta-1,3,5-trienyl}-1-{2-[2-(2-methoxy-ethoxy)-ethoxy]-ethyl}-3-methyl-5-sulfo-3-(3-sulfopropyl)-3H-indolium

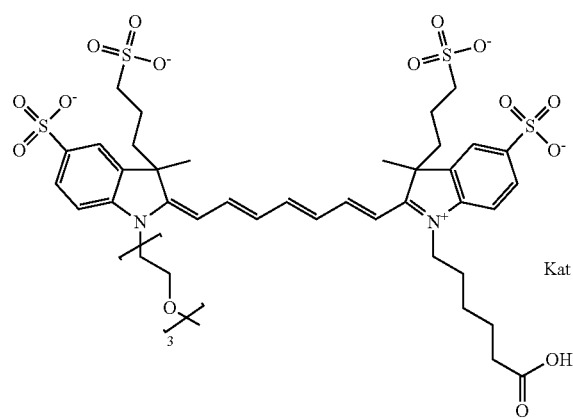

Both 1 mmol 1-(5-carboxypentyl)-3-methyl-2-((1E,3E,5E)-6-phenylamino-hexa-1,3,5-trienyl)-5-sulfo-3-(3-sulfopropyl)-3H-indolium and 1 mmol 1-{2-[2-(2-methoxy-ethoxy)-ethoxy]-ethyl}-dimethyl-5-sulfo-3-(3-sulfo-propyl)-3H-indolium were dissolved in 20 ml acetic acid/acetic anhydride (1/1) followed by the addition of 200 mg sodium acetate. The solution was stirred under reflux for 15 min. After cooling to room temperature, 20 ml diethylether was added. The resulting precipitate (mixture of the diastereomers 755 compound 3 (isomer 1) and 755 compound 3 (isomer 2)) was extracted by suction, washed with ether and dried. The residue is purified by column chromatography (RP-18, acetonitrile/water and concentrated HCl), thereby separating the diastereomers from each other, as described in Example 16.

EXAMPLE 19

Properties of 550 Compounds 1-NHS were compared with commercially available dyes, as shown below.

|  | DyLight 549-NHS | 550 Compound 1-NHS | Alexa Fluor 555-NHS |
|---|---|---|---|
| MW (g/mol) | 982 | 1040.06 | ~1250 |
| Ex (nm) | 562 | 557 | 555 |
| Em (nm) | 576 | 572 | 565 |
| ε (M-1cm-1) | 150,000 | 142,000 (theoretical 150,000) | 150,000 |

The quantum yield (QY) was determined at an excitation wavelength of 500 nm and 530 nm for inventive and commercial compounds, as shown below

|  | QY excitation at 500 nm | QY excitation at 530 nm |
|---|---|---|
| DyLight 549-NHS isomer 2 | 0.110 | 0.093 |
| 550 Compound 1(isomer 1)-NHS | 0.105 | 0.098 |
| 550 Compound 1 (isomer 2)-NHS | 0.096 | 0.090 |

QY measurements were performed in PBS using a Hamamatsu C9920 PL Absolute Quantum Yield Measurement System. The maximum absorbance at a 1 cm pathlength was set to 0.08. The lower values for the excitation at 530 nm was due to the rising emission which was not included in the counting because it was too close to the excitation light.

Absorption profiles for inventive and commercial compounds were determined, and shown in FIG. 1 as indicated, and where DyLight 549-NHS (blue), 550 Compound 1 (isomer 1)-NHS (pink), 550 Compound 1 (isomer 2; lot 1)-NHS (yellow), and 550 Compound 1 (isomer 2; lot 2)-NHS (red) all showed very similar profiles (baseline (100% transmission)).

Figure 2:
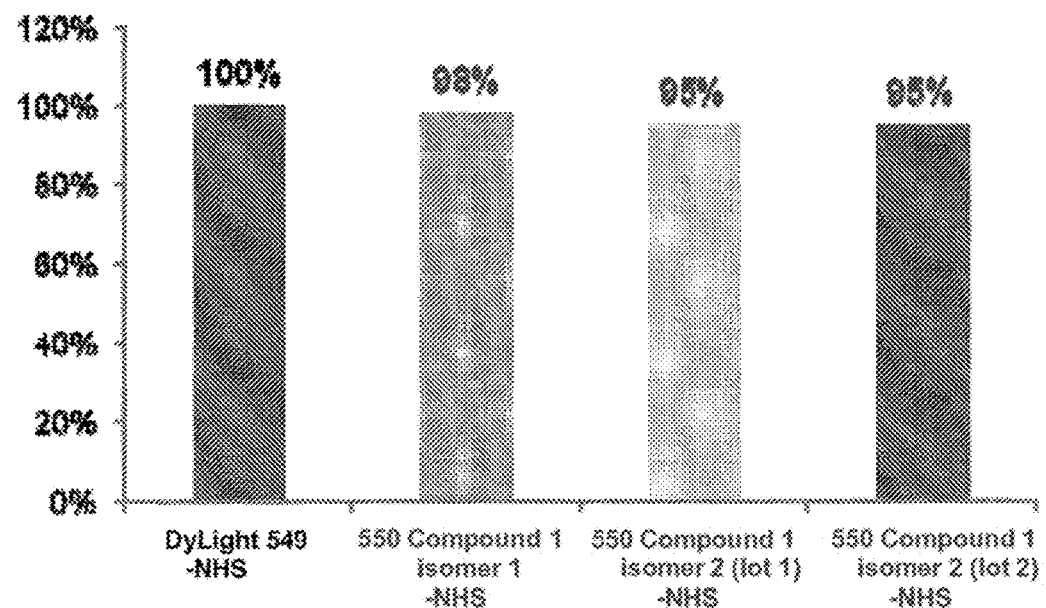
FIG. 2 shows fluorescence intensity of some inventive compounds and commercial dyes.

Fluorescence intensity was measured for DyLight 549 (blue), 550 Compound 1 (isomer 1)-NHS (pink), 550 Compound 1 (isomer 2; lot 1)-NHS (yellow), and 550 Compound 1 (isomer 2; lot 2)-NHS (red) with an excitation and emission of 562 nm/576 nm and compared as a percent fluorescence intensity based on DyLight 549-NHS (FIG. 2). The fluorescence intensities for the inventive compounds were similar to each other and within 5% of DyLight 549-NHS.

EXAMPLE 20

Inventive and commercial compounds, each as the NHS ester, were conjugated to goat anti-mouse (GAM), goat anti-rabbit (GAR) antibodies, and streptavidin (SA). GAM, GAR, and SA, at 10 mg/ml in phosphate buffered saline (PBS), were dialyzed against 50 mM borate buffer, pH 8.5. The compounds were reconstituted in dimethylformamide (DMF) at 10 mg/ml and combined at 2×, 4×, 5×, 7.5×, or 10× molar excess with GAM, GAR, or SA for 2 h at room temperature to label the antibodies or SA.

The labeled compounds, also termed dyes or labels, were subjected to PDDR to remove the unlabeled (free) compound; 100 μl of the packed resin was used per mg of protein purified. The purified antibody-labeled dyes were then diluted 1:50 in PBS and scanned for absorbance from 700 nm to 230 nm to determine the protein concentration, and to determine the mole dye to mole protein ratio. Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the Typhoon 9400 Imager to verify removal of the unconjugated compound. Labeling efficiency was compared, with results showing degree of labeling below.

|  | DyLight 549 | 550 Compound 1 (isomer 1) | 550 Compound 1 (isomer 2; lot 1) | 550 Compound 1 (isomer 2; lot 2) |
|---|---|---|---|---|
| GAM-2X | 1.5 | 1.7 | 1.7 | 1.4 |
| GAM-5X | 2.9 | 3.6 | 3.7 | 3.6 |
| GAM-10X | 5.3 | 6.5 | 6.5 | 6.4 |

|  | DyLight 549 | 550 Compound 1 (isomer 1) | 550 Compound 1 (isomer 2; lot1) | 550 Compound 1 (isomer 2; lot2) |
|---|---|---|---|---|
| GAR-2X | 1.3 | 1.6 | 1.7 | 1.4 |
| GAR-5X | 2.6 | 3.3 | 3.7 | 3.5 |
| GAR-10X | 5.6 | 6.4 | 6.7 | 6.5 |

At 2× molar excess, there was no significant difference in degree of labeling (dye to protein ratio (D/P)) for GAM and GAR between DyLight 549 and the inventive compounds. At 5× and 10× molar excess, the inventive compounds showed better incorporation of dye and higher D/P for GAM and GAR than DyLight 549 conjugates.

|  | DyLight 549 | 550 Compound 1 (isomer 1) | 550 Compound 1 (isomer 2; lot#1) | 550 Compound 1 (isomer 2; lot#2) |
|---|---|---|---|---|
| SA-2X (PBS) | 1.2 | 1.4 | 1.5 | 1.3 |
| SA-4X (PBS) | 2.3 | 2.7 | 2.9 | 2.6 |
| SA-2X (BB) | 1.2 | 1.3 | 1.4 | 1.3 |
| SA-4X (BB) | 2.3 | 2.5 | 2.7 | 2.5 |

At 2× and 4× molar excess for SA conjugates (PBS and borate buffers (BB)), there was no significant difference in D/P for the inventive compounds and DyLight 549.

Figure 3:
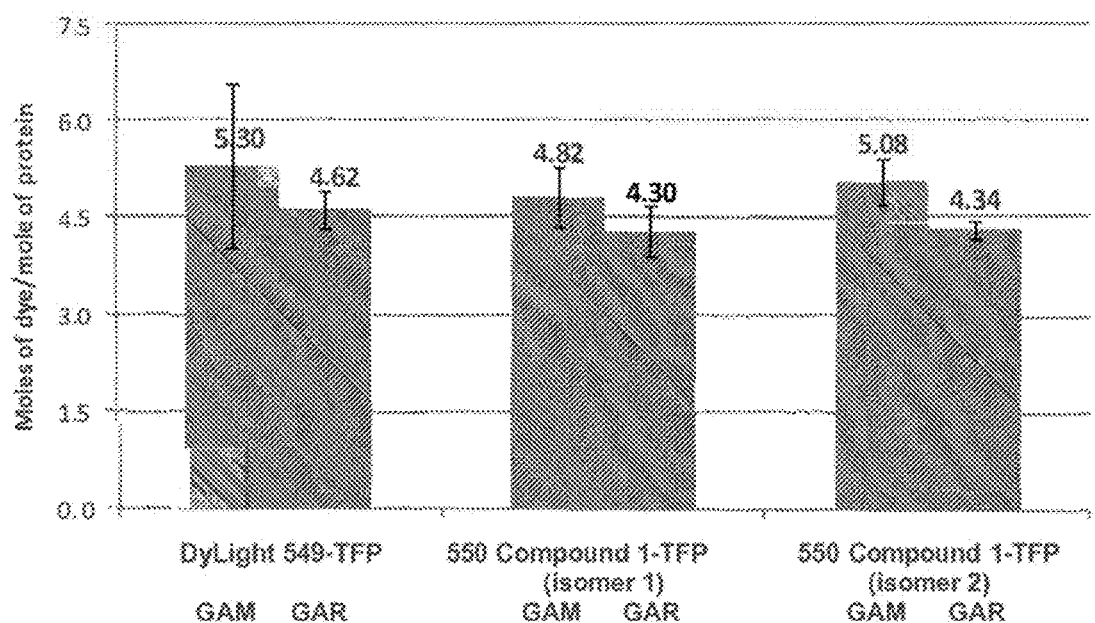
FIG. 3 shows labeling efficiency of some inventive compounds and commercial dyes with one conjugate.

Labeling efficiencies for inventive and commercial compounds, each having a TFP ester, were also compared. Dyes were reconstituted in DMF at 10 mg/ml; antibodies were buffer-exchanged (dialyzed) from PBS pH 7.4 into 50 mM borate buffer pH 8.5. Antibodies were labeled with 5× molar excess of dye and the conjugates were purified with PDRR. The conjugates were scanned and moles of dye per mole of protein (D/P) was calculated. As shown in FIG. 3, 550 Compound 1 (isomer 1)-TFP and 550 Compound 1 (isomer 2)-TFP labeled GAM (blue, first bar in each set) and GAR (red, second bar in each set) with similar efficiency as DyLight 549-TFP. Both 550 Compound 1 (isomer 1)-TFP and 550 Compound 1 (isomer 2)-TFP were similar in labeling efficiency as DyLight 549-TFP.

EXAMPLE 21

Performance of the dye-GAM conjugates, dye-GAR conjugates, and dye-SA conjugates was evaluated in a functional assay. Wells of a 96 white opaque plate were coated with target proteins mouse IgG immunoglobulin, rabbit IgG immunoglobulin, or biotinylated bovine serum albumin (BBSA). One hundred µl mouse or rabbit IgG or BBSA at a concentration of 10 µg/ml was applied to the corresponding wells in columns 1 and 2. The target proteins were serially diluted 1:1 from the wells in columns 2 to 11 using 100 µl PBS. One hundred 100 µl of the samples from the wells in column 11 were discarded. One hundred µl PBS was added to the wells in column 12. The plates were incubated overnight at 4° C. and then blocked 2×200 µl with Thermo Scientific SuperBlock® Blocking Buffer. The coated plates were washed 2×200 µl with PBS-Tween and 1×200 µl with PBS. Conjugates diluted in PBS to 4 µg/ml were added to the corresponding plates (100 µl/well) and then incubated for 1 h in the dark. The plates were washed with 2×200 µl with PBS-Tween and 1×200 µl with PBS and filled with PBS buffer (100 µl/well) prior to scanning on Tecan Safire using 562 $nm_{excitation}$/576 $nm_{emission}$ to detect fluorescence intensity.

As shown in FIGS. 4-11, the relative fluorescence units (RFU) and/or signal-to-background ratio (S/B) of the dyes were compared at various concentrations, using the indicated conjugation conditions.

Figure 4:
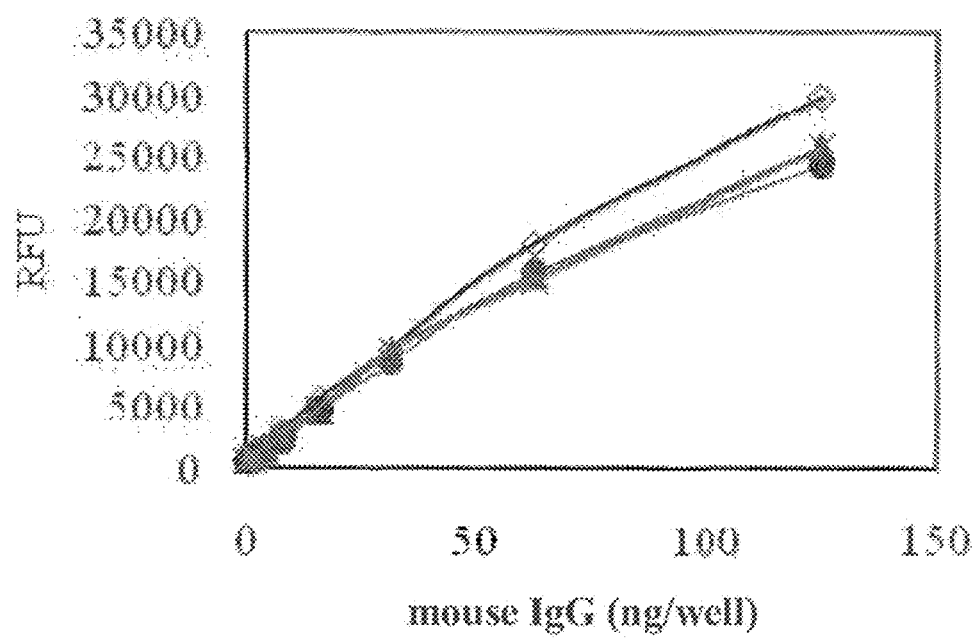
FIG. 4 shows functional assay results with some inventive compounds and commercial dyes with one conjugate produced in one embodiment.

FIG. 4 shows results of a functional assay using GAM conjugated with a 10× molar excess of the dyes (DyLight 549 red open diamond; 550 Compound 1 (isomer 1) blue closed circle; 550 Compound 1 (isomer 2 lot 1) red closed triangle; and 550 Compound 1 (isomer 2 lot 2) light green "X".

Figure 5:
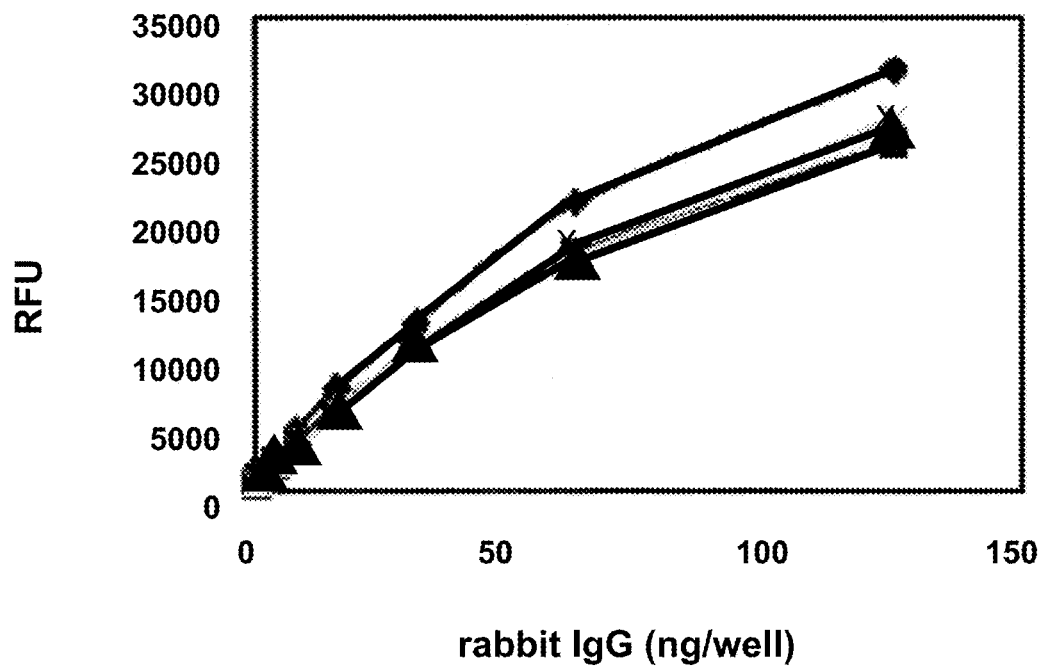
FIG. 5 shows functional assay results with some inventive compounds and commercial dyes with one conjugate produced in one embodiment.

FIG. 5 shows results of a functional assay using GAR conjugated with a 10× molar excess of the dyes (DyLight 549 dark blue closed diamond; 550 Compound 1 (isomer 1) red closed square; 550 Compound 1 (isomer 2 lot 1) yellow closed triangle; and 550 Compound 1 (isomer 2 lot 2) light blue "X".

Figure 6:
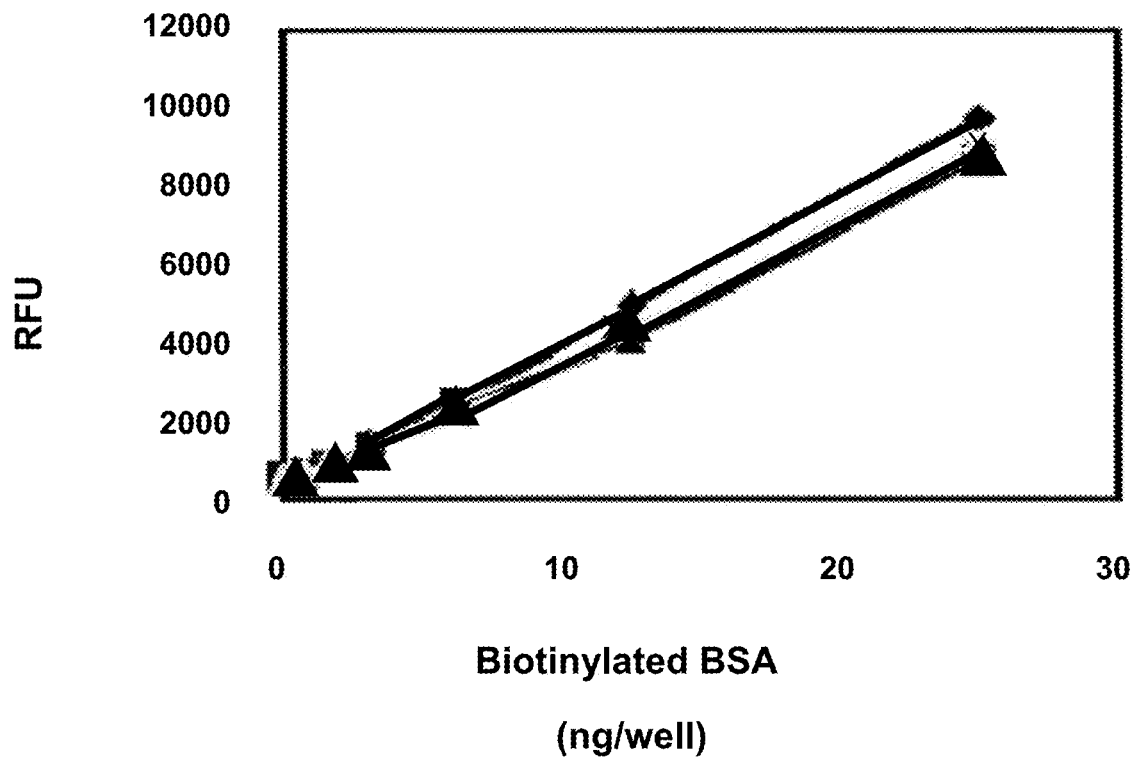
FIG. 6 shows functional assay results with some inventive compounds and commercial dyes with one conjugate produced in one embodiment.
Figure 7:
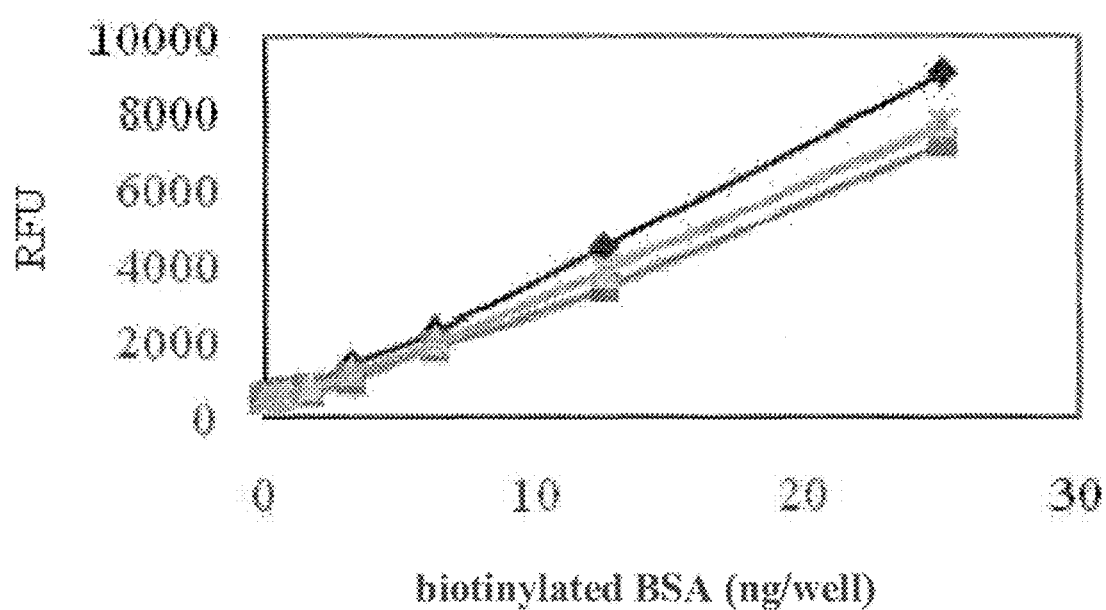
FIG. 7 shows functional assay results with some inventive compounds and commercial dyes with one conjugate produced in one embodiment.

FIGS. 6 and 7 shows results of a functional assay using SA conjugated in the presence of PBS buffer (FIG. 6) or borate buffer (FIG. 7) with a 4× molar excess of the dyes (DyLight 549 dark blue closed diamond; 550 Compound 1 (isomer 1) red closed square; 550 Compound 1 (isomer 2 lot 1) yellow closed triangle; and 550 Compound 1 (isomer 2 lot 2) light blue "X".

Figure 8:
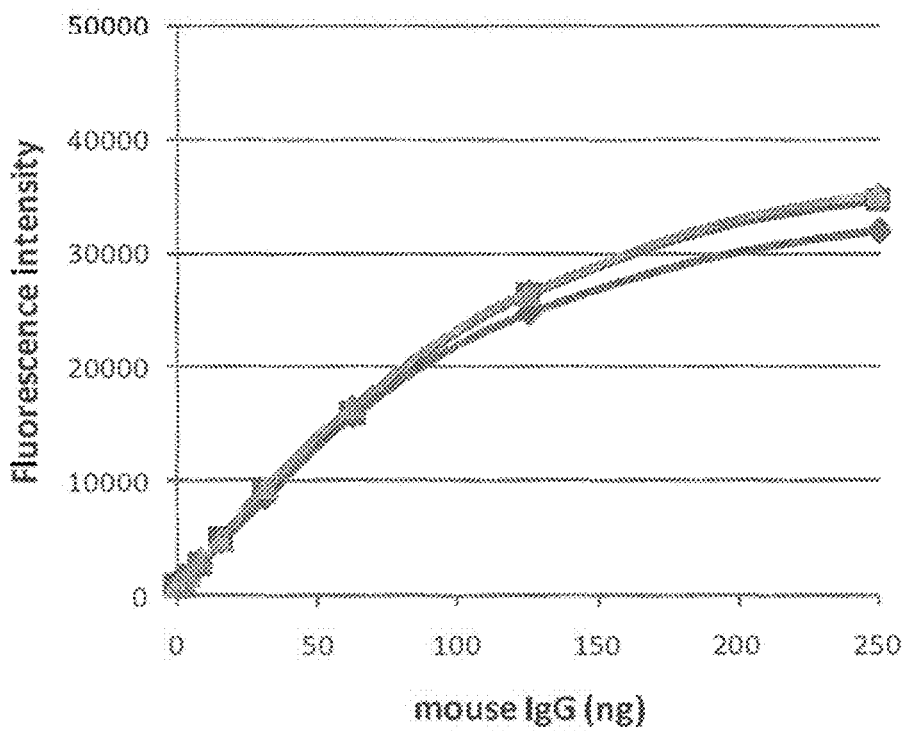
FIG. 8 shows functional assay results with some inventive compounds and commercial dyes with one conjugate produced in one embodiment.
Figure 9:
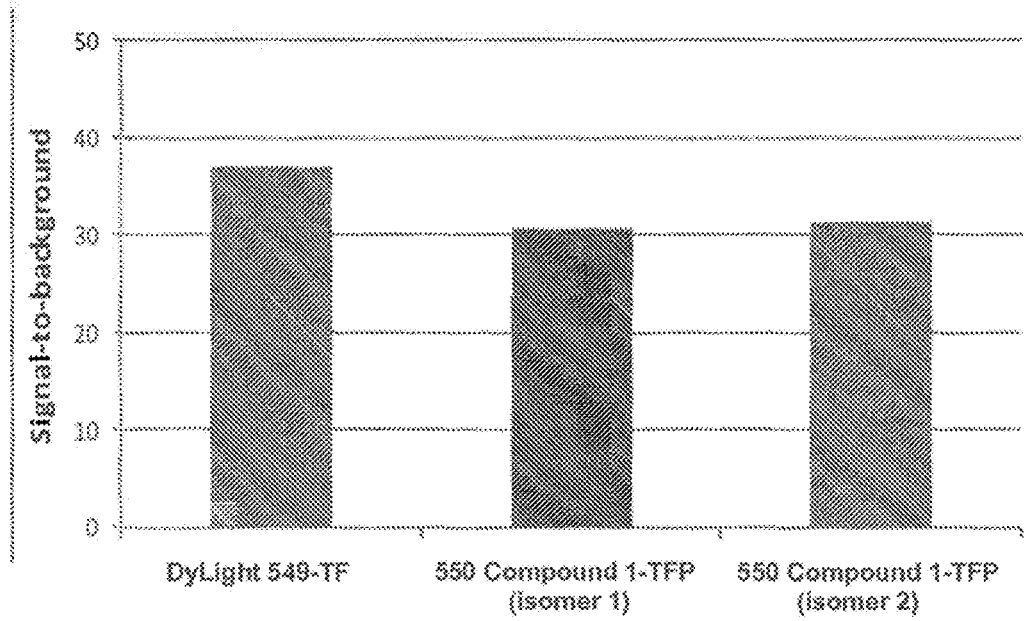
FIG. 9 shows results of the functional assay of FIG. 8 expressed as signal-to-background ratio.

FIG. 8 shows RFU results, and FIG. 9 shows signal-to-background ratio at 125 ng mouse IgG results, of a functional assay using GAM conjugated with a 5× molar excess of TFP ester containing dyes (DyLight 549-TFP blue closed diamond in FIG. 8; 550 Compound 1 (isomer 1)-TFP red closed square in FIG. 8; and 550 Compound 1 (isomer 2)-TFP green closed triangle in FIG. 8. Inventive compounds showed similar performance to DyLight 549-TFP in the plate assay with slightly lower signal-to-background.

Figure 10:
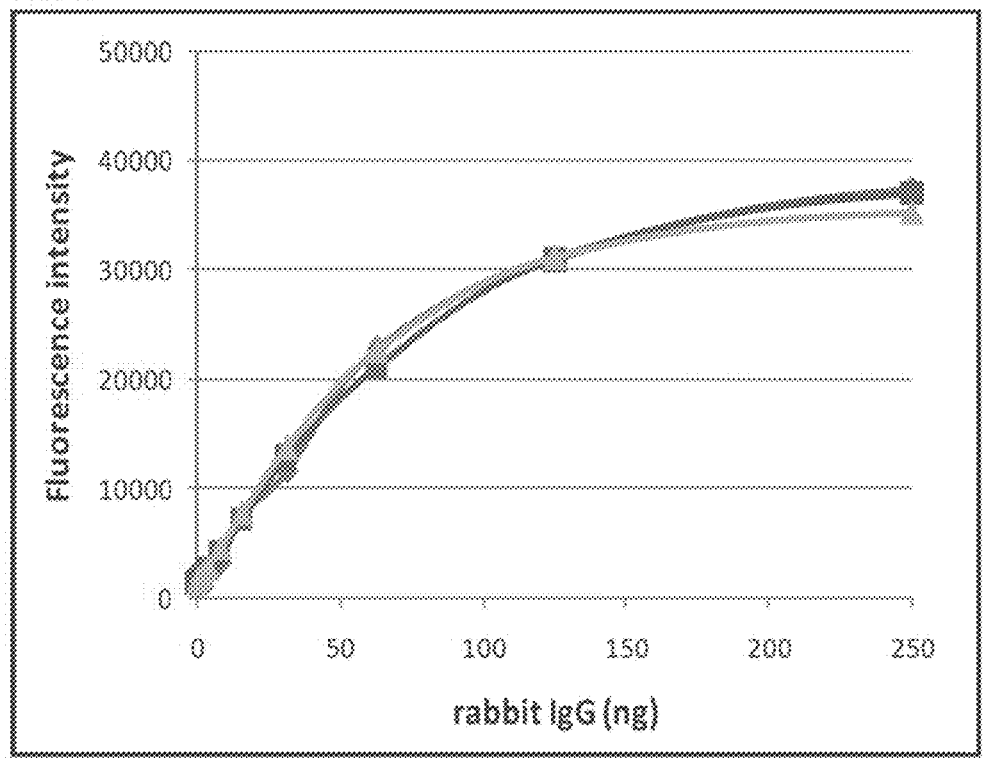
FIG. 10 shows functional assay results with some inventive compounds and commercial dyes with one conjugate produced in one embodiment.
Figure 11:
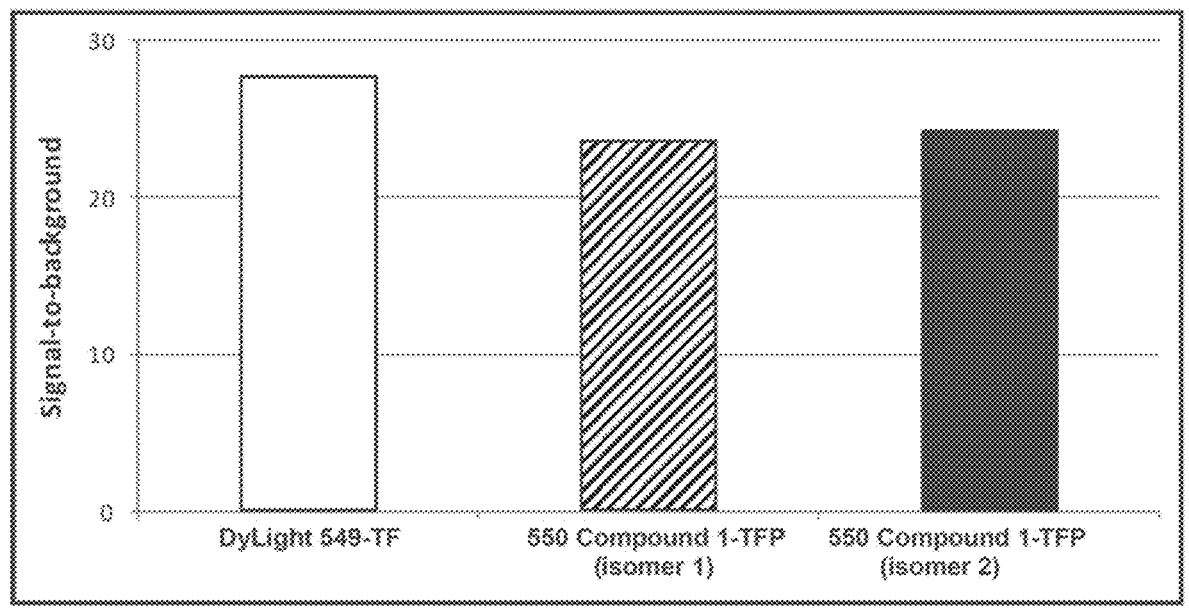
FIG. 11 shows results of the functional assay of FIG. 10 expressed as signal-to-background ratio.

FIG. 10 shows RFU results, and FIG. 11 shows signal-to-background ratio at 125 ng rabbit IgG results, of a functional assay using GAR conjugated with a 5× molar excess of TFP ester containing dyes (DyLight 549-TFP blue closed diamond in FIG. 10; 550 Compound 1 (isomer 1)-TFP red closed square in FIG. 10; and 550 Compound 1 (isomer 2)-TFP green closed triangle in FIG. 10). Inventive compounds showed similar performance to DyLight 549-TFP in the plate assay with slightly lower signal-to-background.

EXAMPLE 22

The inventive compounds and commercial dye were evaluated for immunofluorescence in cell based assays using the following protocol. Plates containing U2OS cells (human osteosarcoma cell line) were fixed in 4% paraformaldehyde in PBS/0.1% Triton X-100 for 15 min at room temperature. The cells were then permeabilized with 2% BSA in PBS/0.1% Triton X-100 for 30 min at room temperature. Diluted primary antibodies in PBS/0.1% Triton X-100 were added to the plates and incubated overnight at 4° C. The plates were washed 3×100 µl with PBS. Based on the calculated protein concentrations, the conjugates were diluted to 4 µg/ml (1:250 from 1 mg/ml stock) in PBS/0.1% Triton X-100 and added to the plates (50 µl/well) and incubated 1 h in the dark at room temperature. The plates were washed 3×100 µl with PBS. One hundred µl of 2 µg/ml Hoechst dye in PBS was added per well. The plates were then scanned on an ArrayScan® Plate Reader for imaging and quantitation.

As shown in FIGS. 12-23 and in the following tables, 550 Compound 1 exhibited fluorescence that was similar or better than DyLight 549.

Figure 12:
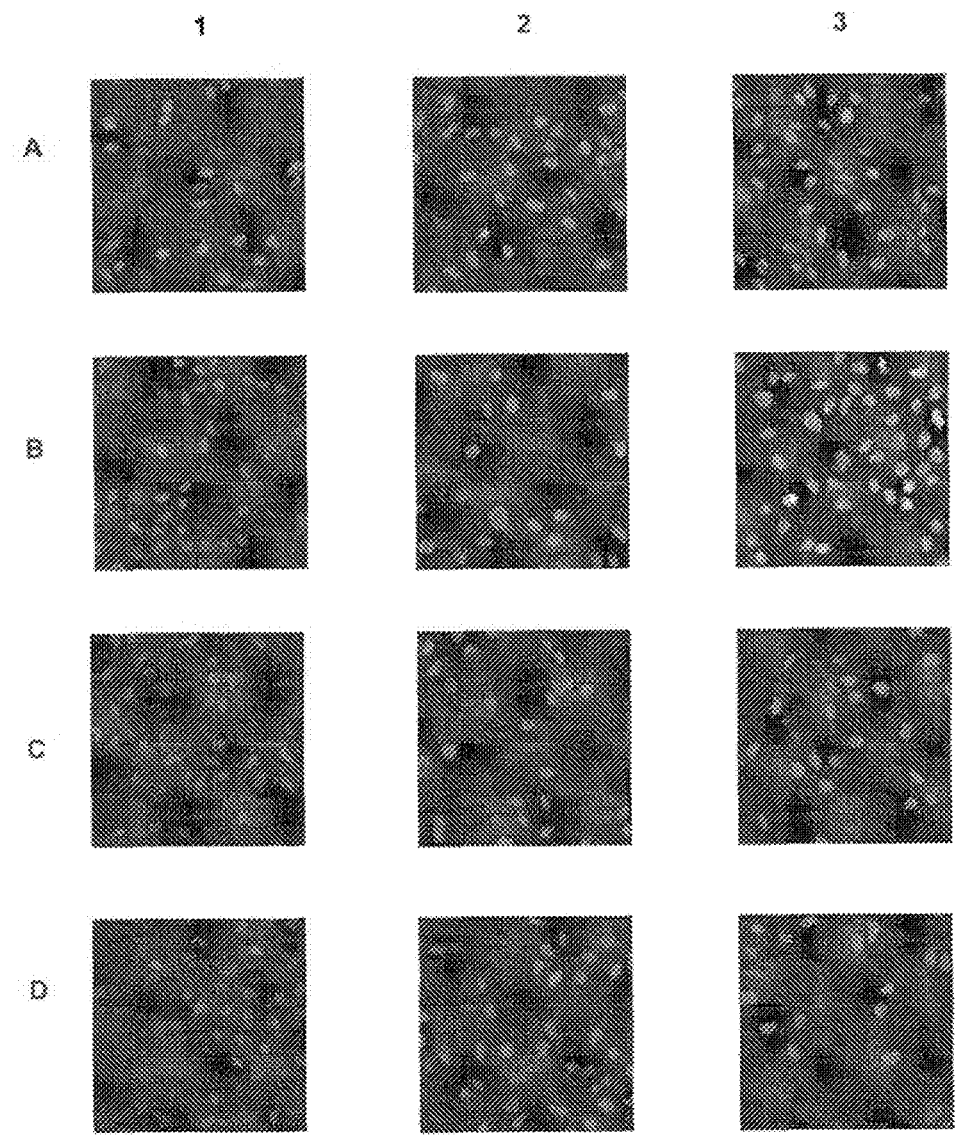
FIG. 12 shows results of an immunofluorescence assay with some inventive compounds and commercial dyes forming a conjugate in one embodiment.

FIG. 12 shows results of an immunofluorescence assay using mouse anti-lamin A as a primary antibody, and either DyLight 549-GAM (row A), 550 Compound 1 (isomer 1)-GAM (row B), 550 Compound 1 (isomer 2/lot1)-GAM (row C), or 550 Compound 1 (isomer 2/lot2)-GAM (row D) as secondary antibody, where the compound was conjugated to GAM (secondary antibody) at 2× molar excess (column 1), 5× molar excess (column 2), or 10× molar excess (column 3). The resulting D/P ratio for the conjugates is shown below:

|  | 2X molar ratio | 5X molar ratio | 10X molar ratio |
|---|---|---|---|
| DyLight 549-GAM | 1.5 | 2.9 | 5.3 |
| 550 Compound 1 (isomer 1)-GAM | 1.7 | 3.6 | 6.5 |
| 550 Compound 1 (isomer 2 lot 1)-GAM | 1.7 | 3.7 | 6.5 |
| 550 Compound 1 (isomer 2/lot 2)-GAM | 1.4 | 3.6 | 6.4 |

550 Compound 1 (isomer 1)-GAM conjugates were equivalent or better than DyLight 549-GAM conjugates. Controls (no primary antibody) showed no non-specific binding from DyLight 549 or inventive compound GAM conjugates.

Figure 13:
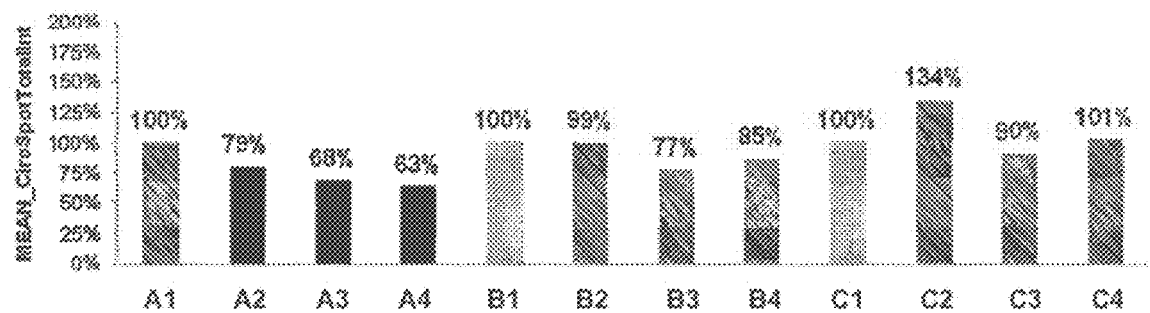
FIG. 13 shows results of the functional assay of FIG. 12 expressed as percent fluorescence intensity.

FIG. 13 shows quantitative analysis, expressed as normalized percent fluorescence intensity, of GAM conjugates formed at a 2× molar ratio (A) (black and gray bars), 5× molar ratio (B) (pink bars), and 10× molar ratio (C) (green bars), to DyLight 549 (1), 550 Compound 1 (isomer 1) (2), 550 Compound 1 (isomer 2 lot1) (3), or 550 Compound 1 (isomer 2 lot 2) (4). This normalized percent fluorescence intensity was the average total intensity of all pixels within a defined area or defined primary objected such as a nucleus, abbreviated as Mean Circ Total Intensity, of the data in FIG. 12 using an ArrayScan HCS. The number of cells analyzed per well was set to 200 (variable from experiment to experiment depending on the cell density).

Figure 14:
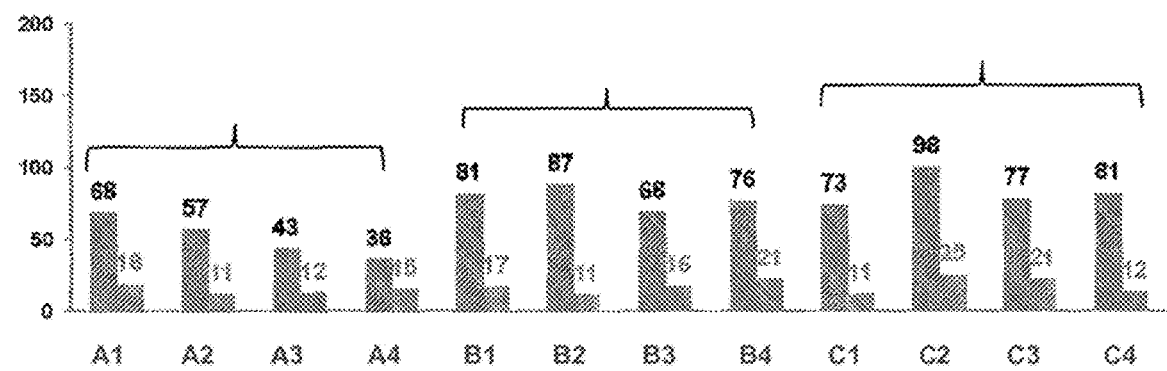
FIG. 14 shows results of the functional assay of FIG. 12 expressed as signal-to-background ratio and signal-to-noise ratio.

FIG. 14 shows quantitative analysis, expressed as signal-to-background (orange bar in each pair) or signal-to-noise (green bar in each pair), of the data in FIG. 12 showing GAM conjugates formed at a 2× molar ratio (A), 5× molar ratio (B), and 10× molar ratio (C), to either DyLight 549 (1), 550 Compound 1 (isomer 1) (2), 550 Compound 1 (isomer 2/lot 1) (3), or 550 Compound 1 (isomer 2/lot2) (4).

Figure 15:
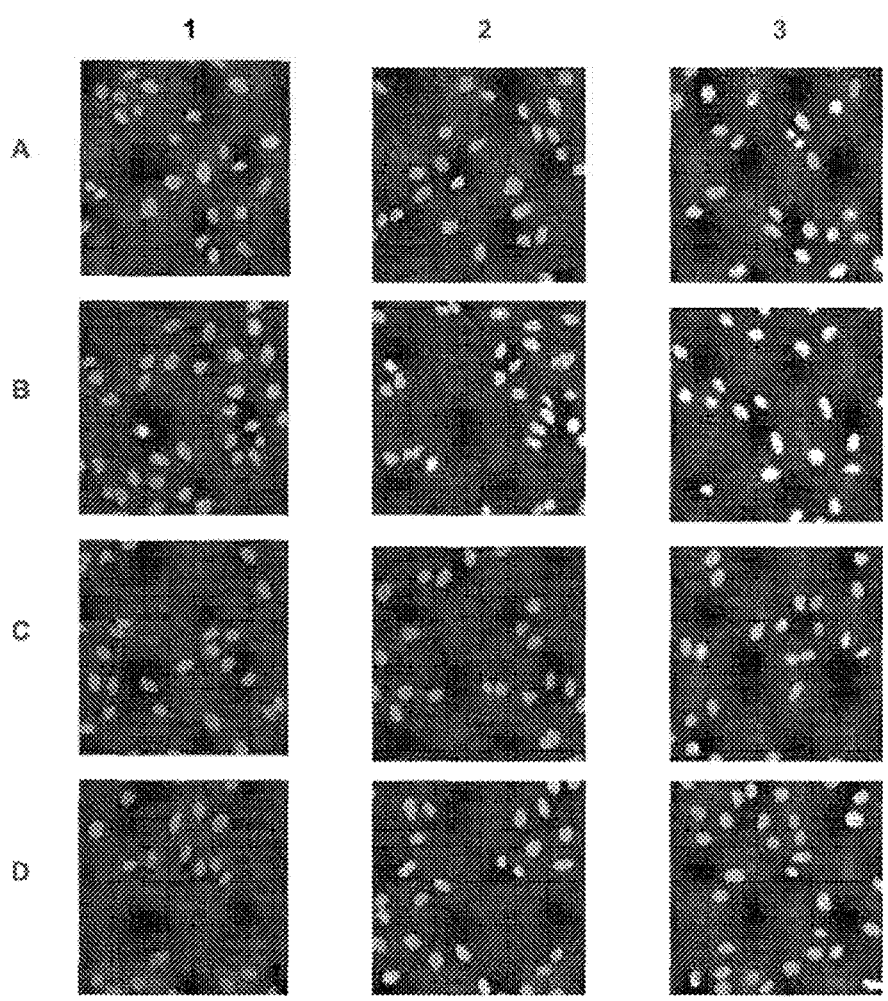
FIG. 15 shows results of an immunofluorescence assay with some inventive compounds and commercial dyes forming a conjugate in one embodiment.

FIG. 15 shows results of an immunofluorescence assay using rabbit anti-lamin B1 as a primary antibody, and either DyLight 549-GAR (row A), 550 Compound 1 (isomer 1)-GAR (row B), 550 Compound 1 (isomer 2/lot 1)-GAR (row C), or 550 Compound 1 (isomer 2/lot 2)-GAR (row D) as secondary antibody, where the compound was conjugated to GAM (secondary antibody) at 2× molar excess (column 1), 5× molar excess (column 2), or 10× molar excess (column 3). The resulting dye protein ratio (D/P) for the conjugates is shown below:

|  | 2X molar ratio | 5X molar ratio | 10X molar ratio |
|---|---|---|---|
| DyLight 549-GAR | 1.3 | 2.6 | 5.6 |
| 550 Compound 1 (isomer 1)-GAR | 1.6 | 3.3 | 6.4 |

-continued

|  | 2X molar ratio | 5X molar ratio | 10X molar ratio |
|---|---|---|---|
| 550 Compound 1 (isomer 2 lot1)-GAR | 1.7 | 3.7 | 6.7 |
| 550 Compound 1 (isomer 2 lot 2)-GAR | 1.4 | 3.5 | 6.5 |

550 Compound 1 (isomer 1)-GAR conjugate was equivalent or better than DyLight 549-GAR conjugate. Controls (no primary antibody) showed no non-specific binding from DyLight 549 or inventive compound GAR conjugates.

Figure 16:
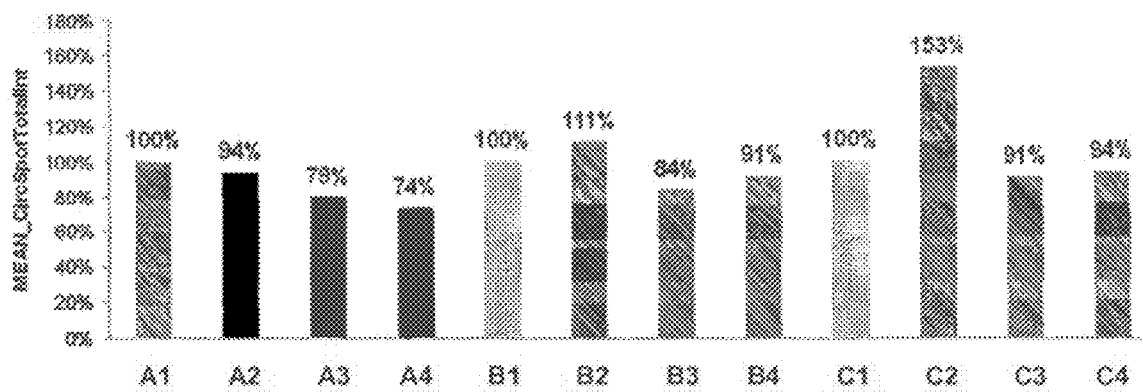
FIG. 16 shows results of the functional assay of FIG. 15 expressed as percent fluorescence intensity.

FIG. 16 shows quantitative analysis, expressed as normalized percent fluorescence intensity, of the data presented in FIG. 15, as described for FIG. 13 above, showing GAR conjugates formed at a 2× molar ratio (A) (black and gray bars), 5× molar ratio (B) (pink bars), and 10× molar ratio (C) (green bars), to either DyLight 549 (1), 550 Compound 1 (isomer 1) (2), 550 Compound 1 (isomer 2/lot1) (3), or 550 Compound 1 (isomer 2/lot2) (4).

Figure 17:
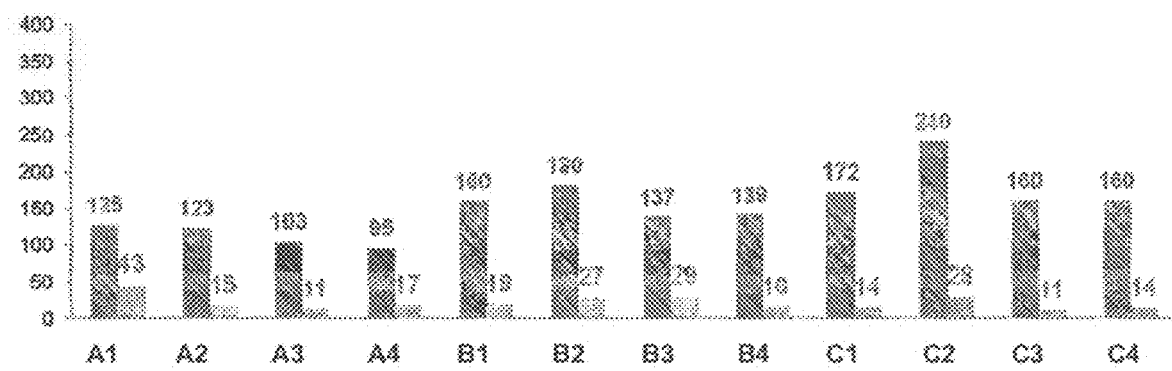
FIG. 17 shows results of the functional assay of FIG. 15 expressed as signal-to-background ratio and signal-to-noise ratio.

FIG. 17 shows quantitative analysis, expressed as signal-to-background (orange bar in each pair) or signal-to-noise (light blue bar in each pair), of the data presented in FIG. 15 showing GAR conjugates formed at a 2× molar ratio (A), a 5× molar ratio (B), and a 10× molar ratio (C), to either DyLight 549 (1), 550 Compound 1 (isomer 1) (2), 550 Compound 1 (isomer 2/lot 1) (3), or 550 Compound 1 (isomer 2/lot2) (4).

Figure 18:
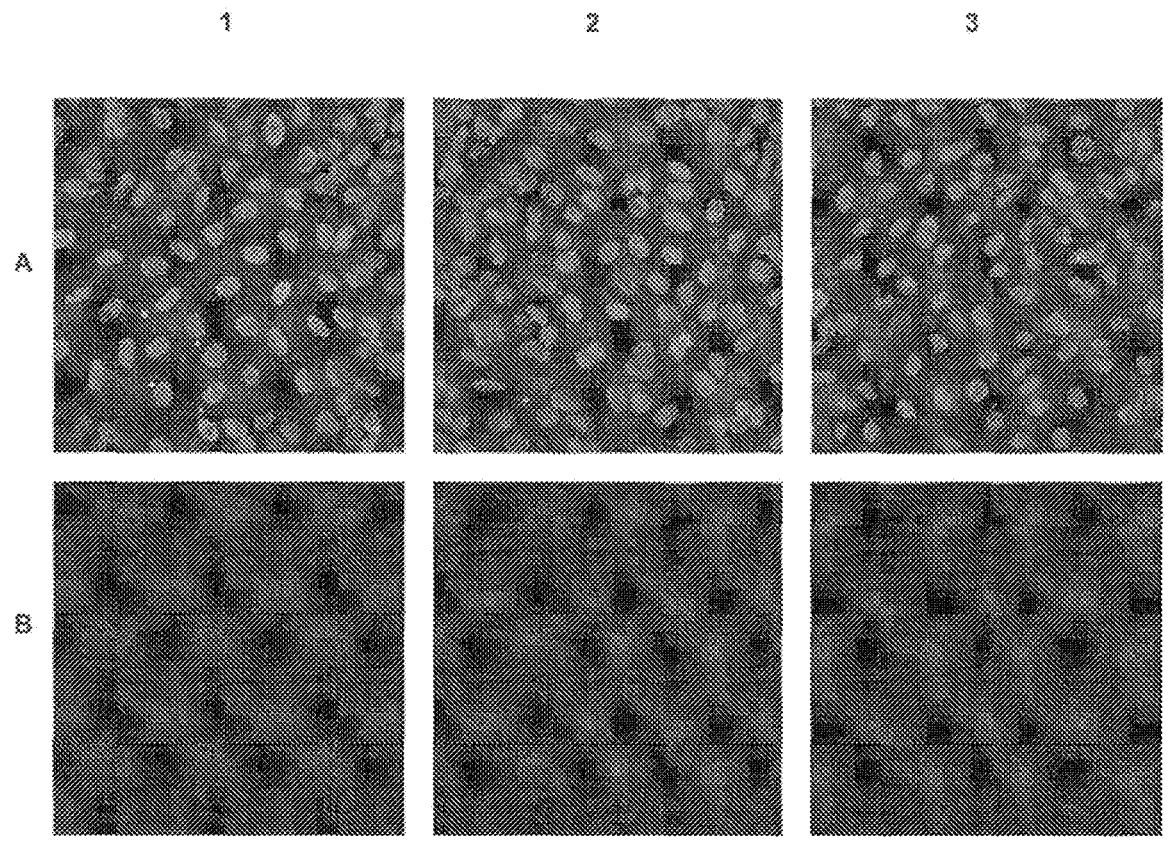
FIG. 18 shows results of an immunofluorescence assay with some inventive compounds and commercial dyes forming a conjugate in one embodiment.

FIG. 18 shows results of an immunofluorescence assay in the presence (row A) or absence (row B) of mouse anti-lamin A as a primary antibody, and either DyLight 549-GAM (column 1), 550 Compound 1 (isomer 1)-GAM (column 2), or 550 Compound 1 (isomer 2)-GAM (column 3), as secondary antibody, where a TFP ester form of the compound was conjugated to GAM (secondary antibody) to result in a 4.1, 4.6, and 4.7 D/P ratio, respectively.

Figure 19:
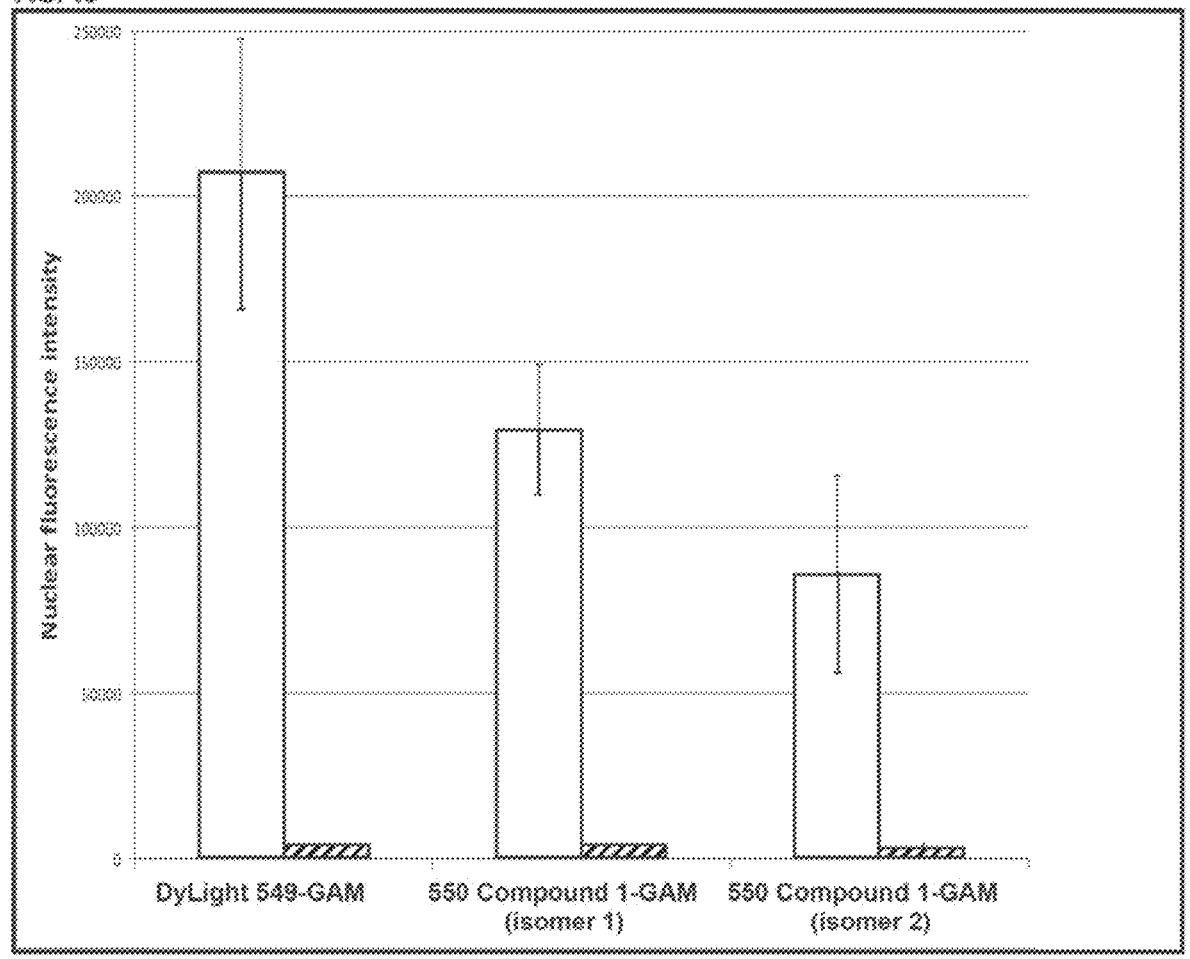
FIG. 19 shows results of the functional assay of FIG. 18 expressed as fluorescence intensity.

FIG. 19 shows quantitative analysis, as described for FIG. 13, expressed as nuclear fluorescence intensity of the data presented in FIG. 18 of the presence (blue bar of each pair) or absence (red bar of each pair) of primary antibody.

Figure 20:
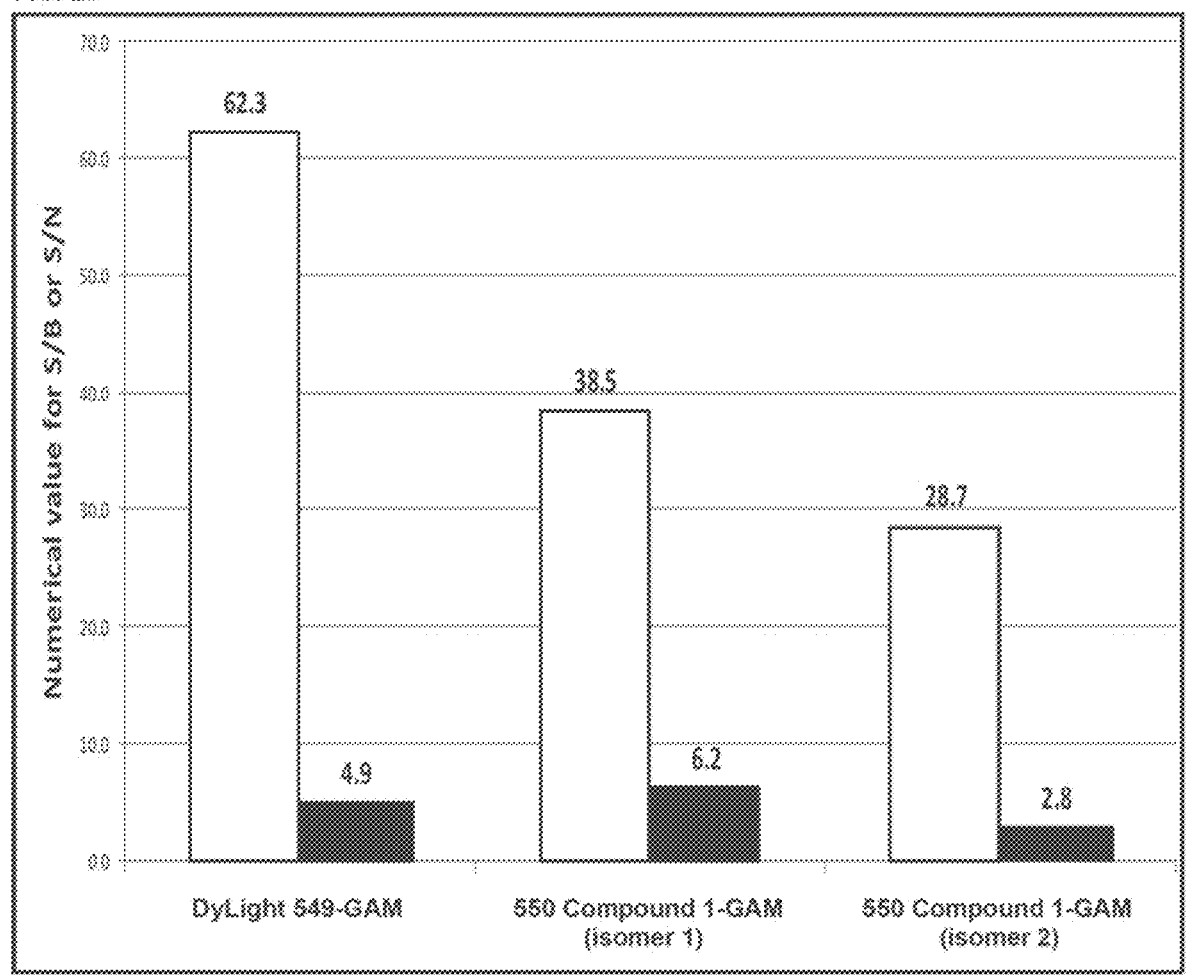
FIG. 20 shows results of the functional assay of FIG. 18 expressed as signal-to-background ratio and signal-to-noise ratio.

FIG. 20 shows quantitative analysis, expressed as signal-to-background (S/B)(green bar in each pair) or signal-to-noise (S/N) (purple bar in each pair), of the data in FIG. 18.

Figure 21:
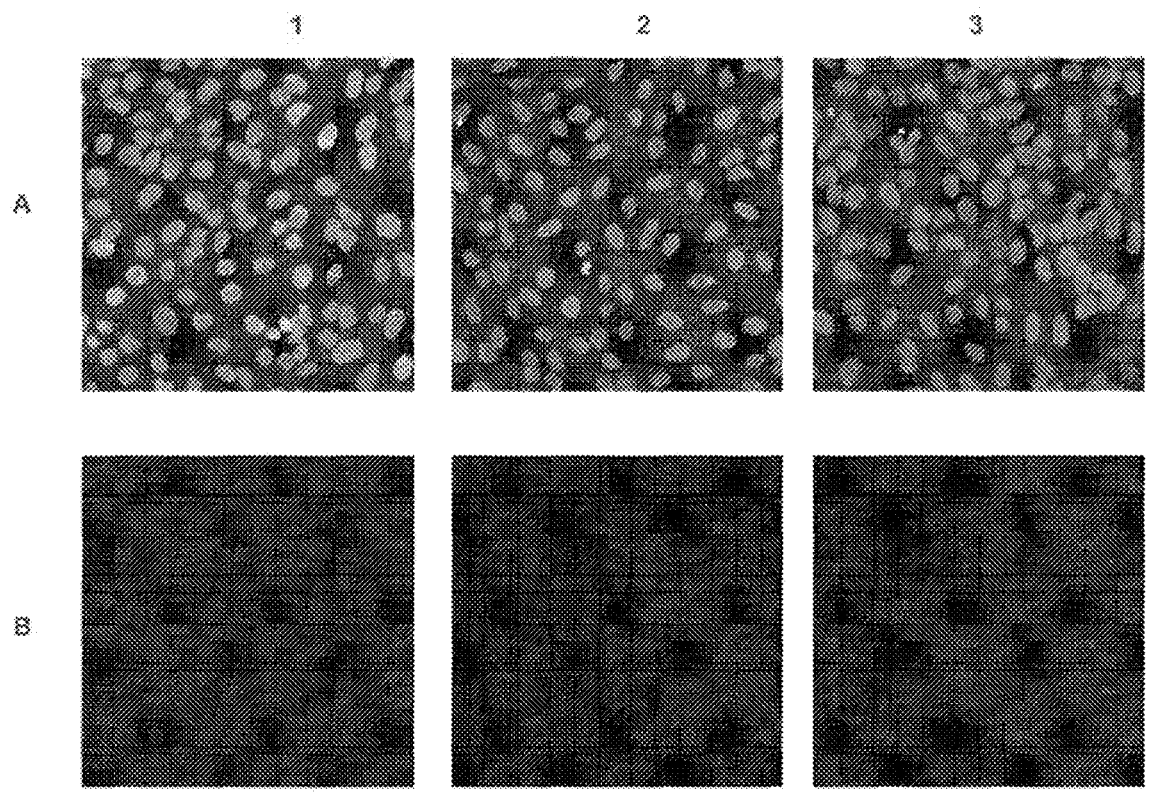
FIG. 21 shows results of an immunofluorescence assay with some inventive compounds and commercial dyes forming a conjugate in one embodiment.

FIG. 21 shows results of an immunofluorescence assay in the presence (row A) or absence (row B) of rabbit anti-lamin B1 as a primary antibody, and either DyLight 549-GAR (column 1), 550 Compound 1 (isomer 1)-GAR (column 2), or 550 Compound 1 (isomer 2)-GAR (column 3), as secondary antibody, where a TFP ester form of the compound was conjugated to GAR (secondary antibody) to result in a 4.3, 4.3, and 4.4 D/P ratio, respectively.

Figure 22:
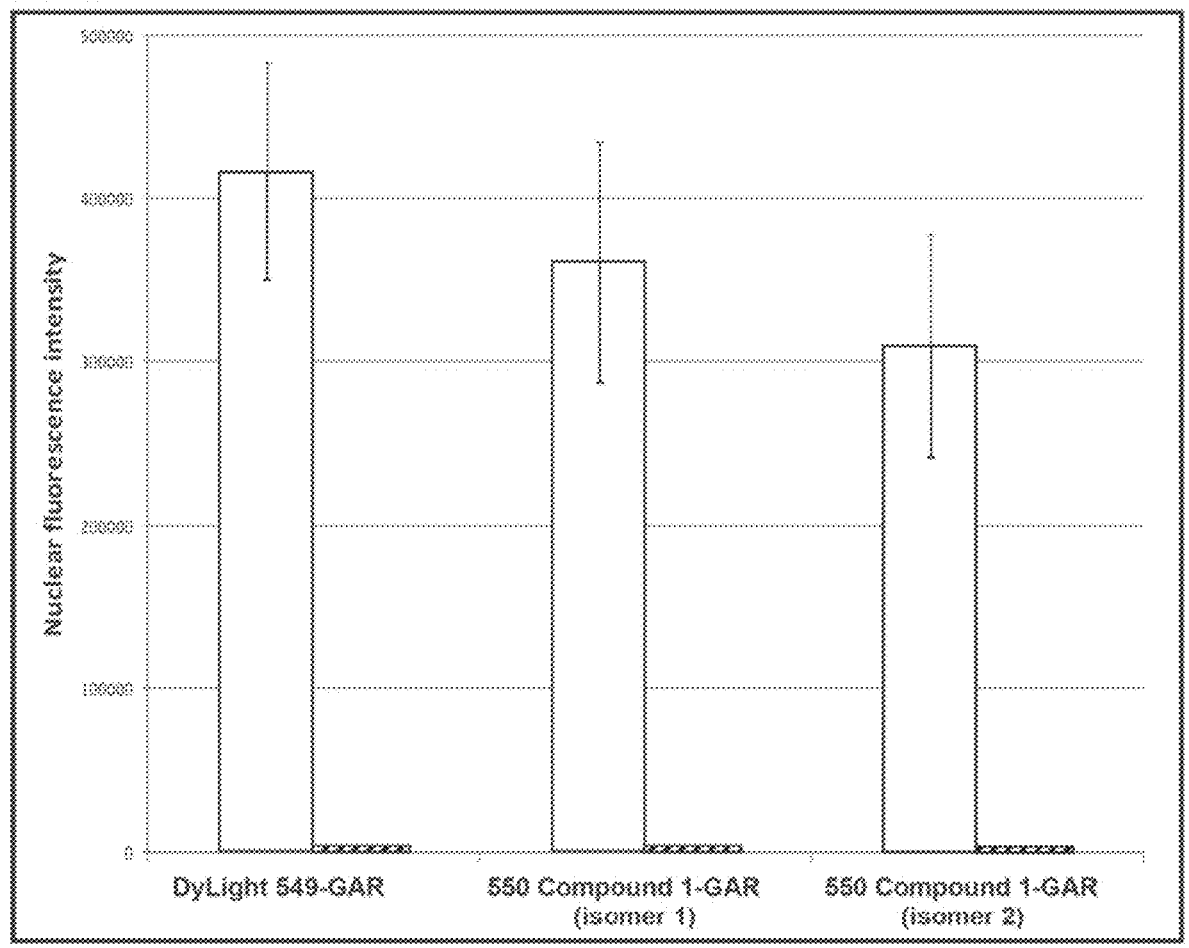
FIG. 22 shows results of the functional assay of FIG. 21 expressed as fluorescence intensity.

FIG. 22 shows quantitative analysis, as described for FIG. 13, expressed as nuclear fluorescence intensity, of the data in FIG. 21 of the presence (blue bar in each pair) or absence (red bar of each pair) of primary antibody.

Figure 23:
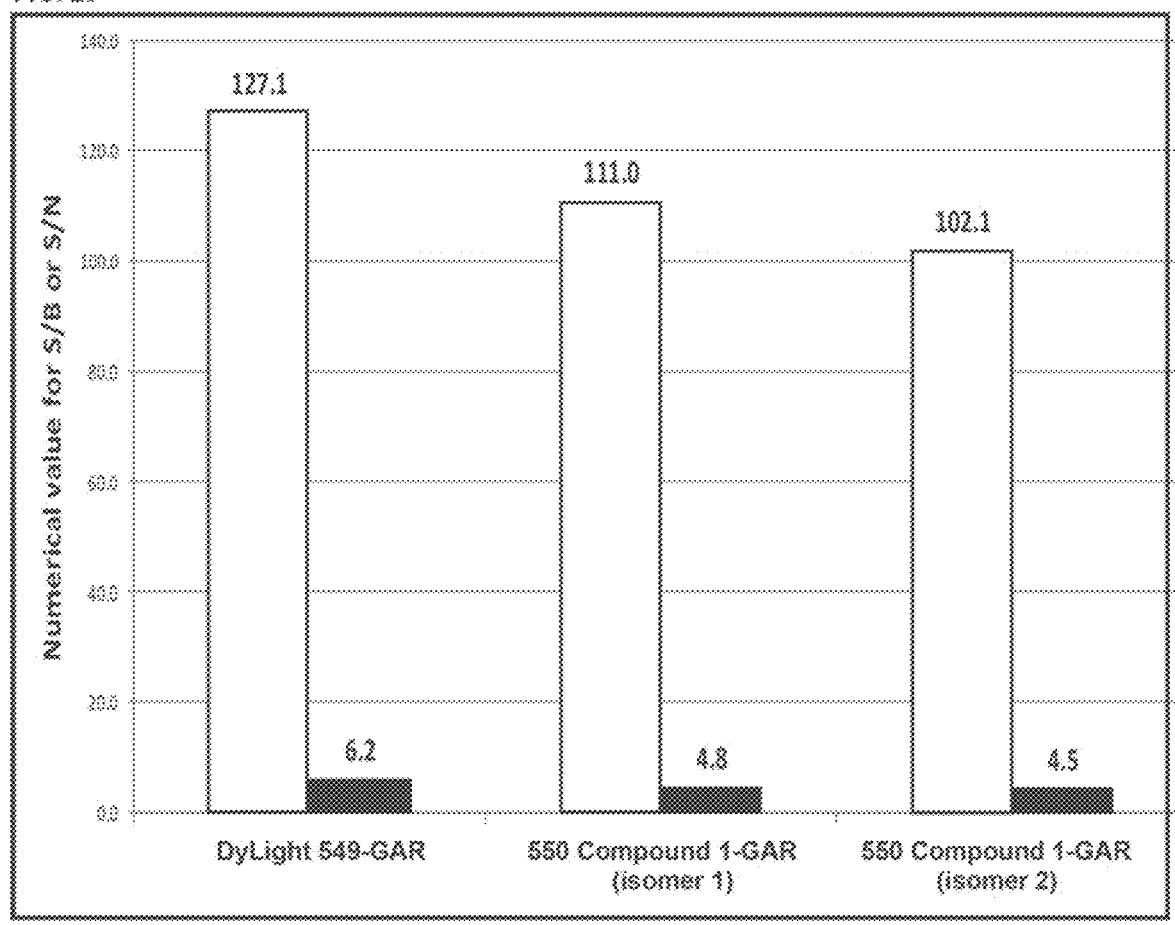
FIG. 23 shows results of the functional assay of FIG. 21 expressed as signal-to-background ratio and signal-to-noise ratio.

FIG. 23 shows quantitative analysis, expressed as signal-to-background (S/B) (green bar in each pair) or signal-to-noise (S/N) (purple bar in each pair), of the data in FIG. 21.

EXAMPLE 23

The inventive compounds were evaluated for stability. All compounds were packed under argon in plastic vials. The vials sere sealed with a drying pad in an aluminium coated pouch, and then stored at 50° C. for seven days. The results of the stability study for selected compounds are shown below:

| Dye | Unit size | Purity at day 1 | Purity at day 7 |
|---|---|---|---|
| 550 Compound 1(isomer 1)-NHS | 1 mg | 96% | 93% |
|  | 50 µg | 95% | 91% |
|  | 15 µg | 95% | 91% |
| 550 Compound 1(isomer 1)-TFP | 1 mg | 97% | 96% |
| 550 Compound 1(isomer 1)-maleimide | 1 mg | 99% | 97% |
| 550 Compound 1(isomer 2)-NHS | 50 µg | 96% | 95% |
|  | 15 µg | 96% | 94% |
| 550 Compound 1(isomer 2)-maleimide | 1 mg | 98% | 97% |

Purity was determined based on ester activity.

EXAMPLE 24

The inventive compounds and commercial dyes were evaluated in direct fluorescence labeling of cell surface proteins using the following protocol. DyLight 549-NHS, 550 Compound 1-NHS, and Whole Cell Stain Orange (Thermo Fisher Scientific) were reconstituted in DMF and diluted to 6 µM in Dulbecco's PBS (DPBS). A total of four 1:1 serial dilutions of the dyes were prepared in DPBS. Frozen IMR90 cells (human lung embryonic fibroblast) on a plate were thawed for 1 h at 37° C. The cell plates were washed two times with DPBS and incubated with dye dilutions for 30 min at room temperature protected from light. The cell plates were then washed three times with DPBS. The cell plates were incubated with 100 µl/well of 1 µg/ml Hoechst dye in DPBS. The cell plates were sealed and imaged using the Thermo Scientific ArrayScan VTI HCS Reader.

Figure 24:
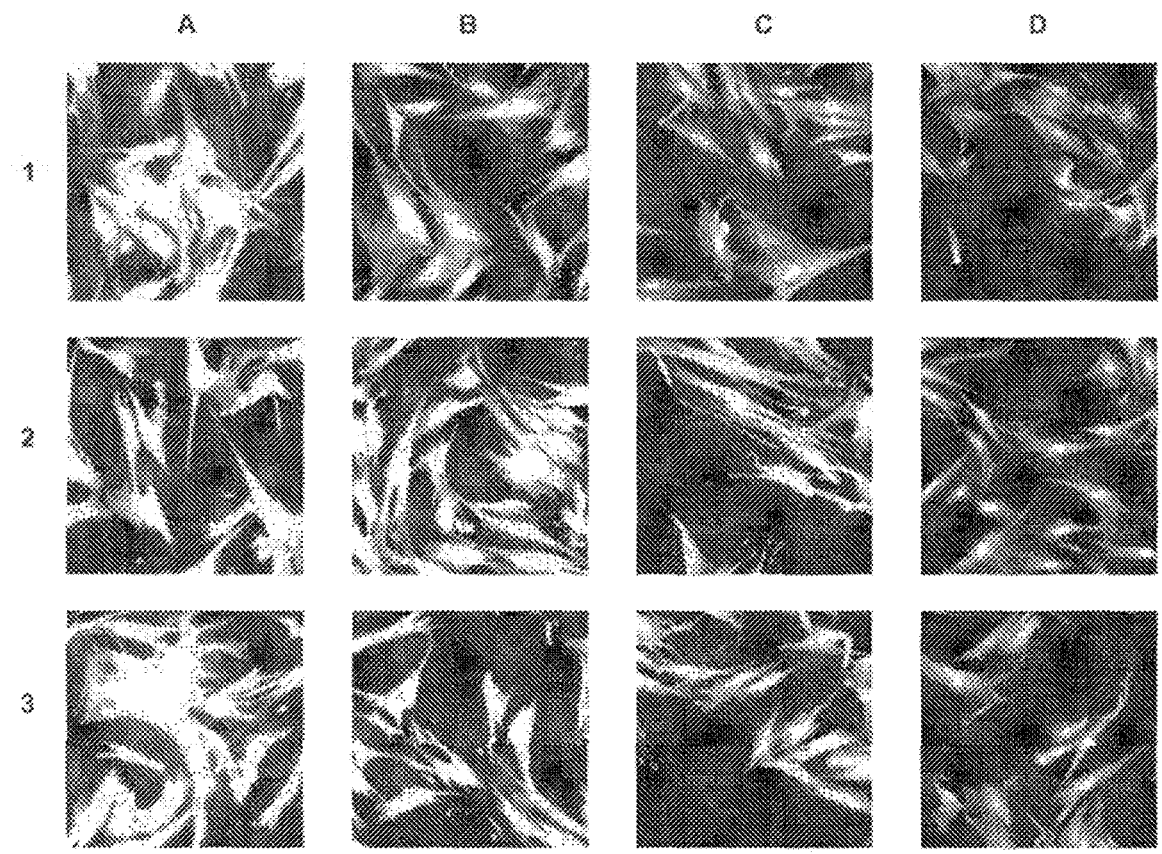
FIG. 24 shows results of direct fluorescence labeling of cell surface proteins with some inventive compounds and commercial dyes in one embodiment.

As shown in FIG. 24, 550 Compound 1-NHS (row 3) performed equivalently as DyLight 549-NHS (row 2) and Whole Cell Stain Orange (row 1) at a concentration of 6 µm (column A), 3 µm (column B), 1.5 µm (column C), and 0.75 µm (column D).

EXAMPLE 25

Evaluation of 650 Compounds 1-3 (compound 1-NHS, compound 2-NHS, and compound 3-NHS, respectively) were compared with commercially available dyes.

| Property | DyLight 649-NHS | 650 Compound 1-NHS | 650 Compound 2-NHS | 650 Compound 3-NHS | Alexa 647-NHS | Cy5 mono ester |
|---|---|---|---|---|---|---|
| MW (g/mol) | 1008 | 1066.10 | 1110.16 | 1154.21 | ~1250 | 791.99 |
| excitation (nm) | 652 (+/−4 nm) | 654 | 654 | 654 | 659 | 650 |
| emission (nm) | 672 (+/−4 nm) | 672 | 672 | 672 | 665 | 670 |
| ε (M−1cm−1) | 250,000 | 223,000 | 250,000 | 250,000 | 250,000 | 250,000 |

Evaluation of 650 Compound 1-TFP was compared with commercially available dyes.

| Property | DyLight 649 isomer 1-TFP | DyLight 649 isomer 2-TFP | 650 Compound 1-TFP |
|---|---|---|---|
| MW (g/mol) | 1059.01 | 1059.01 | 1117.09 |
| Excitation (nm) | 652 | 654 | 654 |
| Emission (nm) | 670 | 672 | 672 |
| ε (M−1cm−1) | 250,000 | 250,000 | 250,000 |

The quantum yield (QY) was determined at an excitation wavelength of 600 nm for inventive and commercial compounds, as shown below

| NHS Forms | QY excitation at 600 nm | QY excitation at 630 nm |
|---|---|---|
| DyLight 649-NHS (isomer 2) | 0.328 | 0.32 |
| 650 Compound 1 (isomer 1)-NHS | 0.335 | 0.319 |
| 650 Compound 1 (isomer 2)-NHS | 0.338 | 0.326 |
| Cy5 | ND | 0.282 |
| Alexa 647 | ND | 0.323 |

QY measurements were performed in PBS using a Hamamatsu C9920 PL Absolute Quantum Yield Measurement System. The maximum absorbance at a 1 cm pathlength was set to 0.08.

Figure 25:
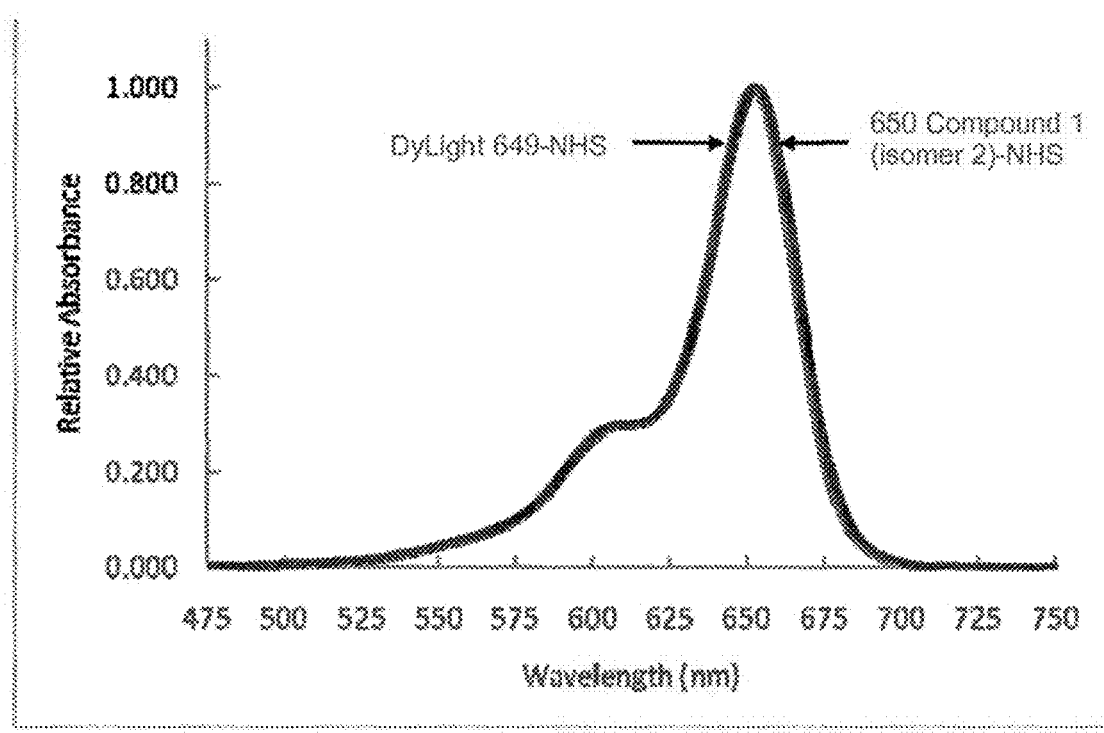
FIG. 25 shows relative absorption profiles of an inventive compound and commercial dye.

Absorption profiles for inventive and commercial compounds were determined as shown in FIG. 25, where DyLight 649-NHS (red line) and 650 Compound 1 (isomer 2)-NHS (blue line) showed very similar profiles.

Figure 26:
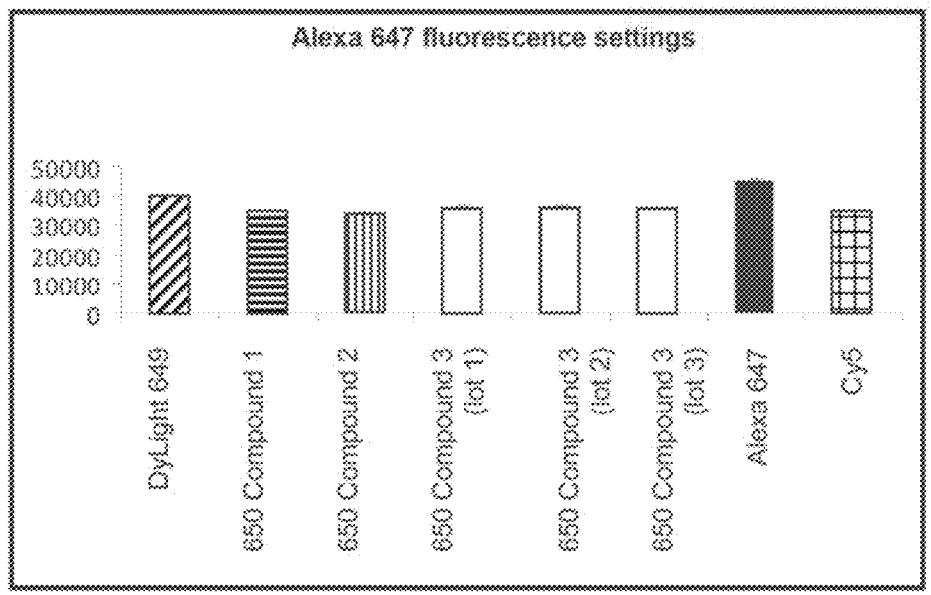
FIG. 26 shows fluorescence intensity of some inventive compounds and commercial dyes assessed at one emission/excitation wavelength.
Figure 27:
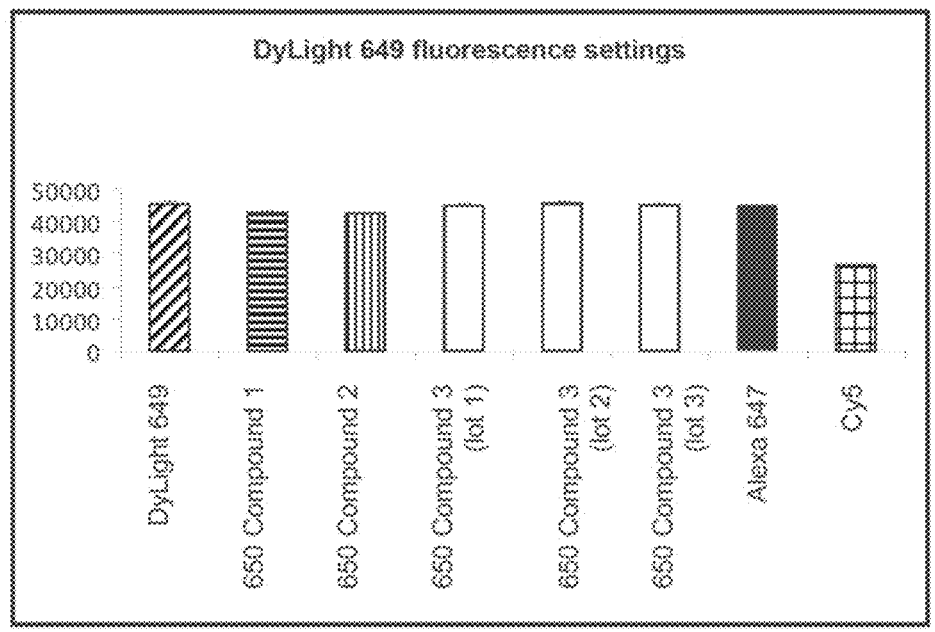
FIG. 27 shows fluorescence intensity of some inventive compounds and commercial dyes assessed at one emission/excitation wavelength.

Fluorescence intensity, in relative fluorescence units (RFU), for inventive and commercial compounds was compared using 650 $nm_{excitation}$/665 $nm_{emission}$ (Alexa 647 settings; FIG. 26) or 654 $nm_{excitation}$/673 $nm_{emission}$ (DyLight 649 settings; FIG. 27), for DyLight 649-NHS, 650 Compound 1-NHS, 650 Compound 2-NHS, and 650 Compound 3-NHS (lots 1, 2, and 3), Alexa 647-NHS, and Cy5. The fluorescence intensities for the inventive compounds were similar to each other and within 5% of DyLight 649-NHS using the DyLight 649 settings.

EXAMPLE 26

Compounds 1, 2, and 3, each as the NHS ester, and DyLight 649-NHS were conjugated to goat anti-mouse (GAM) and goat anti-rabbit (GAR) antibodies. GAM and GAR, at a concentration of 10 mg/ml in phosphate buffered saline (PBS), were dialyzed against 50 mM borate buffer, pH 8.5. The compounds were reconstituted in dimethylformamide (DMF) at 10 mg/ml. To label the antibodies, the compounds were added at 2.5× molar excess and 5× molar excess for 2 h at room temperature. Streptavidin (SA) was reconstituted in PBS buffer, pH 7.2, and 50 mM borate buffer, pH 8.5, and labeled with 2.5× molar excess and 4× molar excess of the compound.

The antibody-labeled compounds, also termed dyes or labels, were subjected to gel filtration chromatography (15 cm×0.8 cm columns) or to the PDDR to remove the unlabeled (free) compound; 100 µl of the packed resin was used per mg of protein purified. The purified antibody-labeled dyes were then diluted 1:100 in PBS and scanned for absorbance from 700 nm to 230 nm to determine the protein concentration, and to determine the mole dye to mole protein ratio. Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the Typhoon 9400 Imager to verify removal of the unconjugated compound. Labeling efficiency was compared using labeling of the compounds to GAM antibody at a 2.5× molar excess of compound, with results shown below.

| Conjugate | Compound/Protein GAM (2.5X molar excess) purified by gel filtration | Compound/Protein GAM (2.5X molar excess) purified on PDRR |
| --- | --- | --- |
| DyLight 649-GAM | 1.8 | 1.9 |
| 650 Compound 1-GAM | 2.4 | 2.3 |
| 650 Compound 2-GAM | 2.0 | 2.0 |
| 650 Compound 3 (lot 1)-GAM | 1.5 | 1.6 |
| 650 Compound 3 (lot 2)-GAM | 1.9 | 2.0 |
| 650 Compound 3 (lot 3)-GAM | 2.0 | 1.9 |
| Alexa647-GAM | 2.2 | 2.2 |
| Cy5-GAM | 1.6 | 1.5 |

Labeling efficiency was compared using labeling of the compounds to GAM antibody at a 5× molar excess of the compound, and to goat anti-rabbit (GAR) at a 5× molar excess of the compound, with results shown below.

| Conjugate | Compound/Protein GAM (5X molar excess) purified by gel filtration | Compound/Protein GAM (5X molar excess) purified on PDRR | Compound/Protein GAR (5X molar excess) purified on PDRR |
| --- | --- | --- | --- |
| DyLight 649-GAM | 3.6 | 3.3 | 2.9 |
| 650 Compound 1-GAM | 3.9 | 3.5 | 3.3 |
| 650 Compound 2-GAM | 3.8 | 3.4 | 2.9 |
| 650 Compound 3 (lot 1)-GAM | 4.0 | 3.6 | 2.4 |
| 650 Compound 3 (lot 2)-GAM | 4.0 | 3.5 | 3.1 |
| 650 Compound 3 (lot 3)-GAM | 3.8 | 3.4 | 3.0 |
| Alexa 647-GAM | 4.2 | 3.8 | 3.5 |
| Cy5-GAM | 3.0 | 2.7 | 2.7 |

Labeling efficiency of GAM and GAR was within 10% of that obtained with DyLight 649-NHS, Alexa 647-NHS, and Cy 5-NHS.

Labeling efficiency was also compared using high molar excess of the dyes with GAM and GAR.

| Test # | Conjugate | Compound/Protein | % free dye* |
| --- | --- | --- | --- |
| 1 | DyLight 649-GAM 5X | 2.8 | 0.5% |
| 2 | DyLight 649-GAM 10X | 6.1 | 0.4% |
| 3 | DyLight 649-GAM 20X | 8.3 | 0.5% |
| 4 | DyLight 649-GAM 25X | 10.8 | 0.5% |
| 5 | 650 Compound 1-GAM 5X | 3.3 | 0.5% |
| 6 | 650 Compound 1-GAM 10X | 6.6 | 0.3% |
| 7 | 650 Compound 1-GAM 20X | 11.3 | 0.3% |
| 8 | 650 Compound 1-GAM 25X | 13.4 | 0.3% |
| 9 | DyLight 649-GAR 5X | 2.7 | 0.4% |
| 10 | DyLight 649-GAR 10X | 5.5 | 0.4% |
| 11 | DyLight 649-GAR 20X | 9.3 | 0.3% |
| 12 | DyLight 649-GAR 25X | 14.0 | 0.3% |
| 13 | 650 Compound 1-GAR 5X | 3.3 | 0.6% |
| 14 | 650 Compound 1-GAR 10X | 5.9 | 0.3% |
| 15 | 650 Compound 1-GAR 20X | 10.6 | 0.3% |
| 16 | 650 Compound 1-GAR 25X | 12.7 | 0.4% |

*Calculated from conjugates separated on SDS-PAGE gels scanned using the Typhoon 9400 Imager.

Labeling efficiency was also compared using labeling of the dyes to streptavidin (SA) at either a 2.5 fold or a 4 fold molar excess of the dye, with SA in PBS, pH 7.2, and borate buffer, pH 8.5.

| Conjugate | Compound/Protein SA in PBS purified by gel filtration | Compound/Protein SA in PBS purified by PDRR | Compound/Protein SA in borate purified by gel filtration | Compound/Protein SA in borate purified by gel PDRR |
|---|---|---|---|---|
| DyLight 649-SA (2.5X) | | | 2.3 | 2.2 |
| 650 Compound 1-SA (2.5X) | | | 2.4 | 2.2 |
| 650 Compound 2-SA (2.5X) | | | 2.2 | 2.0 |
| 650 Compound 3 (lot 1)-SA (2.5X) | | | 1.8 | 1.7 |
| 650 Compound 3 (lot 2)-SA (2.5X) | | | 2.4 | 2.1 |
| 650 Compound 3 (lot 3)-SA (2.5X) | | | 2.3 | 2.2 |
| Alexa 647-SA-(2.5X) | | | 2.6 | 2.4 |
| Cy5-SA (2.5X) | | | 2.3 | 2.0 |
| DyLight 649-SA-4X | 3.5 | 2.6 | 3.5 | 2.9 |
| 650 Compound 1-SA-4X | 3.7 | 3.2 | 3.5 | 2.8 |
| 650 Compound 2-SA-4X | 3.4 | 3.2 | 3.6 | 3.2 |
| 650 Compound 3 (lot 1)-SA-4X | 3.0 | 2.6 | 2.6 | 2.5 |
| 650 Compound 3 (lot 2)-SA-4X | 3.7 | 3.2 | 3.4 | 3.1 |
| 650 Compound 3 (lot 3)-SA-4X | 3.5 | 3.2 | 3.1 | 2.9 |
| Alexa647-SA-4X | 3.9 | 3.5 | 3.9 | 3.4 |
| Cy5-SA-4X | 4.2 | 3.8 | 3.8 | 3.3 |

Labeling efficiency of SA in PBS pH 7.2 was the same with 650 Compound 1-NHS and DyLight 649-NHS. Labeling efficiency of SA in borate pH 8.5 was the same with 650 Compound 1-NHS and DyLight 649-NHS.

TFP-ester forms of the compounds were compared with NHS-ester forms of the compounds. 650 Compound 1 (isomer 2)-TFP, 650 Compound 1 (isomer 1)-TFP, 650 Compound 1 (isomer 2)-TFP, 650 Compound 1-NHS, and DyLight 649-NHS were conjugated to GAM, GAR, and SA. GAM and GAR, at a concentration of 10 mg/ml in phosphate buffered saline (PBS), were dialyzed against 50 mM borate buffer, pH 8.5. The compounds were reconstituted in dimethylformamide (DMF) at 10 mg/ml and used to label antibodies at 5× molar excess of compound for two hours at room temperature to label the antibodies. SA was reconstituted in 50 mM borate buffer, pH 8.5, and combined with 4× molar excess to label the SA.

Figure 28:
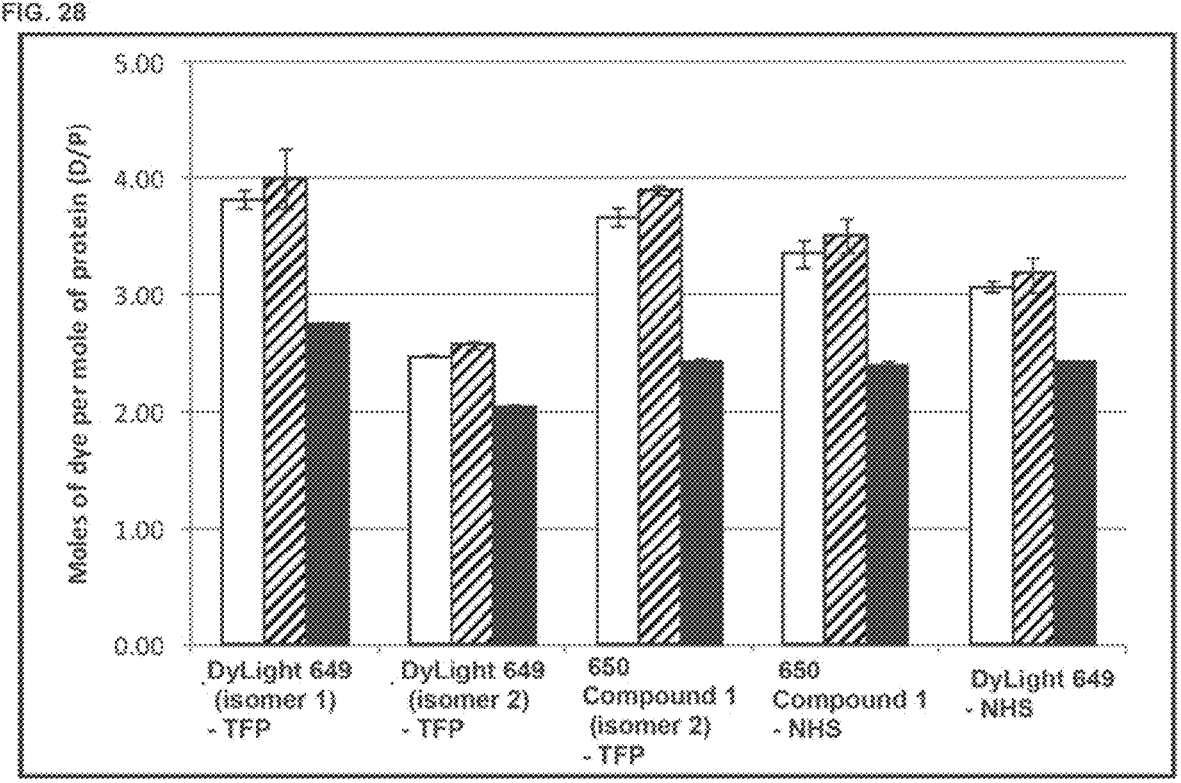
FIG. 28 shows labeling efficiency of some inventive compounds and commercial dyes.

The antibody-conjugated and SA-conjugated compounds, also termed dyes or labels, were subjected to the PDDR to remove the unlabeled (free) compound. The purified antibodies and SA were then diluted 1:25 in PBS and scanned for absorbance from 700 nm to 230 nm to determine the protein concentration, and to determine the mole dye to mole protein ratio. Labeling efficiency is shown below and in FIG. 28, showing the GAM-conjugates (blue bar in each triplet), GAR-conjugates (red bar in each triplet), and SA-conjugates (green bar in each triplet).

| | GAM (5X) | | | GAR (5X) | | | SA (4X) | | |
|---|---|---|---|---|---|---|---|---|---|
| | Average | SD | % CV | Average | SD | % CV | Average | SD | % CV |
| DyLight 649 (isomer 1)-TFP | 3.82 | 0.07 | 1.8% | 4.00 | 0.25 | 6.3% | 2.75 | 0.01 | 0.4% |
| DyLight 649 (isomer 2)-TFP | 2.48 | 0.01 | 0.4% | 2.58 | 0.03 | 1.3% | 2.05 | 0.02 | 0.9% |
| 650 Compound 1 (isomer 2)-TFP | 3.68 | 0.07 | 2.0% | 3.89 | 0.04 | 0.9% | 2.42 | 0.03 | 1.3% |

|  | GAM (5X) | | | GAR (5X) | | | SA (4X) | | |
|---|---|---|---|---|---|---|---|---|---|
|  | Average | SD | % CV | Average | SD | % CV | Average | SD | % CV |
| 650 Compound 1-NHS | 3.36 | 0.12 | 3.7% | 3.51 | 0.15 | 4.1% | 2.40 | 0.03 | 1.2% |
| DyLight 649-NHS | 3.08 | 0.05 | 1.7% | 3.17 | 0.15 | 4.9% | 2.43 | 0.01 | 0.3% |

SD = standard deviation
% CV = % coefficient of variation

EXAMPLE 27

Performance of the dye-GAM conjugates and dye-GAR conjugates was evaluated in a functional assay. Wells of a 96 well white opaque plate were coated with mouse IgG, or rabbit IgG. One hundred µl mouse or rabbit IgG at a concentration of 10 µg/ml was applied to the corresponding wells in columns 1 and 2. The IgG proteins were serially diluted 1:1 from the wells in columns 2 to 11 using 100 µl PBS. One hundred 100 µl of the samples from the wells in column 11 were discarded. One hundred µl PBS was added to the wells in column 12. The plates were incubated overnight at 4° C. and then blocked 2×200 µl with Thermo Scientific SuperBlock® Blocking Buffer. The mouse IgG and rabbit IgG coated plates were washed 2×200 µl with PBS-Tween and 1×200 µl with PBS. Conjugates were diluted in PBS, then 4 µg/ml were added to the corresponding plates (100 µl/well) and then incubated for one hour in the dark. The plates were washed with 2×200 µl with PBS-Tween and 1×200 µl with PBS and filled with PBS buffer (100 µl/well) prior to scanning on Tecan Safire using the Alexa 647 setting (650 $nm_{excitation}$/665 $nm_{emission}$) and the DyLight 649 setting (654 $nm_{excitation}$/673 $nm_{emission}$ to detect fluorescence intensity As shown in FIGS. 29-42, the relative fluorescence units (RFU) and signal-to-background (S/B) ratios of the dyes were compared at various concentrations, using the indicated conjugation conditions. 650 Compound 1-GAM conjugates and 650 Compound 1-GAR conjugates had a higher signal to noise ratios compared to DyLight 649-GAM conjugates and DyLight 649-GAR conjugates, respectively, in the functional assay.

Figure 29:
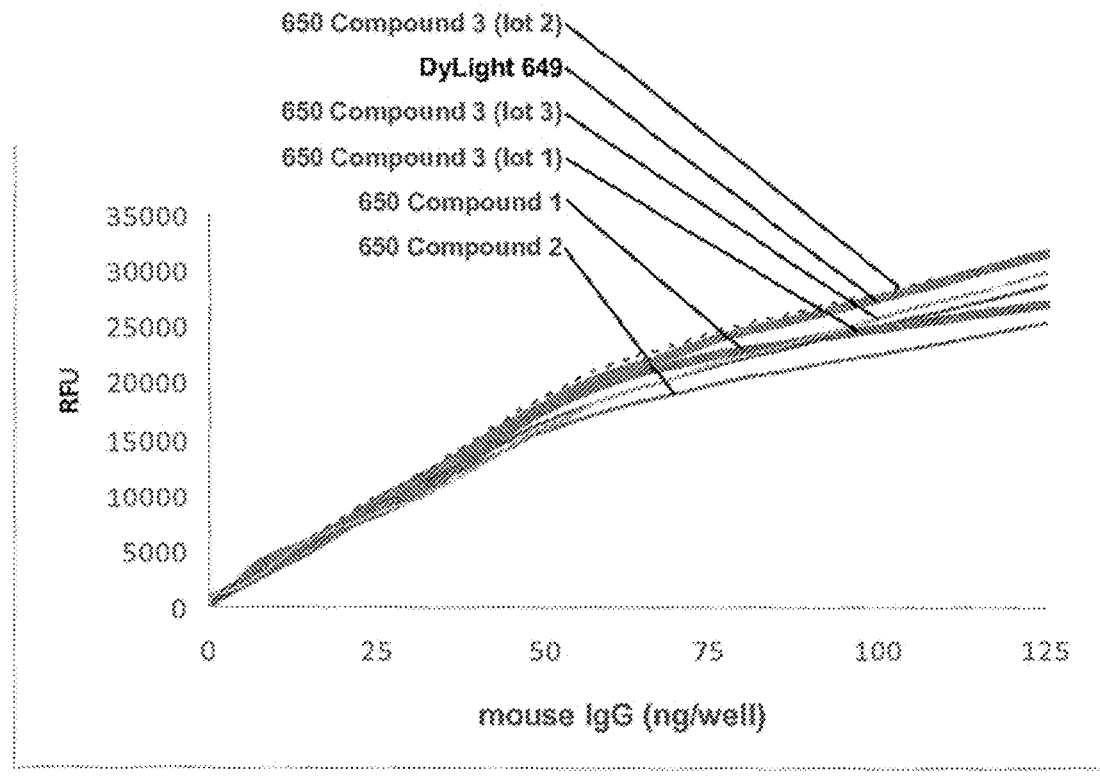
FIG. 29 shows functional assay results with one conjugate.

FIG. 29 shows results of a functional assay using GAM conjugated with a 5× molar excess of the commercial dyes and the inventive compounds (measurement of 650 $nm_{excitation}$/665 $nm_{emission}$) with conjugates purified by gel filtration. The relative fluorescence units (RFU) are shown for each of DyLight 649 (thick green line), 650 Compound 1 (thick blue line), 650 Compound 2 (thin pink line), 650 Compound 3 lot 1 (thin red line), 650 Compound 3 lot 2 (dashed red line), and 650 Compound 3 lot 3 (thin yellow line) were plotted as a function of the coated IgG amount (ng/well).

Figure 30:
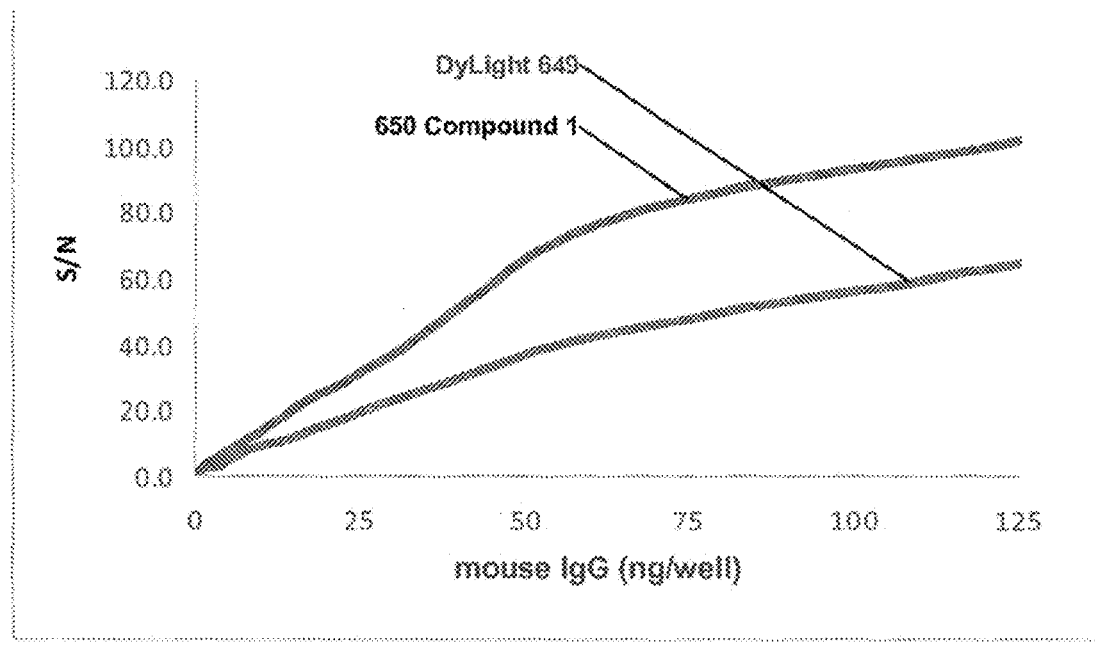
FIG. 30 shows results of the assay of FIG. 4 assay expressed as signal-to-noise.

FIG. 30 shows selected results from FIG. 29, expressed as signal-to-noise ratio (S/N) for DyLight 649 (green line) and 650 Compound 1 (blue line) plotted as a function of the amount of IgG per well (ng/well).

Figure 31:
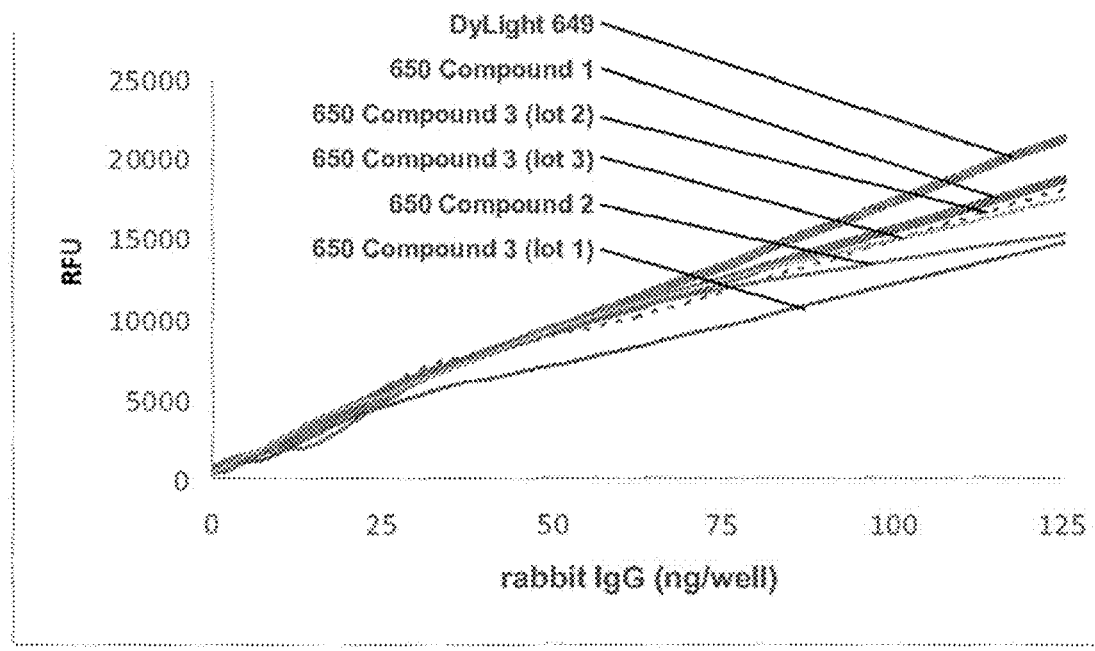
FIG. 31 shows functional assay results with one conjugate.

FIG. 31 shows results of a functional assay using GAR conjugated with 5× molar excess of the commercial dyes and the inventive compounds (measurement of 650 $nm_{excitation}$/665 $nm_{emission}$) with conjugates purified using PDRR. RFU are shown for each of DyLight 649 (thick green line), 650 Compound 1 (thick blue line), 650 Compound 2 (thin pink line), 650 Compound 3 lot 1 (thin red line), 650 Compound 3 lot 2 (dashed red line), and 650 Compound 3 lot 3 (thin yellow line) were plotted as a function of the amount of IgG per well (ng/well).

Figure 32:
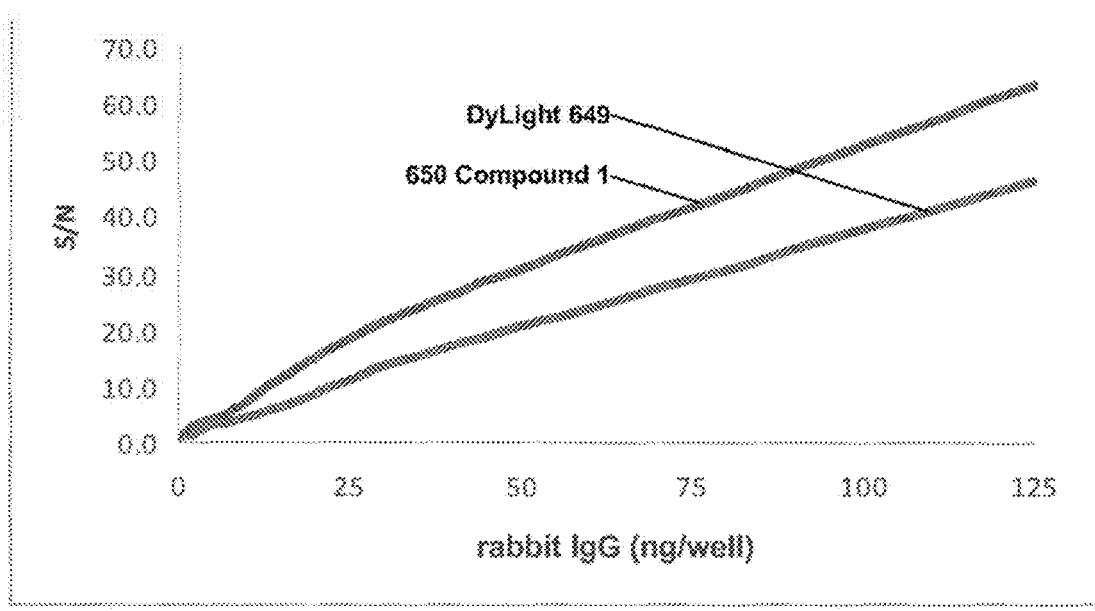
FIG. 32 shows results of the assay of FIG. 6 expressed as signal to noise.

FIG. 32 shows selected results from FIG. 31, expressed as signal to noise ratio (S/N) for Dylight 649 (green line) and 650 Compound 1 (blue line) plotted as a function of the IgG concentration per well (ng/well). S/N was calculated as described above.

Figure 33:
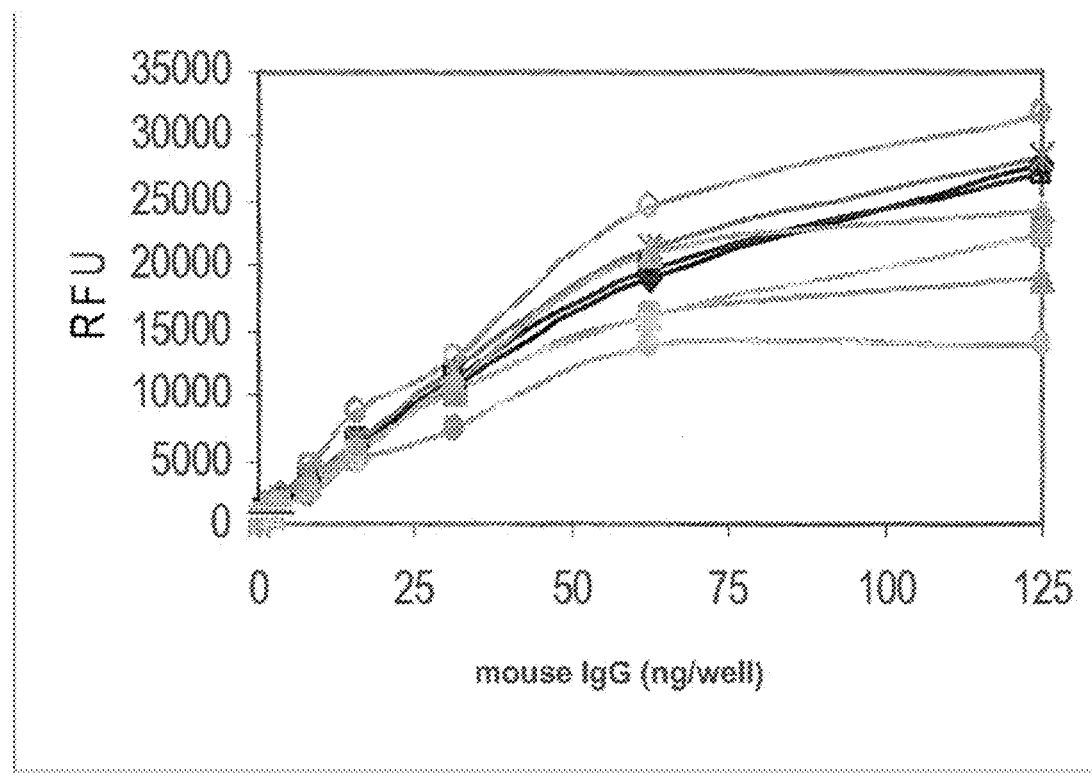
FIG. 33 shows functional assay results with some inventive compounds and commercial dyes.

FIG. 33 shows results of a functional assay using GAM conjugated with the following molar excesses of commercial dyes and the inventive compounds (measurement of 654 $nm_{excitation}$/673 $nm_{emission}$ with conjugates purified using PDRR. RFU are shown for DyLight 649 at each of 5× molar excess (solid black diamond), 10× molar excess (open blue square), 20× molar excess (solid blue triangle), 25× molar excess (solid blue circle), 650 Compound 1 at 5× molar excess (orange "X"), 650 Compound 1 at 10× molar excess (open orange circle), 650 Compound 1 at 20× molar excess (solid orange triangle), and 650 Compound 1 at 25× molar excess (solid beige square) were plotted as a function of the amount of coated IgG per well (ng/well).

Figure 34:
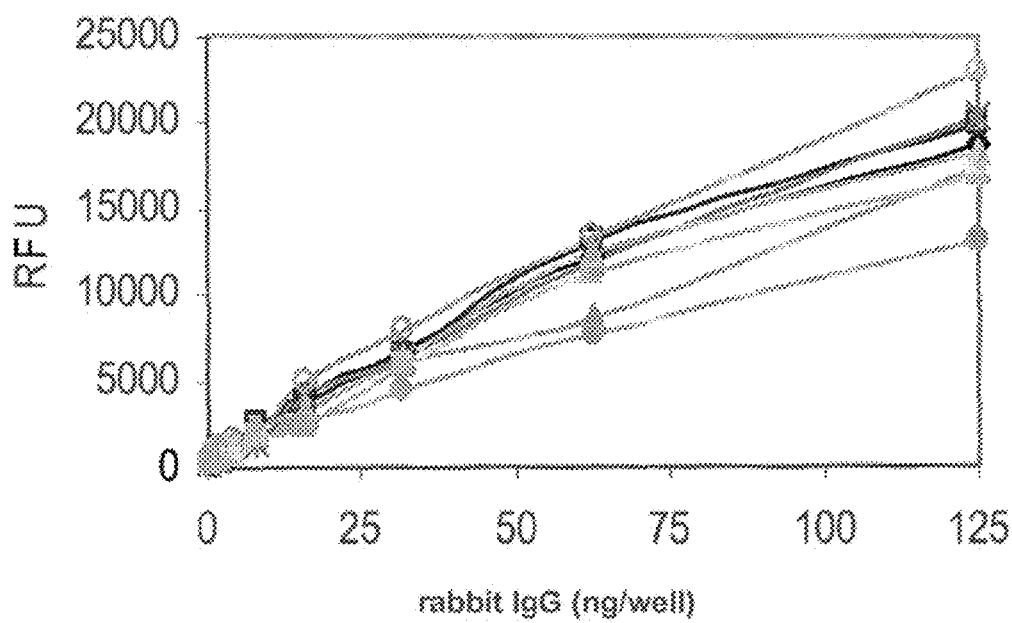
FIG. 34 shows functional assay results with some inventive compounds and commercial dyes.

FIG. 34 shows results of a functional assay using GAR conjugated with the following molar excesses of commercial dyes and the inventive compounds (measured at 650 $nm_{excitation}$/665 $nm_{emission}$) with conjugates purified using PDRR. RFU are shown for DyLight 649 at each of 5× molar excess (solid black diamond), 10× molar excess (open blue square), 20× molar excess (solid blue triangle), 25× molar excess (solid blue circle), 650 Compound 1 at 5× molar excess (red "X"), 650 Compound 1 at 10× molar excess (open orange circle), 650 Compound 1 at 20× molar excess (solid orange triangle), and 650 Compound 1 at 25× molar excess (closed beige square) were plotted as a function of the amount of coated IgG per well (ng/well).

Figure 35:
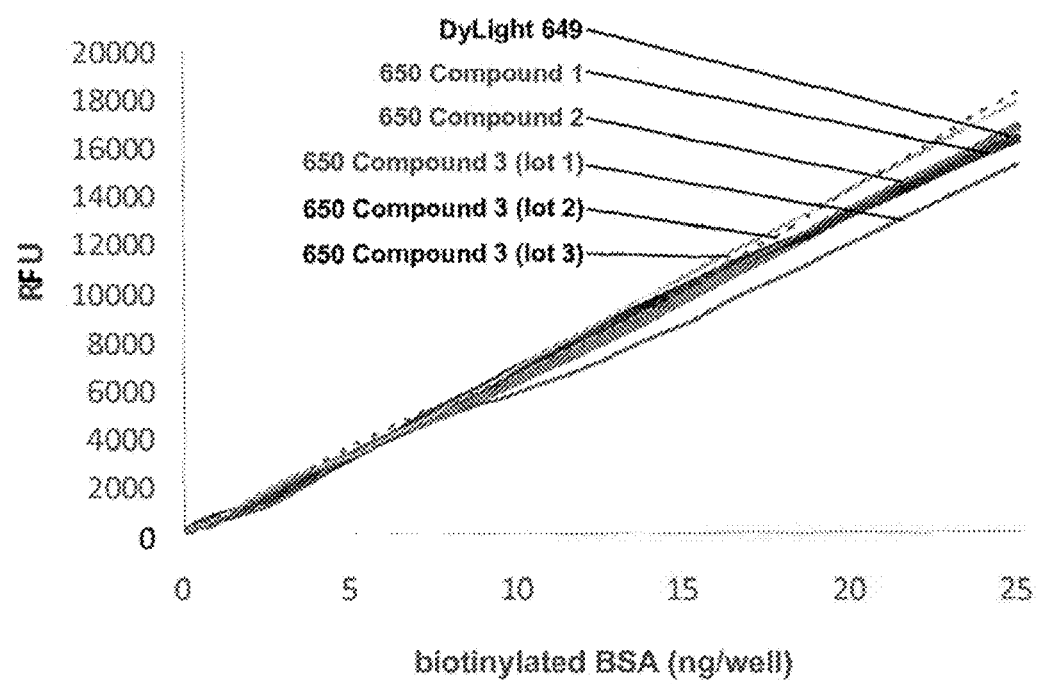
FIG. 35 shows functional assay results with some inventive compounds and commercial dyes.

FIG. 35 shows results of a functional assay using SA conjugated with 4× molar excess of commercial dyes and the inventive compounds (measured at 650 $nm_{excitation}$/665 $nm_{emission}$) with conjugates purified by gel filtration. RFU are shown for DyLight 649 (thick green line), 650 Compound 1 (thick blue line), 650 Compound 2 (solid light middle line at midpoint), 650 Compound 3 lot 1 (thin red line), 650 Compound 3 lot 2 (thin yellow line), and 650 Compound 3 lot 3 (dashed pink line) were plotted as a function of the biotinylated BSA amount per well (ng/well).

Figure 36:
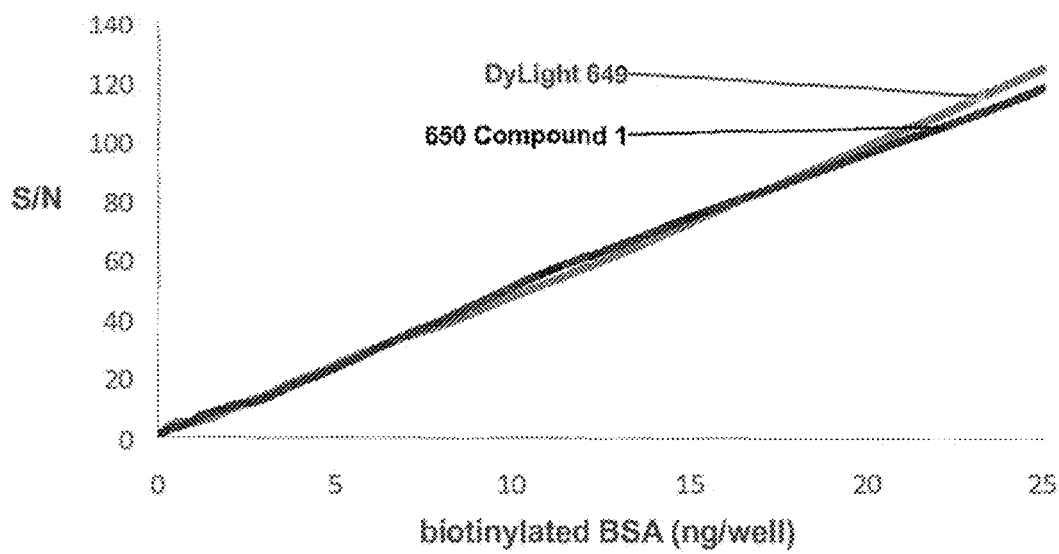
FIG. 36 shows results of the assay of FIG. 10 expressed as signal-to-noise.

FIG. 36 shows selected results from FIG. 35, expressed as S/N for DyLight 649 (green line) and compound 1 (blue line) plotted as a function of the biotinylated BSA amount per well (ng/well).

Conjugates prepared using TFP- and NHS-forms of the compounds were compared in a functional assay. Using the method described above, FIGS. 37-42 show the RFU and the signal-to-background ratio of the compounds compared at various binding target concentrations.

Figure 37:
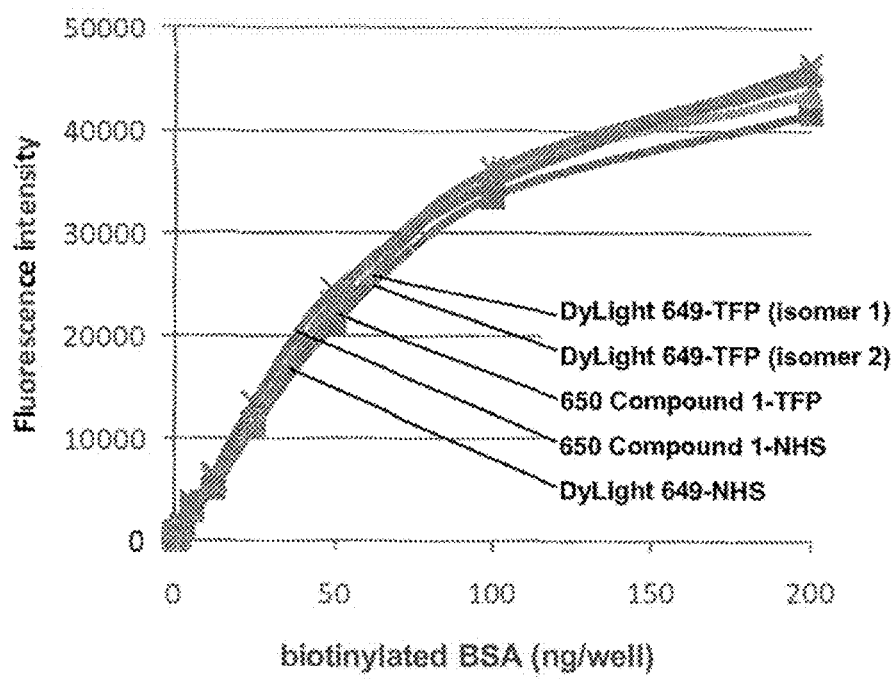
FIG. 37 shows functional assay results with some inventive compounds and commercial dyes.

FIG. 37 shows results in fluorescence intensity of a functional assay using SA conjugated with 4× molar excess of DyLight 649-TFP (isomer 1) (blue diamond), DyLight 649-TFP (isomer 2) (red square), 650 Compound 1-TFP (green triangle), 650 Compound 1-NHS (purple "X"), and DyLight 649-NHS (blue "X").

Figure 38:
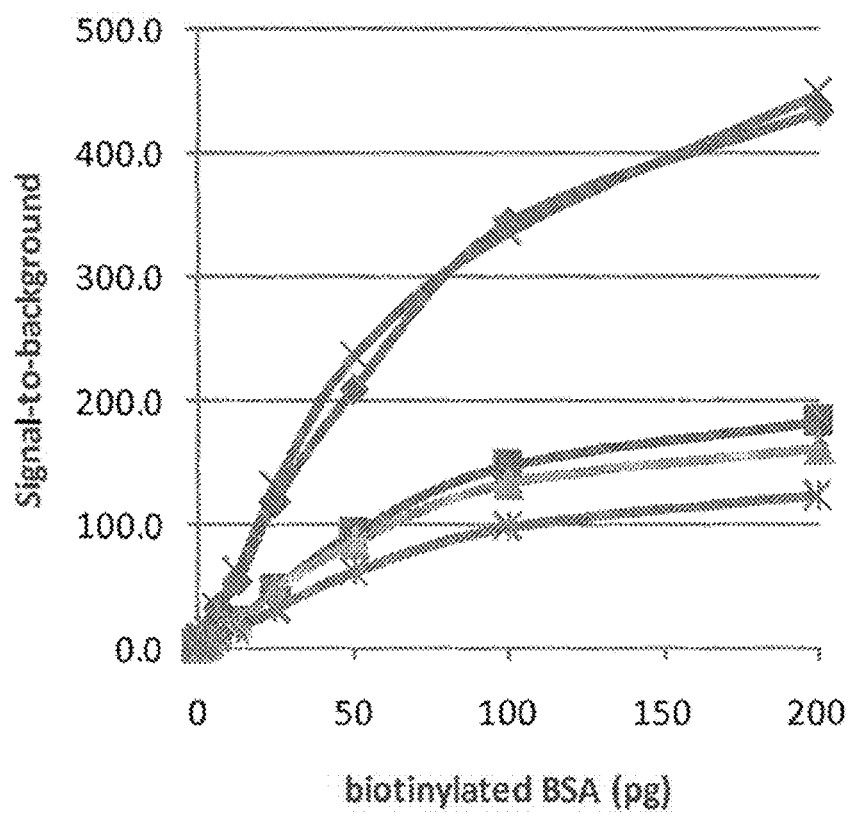
FIG. 38 shows functional assay results with some inventive compounds and commercial dyes.

FIG. 38 shows results in signal-to-background ratio of a functional assay using SA conjugated with 4× molar excess of DyLight 649-TFP (isomer 1) (blue diamond), DyLight 649-TFP (isomer 2) (red square), 650 Compound 1-TFP (green triangle), 650 Compound 1-NHS (purple "X"), and DyLight 649-NHS (blue "X").

Figure 39:
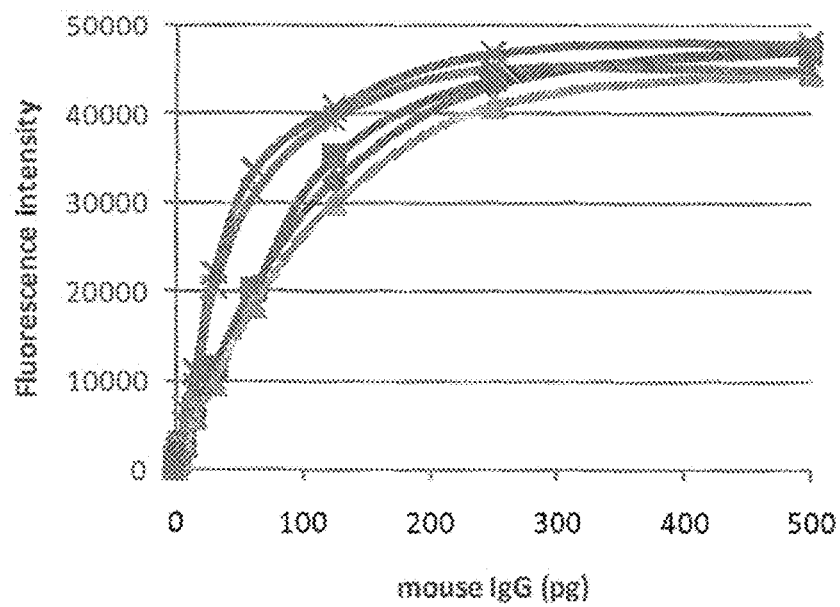
FIG. 39 shows functional assay results with some inventive compounds and commercial dyes.

FIG. 39 shows results in fluorescence intensity of a functional assay using GAM conjugated with 5× molar excess of DyLight 649-TFP (isomer 1) (blue diamond), DyLight 649-TFP (isomer 2) (red square), 650 Compound 1-TFP (green triangle), 650 Compound 1-NHS (purple "X"), and DyLight 649-NHS (blue "X").

Figure 40:
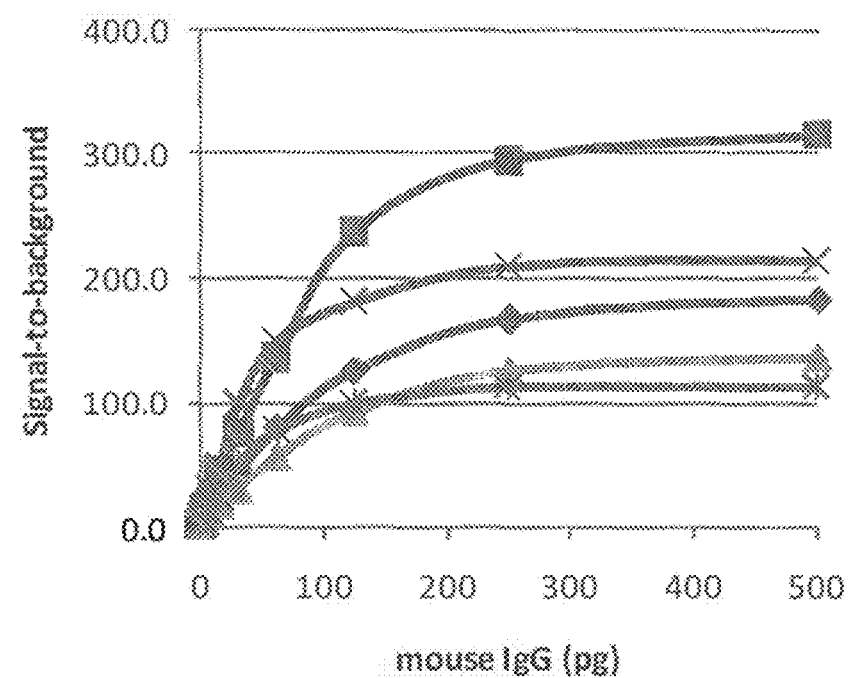
FIG. 40 shows functional assay results with some inventive compounds and commercial dyes.

FIG. 40 shows results in signal-to-background ratio of a functional assay using GAM conjugated with 5× molar excess of DyLight 649-TFP (isomer 1; blue diamond), DyLight 649-TFP (isomer 2; red square), 650 Compound 1-TFP (green triangle), 650 Compound 1-NHS (purple "X"), and DyLight 649-NHS (blue "X").

Figure 41:
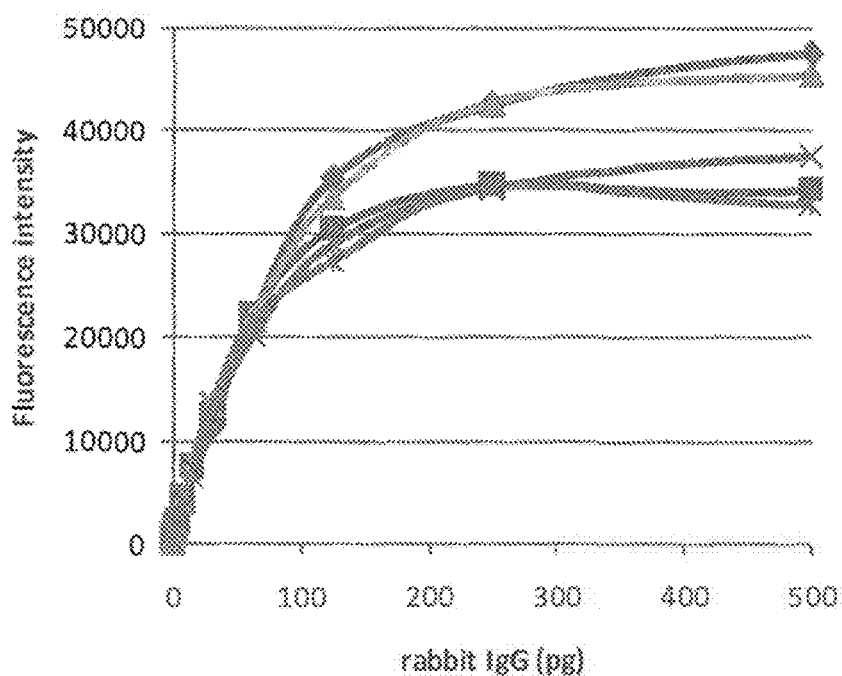
FIG. 41 shows functional assay results with some inventive compounds and commercial dyes.

FIG. 41 shows results in fluorescence intensity of a functional assay using GAR conjugated with 5× molar excess of DyLight 649-TFP (isomer 1; blue diamond), DyLight 649-TFP (isomer 2; red square), 650 Compound 1-TFP (green triangle), 650 Compound 1-NHS (purple "X"), and DyLight 649-NHS (blue "X").

Figure 42:
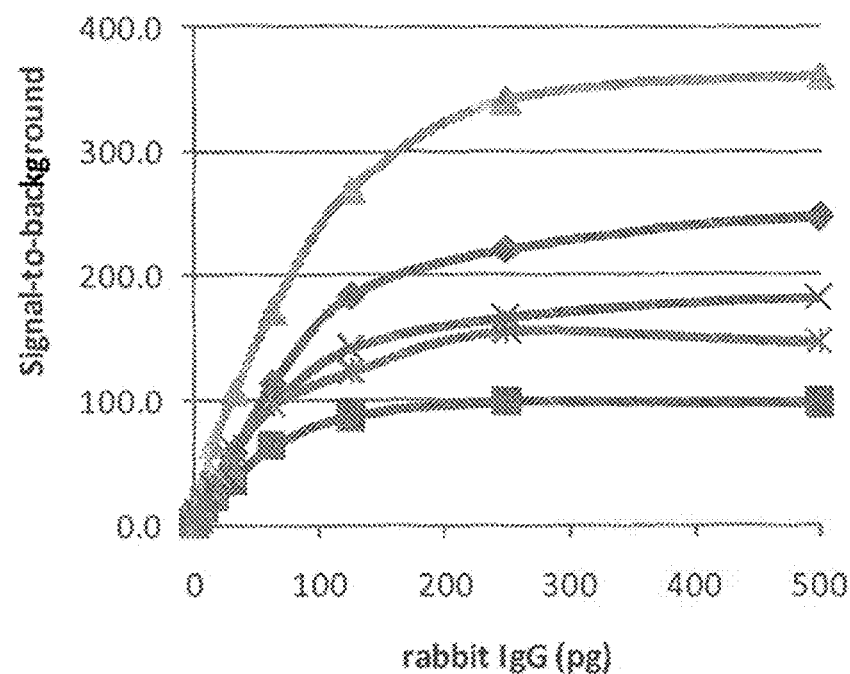
FIG. 42 shows functional assay results with some inventive compounds and commercial dyes.

FIG. 42 shows results in signal-to-background ratio of a functional assay using GAR conjugated with 5× molar excess of DyLight 649-TFP (isomer 1; blue diamond), DyLight 649-TFP (isomer 2; red square), 650 Compound 1-TFP (green triangle), 650 Compound 1-NHS (purple "X"), and DyLight 649-NHS (blue "X").

EXAMPLE 28

The inventive compounds and commercial dyes were evaluated for immunofluorescence in cell based assays using the following protocol. Plates containing A550 cells (adenocarcinoma human alveolar basal epithelial cells, P5, Sep. 23, 2010) and stored at −80° C. were placed at 50° C. for 30 min. The storage buffer (PBS) was removed and then the cells were permeabilized for 15 min (100 µl/well) with 0.1% Triton-X100 in 1×PBS buffer. The plates were blocked for 30 min in 2% BSA in 1×PBS-0.1% Triton-X100 and then incubated with primary antibodies diluted in 2% BSA in 1×PBS, 0.1% Trion-X100, overnight at 4° C. Mouse anti-lamin A (AbCam, diluted as suggested by the manufacturer), rabbit anti-lamin B (AbCam 1:100, 0.3 mg/ml)), or mouse anti-α-tubulin (AbCam, diluted as suggested by the manufacturer) was added to wells of half of the plate. The remaining wells were incubated in blocking buffer only (no primary antibody). After overnight incubation, the antibody solution was removed from the wells, and the plates were washed with PBS-Tween (2×100 µl/well). The labeled secondary antibody conjugates, diluted to 4 µg/ml in PBS were added to corresponding wells and incubated for 1 h at room temperature (about 20° C. to about 22° C.). The plates were washed 3×100 µl/well with PBS and Hoechst stain diluted 1 µg/ml in PBS were added to each well (100 µl/well) of each plate. The plates were then scanned on the Thermo Scientific ArrayScan® HCS Reader for imaging and quantitation.

As shown in the figures and in the following tables, compound 1 exhibited fluorescence that was similar to DyLight 649 dyes, a higher signal-to-background ratio, and a higher signal-to-noise ratio.

| Mouse α-tubulin | | |
|---|---|---|
| Conjugate, molar excess | Signal:Background | Signal:Noise |
| DyLight 649-GAM (commercial) | 52.6 | 12.1 |
| Alexa 647-GAM (freshly purchased from Molecular Probes) | 17.6 | 7.9 |
| DyLight 649-GAM 5X | 19.7 | 8.3 |
| DyLight 649-GAM 10X | 15.0 | 14.3 |
| DyLight 649-GAM 20X | 5.9 | 10.0 |
| DyLight 649-GAM 25X | 1.7 | 4.6 |
| 650 Compound 1-GAM 5X | 33.0 | 95.1 |
| 650 Compound 1-GAM 10X | 17.2 | 7.5 |
| 650 Compound 1-GAM 20X | 6.3 | 8.2 |
| 650 Compound 1-GAM 25X | 6.1 | 7.2 |

| Rabbit anti-lamin B1 | | |
|---|---|---|
| Conjugate, molar excess | Signal:Background | Signal:Noise |
| DyLight 649-GAR (commercial) | 56.9 | 4.4 |
| Alexa647-GAR (freshly purchased from Molecular Probes) | 28.7 | 6.8 |
| DyLight 649-GAR 5X | 44.6 | 12.5 |
| DyLight 649-GAR 10X | 29.0 | 5.5 |
| DyLight 649-GAR 20X | 7.6 | 21.0 |
| DyLight 649-GAR 25X | 5.1 | 7.8 |
| 650 Compound 1-GAR 5X | 36.5 | 8.9 |
| 650 Compound 1-GAR 10X | 46.5 | 11.6 |
| 650 Compound 1-GAR 20X | 20.2 | 48.7 |
| 650 Compound 1-GAR 25X | 8.0 | 4.5 |

Figure 43:
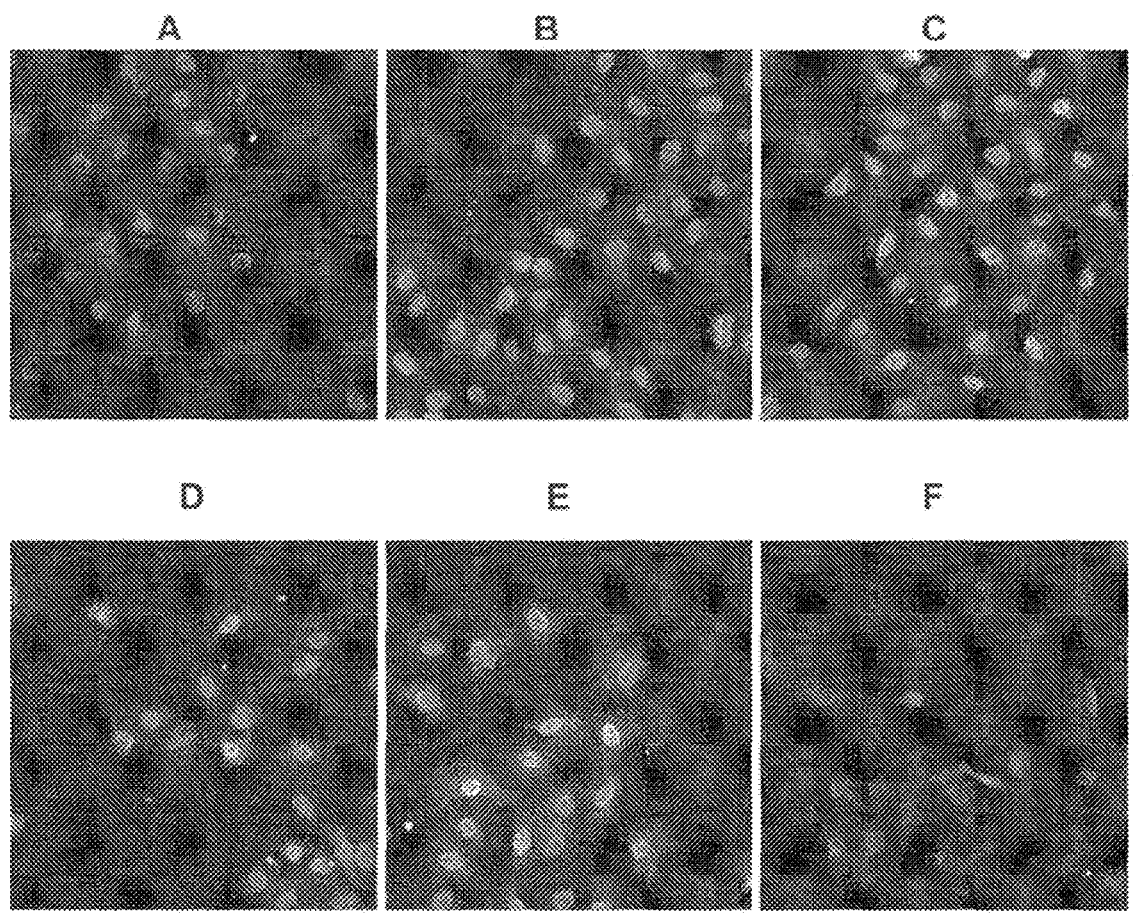
FIG. 43 shows immunofluorescence assay results with some inventive compounds and commercial dyes.

FIG. 43 shows results of an immunofluorescence assay using mouse anti-lamin A as a primary antibody, and commercial dyes and the inventive compounds conjugated to GAM (secondary antibody) at 2.5× molar excess, then purified by gel filtration. Immunofluorescence was obtained for DyLight 649 (A), 650 Compound 1 (B), 650 Compound 2 (C), 650 Compound 3 lot 2 (D), Alexa 647 (E), and Cy5 (F).

Figure 44:
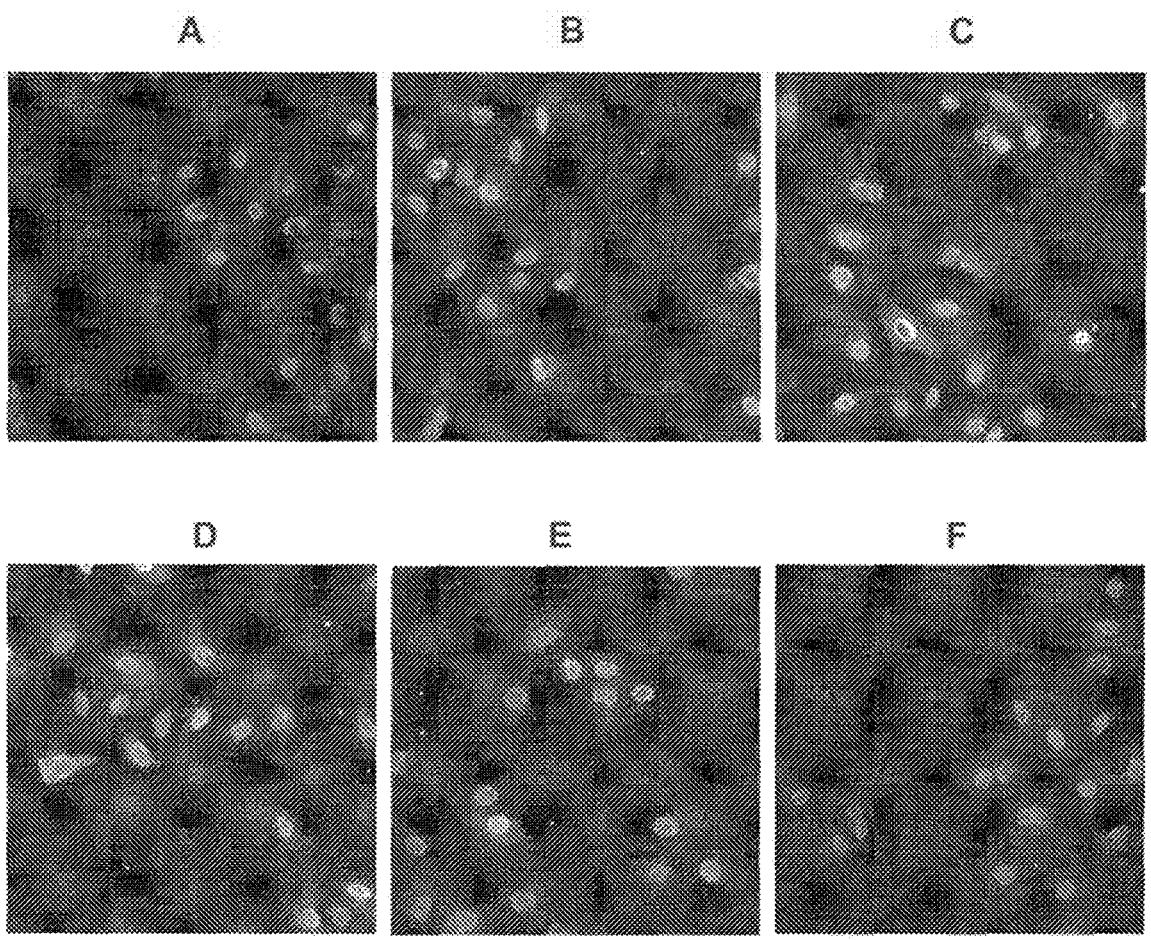
FIG. 44 shows immunofluorescence assay results with some inventive compounds and commercial dyes.

FIG. 44 shows results of an immunofluorescence assay using mouse anti-lamin A as a primary antibody, and commercial dyes and the inventive compounds conjugated to GAM (secondary antibody) at 5× molar excess, then purified by gel filtration. Immunofluorescence was obtained for DyLight 649 (A), 650 Compound 1 (B), 650 Compound 2 (C), 650 Compound 3 lot 2 (D), Alexa647 (E), and Cy5 (F).

Figure 45:
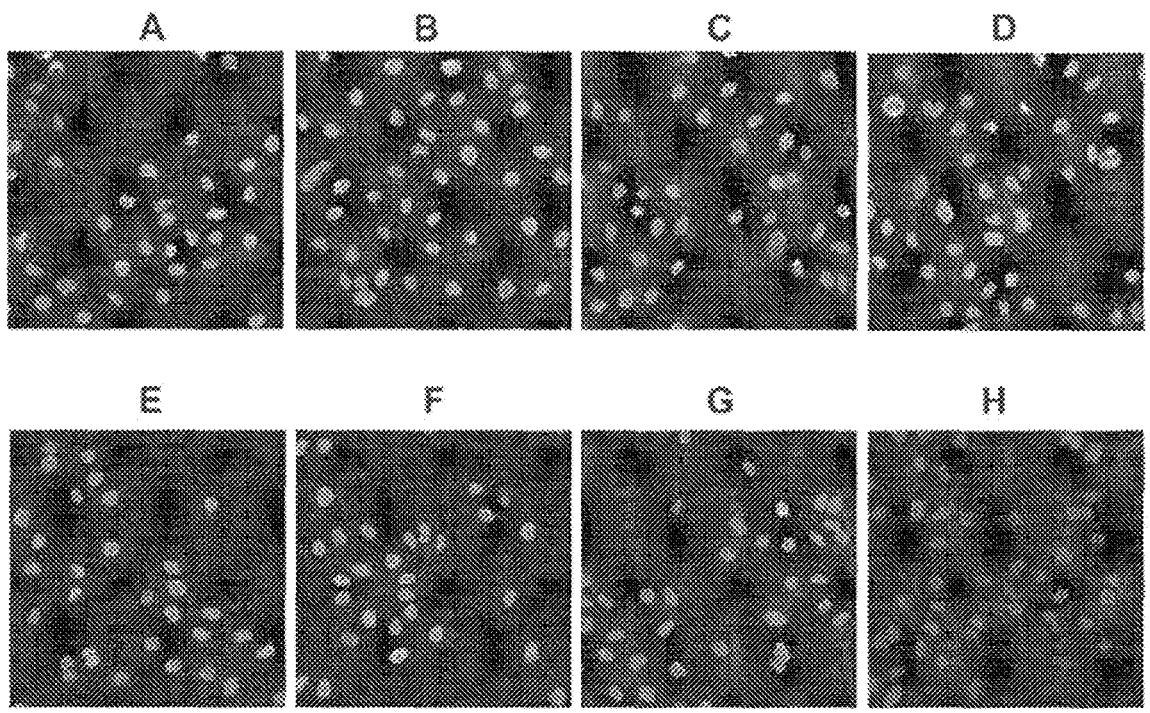
FIG. 45 shows immunofluorescence assay results with some inventive compounds and commercial dyes

FIG. 45 shows results of an immunofluorescence assay using rabbit anti-lamin B1 as a primary antibody, and commercial dyes and the inventive compounds conjugated to GAR (secondary antibody) at 5× molar excess, purified using PDRR. Immunofluorescence was obtained for DyLight 650 (A), compound 1 (B), compound 2 (C), compound 3 lot 1 (D), compound 3 lot 2 (E), compound 3 lot 3 (F), Alexa 647 (G), and Cy5 (H).

Figure 46:
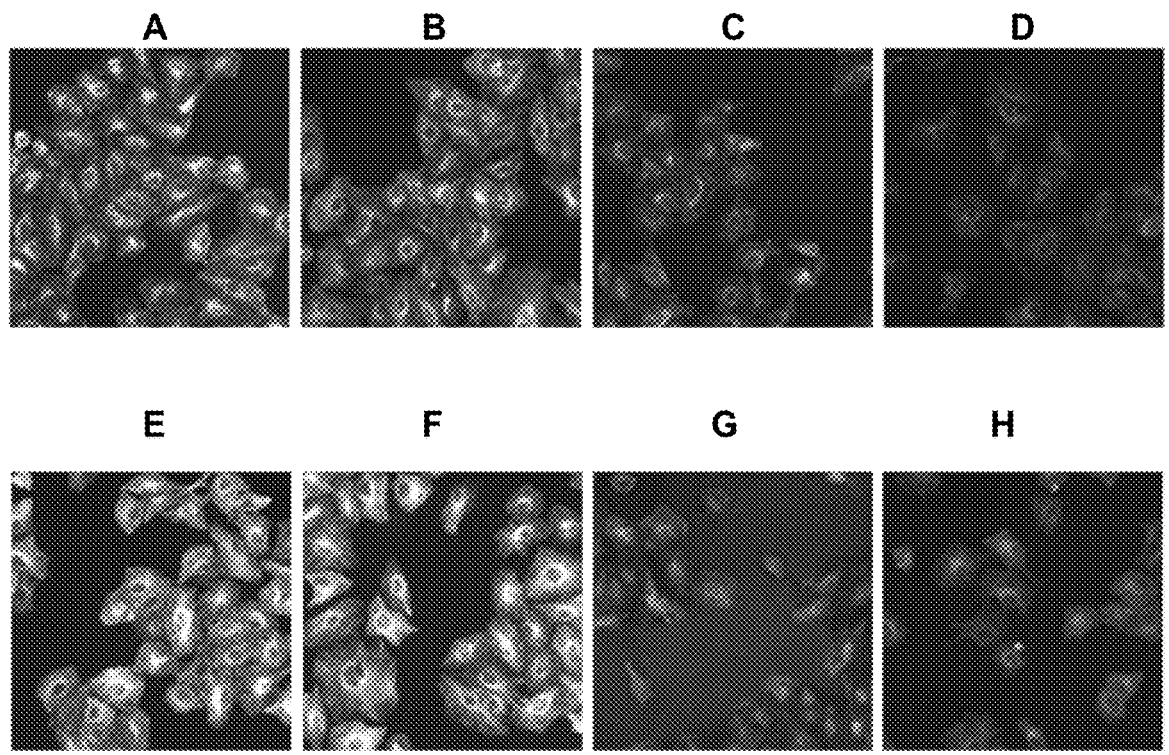
FIG. 46 shows immunofluorescence assay results with some inventive compounds and commercial dyes.

FIG. 46 shows results of an immunofluorescence assay using mouse anti-α tubulin as a primary antibody, and commercial dyes and the inventive compounds conjugated to GAM (secondary antibody) at different molar excess of each dye and compound, purified using PDRR. Immunofluorescence was obtained for DyLight 649 at each of 5× molar excess (A), 10× molar excess (B), 20× molar excess (C), 25× molar excess (D), 650 Compound 1 at 5× molar excess (E), 650 Compound 1 at 10× molar excess (F), 650 Compound 1 at 20× molar excess (G), and 650 Compound 1 at 25× molar excess (H).

The following table shows signal-to-background and signal-to-noise ratios determined from the results of FIG. 46.

| Conjugate, molar excess | Image | Signal:Background | Signal:Noise |
|---|---|---|---|
| DyLight 649-GAM 5X | A | 19.7 | 8.3 |
| DyLight 649-GAM 10X | B | 15 | 14.3 |
| DyLight 649-GAM 20X | C | 5.9 | 10 |
| DyLight 649-GAM 25X | D | 1.7 | 4.6 |
| 650 Compound 1-GAM 5X | E | 33 | 95.1 |
| 650 Compound 1-GAM 10X | F | 17.2 | 7.5 |
| 650 Compound 1-GAM 20X | G | 6.3 | 8.2 |
| 650 Compound 1-GAM 25X | H | 6.1 | 7.2 |

Figure 47:
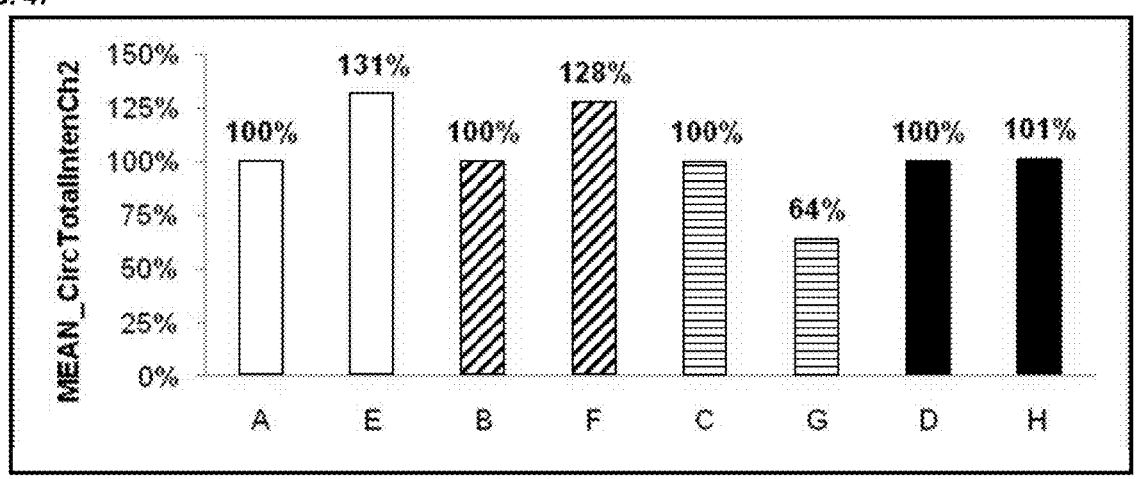
FIG. 47 shows quantitative analysis, expressed as normalized percent fluorescence intensity, of conjugates shown in FIG. 46.

FIG. 47 shows quantitative analysis, expressed as normalized percent fluorescence intensity, of GAM conjugates shown in FIG. 46. This normalized percent fluorescence intensity was the average total intensity of all pixels within a defined area or defined primary objected such as a nucleus, abbreviated as Mean Circ Total Intensity, using an ArrayScan HCS. The number of cells analyzed per well was set to 200 (variable from experiment to experiment depending on the cell density).

Figure 48:
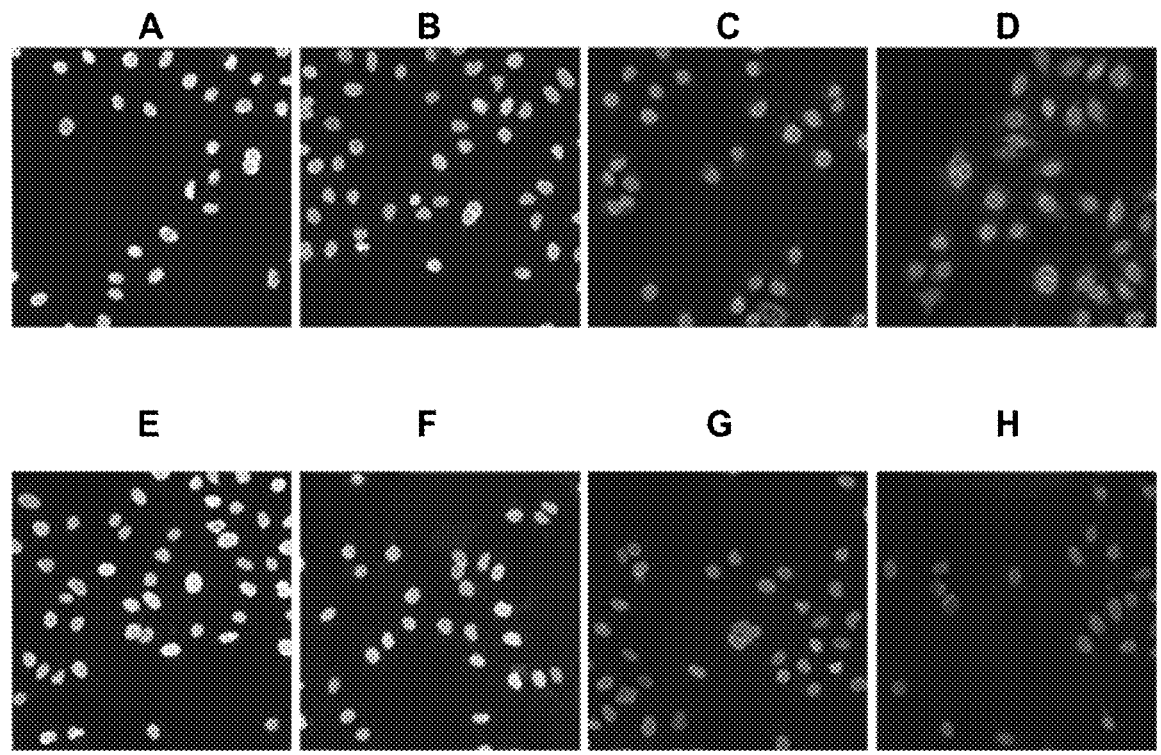
FIG. 48 shows immunofluorescence assay results with some inventive compounds and commercial dyes.

FIG. 48 shows results of an immunofluorescence assay with rabbit anti-lamin B1 as a primary antibody, and commercial dyes and the inventive compounds conjugated to GAR (secondary antibody) at different molar excess of each dye and compound, purified using PDRR. Immunofluorescence was obtained for DyLight 649 at each of 5× molar excess (A), 10× molar excess (B), 20× molar excess (C), 25× molar excess (D), 650 Compound 1 at 5× molar excess (E), 650 Compound 1 at 10× molar excess (F), 650 Compound 1 at 20× molar excess (G), and 650 Compound 1 at 25× molar excess (H).

The following table shows signal-to-background and signal-to-noise ratios determined from the results of FIG. 48.

| Conjugate, molar excess | Image | Signal:Background | Signal:Noise |
|---|---|---|---|
| DyLight 649-GAR 5X | A | 44.6 | 12.5 |
| DyLight 649-GAR 10X | B | 29.0 | 5.5 |
| DyLight 649-GAR 20X | C | 7.6 | 21.0 |
| DyLight 649-GAR 25X | D | 5.1 | 7.8 |
| 650 Compound 1-GAR 5X | E | 36.5 | 8.9 |
| 650 Compound 1-GAR 10X | F | 46.5 | 11.6 |
| 650 Compound 1-GAR 20X | G | 20.2 | 48.7 |
| 650 Compound 1-GAR 25X | H | 8.0 | 4.5 |

Figure 49:
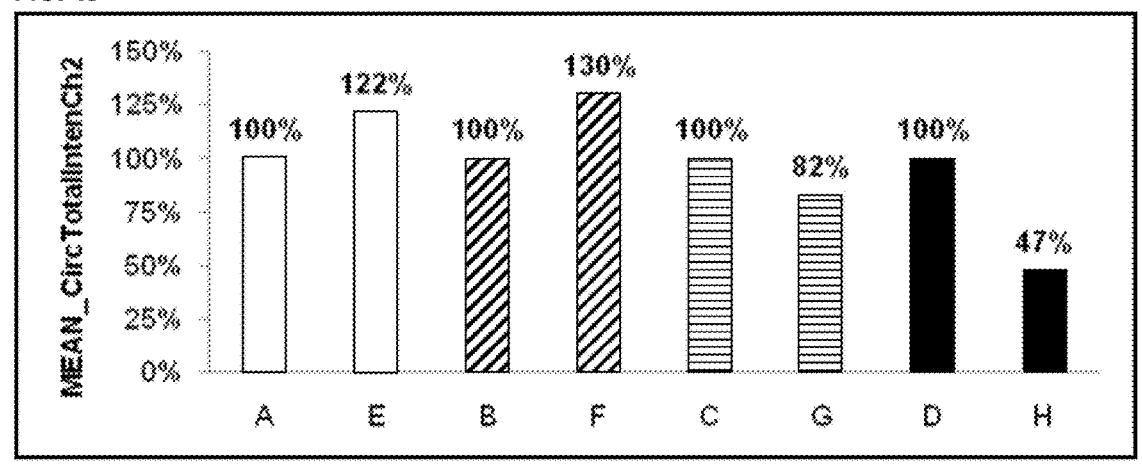
FIG. 49 shows quantitative analysis, expressed as normalized percent fluorescence intensity, of conjugates shown in FIG. 48.

FIG. 49 shows quantitative analysis, expressed as normalized percent fluorescence intensity, of GAM conjugates shown in FIG. 48. This normalized percent fluorescence intensity is the average total intensity of all pixels within a defined area or defined primary object such as a nucleus, abbreviated as Mean Circ Total Intensity, using an ArrayScan HCS. The number of cells analyzed per well was set to 200 (variable from experiment to experiment depending on the cell density).

Figure 50:
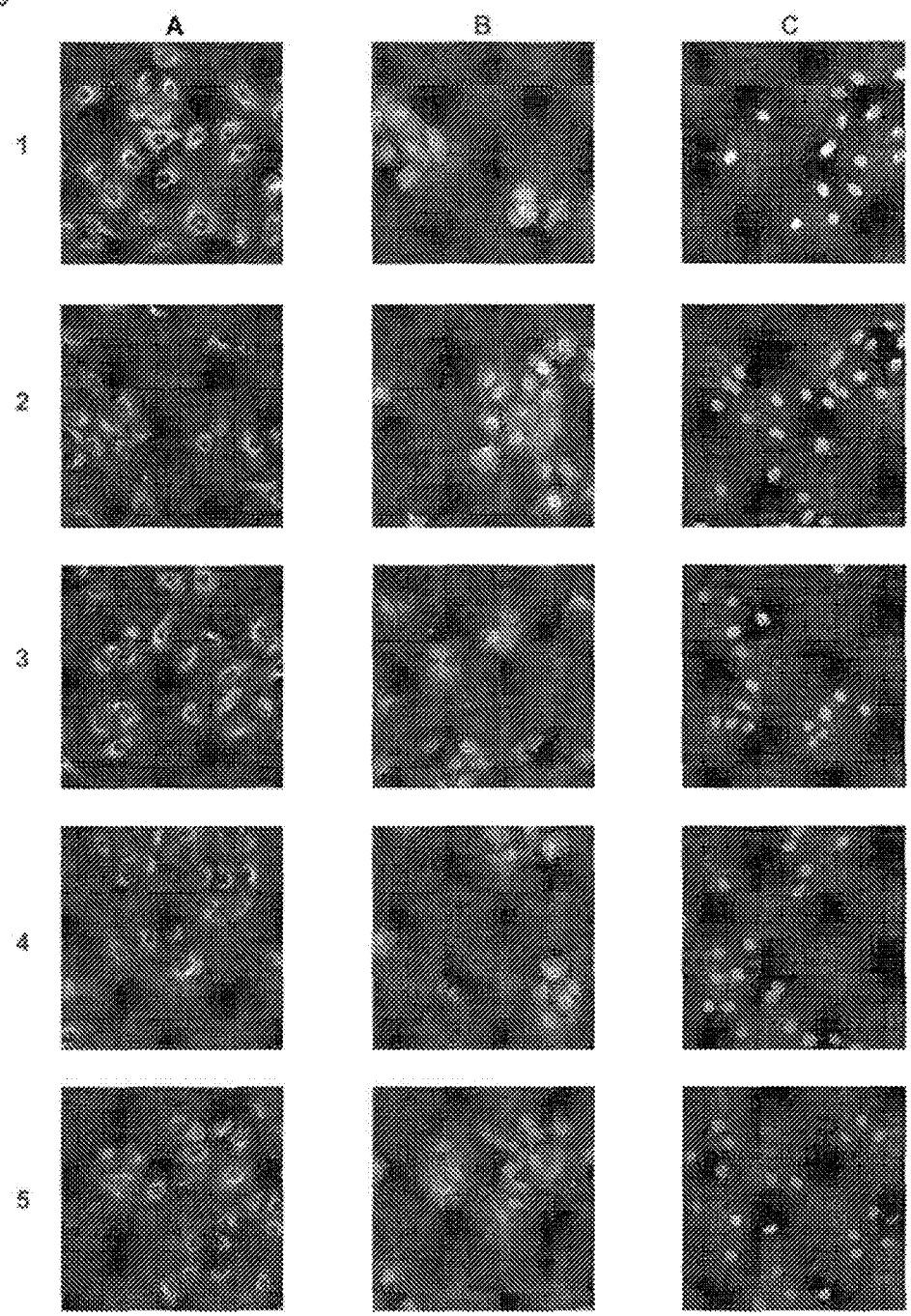
FIG. 50 shows immunofluorescence assay results with some inventive compounds and commercial dyes.

The inventive compounds and commercial dye having a TFP or NHS function were compared in an immunofluorescence cell based assay using the above protocol. As shown in FIG. 50, DyLight 649-TFP (isomer 1; 1A, 1B, and 1C), DyLight 649-TFP (isomer 2; 2A, 2B, and 2C), 650 Compound 1-TFP (isomer 2; 3A, 3B, and 3C), 650 Compound 1-NHS (4A, 4B, and 4C), and DyLight 649-NHS (5A, 5B, and 5C), where all A panels show results of a SA-conjugate, all B panels show results of a GAM-conjugate, and all C panels show results of a GAR-conjugate.

EXAMPLE 29

The inventive compounds were evaluated for stability compared to commercial dyes. All compounds were packed under argon as 1 mg portions in plastic vials. The vials sere sealed with a drying pad in an aluminium coated pouch, and then stored at 50° C. for 14 days. The results of the stability study for selected compounds are shown below:

| Dye | Amount | Purity at day 1 | Purity at day 14 |
|---|---|---|---|
| 650 Compound 1NHS | 1 mg | 97% | 97% |
| 650 Compound 1 TFP | 1 mg | 98% | 97% |

EXAMPLE 30

The inventive compounds and commercial dye were evaluated in direct fluorescence labeling of cell surface proteins. DyLight 649-NHS, 650 Compound 1-NHS, and Whole Cell Stain Orange (Thermo Fisher Scientific) were reconstituted in DMF and diluted to 6 µM in Dulbecco's PBS (DPBS). A total of four 1:1 serial dilutions of the dyes were prepared in DPBS. Frozen IMR90 cells (human lung embryonic fibroblast) on a plate were thawed for 1 h at 37° C. The cell plates were washed two times with DPBS and incubated with diluted dye for 30 min at room temperature, protected from light. The cell plates were then washed three times with DPBS. The cell plates were incubated with 100 µl/well of 1 µg/ml Hoechst dye in DPBS. The cell plates were sealed and imaged using the Thermo Scientific ArrayScan VTI HCS Reader.

Figure 51:
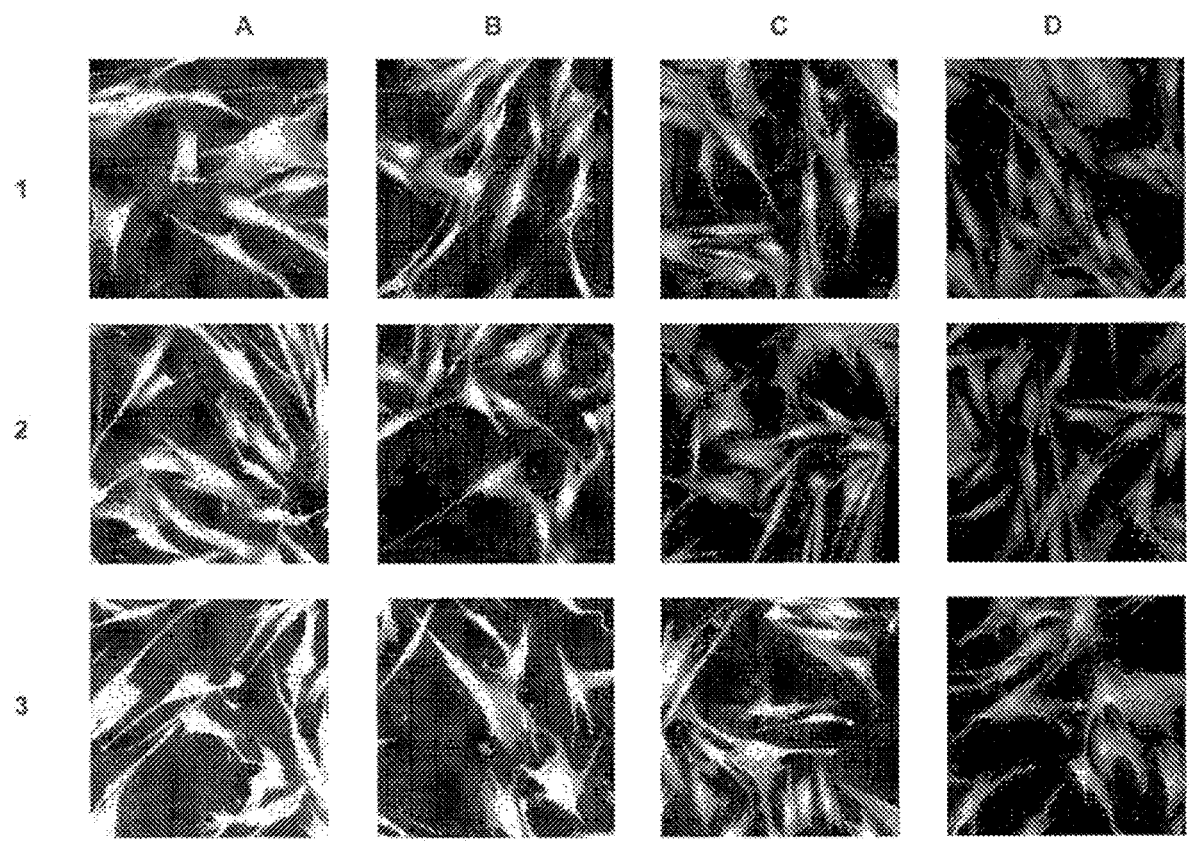
FIG. 51 shows results of direct fluorescence labeling of cell surface proteins with an inventive compound and commercial dyes.

As shown in FIG. 51, 650 Compound 1-NHS (row 3) performed equivalently as DyLight 649-NHS (row 2) and Whole Cell Stain Orange (row 1) at 6 µm (column A), 3 µm (column B), 1.5 µm (column C), and 0.75 µm (column D).

EXAMPLE 31

The inventive compounds are used for in vivo imaging to obtain information about biological tissues that are not readily accessible. The compounds are responsive to light in the near infrared (NIR) region of the spectrum, which is a part of the spectrum that has minimal interference from the absorbance of biological materials. In one embodiment, the compounds are used for fluorescent imaging of targets within animals. For example, in vivo imaging information can be obtained using methods such as X-ray, magnetic resonance imaging, positron emission tomography, ultrasound imaging and probing, and other non-invasive methods used for diagnosing and treating disease. Light in the NIR region, from about 650 nm to about 1000 nm wavelength, can permeate through several centimeters of tissue and therefore, can be used for in vivo imaging. Fluorescent dyes, such as the inventive compounds that are responsive to light in these longer wavelengths, can be used as conjugates with targeting molecules such as antibodies to bind and accumulate in, e.g., diseased tissue such as tumors, and may be used to distinguish healthy from diseased tissue. In some methods, the inventive compound may be attached to a biomolecule, such as a protein, peptide, or a drug, which is localized or retained in the desired tissue environment. Fluorescent in vivo imaging using NIR dyes such as the inventive compounds are diagnostic agents to discretely target disease tissue directly within animals or humans.

For in vivo imaging, the compound or a conjugate of the compound with a targeting agent, is administered to a tissue (e.g., intravenously), permitted to accumulate with excess compound removed by the circulatory system, then the tissue is irradiated with light at an appropriate wavelength. The NIR fluorescent light is recorded and/or an image is generated from the data obtained to specifically detect and visualize the targeted cells or tissues. The dose of compound administered can differ depending upon the specific tissue, application, etc., as long as the method achieves a detectable concentration of the compound in the tissue to be assessed.

EXAMPLE 32

In Vivo Imaging Using 650 Compound 1 (Isomer 1) Conjugated to anti-HER2 Antibody 650 Compound 1 (isomer 1)-NHS is conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for 1 h at room temperature to result in a 650 Compound 1 (isomer 1)-anti-HER2 conjugate.

The conjugation reaction is then subjected to PDDR to remove unlabeled (free) 650 Compound 1 (isomer 1). Ten microgram of the conjugate is injected intravenously (IV) to athymic mice bearing BT474 tumors. The animals are imaged over time at 1, 24, 48, 72, 96, and 120 hours post-injection using Pearl Imager from LI-COR Biosciences (LI-COR Instruments, Lincoln Nebr.).

Upon whole body imaging, fluorescence intensity is observed to be distributed over the whole animal during the first hour imagining and diminishes significantly at 72 hours. After 96 hours, the signal is localized and specific to the tumor.

EXAMPLE 33

In Vivo Imaging Using Either Monosulfonated or Disulfonated 650 Compound 1 (Isomer 1)

The compound may be rendered less hydrophilic, i.e., more hydrophobic, by altering the number of sulfonate groups. Fewer sulfonates render the compound more hydrophobic. In this embodiment, the compound may be more readily retained in a desired tissue or location if the appropriate number of sulfonates is determined. For example, compound penetration into cells is more efficient if fewer sulfonates are on the compound. The compound may contain one, two, three, or four sulfonate groups. Hydrophobic compounds are also known to more efficiently cross the cell membrane, and therefore are more desirable when the target of interest is located within the cell.

Alendronate, a compound that binds to, and is retained in, LNCap prostate cancer cells, is conjugated with disulfonated or monosulfonated 650 Compound 1 (isomer 1) by incubating a solution containing 1 mM disulfonated or monosulfonated 650 Compound 1 (isomer 1)-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 650 Compound 1 (isomer 1)-alendronate (5 nmole) is injected into the tumor. Control mice are injected with free 650 Compound 1 (isomer 1) containing a carboxylic acid residue instead of the reactive NHS ester. X-ray and near infra-red fluorescence images are captured.

Upon imaging the whole mouse, 650 Compound 1 (isomer 1)-alendroneate conjugate is retained in mouse tissue greater than the unconjugated compound; the conjugate is retained in the LNCap cell-induced tumor for at least 18 hrs.

EXAMPLE 34

In Vivo Imaging Using Either Monosulfonated or Disulfonated 650 Compound 1 (Isomer 1)

A drug delivery nanoparticle system conjugated with disulfonated or monosulfonated 650 Compound 1 (isomer 1) is prepared as followed. A solution containing 1 mM disulfonated or monosulfonated 650 Compound 1 (isomer 1)-NHS in 1 ml of PBS is incubated overnight at room temperature with 0.1 mM of an anti-cancer drug conjugated with transferrin in the form of a nanoparticle. The resulting 650 Compound 1 (isomer 1)-nanoparticle conjugate is purified by centrifugation, and then lyophilized.

The 650 Compound 1 (isomer 1)-nanoparticle conjugate (1 nmole) is injected intravenously into the tail vein of a mouse. Control mice are injected with free 650 Compound 1 (isomer 1) dye. X-ray and near infra-red fluorescence images of mouse brain are captured.

650 Compound 1 (isomer 1)-nanoparticle conjugate localizes in the mouse brain for greater than about 24 hours after injection. Tumor size progressively decreases after injection of 650 Compound 1 (isomer 1)-nanoparticle conjugate, compared to 650 Compound 1 (isomer 1)-nanoparticle without the anti-cancer drug.

EXAMPLE 35

The mono-sulfonated derivative could be on any one of six possible positions on the 650 compound, accounting for the stereochemistry around the carbon positions on the rings as well as the non-symmetrical nature of the two ends of each dye. Similarly, the di- and tri-substituted sulfonates could be on multiple possible positions on the inventive compounds.

EXAMPLE 36

Properties of 755 Compounds 1-NHS were compared with commercially available dyes, and shown below.

|  | DyLight 750-NHS | 755 Compound 1 (isomer 1)-NHS; 755 Compound 1 (isomer 2)-NHS | Alexa 750-NHS | Cy7 Mono ester |
|---|---|---|---|---|
| MW (g/mol) | 1034 | 1092.11 | ~1300 | 818.0 |
| Excitation (nm) | 752 | 754 | 755 | 747 |
| Emission (nm) | 778 | 776 | 775 | 776 |
| ε (M−1cm−1) | 220,000 | 220,000 | 240,000 | 200,000 |

The quantum yield (QY) was determined at an excitation wavelength of 710 nm for inventive and commercial compounds, as shown below.

|  | QY with excitation at 710 nm |
| --- | --- |
| 755 Compound 1 (isomer 1)-NHS | 0.119 |
| 755 Compound 1 (isomer 2)-NHS | 0.110 |
| DyLight 750-NHS (isomer 1) | 0.112 |
| DyLight 750-NHS (isomer 2) | 0.102 |
| Cy7-Mono NHS ester | 0.119 |
| Alexa Fluor 750-NHS | 0.108 |

QY measurements were performed in PBS using a Hamamatsu C9920 PL Absolute Quantum Yield Measurement System. The maximum absorbance at a 1 cm path length was set to 0.08.

Figure 52:
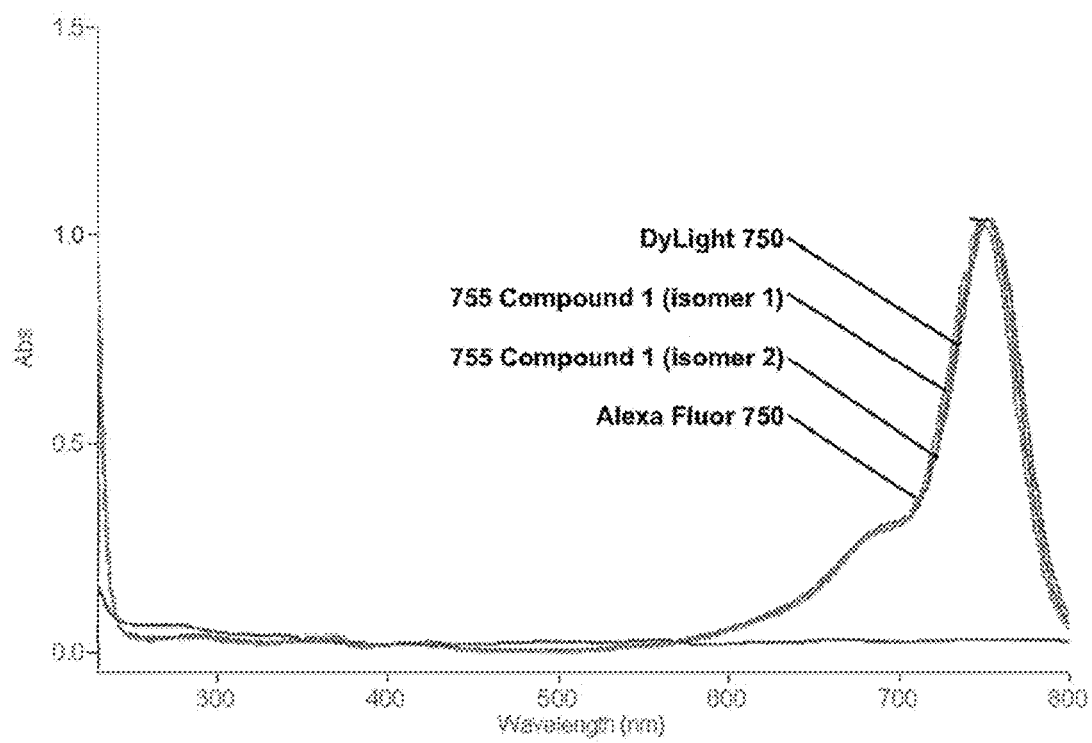
FIG. 52 shows absorption profiles of some inventive compounds and commercial dyes.

Absorption profiles for inventive and commercial compounds were determined, as shown in FIG. 52, where DyLight 750-NHS (red), 755 Compound 1 (isomer 1)-NHS (yellow), 755 Compound 1 (isomer 2)-NHS (blue), and Alexa Fluor 750-NHS (green) all showed very similar profiles (baseline (100% transmission)).

The maximum absorbance peak for DyLight 750 was 751 nm; the maximum absorbance peak for 755 Compound 1 (isomer 1) and (isomer 2) was 753 nm. The maximum absorbance peak (Abs max) in nm for inventive and commercial compounds conjugated to goat anti-mouse IgG (GAM), goat anti-rabbit IgG (GAR), and streptavidin (SA) are shown below:

|  | Abs max GAM | Abs max GAR | Abs max SA |
| --- | --- | --- | --- |
| DyLight 750 | 754-755 | 754-755 | 755 |
| 755 Compound 1 (isomer 1) | 755 | 755 | 761-763 |
| 755 Compound 1 (isomer 2) | 756-757 | 755-757 | 759-760 |
| Alexa 750 | 750-752 | 750-752 | 754 |

EXAMPLE 37

Inventive and commercial compounds, each as the NHS ester, were conjugated to goat anti-mouse (GAM) and goat anti-rabbit (GAR) antibodies, and streptavidin (SA). GAM, GAR, and SA, each at 10 mg/ml in phosphate buffered saline (PBS), were dialyzed against 50 mM borate buffer, pH 8.5. The compounds were reconstituted in dimethylformamide (DMF) at 10 mg/ml and combined at the indicated molar excess with GAM, GAR, or SA for 2 h at room temperature to label the antibodies and SA.

The labeled compounds, also termed dyes or labels, were subjected to PDDR to remove the unlabeled (free) compound; 100 µl of the packed resin was used per mg of protein purified. The purified antibody-labeled dyes were then diluted 1:50 in PBS and scanned for absorbance from 700 nm to 230 nm to determine the protein concentration, and to determine the mole dye to mole protein ratio (D/P). Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the Typhoon 9400 Imager to verify removal of the unconjugated compound. Labeling efficiency was compared for the dye/protein (D/P) conjugates, at the indicated molar excess, with results showing degree of labeling below.

| D/P | 2.5X | 5X | 7.5X | 10X | 15X |
| --- | --- | --- | --- | --- | --- |
| DyLight 750-GAM | 2.3 | 4.6 | 6.3 | 8.3 | 10.4 |
| 755 Compound 1 (isomer 1)-GAM | 2.3 | 4.3 | 5.8 | 7.6 | 10.0 |
| 755 Compound 1 (isomer 2)-GAM | 1.8 | 3.3 | 4.8 | 5.7 | 9.0 |
| Alexa 750-GAM | 2.1 | 4.0 | 5.7 | 7.3 | 9.9 |

| D/P | 2.5X | 5X | 7.5X | 10X | 15X |
| --- | --- | --- | --- | --- | --- |
| DyLight 750-GAR | 2.4 | 4.3 | 6.0 | 7.8 | 10.3 |
| 755 Compound 1 (isomer 1)-GAR | 2.0 | 4.5 | 5.7 | 7.2 | 9.8 |
| 755 Compound 1 (isomer 2)-GAR | 1.7 | 3.2 | 5.6 | 5.8 | 8.5 |
| Alexa 750-GAR | 2.2 | 4.0 | 5.6 | 7.4 | 10.0 |

| D/P | 3X | 5X |
| --- | --- | --- |
| DyLight 750-SA | 2.5 | 4.0 |
| 755 Compound 1 (isomer 1)-SA | 2.1 | 3.3 |
| 755 Compound 1 (isomer 2)-SA | 2.0 | 3.6 |
| Alexa 750-SA | 3.3 | 4.7 |

Labeling efficiency of GAM, GAR, and SA was slightly lower with 755 Compound 1 (isomer 1)-NHS and 755 Compound 1 (isomer 2)-NHS compared to DyLight 750-NHS, however 755 Compound 1 (isomer 1) showed better labeling, especially of antibodies, than 755 Compound 1 (isomer 2). Therefore, the inventive and commercial compounds exhibited comparable labeling efficiencies.

EXAMPLE 38

Performance of the dye-GAM conjugates, dye-GAR conjugates, and dye-SA conjugates was evaluated in a functional assay. Wells of a 96 white opaque plate were coated with target proteins mouse IgG immunoglobulin, rabbit IgG immunoglobulin, or biotinylated bovine serum albumin (BBSA). One hundred µl mouse or rabbit IgG, or BBSA, each at 10 µg/ml was applied to the corresponding wells in columns 1 and 2. Target proteins were serially diluted 1:1 from the wells in columns 2 to 11 using 100 µl PBS. One hundred 100 µl of the samples from the wells in column 11 were discarded. One hundred µl PBS was added to the wells in column 12. The plates were incubated overnight at 4° C. and then blocked 2×200 µl with Thermo Scientific Super-Block® Blocking Buffer. The coated plates were washed 2×200 µl with PBS-Tween and 1×200 µl with PBS. Conjugates diluted in PBS to 4 µg/ml were added to the corresponding plates (100 µl/well) and then incubated for 1 h in the dark. The plates were washed with 2×200 µl with PBS-Tween and 1×200 µl with PBS and filled with PBS buffer (100 µl/well) prior to scanning on Tecan Safire using 754 $nm_{excitation}$/776 $nm_{emission}$, or on LICOR Odyssey using the "800" channel, to detect fluorescence intensity.

As shown in FIGS. 53-81, the relative fluorescence units (RFU), raw intensity, or signal-to-background ratio (S/B) of dyes were compared at various concentrations of mouse IgG (MsIgG), rabbit IgG (RbIgG), or biotinylated bovine serum albumin (BBSA), using the indicated conjugation conditions.

Figure 53:
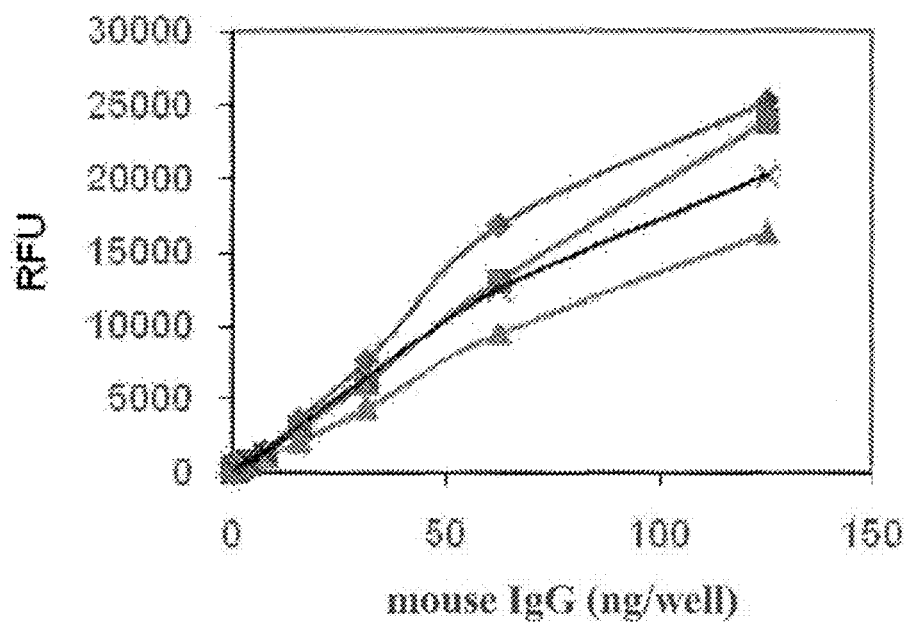
FIG. 53 shows functional assay results with some inventive compounds and commercial dyes.

FIG. 53 shows results of a functional assay, measured on Tecan Safire, using GAM conjugated with 2.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 54:
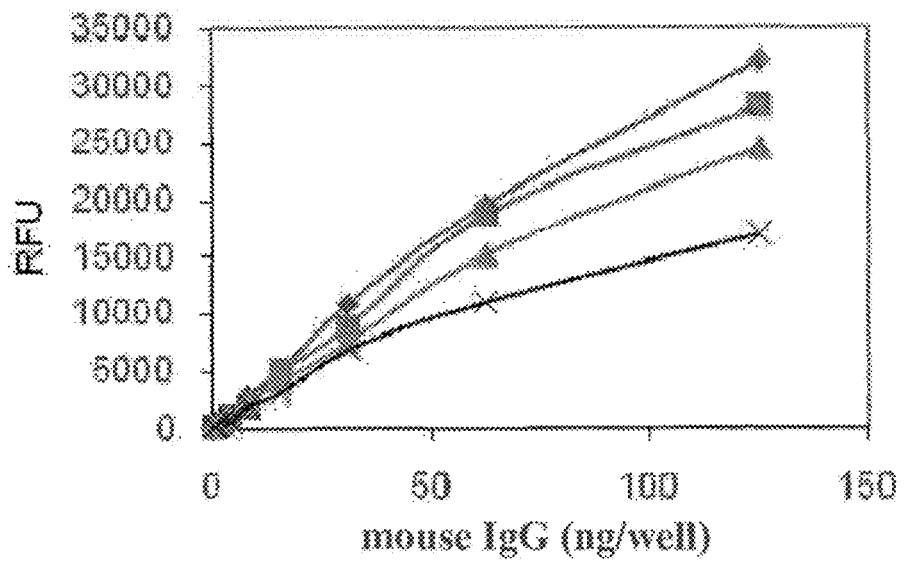
FIG. 54 shows functional assay results with some inventive compounds and commercial dyes.

FIG. 54 shows results of a functional assay, measured on Tecan Safire, using GAM conjugated with 7.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 55:
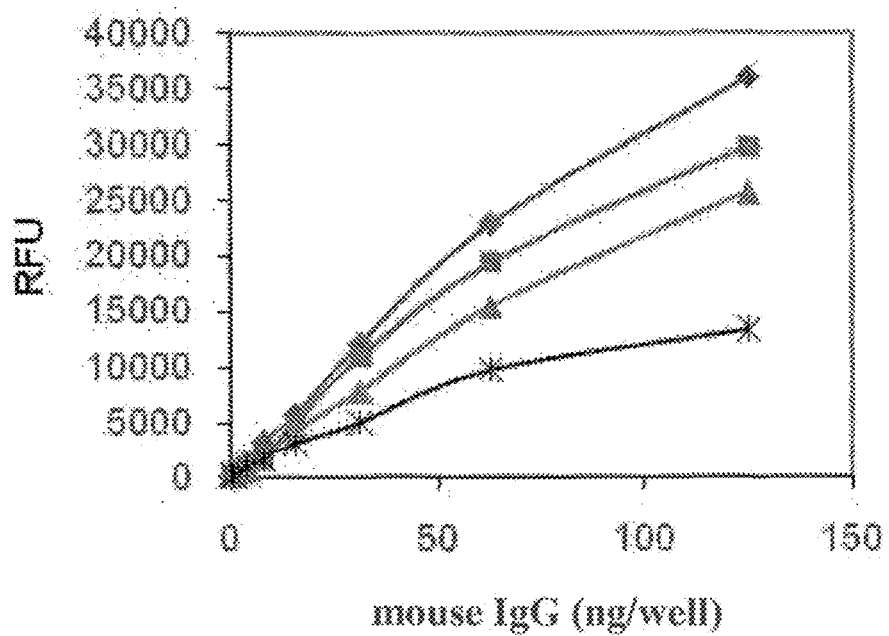
FIG. 55 shows functional assay results with some inventive compounds and commercial dyes.

FIG. 55 shows results of a functional assay, measured on Tecan Safire, using GAM conjugated with 10× molar excess of the dyes DyLight 750 (blue diamond); 755 Compound 1 (isomer 1) (red square); 755 Compound 1 (isomer 2) (green triangle); and Alexa Fluor 750 (black "X").

Figures 56, 57:
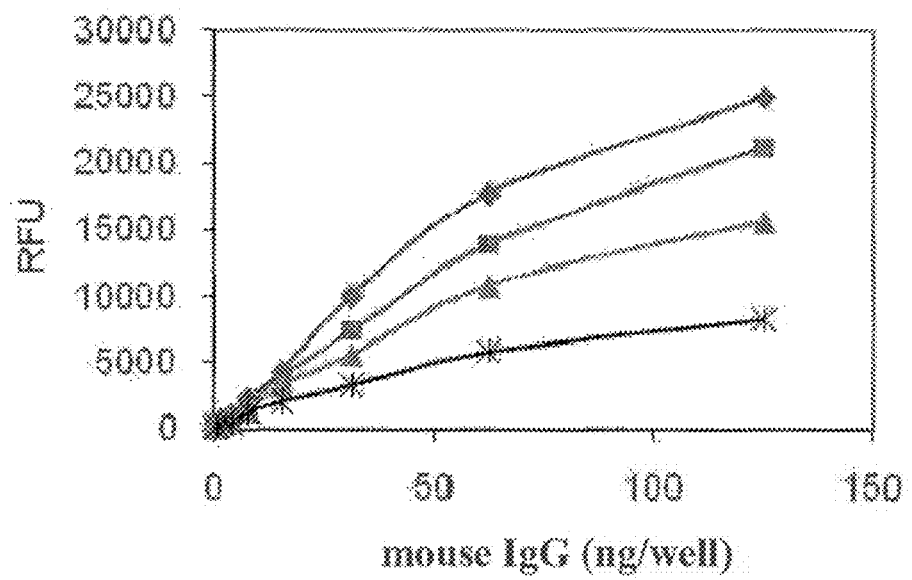
FIG. 56 shows functional assay results with some inventive compounds and commercial dyes.
FIG. 57 shows signal-to-background ratio of a functional assay with some inventive compounds and commercial dyes.

FIG. 56 shows results of a functional assay, measured on Tecan Safire, using GAM conjugated with 15× molar excess of the dyes DyLight 750 (blue diamond); 755 Compound 1 (isomer 1) (red square); 755 Compound 1 (isomer 2) (green triangle); and Alexa Fluor 750 (black "X").

FIG. 57 shows signal-to-background ratio (S/B) at 125 ng mouse IgG results of a functional assay using GAM conjugated with 2.5×, 7.5×, 10×, or 15× molar excess of NHS ester containing dyes. Inventive compounds showed similar performance to DyLight 750-NHS in the plate assay with slightly lower S/B, and showed better performance than Alexa Fluor 750 at higher molar excesses. All dyes exhibited signal quenching at 10× and 15× molar excesses.

Figure 58:
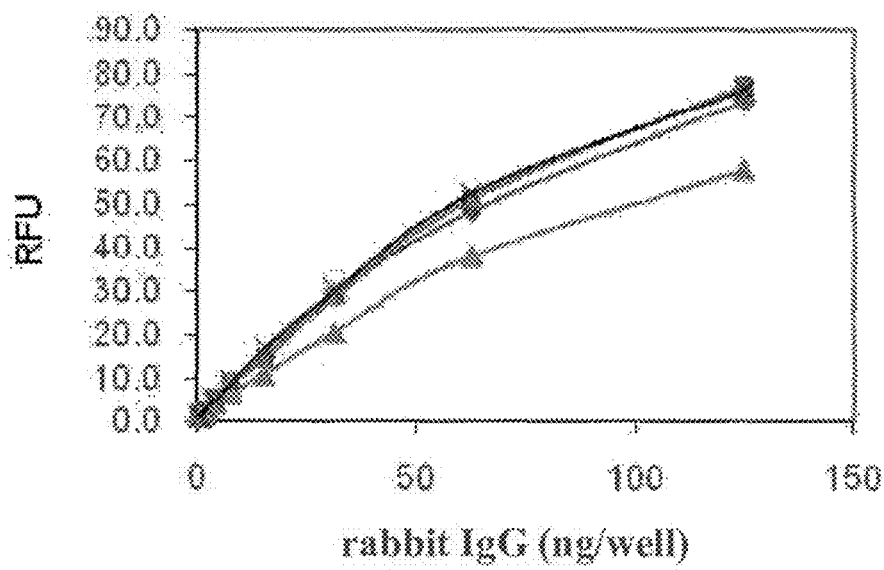
FIG. 58 shows functional assay results with some inventive compounds and commercial dyes.

FIG. 58 shows results of a functional assay, measured on Tecan Safire, using GAR conjugated with 2.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 59:
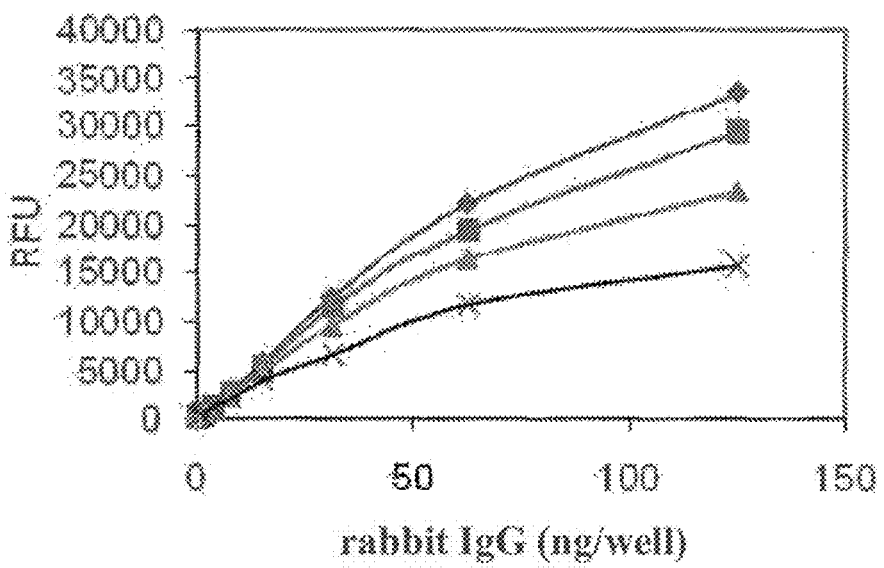
FIG. 59 shows functional assay results with some inventive compounds and commercial dyes.

FIG. 59 shows results of a functional assay, measured on Tecan Safire, using GAR conjugated with 7.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 60:
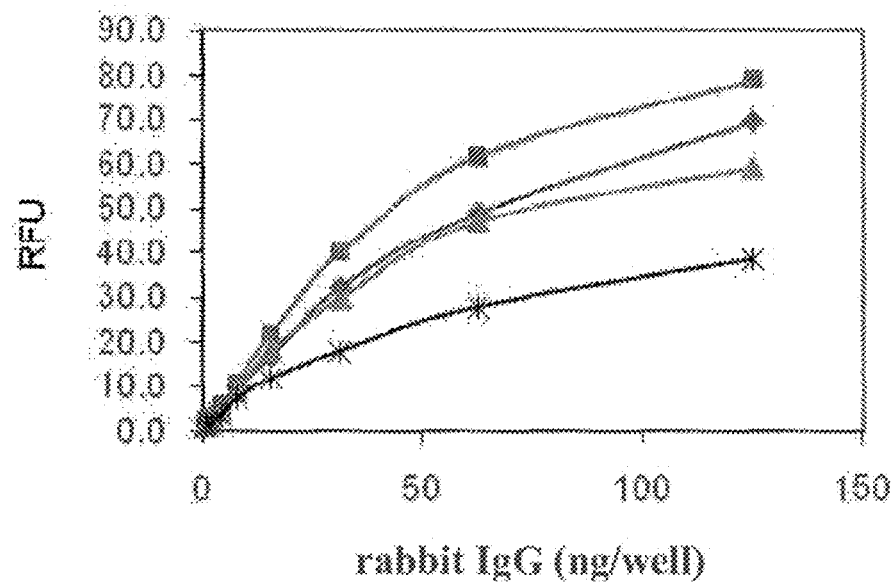
FIG. 60 shows functional assay results with some inventive compounds and commercial dyes.

FIG. 60 shows results of a functional assay, measured on Tecan Safire, using GAR conjugated with 10× molar excess of the dyes DyLight 750 (blue diamond); 755 Compound 1 (isomer 1) (red square); 755 Compound 1 (isomer 2) (green triangle); and Alexa Fluor 750 (black "X").

Figure 61:
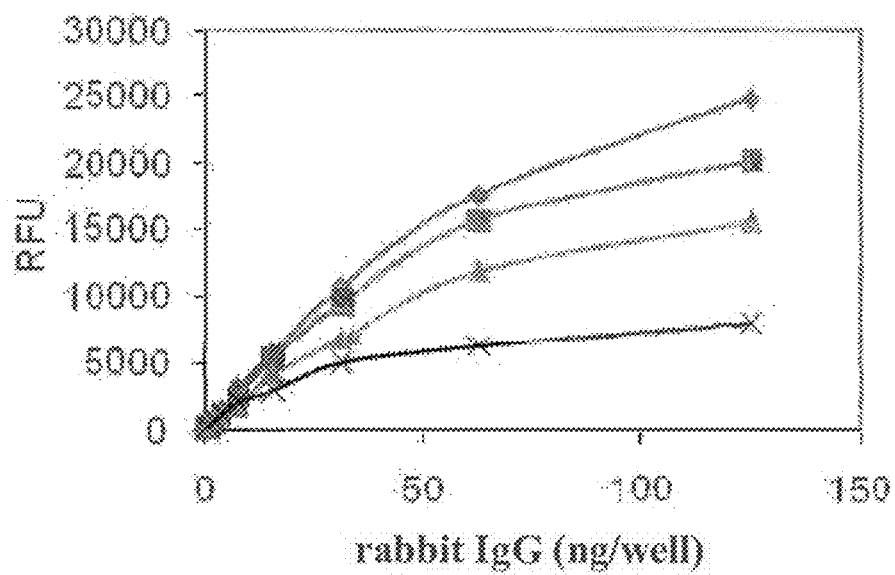
FIG. 61 shows functional assay results with some inventive compounds and commercial dyes.

FIG. 61 shows results of a functional assay, measured on Tecan Safire, using GAR conjugated with 15× molar excess of the dyes DyLight 750 (blue diamond); 755 Compound 1 (isomer 1) (red square); 755 Compound 1 (isomer 2) (green triangle); and Alexa Fluor 750 (black "X").

Figures 62, 63:
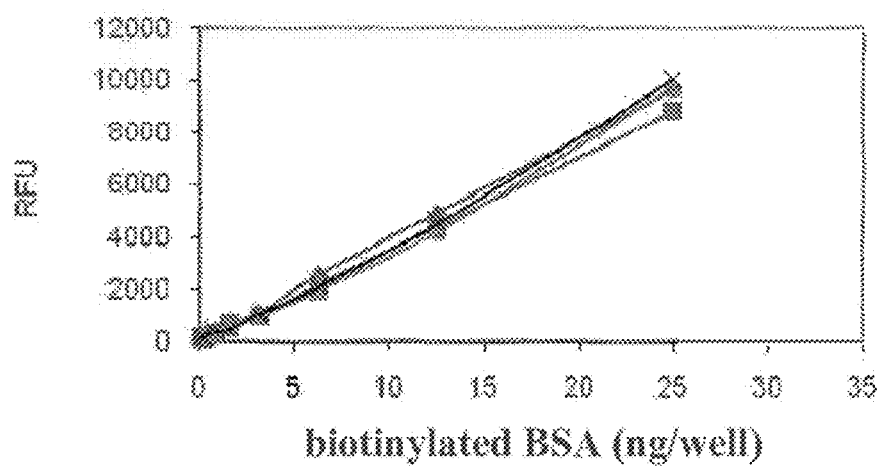
FIG. 62 shows signal-to-background ratio of a functional assay with some inventive compounds and commercial dyes.
FIG. 63 shows functional assay results with some inventive compounds and commercial dyes.

FIG. 62 shows signal to background ratio (S/B) at 125 ng rabbit IgG) results of a functional assay using GAR conjugated with 2.5×, 7.5×, 10×, or 15× molar excess of NHS ester containing dyes. Inventive compounds showed similar performance to DyLight 750-NHS in the plate assay with slightly lower S/B, and showed better performance than Alexa Fluor 750 at higher molar excesses. All dyes exhibited signal quenching at 10× and 15× molar excesses.

755 Compound 1 (isomer 1)-GAR showed similar binding intensity to DyLight 750-GAR (2.5× condition) and increased intensity compared to DyLight 750-GAR (10× condition). All dyes exhibited signal quenching at 15× molar excess.

FIG. 63 shows results of a functional assay, measured on Tecan Safire, using SA conjugated with 3× molar excess of the dyes DyLight 750 (blue diamond); 755 Compound 1 (isomer 1) (red square); 755 Compound 1 (isomer 2) (green triangle); and Alexa Fluor 750 (black "X").

Figures 64, 65:
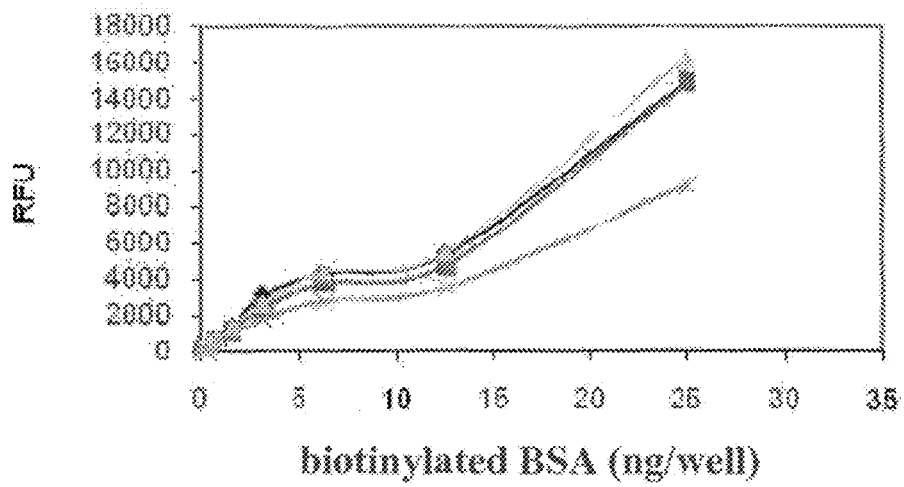
FIG. 64 shows functional assay results with some inventive compounds and commercial dyes.
FIG. 65 shows signal-to-background ratio of a functional assay with some inventive compounds and commercial dyes.

FIG. 64 shows results of a functional assay, measured on Tecan Safire, using SA conjugated with 5× molar excess of the dyes DyLight 750 (blue diamond); 755 Compound 1 (isomer 1) (red square); 755 Compound 1 (isomer 2) (green triangle); and Alexa Fluor 750 (black "X").

FIG. 65 shows signal-to-background ratio (S/B) at 25 ng BBSA results of a functional assay using SA conjugated with either 3× or 5× molar excess of NHS ester containing dyes. Inventive compounds showed similar performance to DyLight 750-NHS in the plate assay with equivalent or slightly lower S/B, and showed better performance than Alexa Fluor 750.

Figure 66:
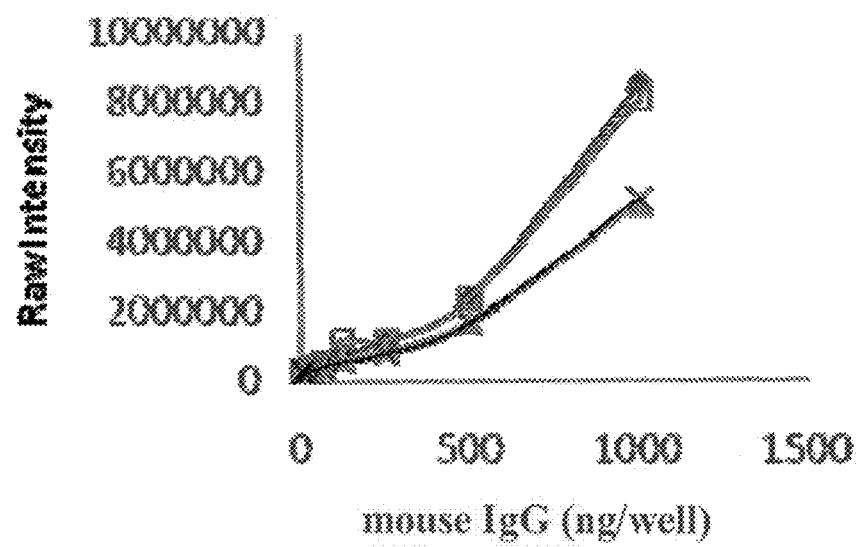
FIG. 66 shows functional assay results with some inventive compounds and commercial dyes.

FIG. 66 shows results of a functional assay, measured on LICOR Odyssey, using GAM conjugated with 2.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 67:
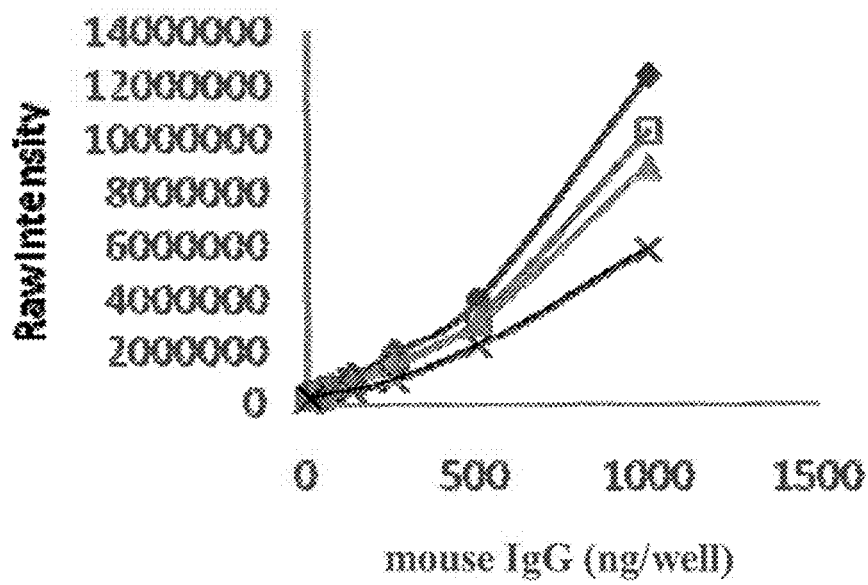
FIG. 67 shows functional assay results with some inventive compounds and commercial dyes.

FIG. 67 shows results of a functional assay, measured on LICOR Odyssey, using GAM conjugated with 7.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 68:
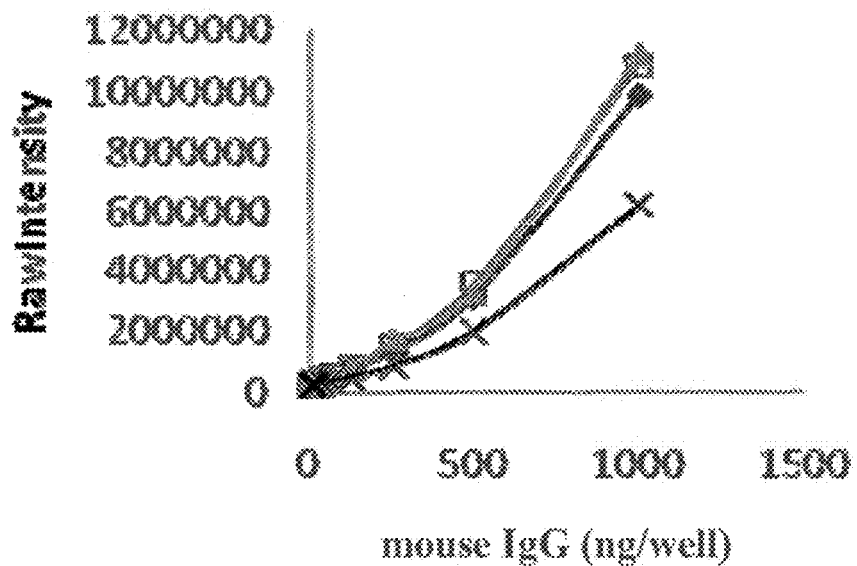
FIG. 68 shows functional assay results with some inventive compounds and commercial dyes.

FIG. 68 shows results of a functional assay, measured on LICOR Odyssey, using GAM conjugated with 10× molar excess of the dyes DyLight 750 (blue diamond); 755 Compound 1 (isomer 1) (red square); 755 Compound 1 (isomer 2) (green triangle); and Alexa Fluor 750 (black "X").

Figure 69:
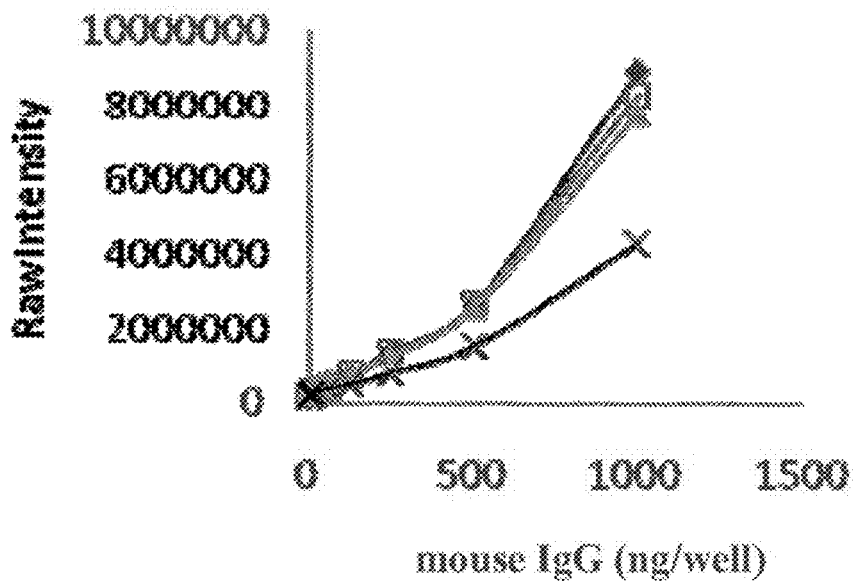
FIG. 69 shows functional assay results with some inventive compounds and commercial dyes.

FIG. 69 shows results of a functional assay, measured on LICOR Odyssey, using GAM conjugated with 15× molar excess of the dyes (DyLight 750 (blue diamond); 755 Compound 1 (isomer 1) (red square); 755 Compound 1 (isomer 2) (green triangle); and Alexa Fluor 750 (black "X").

FIGS. 70 (signal-to-background ratio at 125 ng mouse IgG) and 71 (signal-to-background ratio at 1000 ng mouse IgG) show S/B results of a functional assay using GAM conjugated with 2.5×, 7.5×, 10×, or 15× molar excess of NHS ester containing dyes. At 2.5× molar excess, GAM conjugated to DyLight 750 and 755 Compound 1 (isomer 1) showed similar performance; 755 Compound 1 (isomer 2) and Alexa 750 exhibited similar performance, but less than DyLight 750 and 755 Compound 1 (isomer 1). At 7.5× molar excess, DyLight 750 showed the best performance, followed by 755 Compound 1 (isomer 1), 755 Compound 1 (isomer 2), and Alexa 750, respectively. At 10× molar excess, the DyLight 750 and 755 Compound 1 conjugates showed similar performance, and were better than Alexa 750. All dyes exhibited signal quenching at 15× molar excess.

Figure 72:
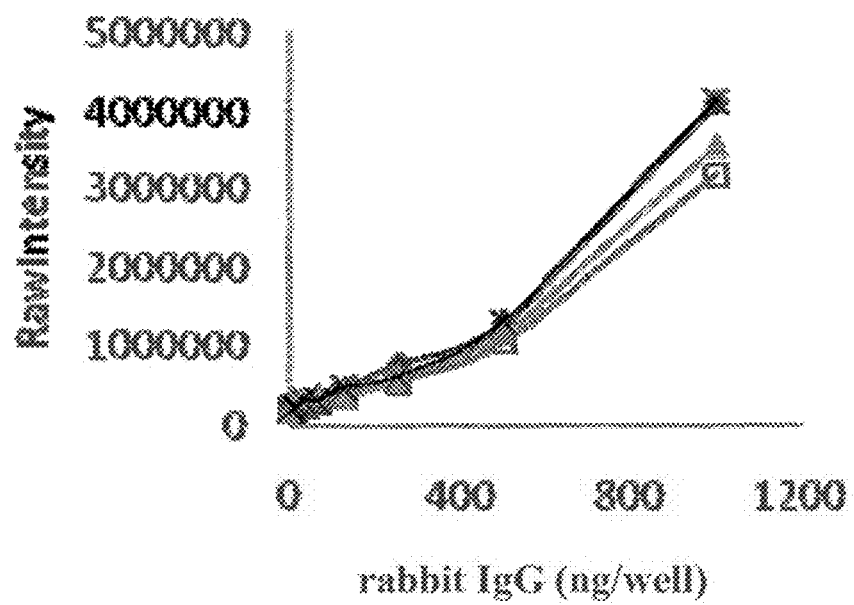
FIG. 72 shows functional assay results with some inventive compounds and commercial dyes.

FIG. 72 shows results of a functional assay, measured on LICOR Odyssey, using GAR conjugated with 2.5× molar excess of the dyes DyLight 750 (blue diamond; 755 Compound 1 (isomer 1) (red square); 755 Compound 1 (isomer 2) (green triangle); and Alexa Fluor 750 (black "X").

Figure 73:
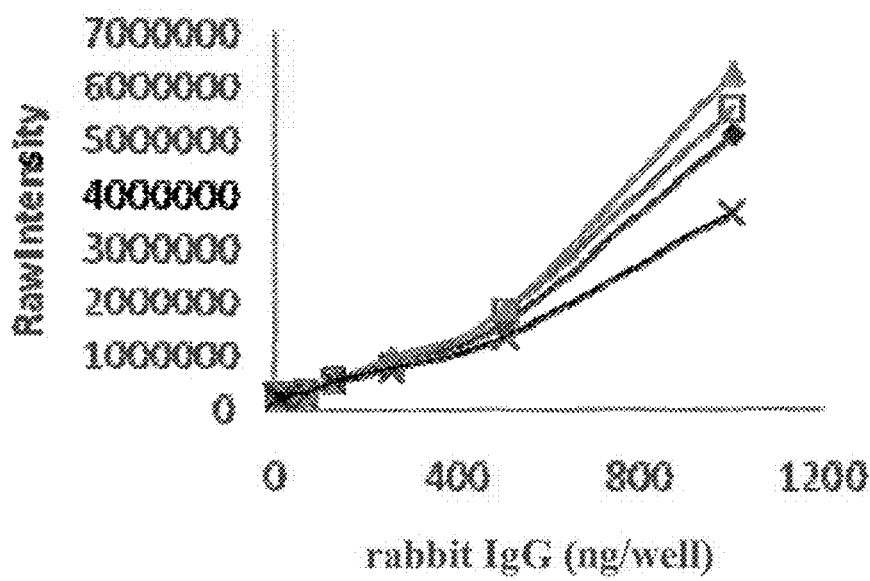
FIG. 73 shows functional assay results with some inventive compounds and commercial dyes.

FIG. 73 shows results of a functional assay, measured on LICOR Odyssey, using GAR conjugated with 7.5× molar excess of the dyes DyLight 750 (blue diamond); 755 Compound 1 (isomer 1) (red square); 755 Compound 1 (isomer 2) (green triangle); and Alexa Fluor 750 (black "X").

Figure 74:
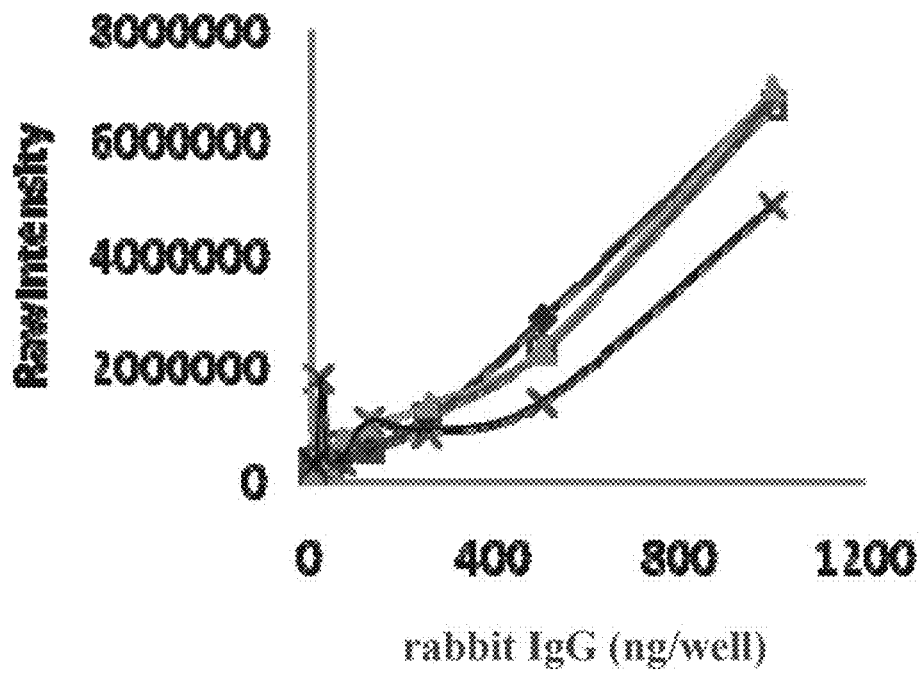
FIG. 74 shows functional assay results with some inventive compounds and commercial dyes.

FIG. 74 shows results of a functional assay, measured on LICOR Odyssey, using GAR conjugated with 10× molar excess of the dyes DyLight 750 (blue diamond); 755 Compound 1 (isomer 1) (red square); 755 Compound 1 (isomer 2) (green triangle); and Alexa Fluor 750 (black "X").

Figure 75:
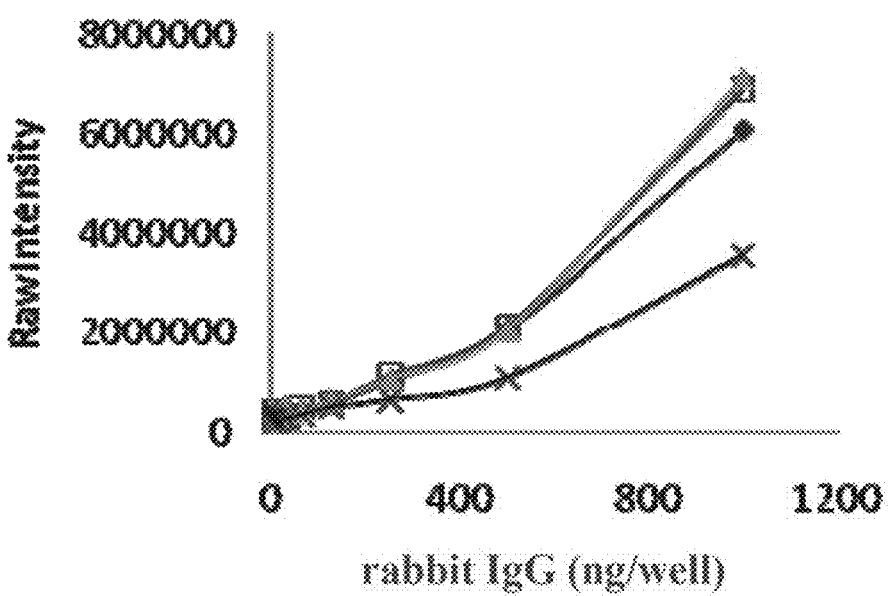
FIG. 75 shows functional assay results with some inventive compounds and commercial dyes.

FIG. 75 shows results of a functional assay, measured on LICOR Odyssey, using GAR conjugated with 15× molar excess of the dyes DyLight 750 (blue diamond); 755 Compound 1 (isomer 1) (red square); 755 Compound 1 (isomer 2) (green triangle); and Alexa Fluor 750 (black "X").

FIGS. 76 (signal-to-background ratio at 125 ng mouse IgG) and 77 (signal-to-background ratio at 1000 ng mouse IgG) show S/B results of a functional assay using GAR conjugated with 2.5×, 7.5×, 10×, or 15× molar excess of NHS ester containing dyes. At 2.5× molar excess, GAR conjugated to DyLight 750, 755 Compound 1 (isomer 1), and 755 Compound 1 (isomer 2) exhibited lower performance compared to Alexa 750, but at 7.5× molar excess, DyLight 750, 755 Compound 1 (isomer 1), and 755 Compound 1 (isomer 2) all exhibited similar performance and were superior to Alexa 750.

Figure 78:
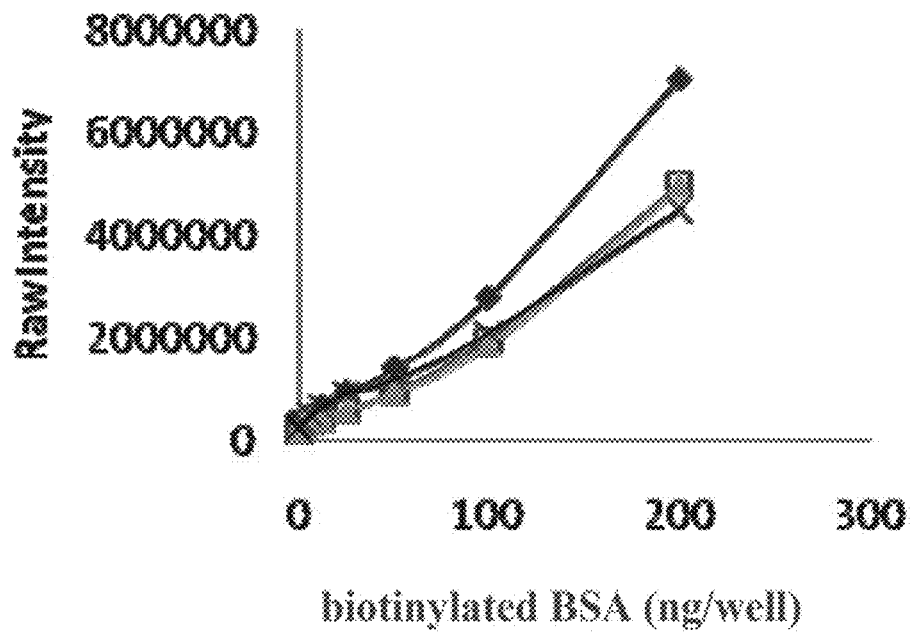
FIG. 78 shows functional assay results with some inventive compounds and commercial dyes.

FIG. 78 shows results of a functional assay, measured on LICOR Odyssey, using SA conjugated with 3× molar excess of the dyes (DyLight 750 (blue diamond); 755 Compound 1 (isomer 1) (red square); 755 Compound 1 (isomer 2) (green triangle); and Alexa Fluor 750 (black "X").

Figure 79:
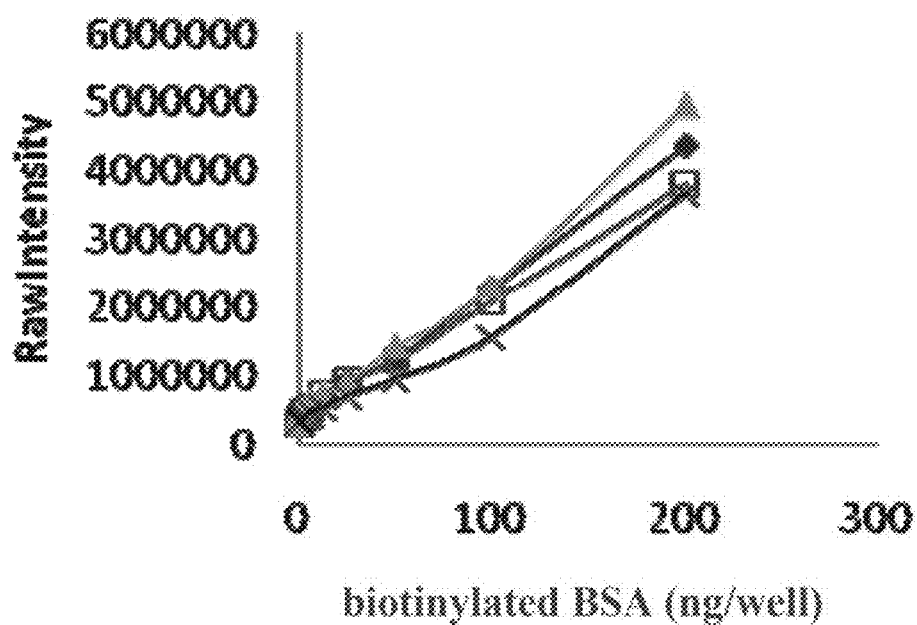
FIG. 79 shows functional assay results with some inventive compounds and commercial dyes.

FIG. 79 shows results of a functional assay, measured on LICOR Odyssey, using SA conjugated with 5× molar excess of the dyes DyLight 750 (blue diamond); 755 Compound 1 (isomer 1) (red square); 755 Compound 1 (isomer 2) (green triangle); and Alexa Fluor 750 (black "X").

FIGS. 80 (3× molar excess) and 81 (5× molar excess) show S/B results of a functional assay using SA conjugated with 3× or 5× of NHS ester containing dyes, with 200 ng or 25 ng of BBSA coating. At 3× molar excess, Dylight 750 exhibited superior performance than the other conjugates. At 5× molar excess, 755 Compound 1 (isomer 2) exhibited slightly better performance than the other conjugates.

EXAMPLE 39

The inventive compound 755 Compound 1 (isomer 1)-NHS was evaluated for stability. The compound was packed under argon in plastic vials. The vials sere sealed with a drying pad in an aluminium coated pouch, and then stored at 50° C. for 14 days. Purity was determined by HPLC before and after storage. The results of the stability study are shown below:

| Unit size | Purity at day 1 | Purity at day 14 |
| --- | --- | --- |
| 1 mg | 99% | 98% |
| 60 µg | 99% | 97% |
| 50 µg | 99% | 97% |
| 15 µg | 99% | 96% |

EXAMPLE 40

In Vivo Imaging Using 755 Compound 1 (Isomer 1) Conjugated to anti-HER2 Antibody 755 Compound 1 (isomer 1)-NHS was conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for 1 h at room temperature to result in a 755 Compound 1 (isomer 1)-anti-HER2 conjugate. The conjugation reaction was then subjected to PDDR to remove unlabeled (free) 755 Compound 1 (isomer 1). Ten microgram of the conjugate is injected intravenously (IV) to athymic mice bearing BT474 tumors. The animals were imaged over time at 1, 24, 48, 72, 96, and 120 hours post-injection using Pearl Imager from LI-COR Biosciences (LI-COR Instruments; Lincoln Nebr.).

Upon whole body imaging, fluorescence intensity was observed to be distributed over the whole animal during the first hour imagining and diminishes significantly at 72 hours. After 96 hours, the signal is localized and specific to the tumor.

EXAMPLE 41

In Vivo Imaging Using Either Monosulfonated or Disulfonated 755 Compound 1 (Isomer 1)

The compound may be rendered less hydrophilic, i.e., more hydrophobic by altering the number of sulfonate groups. The fewer sulfonates, the more hydrophobic the compound becomes. In this embodiment, the compound may be more readily retained in a desired tissue or location if the appropriate number of sulfonates is determined. For example, compound penetration into cells is more efficient if fewer sulfonates are present on the molecule. the compound may contain one, two, three, or four sulfonate groups. Hydrophobic compounds are also known to more efficiently cross the cell membrane, and therefore are more desirable when the target of interest is located within the cell.

Alendronate, a compound that binds to, and is retained in, LNCap prostate cancer cells, is conjugated with disulfonated or monosulfonated 755 Compound 1 (isomer 1) by incubating a solution containing 1 mM disulfonated or monosulfonated 755 Compound 1 (isomer 1)-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 755 Compound 1 (isomer 1)-alendronate (5 nmole) is injected into the tumor. Control mice are injected with free 755 Compound 1 (isomer 1) containing a carboxylic acid residue instead of the reactive NHS ester. X-ray and near infra-red fluorescence images are captured.

Upon imaging the whole mouse, 755 Compound 1 (isomer 1)-alendroneate conjugate is retained in mouse tissue greater than the unconjugated compound; the conjugate is retained in the LNCap cell-induced tumor for at least 18 hrs.

EXAMPLE 42

In Vivo Imaging Using Either Monosulfonated or Disulfonated 755 Compound 1 (Isomer 1)

A drug delivery nanoparticle system conjugated with disulfonated or monosulfonated 755 Compound 1 (isomer 1) is prepared as followed. A solution containing 1 mM disulfonated or monosulfonated 755 Compound 1 (isomer 1)-NHS in 1 ml of PBS is incubated overnight at room temperature with 0.1 mM of an anti-cancer drug conjugated with transferrin in the form of a nanoparticle. The resulting 755 Compound 1 (isomer 1)-nanoparticle conjugate is purified by centrifugation, and then lyophilized.

The 755 Compound 1 (isomer 1)-nanoparticle conjugate (1 nmole) is injected intravenously into the tail vein of a mouse. Control mice are injected with free 755 Compound 1 (isomer 1) dye. X-ray and near infra-red fluorescence images of mouse brain are captured.

755 Compound 1 (isomer 1)-nanoparticle conjugate localizes in the mouse brain for greater than about 24 hours after injection. Tumor size progressively decreases after injection of 755 Compound 1 (isomer 1)-nanoparticle conjugate, compared to 755 Compound 1 (isomer 1)-nanoparticle without the anti-cancer drug.

EXAMPLE 43

The mono-sulfonated derivative could be on any one of six possible positions on the 755 compound, accounting for the stereochemistry around the carbon positions on the rings as well as the non-symmetrical nature of the two ends of each dye. Similarly, the di- and tri-substituted sulfonates could be on multiple possible positions on the inventive compounds.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A compound of general formula I

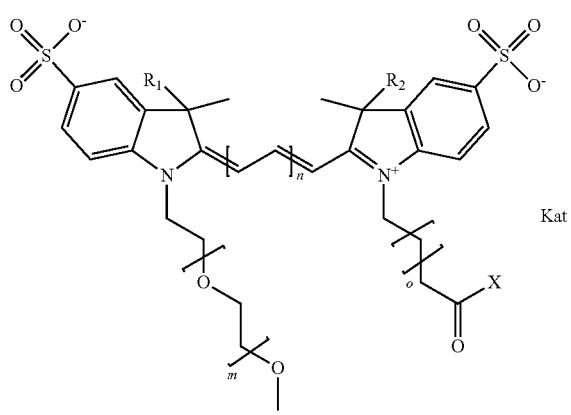

where each of $R^1$ and $R^2$ is the same or different and is independently selected from the group consisting of an alkyl and sulfoalkyl group;

X is selected from the group consisting of —OH, —SH, —NH$_2$, —NH—NH$_2$, —F, —Cl, —Br, and —I, Kat is one or more cations needed to balance the negative charge of the compound;

m is 0;

o is an integer from 0 to 12 inclusive; and n is an integer from 1 to 3 inclusive.

2. A compound of general formula II

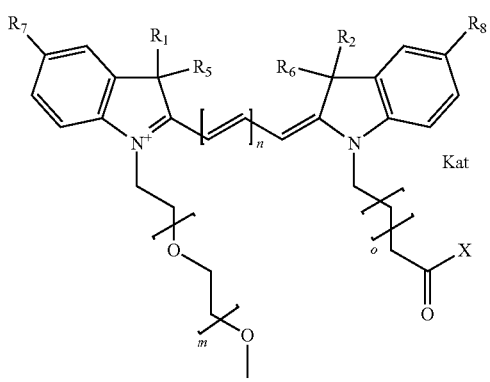

where:

each of $R^1$, $R^2$, $R^5$, and $R^6$ is the same or different and is independently selected from the group consisting of an alkyl and sulfoalkyl group;

each of $R^7$ and $R^8$ is the same or different and is independently selected from either H or SO$_3$;

X is selected from the group consisting of —OH, —SH, —NH$_2$, —NH—NH$_2$, —F, —Cl, —Br, and —I;

Kat is one or more cations needed to balance the negative charge of the compound;

m is 0;

o is an integer from 0 to 12 inclusive; and n is an integer from 1 to 3 inclusive.

3. The compound of claim 2 selected from the group consisting of

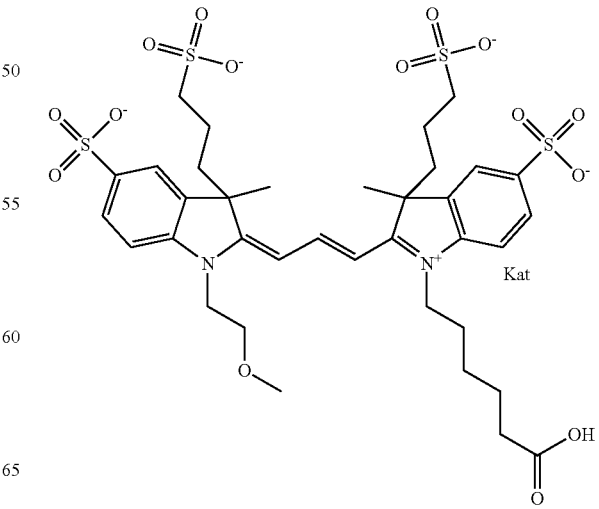

-continued

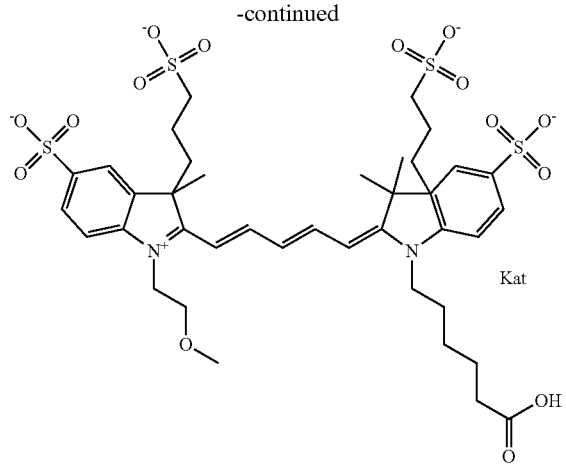

and

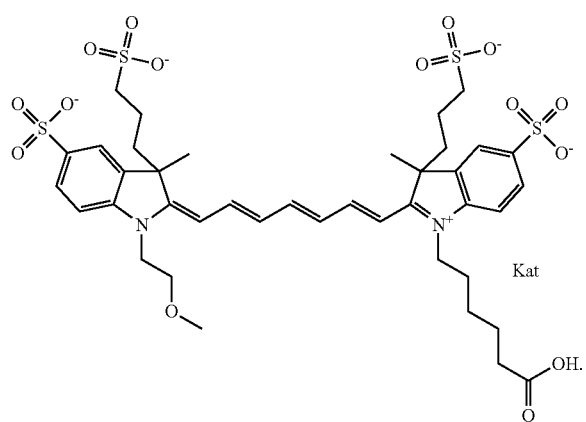

4. A compound of general formula IV

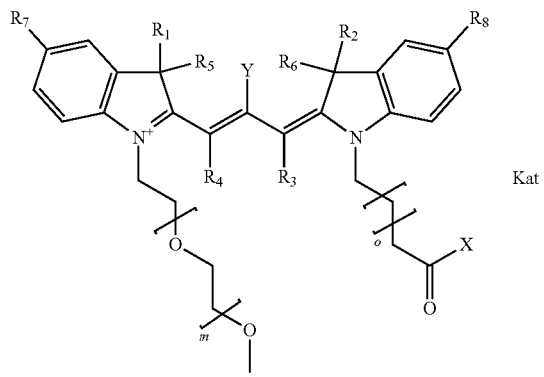

where:
each of $R^1$, $R^2$, $R^5$, and $R^6$ is the same or different and is independently selected from an alkyl and sulfoalkyl group;
each of $R^7$ and $R^8$ is the same or different and is independently selected from H or $SO_3$;
X is selected from —OH, —SH, —NH$_2$, —NH—NH$_2$, —F, —Cl, —Br, and —I;

Kat is one or more cations needed to balance the negative charge of the compound;
m is 0;
o is an integer from 0 to 12 inclusive;
each of $R^3$ and $R^4$ is the same or different and is independently hydrogen, an aliphatic group, or a heteroaliphatic group; and
Y is selected from the group consisting of hydrogen, alkyl, sulfoalkyl, fluorine, chlorine, or bromine.

5. The compound of claim 2 conjugated to at least one biomolecule selected from protein, antibody, enzyme, nucleoside triphosphate, oligonucleotide, biotin, hapten, cofactor, lectin, antibody binding protein, carotenoid, hormone, neurotransmitter, growth factor, toxin, biological cell, lipid, receptor binding drug, organic polymer carrier material, and inorganic polymeric carrier material.

6. A method of labelling at least one biomolecule, the method comprising combining a composition comprising at least one excipient and a compound of claim 2 in an effective concentration to at least one biomolecule under conditions sufficient for binding the compound to the biomolecule.

7. The method of claim 6, wherein the at least one biomolecule is selected from protein, antibody, enzyme, nucleoside triphosphate, oligonucleotide, biotin, hapten, cofactor, lectin, antibody binding protein, carotenoid, hormone, neurotransmitter, growth factors, toxin, biological cell, lipid, receptor binding drug, fluorescent proteins, organic polymer carrier material, and inorganic polymeric carrier material.

8. A method of detecting at least one biomolecule, the method comprising combining a composition comprising at least one excipient and at least one compound of claim 2 in an effective concentration to the at least one biomolecule under conditions sufficient for binding the compound to the biomolecule, resulting in the at least one compound of claim 2 being bound to the at least one biomolecule; and detecting the biomolecule-bound compound.

9. The method of claim 8, wherein the at least one biomolecule is selected from protein, antibody, enzyme, nucleoside triphosphate, oligonucleotide, biotin, hapten, cofactor, lectin, antibody binding protein, carotenoid, hormone, neurotransmitter, growth factors, toxin, biological cell, lipid, receptor binding drug, fluorescent proteins, organic polymer carrier material, and inorganic polymeric carrier material.

10. The method of claim 8, wherein the at least one biomolecule is detected in an assay selected from fluorescence microscopy, flow cytometry, in vivo imaging, immunoassay, hybridization, chromatographic assay, electrophoretic assay, microwell plate based assay, fluorescence resonance energy transfer (FRET) system, high throughput screening, or microarray.

11. The method of claim 8, wherein the biomolecule is detected by in vivo imaging comprising combining the biomolecule-bound compound to at least one of a biological sample, tissue, or organism; and detecting the biomolecule within the at least one of a biological sample, tissue or organism.

12. A kit for performing an assay to detect at least one biomolecule in a sample, the kit comprising at least one compound of claim 2 and at least one excipient, and instructions for use to detect a biomolecule in a sample.

* * * * *

UNITED STATES PATENT AND TRADEMARK OFFICE
CERTIFICATE OF CORRECTION

PATENT NO. : 11,053,222 B2  Page 1 of 1
APPLICATION NO. : 16/436512
DATED : July 6, 2021
INVENTOR(S) : Greg Hermanson et al.

It is certified that error appears in the above-identified patent and that said Letters Patent is hereby corrected as shown below:

In the Claims

In Claim 3, Column 145, Lines 1-20, please replace the existing compound with:

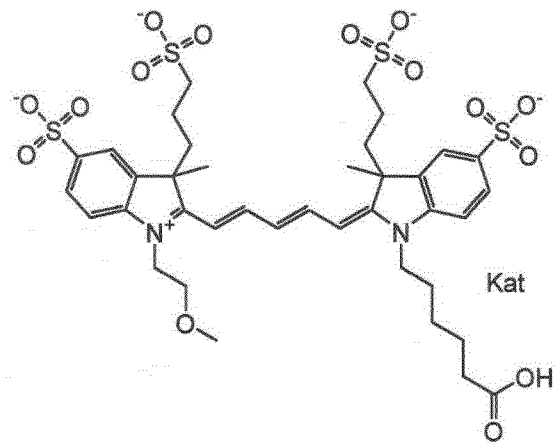

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*